US011534450B2

(12) United States Patent
Pauza et al.

(10) Patent No.: US 11,534,450 B2
(45) **Date of Patent: *Dec. 27, 2022**

(54) METHODS AND COMPOSITIONS FOR THE ACTIVATION OF GAMMA-DELTA T-CELLS

(71) Applicant: American Gene Technologies International Inc., Rockville, MD (US)

(72) Inventors: Charles David Pauza, Baltimore, MD (US); Haishan Li, North Potomac, MD (US); Tyler Lahusen, Frederick, MD (US); Mei-Ling Liou, Germantown, MD (US)

(73) Assignee: American Gene Technologies International Inc., Rockville, MD (US)

(*) Notice: Subject to any disclaimer, the term of this patent is extended or adjusted under 35 U.S.C. 154(b) by 225 days.

This patent is subject to a terminal disclaimer.

(21) Appl. No.: 16/988,427

(22) Filed: Aug. 7, 2020

(65) Prior Publication Data

US 2021/0008093 A1 Jan. 14, 2021

Related U.S. Application Data

(63) Continuation of application No. 16/530,908, filed on Aug. 2, 2019, now Pat. No. 10,772,905, which is a continuation of application No. 16/132,247, filed on Sep. 14, 2018, now Pat. No. 10,420,789, which is a continuation of application No. 15/904,131, filed on Feb. 23, 2018, now Pat. No. 10,137,144, which is a continuation-in-part of application No. 15/652,080, filed on Jul. 17, 2017, now Pat. No. 9,914,938, which is a continuation of application No. PCT/US2017/013399, filed on Jan. 13, 2017.

(60) Provisional application No. 62/279,474, filed on Jan. 15, 2016.

(51) Int. Cl.

| | |
|---|---|
| ***A61K 31/7105*** | (2006.01) |
| ***C12N 15/113*** | (2010.01) |
| ***C12N 15/86*** | (2006.01) |
| ***A61P 35/02*** | (2006.01) |
| ***A61K 47/68*** | (2017.01) |
| ***A61K 47/69*** | (2017.01) |
| ***A61K 31/675*** | (2006.01) |
| *C12Q 1/68* | (2018.01) |

(52) U.S. Cl.

CPC ........ *A61K 31/7105* (2013.01); *A61K 31/675* (2013.01); *A61K 47/6807* (2017.08); *A61K 47/6901* (2017.08); *A61P 35/02* (2018.01); *C12N 15/1137* (2013.01); *C12N 15/86* (2013.01); *C12Y 205/0101* (2013.01); *A61K 2300/00* (2013.01); *C12N 2310/14* (2013.01); *C12N 2310/531* (2013.01); *C12N 2330/51* (2013.01); *C12N 2740/16032* (2013.01); *C12N 2740/16043* (2013.01); *C12N 2740/16045* (2013.01); *C12N 2750/14143* (2013.01); *C12N 2810/6072* (2013.01)

(58) Field of Classification Search

None

See application file for complete search history.

(56) References Cited

U.S. PATENT DOCUMENTS

| | | | |
|---|---|---|---|
| 9,834,790 | B1 | 12/2017 | Pauza et al. |
| 9,914,938 | B2 | 3/2018 | Pauza et al. |
| 10,023,880 | B2 | 7/2018 | Pauza et al. |
| 10,036,040 | B2 | 7/2018 | Pauza et al. |
| 10,428,350 | B2 | 10/2019 | Pauza et al. |
| 10,472,649 | B2 | 11/2019 | Pauza et al. |
| 10,767,183 | B2 | 9/2020 | Lahusen et al. |
| 2004/0180847 | A1 | 9/2004 | Dobie et al. |
| 2016/0287635 | A1 | 10/2016 | Hariri et al. |
| 2020/0017570 | A1 | 1/2020 | Walcheck et al. |
| 2020/0354679 | A1 | 11/2020 | Niazi |

FOREIGN PATENT DOCUMENTS

| | | |
|---|---|---|
| WO | WO2010111522 | 9/2010 |
| WO | WO2010119039 | 10/2010 |
| WO | WO2012071559 | 5/2011 |
| WO | WO2013056148 | 4/2013 |
| WO | WO2014195159 | 12/2014 |
| WO | WO2017165641 | 9/2017 |

OTHER PUBLICATIONS

EP Office Action in European Application No. 17739028.3 , dated Mar. 18, 2022, 5 pages.

Chen et al., "An unconventional TRAIL to cancer therapy", Eur J Immunol, 2013, 43: 3159-3162.

Li et al., "Reduced Expression of the Mevalonate Pathway Enzyme Farnesyl Pyrophosphate Synthase Unveils Recognition of Tumor Cells by Vγ9V62 T Cells", J Immunol, 2009, 182 (12) 8118-8124.

Riaño et al., "Vγ9Vδ2 TCR-activation by phosphorylated antigens requires butyrophilin 3 AI (BTN3A1) and additional genes on human chromosome 6", Eur J Immunol, 2014, 44: 2571-2576.

U.S. Non-Final Office Action in U.S. Appl. No. 16/614,682, dated Feb. 28, 2022, 75 pages.

Altschul et al., "Basic local alignment search tool", J. Mol. Biol., May 1990, 215:403-410.

Altschul et al., "Gapped BLAST and PSI-BLAST: a new generation of protein database search programs", Nucleic Acids Res., Jul. 1997, 25(17):3389-3402.

(Continued)

*Primary Examiner* — Sean McGarry

(74) *Attorney, Agent, or Firm* — DLA Piper LLP (US)

(57) ABSTRACT

The present invention relates generally to methods and compositions for gene therapy and immunotherapy that activate gamma delta T-cells, and in particular, can be used in the treatment of various cancers and infectious diseases.

20 Claims, 15 Drawing Sheets

Specification includes a Sequence Listing.

(56) References Cited

OTHER PUBLICATIONS

Ausubel et al., "Short Protocols in Molecular Biology: A Compendium of Methods from Current Protocols" in Molecular Biology, Wiley, John & Sons, Inc., 2002, 1 page.
Berge et al. "Pharmaceutical salts", J Pharm Sci, Jan. 1977, 66(1):1-19.
Coligan et al., "Current Protocols in Protein Science", Short Protocols in Protein Science, 1996, 24:409, 1 page.
Deveraux et al., "A comprehensive set of sequence analysis programs for the VAX", Nucleic Acids Research, 1984, 12(1):387-395.
Gagniuc et al., "Eukaryotic genomes may exhibit up to 10 generic classes of gene promoters", BMC Genomics, 2012, 13:512, 17 pages.
Harlow et al., "Antibodies: A Laboratory Manual", Cold Spring Harbor Laboratory Press, 1998, 1 page.
JP Office Action in Japanese Application No. 2021-045605, dated Apr. 1, 2022, 5 pages (with English translation).
Myers et al., "Optimal alignments in linear space", CABIOS, 1989, 4:11-17.
Needleman et al., "A general method applicable to the search for similarities in the amino acid sequence of two proteins", Mol. Biol., 1970, 48:444-453.
Pauza et al., "Evolution and function of the TCR Vgamma9 chain repertoire: It's good to be public", Cell Immunol., Jul. 2015, 296(1):22-30.
Pauza et al., "γδ T cells in HIV disease: past, present, and future", Frontiers in Immunol., Jan. 2015, 5:687, 12 pages.
Pearson et al., "Improved tools for biological sequence comparison", Proc. Nat'l. Acad. Sci., Apr. 1988, 85:2444-2448.
Remington's Pharmaceutical Sciences, 17th ed., Mack Publishing Company, Easton, Pa., 1985, p. 1418.
Sambrook et al., Molecular Cloning: A Laboratory Manual, 3rd ed., Cold Spring Harbor Laboratory Press, 2000, 2272 pages.
Smith et al., "Comparison of Biosequences", Adv. Appl. Math., 1981, 2:482-489.
CN Office Action in Chinese Application No. 201780017712.6, dated Nov. 3, 2021, 18 pages (with English translation).
Cheng et al., "Establishment, Characterization, and Successful Adaptive Therapy Against Human Tumors of NKG Cell, a New Human NK Cell Line", Cell Transplantation, Jun. 2011, 20:1731-1746.
Herrera et al., "Adult peripheral blood and umbilical cord blood NK cells are good sources for effective CAR therapy against CD19 positive leukemic cells", Scientific Reports, Dec. 2019, 9(18729), 2 pages.
Mensali et al., "NK cells specifically TCR-dressed to kill cancer cells", EBioMedicine, Jan. 2019, 40:106-117.
PCT International Search Report and Written Opinion in International Application No. PCT/US2022/013422, dated May 13, 2022, 20 pages.
Shalova et al., "CD16 Regulates TRIF-Dependent TLR4 Response in Human Monocytes and Their Subsets", The Journal of Immunology, 2012, 188:3584-3593.
Fujiwara et al, "A Nucleolar Stress-Specific p53-miR-101 Molecular Circuit Functions as an Intrinsic Tumor-Suppressor Network," EBioMedicine 33, pp. 33-48, 2018.
Tian et al., "MicroRNA-30a Promotes Chondrogenic Differentiation of Mesenchymal Stem Cells Through Inhibiting Delta-Like 4 Expression," Life Sciences, 148, pp. 220-228, 2016.
Wang et al., "Kinesin Family Member 11 is a Potential Therapeutic Target and is Suppressed by MicroRNA-30a in Breast Cancer," Molecular Carcinogenesis, 59, pp. 908-922, 2020.
Ueda et al, "CD47-dependent molecular mechanisms of blood outgrowth endothelial call attachment on cholesterol-modified polyurethane," Biomaterials, vol. 31, No. 25, pp. 6394-6399, Sep. 1, 2010.
Sandstrom et al, The Intracellular B30.2 Domain of Butrophilin 3A1 Binds Phosphoantigens to Mediate Activation of Human Vγ9Vδ2 T Cells, Immunity, vol. 40, No. 4, pp. 490-500, 2014.
Wilkin et al. "Isolation and Sequence of the Human Farnesyl Pyrophosphate Synthetase eDNA," The Journal of Biological Chemestry, vol. 265, No. 8, pp. 4607-4614, Mar. 15, 1990.
USPTO; Final Office Action dated Aug. 2, 2022 is U.S. Appl. No. 16/614,682.
JP Office Action dated Jul. 11, 2022 in App. No. 2018-536892.
JP Office Action dated Jul. 12, 2022 in App. No. 2021-523916.
EPO; Extended Search Report dated Jul. 4, 2022 in EP Application No. 22154806.8.
EPO; Extended Search Report dated Jul. 21, 2022 in EP Application No. 19883230.5.

SEQUENCE LISTING

```
<160> NUMBER OF SEQ ID NOS: 65

<210> SEQ ID NO 1
<211> LENGTH: 53
<212> TYPE: DNA
<213> ORGANISM: Artificial Sequence
<220> FEATURE:
<223> OTHER INFORMATION: FDPS shRNA sequence #1

<400> SEQUENCE: 1

gtcctggagt acaatgccat tctcgagaat ggcattgtac tccaggactt ttt           53


<210> SEQ ID NO 2
<211> LENGTH: 53
<212> TYPE: DNA
<213> ORGANISM: Artificial Sequence
<220> FEATURE:
<223> OTHER INFORMATION: FDPS shRNA sequence #2

<400> SEQUENCE: 2

gcaggatttc gttcagcact tctcgagaag tgctgaacga aatcctgctt ttt           53


<210> SEQ ID NO 3
```

<211> LENGTH: 53
<212> TYPE: DNA
<213> ORGANISM: Artificial Sequence
<220> FEATURE:
<223> OTHER INFORMATION: FDPS shRNA sequence #3

<400> SEQUENCE: 3
gccatgtaca tggcaggaat tctcgagaat tcctgccatg tacatggctt ttt 53

<210> SEQ ID NO 4
<211> LENGTH: 53
<212> TYPE: DNA
<213> ORGANISM: Artificial Sequence
<220> FEATURE:
<223> OTHER INFORMATION: FDPS shRNA sequence #4

<400> SEQUENCE: 4
gcagaaggag gctgagaaag tctcgagact ttctcagcct ccttctgctt ttt 53

<210> SEQ ID NO 5
<211> LENGTH: 116
<212> TYPE: DNA
<213> ORGANISM: Artificial Sequence
<220> FEATURE:
<223> OTHER INFORMATION: miR30 FDPS sequence #1

<400> SEQUENCE: 5
aaggtatatt gctgttgaca gtgagcgaca ctttctcagc ctccttctgc gtgaagccac 60
agatggcaga aggaggctga gaaagtgctg cctactgcct cggacttcaa ggggct 116

<210> SEQ ID NO 6
<211> LENGTH: 114
<212> TYPE: DNA
<213> ORGANISM: Artificial Sequence
<220> FEATURE:
<223> OTHER INFORMATION: miR30 FDPS sequence #2

<400> SEQUENCE: 6
aaggtatatt gctgttgaca gtgagcgaca ctttctcagc ctccttctgc gtgaagccac 60
agatggcaga agggctgaga aagtgctgcc tactgcctcg gacttcaagg ggct 114

<210> SEQ ID NO 7
<211> LENGTH: 91
<212> TYPE: DNA
<213> ORGANISM: Artificial Sequence
<220> FEATURE:
<223> OTHER INFORMATION: miR30 FDPS sequence #3

<400> SEQUENCE: 7
tgctgttgac agtgagcgac tttctcagcc tccttctgcg tgaagccaca gatggcagaa 60
ggaggctgag aaagttgcct actgcctcgg a 91

<210> SEQ ID NO 8
<211> LENGTH: 115
<212> TYPE: DNA
<213> ORGANISM: Artificial Sequence
<220> FEATURE:
<223> OTHER INFORMATION: miR155 FDPS sequence #1

<400> SEQUENCE: 8
cctggaggct tgctgaaggc tgtatgctga ctttctcagc ctccttctgc ttttggccac 60
tgactgagca gaagggctga gaaagtcagg acacaaggcc tgttactagc actca 115

-continued

<210> SEQ ID NO 9
<211> LENGTH: 114
<212> TYPE: DNA
<213> ORGANISM: Artificial Sequence
<220> FEATURE:
<223> OTHER INFORMATION: miR21 FDPS sequence #1

<400> SEQUENCE: 9
catctccatg gctgtaccac cttgtcggga ctttctcagc ctccttctgc ctgttgaatc 60
tcatggcaga aggaggcgag aaagtctgac attttggtat ctttcatctg acca 114

<210> SEQ ID NO 10
<211> LENGTH: 114
<212> TYPE: DNA
<213> ORGANISM: Artificial Sequence
<220> FEATURE:
<223> OTHER INFORMATION: miR185 FDPS sequence #1

<400> SEQUENCE: 10
gggcctggct cgagcagggg gcgagggata ctttctcagc ctccttctgc tggtcccctc 60
cccgcagaag gaggctgaga aagtccttcc ctcccaatga ccgcgtcttc gtcg 114

<210> SEQ ID NO 11
<211> LENGTH: 228
<212> TYPE: DNA
<213> ORGANISM: Artificial Sequence
<220> FEATURE:
<223> OTHER INFORMATION: Rous Sarcoma virus (RSV) promoter

<400> SEQUENCE: 11
gtagtcttat gcaatactct tgtagtcttg caacatggta acgatgagtt agcaacatgc 60
cttacaagga gagaaaaagc accgtgcatg ccgattggtg gaagtaaggt ggtacgatcg 120
tgccttatta ggaaggcaac agacgggtct gacatggatt ggacgaacca ctgaattgcc 180
gcattgcaga gatattgtat ttaagtgcct agctcgatac aataaacg 228

<210> SEQ ID NO 12
<211> LENGTH: 180
<212> TYPE: DNA
<213> ORGANISM: Artificial Sequence
<220> FEATURE:
<223> OTHER INFORMATION: 5' Long terminal repeat (LTR)

<400> SEQUENCE: 12
ggtctctctg gttagaccag atctgagcct gggagctctc tggctaacta gggaacccac 60
tgcttaagcc tcaataaagc ttgccttgag tgcttcaagt agtgtgtgcc cgtctgttgt 120
gtgactctgg taactagaga tccctcagac ccttttagtc agtgtggaaa atctctagca 180

<210> SEQ ID NO 13
<211> LENGTH: 41
<212> TYPE: DNA
<213> ORGANISM: Artificial Sequence
<220> FEATURE:
<223> OTHER INFORMATION: Psi Packaging signal

<400> SEQUENCE: 13
tacgccaaaa attttgacta gcggaggcta gaaggagaga g 41

<210> SEQ ID NO 14
<211> LENGTH: 233
<212> TYPE: DNA
<213> ORGANISM: Artificial Sequence
<220> FEATURE:

<223> OTHER INFORMATION: Rev response element (RRE)

<400> SEQUENCE: 14
aggagctttg ttccttgggt tcttgggagc agcaggaagc actatgggcg cagcctcaat 60
gacgctgacg gtacaggcca gacaattatt gtctggtata gtgcagcagc agaacaattt 120
gctgagggct attgaggcgc aacagcatct gttgcaactc acagtctggg gcatcaagca 180
gctccaggca agaatcctgg ctgtggaaag atacctaaag gatcaacagc tcc 233

<210> SEQ ID NO 15
<211> LENGTH: 118
<212> TYPE: DNA
<213> ORGANISM: Artificial Sequence
<220> FEATURE:
<223> OTHER INFORMATION: Central polypurine tract (cPPT)

<400> SEQUENCE: 15
ttttaaaaga aaagggggga ttggggggta cagtgcaggg gaaagaatag tagacataat 60
agcaacagac atacaaacta aagaattaca aaaacaaatt acaaaattca aaatttta 118

<210> SEQ ID NO 16
<211> LENGTH: 217
<212> TYPE: DNA
<213> ORGANISM: Artificial Sequence
<220> FEATURE:
<223> OTHER INFORMATION: Polymerase III shRNA promoters; H1 promoter

<400> SEQUENCE: 16
gaacgctgac gtcatcaacc cgctccaagg aatcgcgggc ccagtgtcac taggcgggaa 60
cacccagcgc gcgtgcgccc tggcaggaag atggctgtga gggacagggg agtggcgccc 120
tgcaatattt gcatgtcgct atgtgttctg ggaaatcacc ataaacgtga aatgtctttg 180
gatttgggaa tcttataagt tctgtatgag accactt 217

<210> SEQ ID NO 17
<211> LENGTH: 590
<212> TYPE: DNA
<213> ORGANISM: Artificial Sequence
<220> FEATURE:
<223> OTHER INFORMATION: Long WPRE sequence

<400> SEQUENCE: 17
aatcaacctc tgattacaaa atttgtgaaa gattgactgg tattcttaac tatgttgctc 60
cttttacgct atgtggatac gctgctttaa tgcctttgta tcatgctatt gcttcccgta 120
tggctttcat tttctcctcc ttgtataaat cctggttgct gtctctttat gaggagttgt 180
ggcccgttgt caggcaacgt ggcgtggtgt gcactgtgtt tgctgacgca acccccactg 240
gttggggcat tgccaccacc tgtcagctcc tttccgggac tttcgctttc cccctcccta 300
ttgccacggc ggaactcatc gccgcctgcc ttgcccgctg ctggacaggg gctcggctgt 360
tgggcactga caattccgtg gtgttgtcgg ggaaatcatc gtcctttcct tggctgctcg 420
cctgtgttgc cacctggatt ctgcgcggga cgtccttctg ctacgtccct tcggccctca 480
atccagcgga ccttccttcc cgcggcctgc tgccggctct gcggcctctt ccgcgtcttc 540
gccttcgccc tcagacgagt cggatctccc tttgggccgc ctccccgcct 590

<210> SEQ ID NO 18
<211> LENGTH: 250
<212> TYPE: DNA
<213> ORGANISM: Artificial Sequence
<220> FEATURE:
<223> OTHER INFORMATION: 3' delta LTR

<400> SEQUENCE: 18
tggaagggct aattcactcc caacgaagat aagatctgct ttttgcttgt actgggtctc 60
tctggttaga ccagatctga gcctgggagc tctctggcta actagggaac ccactgctta 120
agcctcaata aagcttgcct tgagtgcttc aagtagtgtg tgcccgtctg ttgtgtgact 180
ctggtaacta gagatccctc agaccctttt agtcagtgtg gaaaatctct agcagtagta 240
gttcatgtca 250

<210> SEQ ID NO 19
<211> LENGTH: 290
<212> TYPE: DNA
<213> ORGANISM: Artificial Sequence
<220> FEATURE:
<223> OTHER INFORMATION: Helper/Rev; Chicken beta actin (CAG) promoter; Transcription

<400> SEQUENCE: 19
gctattacca tgggtcgagg tgagccccac gttctgcttc actctcccca tctccccccc 60
ctccccaccc ccaattttgt atttatttat tttttaatta ttttgtgcag cgatgggggc 120
gggggggggg ggggcgcgcg ccaggcgggg cggggcgggg cgaggggcgg ggcggggcga 180
ggcggagagg tgcggcggca gccaatcaga gcggcgcgct ccgaaagttt ccttttatgg 240
cgaggcggcg gcggcggcgg ccctataaaa agcgaagcgc gcggcgggcg 290

<210> SEQ ID NO 20
<211> LENGTH: 1503
<212> TYPE: DNA
<213> ORGANISM: Artificial Sequence
<220> FEATURE:
<223> OTHER INFORMATION: Helper/Rev; HIV Gag; Viral capsid

<400> SEQUENCE: 20
atgggtgcga gagcgtcagt attaagcggg ggagaattag atcgatggga aaaaattcgg 60
ttaaggccag ggggaaagaa aaaatataaa ttaaaacata tagtatgggc aagcagggag 120
ctagaacgat tcgcagttaa tcctggcctg ttagaaacat cagaaggctg tagacaaata 180
ctgggacagc tacaaccatc ccttcagaca ggatcagaag aacttagatc attatataat 240
acagtagcaa ccctctattg tgtgcatcaa aggatagaga taaaagacac caaggaagct 300
ttagacaaga tagaggaaga gcaaaacaaa agtaagaaaa aagcacagca agcagcagct 360
gacacaggac acagcaatca ggtcagccaa aattacccta tagtgcagaa catccagggg 420
caaatggtac atcaggccat atcacctaga actttaaatg catgggtaaa agtagtagaa 480
gagaaggctt tcagcccaga agtgataccc atgttttcag cattatcaga aggagccacc 540
ccacaagatt taaacaccat gctaaacaca gtggggggac atcaagcagc catgcaaatg 600
ttaaaagaga ccatcaatga ggaagctgca gaatgggata gagtgcatcc agtgcatgca 660
gggcctattg caccaggcca gatgagagaa ccaaggggaa gtgacatagc aggaactact 720
agtacccttc aggaacaaat aggatggatg acacataatc cacctatccc agtaggagaa 780
atctataaaa gatggataat cctgggatta aataaaatag taagaatgta tagccctacc 840
agcattctgg acataagaca aggaccaaag gaacccttta gagactatgt agaccgattc 900
tataaaactc taagagccga gcaagcttca caagaggtaa aaaattggat gacagaaacc 960
ttgttggtcc aaaatgcgaa cccagattgt aagactattt taaaagcatt gggaccagga 1020

-continued

```
gcgacactag aagaaatgat gacagcatgt cagggagtgg ggggacccgg ccataaagca   1080

agagttttgg ctgaagcaat gagccaagta acaaatccag ctaccataat gatacagaaa   1140

ggcaatttta ggaaccaaag aaagactgtt aagtgtttca attgtggcaa agaagggcac   1200

atagccaaaa attgcagggc ccctaggaaa aagggctgtt ggaaatgtgg aaaggaagga   1260

caccaaatga aagattgtac tgagagacag gctaattttt tagggaagat ctggccttcc   1320

cacaagggaa ggccagggaa ttttcttcag agcagaccag agccaacagc cccaccagaa   1380

gagagcttca ggtttgggga agagacaaca actccctctc agaagcagga gccgatagac   1440

aaggaactgt atcctttagc ttccctcaga tcactctttg gcagcgaccc ctcgtcacaa   1500

taa                                                                 1503
```

<210> SEQ ID NO 21
<211> LENGTH: 1872
<212> TYPE: DNA
<213> ORGANISM: Artificial Sequence
<220> FEATURE:
<223> OTHER INFORMATION: Helper/Rev; HIV Pol; Protease and reverse transcriptase

<400> SEQUENCE: 21

```
atgaatttgc caggaagatg gaaaccaaaa atgatagggg gaattggagg ttttatcaaa     60

gtaggacagt atgatcagat actcatagaa atctgcggac ataaagctat aggtacagta    120

ttagtaggac ctacacctgt caacataatt ggaagaaatc tgttgactca gattggctgc    180

actttaaatt ttcccattag tcctattgag actgtaccag taaaattaaa gccaggaatg    240

gatggcccaa aagttaaaca atggccattg acagaagaaa aaataaaagc attagtagaa    300

atttgtacag aaatggaaaa ggaaggaaaa atttcaaaaa ttgggcctga aaatccatac    360

aatactccag tatttgccat aaagaaaaaa gacagtacta aatggagaaa attagtagat    420

ttcagagaac ttaataagag aactcaagat ttctgggaag ttcaattagg aataccacat    480

cctgcagggt taaaacagaa aaaatcagta acagtactgg atgtgggcga tgcatatttt    540

tcagttccct tagataaaga cttcaggaag tatactgcat ttaccatacc tagtataaac    600

aatgagacac cagggattag atatcagtac aatgtgcttc cacagggatg gaaaggatca    660

ccagcaatat tccagtgtag catgacaaaa atcttagagc cttttagaaa acaaaatcca    720

gacatagtca tctatcaata catggatgat ttgtatgtag gatctgactt agaaataggg    780

cagcatagaa caaaaataga ggaactgaga caacatctgt tgaggtgggg atttaccaca    840

ccagacaaaa aacatcagaa agaacctcca ttcctttgga tgggttatga actccatcct    900

gataaatgga cagtacagcc tatagtgctg ccagaaaagg acagctggac tgtcaatgac    960

atacagaaat tagtgggaaa attgaattgg gcaagtcaga tttatgcagg gattaaagta   1020

aggcaattat gtaaacttct taggggaacc aaagcactaa cagaagtagt accactaaca   1080

gaagaagcag agctagaact ggcagaaaac agggagattc taaaagaacc ggtacatgga   1140

gtgtattatg acccatcaaa agacttaata gcagaaatac agaagcaggg gcaaggccaa   1200

tggacatatc aaatttatca agagccattt aaaaatctga aaacaggaaa atatgcaaga   1260

atgaagggtg cccacactaa tgatgtgaaa caattaacag aggcagtaca aaaaatagcc   1320

acagaaagca tagtaatatg gggaaagact cctaaattta aattacccat acaaaaggaa   1380

acatggaaag catggtggac agagtattgg caagccacct ggattcctga gtgggagttt   1440

gtcaataccc ctcccttagt gaagttatgg taccagttag agaaagaacc cataatagga   1500
```

-continued gcagaaactt tctatgtaga tggggcagcc aatagggaaa ctaaattagg aaaagcagga 1560
tatgtaactg acagaggaag acaaaaagtt gtccccctaa cggacacaac aaatcagaag 1620
actgagttac aagcaattca tctagctttg caggattcgg gattagaagt aaacatagtg 1680
acagactcac aatatgcatt gggaatcatt caagcacaac cagataagag tgaatcagag 1740
ttagtcagtc aaataataga gcagttaata aaaaaggaaa aagtctacct ggcatgggta 1800
ccagcacaca aaggaattgg aggaaatgaa caagtagatg ggttggtcag tgctggaatc 1860
aggaaagtac ta 1872

<210> SEQ ID NO 22
<211> LENGTH: 867
<212> TYPE: DNA
<213> ORGANISM: Artificial Sequence
<220> FEATURE:
<223> OTHER INFORMATION: Helper Rev; HIV Integrase; Integration of viral RNA

<400> SEQUENCE: 22
tttttagatg gaatagataa ggcccaagaa gaacatgaga aatatcacag taattggaga 60
gcaatggcta gtgattttaa cctaccacct gtagtagcaa aagaaatagt agccagctgt 120
gataaatgtc agctaaaagg ggaagccatg catggacaag tagactgtag cccaggaata 180
tggcagctag attgtacaca tttagaagga aaagttatct tggtagcagt tcatgtagcc 240
agtggatata tagaagcaga agtaattcca gcagagacag ggcaagaaac agcatacttc 300
ctcttaaaat tagcaggaag atggccagta aaaacagtac atacagacaa tggcagcaat 360
ttcaccagta ctacagttaa ggccgcctgt tggtgggcgg ggatcaagca ggaatttggc 420
attccctaca atccccaaag tcaaggagta atagaatcta tgaataaaga attaaagaaa 480
attataggac aggtaagaga tcaggctgaa catcttaaga cagcagtaca aatggcagta 540
ttcatccaca attttaaaag aaaagggggg attggggggt acagtgcagg ggaaagaata 600
gtagacataa tagcaacaga catacaaact aaagaattac aaaaacaaat tacaaaaatt 660
caaaattttc gggtttatta cagggacagc agagatccag tttggaaagg accagcaaag 720
ctcctctgga aaggtgaagg ggcagtagta atacaagata atagtgacat aaaagtagtg 780
ccaagaagaa aagcaaagat catcagggat tatggaaaac agatggcagg tgatgattgt 840
gtggcaagta gacaggatga ggattaa 867

<210> SEQ ID NO 23
<211> LENGTH: 234
<212> TYPE: DNA
<213> ORGANISM: Artificial Sequence
<220> FEATURE:
<223> OTHER INFORMATION: Helper/Rev; HIV RRE; Binds Rev element

<400> SEQUENCE: 23
aggagctttg ttccttgggt tcttgggagc agcaggaagc actatgggcg cagcgtcaat 60
gacgctgacg gtacaggcca gacaattatt gtctggtata gtgcagcagc agaacaattt 120
gctgagggct attgaggcgc aacagcatct gttgcaactc acagtctggg gcatcaagca 180
gctccaggca agaatcctgg ctgtggaaag atacctaaag gatcaacagc tcct 234

<210> SEQ ID NO 24
<211> LENGTH: 351
<212> TYPE: DNA
<213> ORGANISM: Artificial Sequence
<220> FEATURE:
<223> OTHER INFORMATION: Helper/Rev; HIV Rev; Nuclear export and stabilize viral mRNA

<400> SEQUENCE: 24
atggcaggaa gaagcggaga cagcgacgaa gaactcctca aggcagtcag actcatcaag 60
tttctctatc aaagcaaccc acctcccaat cccgagggga cccgacaggc ccgaaggaat 120
agaagaagaa ggtggagaga gagacagaga cagatccatt cgattagtga acggatcctt 180
agcacttatc tgggacgatc tgcggagcct gtgcctcttc agctaccacc gcttgagaga 240
cttactcttg attgtaacga ggattgtgga acttctggga cgcagggggt gggaagccct 300
caaatattgg tggaatctcc tacaatattg gagtcaggag ctaaagaata g 351

<210> SEQ ID NO 25
<211> LENGTH: 577
<212> TYPE: DNA
<213> ORGANISM: Artificial Sequence
<220> FEATURE:
<223> OTHER INFORMATION: Envelope; CMV promoter; Transcription

<400> SEQUENCE: 25
acattgatta ttgactagtt attaatagta atcaattacg gggtcattag ttcatagccc 60
atatatggag ttccgcgtta cataacttac ggtaaatggc ccgcctggct gaccgcccaa 120
cgacccccgc ccattgacgt caataatgac gtatgttccc atagtaacgc caatagggac 180
tttccattga cgtcaatggg tggagtattt acggtaaact gcccacttgg cagtacatca 240
agtgtatcat atgccaagta cgccccctat tgacgtcaat gacggtaaat ggcccgcctg 300
gcattatgcc cagtacatga ccttatggga ctttcctact tggcagtaca tctacgtatt 360
agtcatcgct attaccatgg tgatgcggtt ttggcagtac atcaatgggc gtggatagcg 420
gtttgactca cggggatttc caagtctcca ccccattgac gtcaatggga gtttgttttg 480
gcaccaaaat caacgggact ttccaaaatg tcgtaacaac tccgccccat tgacgcaaat 540
gggcggtagg cgtgtacggt gggaggtcta tataagc 577

<210> SEQ ID NO 26
<211> LENGTH: 1519
<212> TYPE: DNA
<213> ORGANISM: Artificial Sequence
<220> FEATURE:
<223> OTHER INFORMATION: Envelope; VSV-G; Glycoprotein envelope-cell entry

<400> SEQUENCE: 26
atgaagtgcc ttttgtactt agccttttta ttcattgggg tgaattgcaa gttcaccata 60
gtttttccac acaaccaaaa aggaaactgg aaaaatgttc cttctaatta ccattattgc 120
ccgtcaagct cagatttaaa ttggcataat gacttaatag gcacagcctt acaagtcaaa 180
atgcccaaga gtcacaaggc tattcaagca gacggttgga tgtgtcatgc ttccaaatgg 240
gtcactactt gtgatttccg ctggtatgga ccgaagtata taacacattc catccgatcc 300
ttcactccat ctgtagaaca atgcaaggaa agcattgaac aaacgaaaca aggaacttgg 360
ctgaatccag gcttccctcc tcaaagttgt ggatatgcaa ctgtgacgga tgccgaagca 420
gtgattgtcc aggtgactcc tcaccatgtg ctggttgatg aatacacagg agaatgggtt 480
gattcacagt tcatcaacgg aaaatgcagc aattacatat gccccactgt ccataactct 540
acaacctggc attctgacta taaggtcaaa gggctatgtg attctaacct catttccatg 600

-continued

```
gacatcacct tcttctcaga ggacggagag ctatcatccc tgggaaagga gggcacaggg    660

ttcagaagta actactttgc ttatgaaact ggaggcaagg cctgcaaaat gcaatactgc    720

aagcattggg gagtcagact cccatcaggt gtctggttcg agatggctga taaggatctc    780

tttgctgcag ccagattccc tgaatgccca gaagggtcaa gtatctctgc tccatctcag    840

acctcagtgg atgtaagtct aattcaggac gttgagagga tcttggatta ttccctctgc    900

caagaaacct ggagcaaaat cagagcgggt cttccaatct ctccagtgga tctcagctat    960

cttgctccta aaaacccagg aaccggtcct gctttcacca taatcaatgg taccctaaaa   1020

tactttgaga ccagatacat cagagtcgat attgctgctc caatcctctc aagaatggtc   1080

ggaatgatca gtggaactac cacagaaagg gaactgtggg atgactgggc accatatgaa   1140

gacgtggaaa ttggacccaa tggagttctg aggaccagtt caggatataa gtttccttta   1200

tacatgattg gacatggtat gttggactcc gatcttcatc ttagctcaaa ggctcaggtg   1260

ttcgaacatc ctcacattca agacgctgct tcgcaacttc ctgatgatga gagtttattt   1320

tttggtgata ctgggctatc caaaaatcca atcgagcttg tagaaggttg gttcagtagt   1380

tggaaaagct ctattgcctc tttttcttt atcatagggt taatcattgg actattcttg   1440

gttctccgag ttggtatcca tctttgcatt aaattaaagc acaccaagaa aagacagatt   1500

tatacagaca tagagatga                                                1519
```

<210> SEQ ID NO 27
<211> LENGTH: 352
<212> TYPE: DNA
<213> ORGANISM: Artificial Sequence
<220> FEATURE:
<223> OTHER INFORMATION: Helper/Rev; CMV early (CAG) enhancer; Enhance Transcription

<400> SEQUENCE: 27

```
tagttattaa tagtaatcaa ttacggggtc attagttcat agcccatata tggagttccg     60

cgttacataa cttacggtaa atggcccgcc tggctgaccg cccaacgacc cccgcccatt    120

gacgtcaata atgacgtatg ttcccatagt aacgccaata gggactttcc attgacgtca    180

atgggtggac tatttacggt aaactgccca cttggcagta catcaagtgt atcatatgcc    240

aagtacgccc cctattgacg tcaatgacgg taaatggccc gcctggcatt atgcccagta    300

catgacctta tgggactttc ctacttggca gtacatctac gtattagtca tc            352
```

<210> SEQ ID NO 28
<211> LENGTH: 960
<212> TYPE: DNA
<213> ORGANISM: Artificial Sequence
<220> FEATURE:
<223> OTHER INFORMATION: Helper/Rev; Chicken beta actin intron; Enhance gene expression

<400> SEQUENCE: 28

```
ggagtcgctg cgttgccttc gccccgtgcc ccgctccgcg ccgcctcgcg ccgcccgccc     60

cggctctgac tgaccgcgtt actcccacag gtgagcgggc gggacggccc ttctcctccg    120

ggctgtaatt agcgcttggt ttaatgacgg ctcgtttctt ttctgtggct gcgtgaaagc    180

cttaaagggc tccgggaggg ccctttgtgc ggggggggagc ggctcggggg gtgcgtgcgt    240

gtgtgtgtgc gtggggagcg ccgcgtgcgg cccgcgctgc ccggcggctg tgagcgctgc    300

gggcgcggcg cggggctttg tgcgctccgc gtgtgcgcga ggggagcgcg gccgggggcg    360

gtgccccgcg gtgcgggggg gctgcgaggg gaacaaaggc tgcgtgcggg gtgtgtgcgt    420
```

gggggggtga gcagggggtg tgggcgcggc ggtcgggctg taaccccccc ctgcaccccc 480
ctccccgagt tgctgagcac ggcccggctt cgggtgcggg gctccgtgcg gggcgtggcg 540
cggggctcgc cgtgccgggc gggggggtggc ggcaggtggg ggtgccgggc ggggcggggc 600
cgcctcgggc cggggagggc tcgggggagg ggcgcggcgg ccccggagcg ccggcggctg 660
tcgaggcgcg gcgagccgca gccattgcct tttatggtaa tcgtgcgaga gggcgcaggg 720
acttcctttg tcccaaatct ggcggagccg aaatctggga ggcgccgccg caccccctct 780
agcgggcgcg ggcgaagcgg tgcggcgccg gcaggaagga aatgggcggg gagggccttc 840
gtgcgtcgcc gcgccgccgt ccccttctcc atctccagcc tcggggctgc cgcaggggga 900
cggctgcctt cgggggggac ggggcagggc ggggttcggc ttctggcgtg tgaccggcgg 960

<210> SEQ ID NO 29
<211> LENGTH: 448
<212> TYPE: DNA
<213> ORGANISM: Artificial Sequence
<220> FEATURE:
<223> OTHER INFORMATION: Helper/Rev; Rabbit beta globin poly A; RNA stability

<400> SEQUENCE: 29
agatcttttt ccctctgcca aaaattatgg ggacatcatg aagccccttg agcatctgac 60
ttctggctaa taaaggaaat ttattttcat tgcaatagtg tgttggaatt ttttgtgtct 120
ctcactcgga aggacatatg ggagggcaaa tcatttaaaa catcagaatg agtatttggt 180
ttagagtttg gcaacatatg ccatatgctg gctgccatga acaaaggtgg ctataaagag 240
gtcatcagta tatgaaacag ccccctgctg tccattcctt attccataga aaagccttga 300
cttgaggtta gatttttttt atattttgtt ttgtgttatt tttttcttta acatccctaa 360
aattttcctt acatgtttta ctagccagat ttttcctcct ctcctgacta ctcccagtca 420
tagctgtccc tcttctctta tgaagatc 448

<210> SEQ ID NO 30
<211> LENGTH: 573
<212> TYPE: DNA
<213> ORGANISM: Artificial Sequence
<220> FEATURE:
<223> OTHER INFORMATION: Envelope; Beta globin intron; Enhance gene expression

<400> SEQUENCE: 30
gtgagtttgg ggacccttga ttgttctttc tttttcgcta ttgtaaaatt catgttatat 60
ggagggggca aagttttcag ggtgttgttt agaatgggaa gatgtccctt gtatcaccat 120
ggaccctcat gataattttg tttctttcac tttctactct gttgacaacc attgtctcct 180
cttattttct tttcattttc tgtaactttt tcgttaaact ttagcttgca tttgtaacga 240
atttttaaat tcacttttgt ttatttgtca gattgtaagt actttctcta atcacttttt 300
tttcaaggca atcagggtat attatattgt acttcagcac agttttagag aacaattgtt 360
ataattaaat gataaggtag aatatttctg catataaatt ctggctggcg tggaaatatt 420
cttattggta gaaacaacta caccctggtc atcatcctgc ctttctcttt atggttacaa 480
tgatatacac tgtttgagat gaggataaaa tactctgagt ccaaaccggg cccctctgct 540
aaccatgttc atgccttctt ctctttccta cag 573

<210> SEQ ID NO 31

-continued

<211> LENGTH: 450
<212> TYPE: DNA
<213> ORGANISM: Artificial Sequence
<220> FEATURE:
<223> OTHER INFORMATION: Envelope; Rabbit beta globin poly A; RNA
stability

<400> SEQUENCE: 31
agatcttttt ccctctgcca aaaattatgg ggacatcatg aagccccttg agcatctgac 60
ttctggctaa taaaggaaat ttattttcat tgcaatagtg tgttggaatt ttttgtgtct 120
ctcactcgga aggacatatg ggagggcaaa tcatttaaaa catcagaatg agtatttggt 180
ttagagtttg gcaacatatg cccatatgct ggctgccatg aacaaaggtt ggctataaag 240
aggtcatcag tatatgaaac agccccctgc tgtccattcc ttattccata gaaaagcctt 300
gacttgaggt tagatttttt ttatattttg ttttgtgtta tttttttctt taacatccct 360
aaaattttcc ttacatgttt tactagccag atttttcctc ctctcctgac tactcccagt 420
catagctgtc cctcttctct tatggagatc 450

<210> SEQ ID NO 32
<211> LENGTH: 31
<212> TYPE: DNA
<213> ORGANISM: Artificial Sequence
<220> FEATURE:
<223> OTHER INFORMATION: Primer

<400> SEQUENCE: 32
taagcagaat tcatgaattt gccaggaaga t 31

<210> SEQ ID NO 33
<211> LENGTH: 36
<212> TYPE: DNA
<213> ORGANISM: Artificial Sequence
<220> FEATURE:
<223> OTHER INFORMATION: Primer

<400> SEQUENCE: 33
ccatacaatg aatggacact aggcggccgc acgaat 36

<210> SEQ ID NO 34
<211> LENGTH: 2745
<212> TYPE: DNA
<213> ORGANISM: Artificial Sequence
<220> FEATURE:
<223> OTHER INFORMATION: Gag, Pol, Integrase fragment

<400> SEQUENCE: 34
gaattcatga atttgccagg aagatggaaa ccaaaaatga tagggggaat tggaggtttt 60
atcaaagtaa gacagtatga tcagatactc atagaaatct gcggacataa agctataggt 120
acagtattag taggacctac acctgtcaac ataattggaa gaaatctgtt gactcagatt 180
ggctgcactt taaattttcc cattagtcct attgagactg taccagtaaa attaaagcca 240
ggaatggatg gcccaaaagt taaacaatgg ccattgacag aagaaaaaat aaaagcatta 300
gtagaaattt gtacagaaat ggaaaaggaa ggaaaaattt caaaaattgg gcctgaaaat 360
ccatacaata ctccagtatt tgccataaag aaaaaagaca gtactaaatg gagaaaatta 420
gtagatttca gagaacttaa taagagaact caagatttct gggaagttca attaggaata 480
ccacatcctg cagggttaaa acagaaaaaa tcagtaacag tactggatgt gggcgatgca 540
tatttttcag ttcccttaga taaagacttc aggaagtata ctgcatttac catacctagt 600

-continued

```
ataaacaatg agacaccagg gattagatat cagtacaatg tgcttccaca gggatggaaa    660
ggatcaccag caatattcca gtgtagcatg acaaaaatct tagagccttt tagaaaacaa    720
aatccagaca tagtcatcta tcaatacatg gatgatttgt atgtaggatc tgacttagaa    780
atagggcagc atagaacaaa aatagaggaa ctgagacaac atctgttgag gtggggattt    840
accacaccag acaaaaaaca tcagaaagaa cctccattcc tttggatggg ttatgaactc    900
catcctgata aatggacagt acagcctata gtgctgccag aaaaggacag ctggactgtc    960
aatgacatac agaaattagt gggaaaattg aattgggcaa gtcagattta tgcagggatt   1020
aaagtaaggc aattatgtaa acttcttagg ggaaccaaag cactaacaga agtagtacca   1080
ctaacagaag aagcagagct agaactggca gaaaacaggg agattctaaa agaaccggta   1140
catggagtgt attatgaccc atcaaaagac ttaatagcag aaatacagaa gcaggggcaa   1200
ggccaatgga catatcaaat ttatcaagag ccatttaaaa atctgaaaac aggaaagtat   1260
gcaagaatga agggtgccca cactaatgat gtgaaacaat taacagaggc agtacaaaaa   1320
atagccacag aaagcatagt aatatgggga aagactccta aatttaaatt acccatacaa   1380
aaggaaacat gggaagcatg gtggacagag tattggcaag ccacctggat tcctgagtgg   1440
gagtttgtca ataccccctcc cttagtgaag ttatggtacc agttagagaa agaacccata   1500
ataggagcag aaactttcta tgtagatggg gcagccaata gggaaactaa attaggaaaa   1560
gcaggatatg taactgacag aggaagacaa aaagttgtcc ccctaacgga cacaacaaat   1620
cagaagactg agttacaagc aattcatcta gctttgcagg attcgggatt agaagtaaac   1680
atagtgacag actcacaata tgcattggga atcattcaag cacaaccaga taagagtgaa   1740
tcagagttag tcagtcaaat aatagagcag ttaataaaaa aggaaaaagt ctacctggca   1800
tgggtaccag cacacaaagg aattggagga aatgaacaag tagataaatt ggtcagtgct   1860
ggaatcagga aagtactatt tttagatgga atagataagg cccaagaaga acatgagaaa   1920
tatcacagta attggagagc aatggctagt gattttaacc taccacctgt agtagcaaaa   1980
gaaatagtag ccagctgtga taaatgtcag ctaaaagggg aagccatgca tggacaagta   2040
gactgtagcc caggaatatg gcagctagat tgtacacatt tagaaggaaa agttatcttg   2100
gtagcagttc atgtagccag tggatatata gaagcagaag taattccagc agagacaggg   2160
caagaaacag catacttcct cttaaaatta gcaggaagat ggccagtaaa aacagtacat   2220
acagacaatg gcagcaattt caccagtact acagttaagg ccgcctgttg gtgggcgggg   2280
atcaagcagg aatttggcat tccctacaat ccccaaagtc aaggagtaat agaatctatg   2340
aataaagaat taaagaaaat tataggacag gtaagagatc aggctgaaca tcttaagaca   2400
gcagtacaaa tggcagtatt catccacaat tttaaaagaa aaggggggat tggggggtac   2460
agtgcagggg aaagaatagt agacataata gcaacagaca tacaaactaa agaattacaa   2520
aaacaaatta caaaaattca aaattttcgg gtttattaca gggacagcag agatccagtt   2580
tggaaaggac cagcaaagct cctctggaaa ggtgaagggg cagtagtaat acaagataat   2640
agtgacataa aagtagtgcc aagaagaaaa gcaaagatca tcagggatta tggaaaacag   2700
atggcaggtg atgattgtgt ggcaagtaga caggatgagg attaa                   2745
```

<210> SEQ ID NO 35
<211> LENGTH: 1586
<212> TYPE: DNA
<213> ORGANISM: Artificial Sequence
<220> FEATURE:
<223> OTHER INFORMATION: DNA Fragment containing Rev, RRE and rabbit beta globin poly A

<400> SEQUENCE: 35
tctagaatgg caggaagaag cggagacagc gacgaagagc tcatcagaac agtcagactc 60
atcaagcttc tctatcaaag caacccacct cccaatcccg aggggacccg acaggcccga 120
aggaatagaa gaagaaggtg gagagagaga cagagacaga tccattcgat tagtgaacgg 180
atccttggca cttatctggg acgatctgcg gagcctgtgc ctcttcagct accaccgctt 240
gagagactta ctcttgattg taacgaggat tgtggaactt ctgggacgca gggggtggga 300
agccctcaaa tattggtgga atctcctaca atattggagt caggagctaa agaatagagg 360
agctttgttc cttgggttct tgggagcagc aggaagcact atgggcgcag cgtcaatgac 420
gctgacggta caggccagac aattattgtc tggtatagtg cagcagcaga acaatttgct 480
gagggctatt gaggcgcaac agcatctgtt gcaactcaca gtctggggca tcaagcagct 540
ccaggcaaga atcctggctg tggaaagata cctaaaggat caacagctcc tagatctttt 600
tccctctgcc aaaaattatg gggacatcat gaagcccctt gagcatctga cttctggcta 660
ataaaggaaa tttattttca ttgcaatagt gtgttggaat tttttgtgtc tctcactcgg 720
aaggacatat gggagggcaa atcatttaaa acatcagaat gagtatttgg tttagagttt 780
ggcaacatat gccatatgct ggctgccatg aacaaaggtg gctataaaga ggtcatcagt 840
atatgaaaca gccccctgct gtccattcct tattccatag aaaagccttg acttgaggtt 900
agattttttt tatattttgt tttgtgttat ttttttcttt aacatcccta aaattttcct 960
tacatgtttt actagccaga tttttcctcc tctcctgact actcccagtc atagctgtcc 1020
ctcttctctt atgaagatcc ctcgacctgc agcccaagct tggcgtaatc atggtcatag 1080
ctgtttcctg tgtgaaattg ttatccgctc acaattccac acaacatacg agccggaagc 1140
ataaagtgta aagcctgggg tgcctaatga gtgagctaac tcacattaat tgcgttgcgc 1200
tcactgcccg ctttccagtc gggaaacctg tcgtgccagc ggatccgcat ctcaattagt 1260
cagcaaccat agtcccgccc ctaactccgc ccatcccgcc cctaactccg cccagttccg 1320
cccattctcc gccccatggc tgactaattt tttttattta tgcagaggcc gaggccgcct 1380
cggcctctga gctattccag aagtagtgag gaggcttttt tggaggccta ggcttttgca 1440
aaaagctaac ttgtttattg cagcttataa tggttacaaa taaagcaata gcatcacaaa 1500
tttcacaaat aaagcatttt tttcactgca ttctagttgt ggtttgtcca aactcatcaa 1560
tgtatcttat cagcggccgc cccggg 1586

<210> SEQ ID NO 36
<211> LENGTH: 1614
<212> TYPE: DNA
<213> ORGANISM: Artificial Sequence
<220> FEATURE:
<223> OTHER INFORMATION: DNA fragment containing the CAG
enhancer/promoter/intron sequence

<400> SEQUENCE: 36
acgcgttagt tattaatagt aatcaattac ggggtcatta gttcatagcc catatatgga 60
gttccgcgtt acataactta cggtaaatgg cccgcctggc tgaccgccca acgacccccg 120
cccattgacg tcaataatga cgtatgttcc catagtaacg ccaataggga ctttccattg 180
acgtcaatgg gtggactatt tacggtaaac tgcccacttg gcagtacatc aagtgtatca 240
tatgccaagt acgcccccta ttgacgtcaa tgacggtaaa tggcccgcct ggcattatgc 300

```
ccagtacatg accttatggg actttcctac ttggcagtac atctacgtat tagtcatcgc    360

tattaccatg ggtcgaggtg agccccacgt tctgcttcac tctccccatc tcccccccct    420

ccccaccccc aattttgtat ttatttattt tttaattatt ttgtgcagcg atgggggcgg    480

gggggggggg ggcgcgcgcc aggcggggcg gggcggggcg aggggcgggg cggggcgagg    540

cggagaggtg cggcggcagc caatcagagc ggcgcgctcc gaaagtttcc ttttatggcg    600

aggcggcggc ggcggcggcc ctataaaaag cgaagcgcgc ggcgggcggg agtcgctgcg    660

ttgccttcgc cccgtgcccc gctccgcgcc gcctcgcgcc gcccgccccg gctctgactg    720

accgcgttac tcccacaggt gagcgggcgg gacggccctt ctcctccggg ctgtaattag    780

cgcttggttt aatgacggct cgtttctttt ctgtggctgc gtgaaagcct taaagggctc    840

cgggagggcc ctttgtgcgg ggggggagcgg ctcgggggt gcgtgcgtgt gtgtgtgcgt    900

ggggagcgcc gcgtgcggcc cgcgctgccc ggcggctgtg agcgctgcgg gcgcggcgcg    960

gggctttgtg cgctccgcgt gtgcgcgagg ggagcgcggc cgggggcggt gccccgcggt   1020

gcgggggggc tgcgagggga acaaaggctg cgtgcggggt gtgtgcgtgg gggggtgagc   1080

agggggtgtg ggcgcggcgg tcgggctgta acccccccct gcaccccct ccccgagttg   1140

ctgagcacgg cccggcttcg ggtgcggggc tccgtgcggg gcgtggcgcg gggctcgccg   1200

tgccgggcgg ggggtggcgg caggtggggg tgccgggcgg ggcggggccg cctcgggccg   1260

gggagggctc gggggagggg cgcggcggcc ccggagcgcc ggcggctgtc gaggcgcggc   1320

gagccgcagc cattgccttt tatggtaatc gtgcgagagg gcgcagggac ttcctttgtc   1380

ccaaatctgg cggagccgaa atctgggagg cgccgccgca cccctctag cgggcgcggg   1440

cgaagcggtg cggcgccggc aggaaggaaa tgggcgggga gggccttcgt gcgtcgccgc   1500

gccgccgtcc ccttctccat ctccagcctc ggggctgccg cagggggacg gctgccttcg   1560

gggggacgg ggcagggcgg ggttcggctt ctggcgtgtg accggcggga attc          1614
```

```
<210> SEQ ID NO 37
<211> LENGTH: 1531
<212> TYPE: DNA
<213> ORGANISM: Artificial Sequence
<220> FEATURE:
<223> OTHER INFORMATION: DNA fragment containing VSV-G

<400> SEQUENCE: 37

gaattcatga agtgcctttt gtacttagcc tttttattca ttggggtgaa ttgcaagttc     60

accatagttt ttccacacaa ccaaaaagga aactggaaaa atgttccttc taattaccat    120

tattgcccgt caagctcaga tttaaattgg cataatgact taataggcac agccttacaa    180

gtcaaaatgc ccaagagtca caaggctatt caagcagacg gttggatgtg tcatgcttcc    240

aaatgggtca ctacttgtga tttccgctgg tatggaccga agtatataac acattccatc    300

cgatccttca ctccatctgt agaacaatgc aaggaaagca ttgaacaaac gaaacaagga    360

acttggctga atccaggctt ccctcctcaa agttgtggat atgcaactgt gacggatgcc    420

gaagcagtga ttgtccaggt gactcctcac catgtgctgg ttgatgaata cacaggagaa    480

tgggttgatt cacagttcat caacggaaaa tgcagcaatt acatatgccc cactgtccat    540

aactctacaa cctggcattc tgactataag gtcaaagggc tatgtgattc taacctcatt    600

tccatggaca tcaccttctt ctcagaggac ggagagctat catccctggg aaaggagggc    660

acagggttca gaagtaacta ctttgcttat gaaactggag gcaaggcctg caaaatgcaa    720

tactgcaagc attggggagt cagactccca tcaggtgtct ggttcgagat ggctgataag    780
```

```
gatctctttg ctgcagccag attccctgaa tgcccagaag ggtcaagtat ctctgctcca    840
tctcagacct cagtggatgt aagtctaatt caggacgttg agaggatctt ggattattcc    900
ctctgccaag aaacctggag caaaatcaga gcgggtcttc caatctctcc agtggatctc    960
agctatcttg ctcctaaaaa cccaggaacc ggtcctgctt tcaccataat caatggtacc   1020
ctaaaatact ttgagaccag atacatcaga gtcgatattg ctgctccaat cctctcaaga   1080
atggtcggaa tgatcagtgg aactaccaca gaaagggaac tgtgggatga ctgggcacca   1140
tatgaagacg tggaaattgg acccaatgga gttctgagga ccagttcagg atataagttt   1200
cctttataca tgattggaca tggtatgttg gactccgatc ttcatcttag ctcaaaggct   1260
caggtgttcg aacatcctca cattcaagac gctgcttcgc aacttcctga tgatgagagt   1320
ttattttttg gtgatactgg gctatccaaa aatccaatcg agcttgtaga aggttggttc   1380
agtagttgga aaagctctat tgcctctttt ttctttatca tagggttaat cattggacta   1440
ttcttggttc tccgagttgg tatccatctt tgcattaaat taaagcacac caagaaaaga   1500
cagatttata cagacataga gatgagaatt c                                  1531
```

<210> SEQ ID NO 38
<211> LENGTH: 884
<212> TYPE: DNA
<213> ORGANISM: Artificial Sequence
<220> FEATURE:
<223> OTHER INFORMATION: RSV promoter and HIV Rev

<400> SEQUENCE: 38

```
caattgcgat gtacgggcca gatatacgcg tatctgaggg gactagggtg tgtttaggcg     60
aaaagcgggg cttcggttgt acgcggttag gagtcccctc aggatatagt agtttcgctt    120
ttgcataggg agggggaaat gtagtcttat gcaatacact tgtagtcttg caacatggta    180
acgatgagtt agcaacatgc cttacaagga gagaaaaagc accgtgcatg ccgattggtg    240
gaagtaaggt ggtacgatcg tgccttatta ggaaggcaac agacaggtct gacatggatt    300
ggacgaacca ctgaattccg cattgcagag ataattgtat ttaagtgcct agctcgatac    360
aataaacgcc atttgaccat tcaccacatt ggtgtgcacc tccaagctcg agctcgttta    420
gtgaaccgtc agatcgcctg gagacgccat ccacgctgtt ttgacctcca tagaagacac    480
cgggaccgat ccagcctccc ctcgaagcta gcgattaggc atctcctatg gcaggaagaa    540
gcggagacag cgacgaagaa ctcctcaagg cagtcagact catcaagttt ctctatcaaa    600
gcaacccacc tcccaatccc gaggggaccc gacaggcccg aaggaataga agaagaaggt    660
ggagagagag acagagacag atccattcga ttagtgaacg gatccttagc acttatctgg    720
gacgatctgc ggagcctgtg cctcttcagc taccaccgct tgagagactt actcttgatt    780
gtaacgagga ttgtggaact tctgggacgc agggggtggg aagccctcaa atattggtgg    840
aatctcctac aatattggag tcaggagcta aagaatagtc taga                     884
```

<210> SEQ ID NO 39
<211> LENGTH: 1104
<212> TYPE: DNA
<213> ORGANISM: Artificial Sequence
<220> FEATURE:
<223> OTHER INFORMATION: Elongation Factor-1 alpha (EF1-alpha) promoter

<400> SEQUENCE: 39

```
ccggtgccta gagaaggtgg cgcggggtaa actgggaaag tgatgtcgtg tactggctcc     60
```

gcctttttcc cgagggtggg ggagaaccgt atataagtgc agtagtcgcc gtgaacgttc 120
tttttcgcaa cgggtttgcc gccagaacac aggtaagtgc cgtgtgtggt tcccgcgggc 180
ctggcctctt tacgggttat ggcccttgcg tgccttgaat tacttccacg cccctggctg 240
cagtacgtga ttcttgatcc cgagcttcgg gttggaagtg ggtgggagag ttcgaggcct 300
tgcgcttaag gagccccttc gcctcgtgct tgagttgagg cctggcctgg gcgctggggc 360
cgccgcgtgc gaatctggtg gcaccttcgc gcctgtctcg ctgctttcga taagtctcta 420
gccatttaaa atttttgatg acctgctgcg acgctttttt tctggcaaga tagtcttgta 480
aatgcgggcc aagatctgca cactggtatt tcggtttttg gggccgcggg cggcgacggg 540
gcccgtgcgt cccagcgcac atgttcggcg aggcggggcc tgcgagcgcg gccaccgaga 600
atcggacggg ggtagtctca agctggccgg cctgctctgg tgcctggcct cgcgccgccg 660
tgtatcgccc cgccctgggc ggcaaggctg gcccggtcgg caccagttgc gtgagcggaa 720
agatggccgc ttcccggccc tgctgcaggg agctcaaaat ggaggacgcg gcgctcggga 780
gagcgggcgg gtgagtcacc cacacaaagg aaaagggcct ttccgtcctc agccgtcgct 840
tcatgtgact ccacggagta ccgggcgccg tccaggcacc tcgattagtt ctcgagcttt 900
tggagtacgt cgtctttagg ttggggggag gggttttatg cgatggagtt tccccacact 960
gagtgggtgg agactgaagt taggccagct tggcacttga tgtaattctc cttggaattt 1020 gcccttttttg agtttggatc ttggttcatt ctcaagcctc agacagtggt tcaaagtttt 1080
tttcttccat ttcaggtgtc gtga 1104

<210> SEQ ID NO 40
<211> LENGTH: 511
<212> TYPE: DNA
<213> ORGANISM: Artificial Sequence
<220> FEATURE:
<223> OTHER INFORMATION: Promoter; PGK

<400> SEQUENCE: 40
ggggttgggg ttgcgccttt tccaaggcag ccctgggttt gcgcagggac gcggctgctc 60
tgggcgtggt tccgggaaac gcagcggcgc cgaccctggg tctcgcacat tcttcacgtc 120
cgttcgcagc gtcacccgga tcttcgccgc tacccttgtg ggcccccccgg cgacgcttcc 180 tgctccgccc ctaagtcggg aaggttcctt gcggttcgcg gcgtgccgga cgtgacaaac 240
ggaagccgca cgtctcacta gtaccctcgc agacggacag cgccagggag caatggcagc 300
gcgccgaccg cgatgggctg tggccaatag cggctgctca gcagggcgcg ccgagagcag 360
cggccgggaa ggggcggtgc gggaggcggg gtgtggggcg gtagtgtggg ccctgttcct 420
gcccgcgcgg tgttccgcat tctgcaagcc tccggagcgc acgtcggcag tcggctccct 480
cgttgaccga atcaccgacc tctctcccca g 511

<210> SEQ ID NO 41
<211> LENGTH: 1162
<212> TYPE: DNA
<213> ORGANISM: Artificial Sequence
<220> FEATURE:
<223> OTHER INFORMATION: Promoter; UbC

<400> SEQUENCE: 41
gcgccgggtt ttggcgcctc ccgcgggcgc ccccctcctc acggcgagcg ctgccacgtc 60
agacgaaggg cgcaggagcg ttcctgatcc ttccgcccgg acgctcagga cagcggcccg 120
ctgctcataa gactcggcct tagaacccca gtatcagcag aaggacattt taggacggga 180

-continued

```
cttgggtgac tctagggcac tggttttctt tccagagagc ggaacaggcg aggaaaagta    240

gtcccttctc ggcgattctg cggagggatc tccgtggggc ggtgaacgcc gatgattata    300

taaggacgcg ccgggtgtgg cacagctagt tccgtcgcag ccgggatttg ggtcgcggtt    360

cttgtttgtg gatcgctgtg atcgtcactt ggtgagttgc gggctgctgg gctggccggg    420

gctttcgtgg ccgccgggcc gctcggtggg acggaagcgt gtggagagac cgccaagggc    480

tgtagtctgg gtccgcgagc aaggttgccc tgaactgggg gttgggggga gcgcacaaaa    540

tggcggctgt tcccgagtct tgaatggaag acgcttgtaa ggcgggctgt gaggtcgttg    600

aaacaaggtg gggggcatgg tgggcggcaa gaacccaagg tcttgaggcc ttcgctaatg    660

cgggaaagct cttattcggg tgagatgggc tggggcacca tctggggacc ctgacgtgaa    720

gtttgtcact gactggagaa ctcgggtttg tcgtctggtt gcgggggcgg cagttatgcg    780

gtgccgttgg gcagtgcacc cgtacctttg ggagcgcgcg cctcgtcgtg tcgtgacgtc    840

acccgttctg ttggcttata atgcagggtg ggccacctg ccggtaggtg tgcggtaggc    900

ttttctccgt cgcaggacgc agggttcggg cctagggtag gctctcctga atcgacaggc    960

gccggacctc tggtgagggg agggataagt gaggcgtcag tttctttggt cggttttatg   1020

tacctatctt cttaagtagc tgaagctccg gttttgaact atgcgctcgg ggttggcgag   1080

tgtgttttgt gaagtttttt aggcaccttt tgaaatgtaa tcatttgggt caatatgtaa   1140

ttttcagtgt tagactagta aa                                            1162
```

<210> SEQ ID NO 42
<211> LENGTH: 120
<212> TYPE: DNA
<213> ORGANISM: Artificial Sequence
<220> FEATURE:
<223> OTHER INFORMATION: Poly A; SV40

<400> SEQUENCE: 42

```
gtttattgca gcttataatg gttacaaata aagcaatagc atcacaaatt tcacaaataa     60

agcatttttt tcactgcatt ctagttgtgg tttgtccaaa ctcatcaatg tatcttatca    120
```

<210> SEQ ID NO 43
<211> LENGTH: 227
<212> TYPE: DNA
<213> ORGANISM: Artificial Sequence
<220> FEATURE:
<223> OTHER INFORMATION: Poly A; bGH

<400> SEQUENCE: 43

```
gactgtgcct tctagttgcc agccatctgt tgtttgcccc tcccccgtgc cttccttgac     60

cctggaaggt gccactccca ctgtcctttc ctaataaaat gaggaaattg catcgcattg    120

tctgagtagg tgtcattcta ttctgggggg tggggtgggg caggacagca agggggagga    180

ttgggaagac aatagcaggc atgctgggga tgcggtgggc tctatgg                 227
```

<210> SEQ ID NO 44
<211> LENGTH: 1695
<212> TYPE: DNA
<213> ORGANISM: Artificial Sequence
<220> FEATURE:
<223> OTHER INFORMATION: Envelope; RD114

<400> SEQUENCE: 44

```
atgaaactcc caacaggaat ggtcatttta tgtagcctaa taatagttcg ggcagggttt     60
```

-continued gacgaccccc gcaaggctat cgcattagta caaaaacaac atggtaaacc atgcgaatgc 120
agcggagggc aggtatccga ggccccaccg aactccatcc aacaggtaac ttgcccaggc 180
aagacggcct acttaatgac caaccaaaaa tggaaatgca gagtcactcc aaaaaatctc 240
acccctagcg gggagaact ccagaactgc ccctgtaaca ctttccagga ctcgatgcac 300
agttcttgtt atactgaata ccggcaatgc agggcgaata ataagacata ctacacggcc 360
accttgctta aaatacggtc tgggagcctc aacgaggtac agatattaca aaaccccaat 420
cagctcctac agtccccttg taggggctct ataaatcagc ccgtttgctg gagtgccaca 480
gcccccatcc atatctccga tggtggagga cccctcgata ctaagagagt gtggacagtc 540
caaaaaaggc tagaacaaat tcataaggct atgcatcctg aacttcaata ccacccctta 600
gccctgccca aagtcagaga tgaccttagc cttgatgcac ggacttttga tatcctgaat 660
accactttta ggttactcca gatgtccaat tttagccttg cccaagattg ttggctctgt 720
ttaaaactag gtacccctac ccctcttgcg atacccactc cctctttaac ctactcccta 780
gcagactccc tagcgaatgc ctcctgtcag attatacctc ccctcttggt tcaaccgatg 840
cagttctcca actcgtcctg tttatcttcc cctttcatta acgatacgga acaaatagac 900
ttaggtgcag tcacctttac taactgcacc tctgtagcca atgtcagtag tcctttatgt 960
gccctaaacg ggtcagtctt cctctgtgga aataacatgg catacaccta tttaccccaa 1020
aactggacag gactttgcgt ccaagcctcc ctcctccccg acattgacat catcccgggg 1080
gatgagccag tccccattcc tgccattgat cattatatac atagacctaa acgagctgta 1140
cagttcatcc ctttactagc tggactggga atcaccgcag cattcaccac cggagctaca 1200
ggcctaggtg tctccgtcac ccagtataca aaattatccc atcagttaat atctgatgtc 1260
caagtcttat ccggtaccat acaagattta caagaccagg tagactcgtt agctgaagta 1320
gttctccaaa ataggagggg actggaccta ctaacggcag aacaaggagg aatttgttta 1380
gccttacaag aaaaatgctg tttttatgct aacaagtcag gaattgtgag aaacaaaata 1440
agaaccctac aagaagaatt acaaaaacgc agggaaagcc tggcatccaa ccctctctgg 1500
accgggctgc agggctttct tccgtacctc ctacctctcc tgggacccct actcaccctc 1560
ctactcatac taaccattgg gccatgcgtt ttcaatcgat tggtccaatt tgttaaagac 1620
aggatctcag tggtccaggc tctggttttg actcagcaat atcaccagct aaaacccata 1680
gagtacgagc catga 1695

<210> SEQ ID NO 45
<211> LENGTH: 2013
<212> TYPE: DNA
<213> ORGANISM: Artificial Sequence
<220> FEATURE:
<223> OTHER INFORMATION: Envelope; GALV

<400> SEQUENCE: 45
atgcttctca cctcaagccc gcaccacctt cggcaccaga tgagtcctgg gagctggaaa 60
agactgatca tcctcttaag ctgcgtattc ggagacggca aaacgagtct gcagaataag 120
aacccccacc agcctgtgac cctcacctgg caggtactgt cccaaactgg ggacgttgtc 180
tgggacaaaa aggcagtcca gccccttgg acttggtggc cctctcttac acctgatgta 240
tgtgccctgg cggccggtct tgagtcctgg gatatcccgg gatccgatgt atcgtcctct 300
aaaagagtta gacctcctga ttcagactat actgccgctt ataagcaaat cacctgggga 360
gccatagggt gcagctaccc tcgggctagg accaggatgg caaattcccc cttctacgtg 420
tgtccccgag ctggccgaac ccattcagaa gctaggaggt gtggggggct agaatcccta 480
tactgtaaag aatggagttg tgagaccacg ggtaccgttt attggcaacc caagtcctca 540
tgggacctca taactgtaaa atgggaccaa aatgtgaaat gggagcaaaa atttcaaaag 600
tgtgaacaaa ccggctggtg taacccccctc aagatagact tcacagaaaa aggaaaactc 660
tccagagatt ggataacgga aaaaacctgg gaattaaggt tctatgtata tggacaccca 720
ggcatacagt tgactatccg cttagaggtc actaacatgc cggttgtggc agtgggccca 780
gaccctgtcc ttgcggaaca gggacctcct agcaagcccc tcactctccc tctctcccca 840
cggaaagcgc cgcccacccc tctacccccg gcggctagtg agcaaacccc tgcggtgcat 900
ggagaaactg ttaccctaaa ctctccgcct cccaccagtg gcgaccgact ctttggcctt 960
gtgcaggggg ccttcctaac cttgaatgct accaacccag gggccactaa gtcttgctgg 1020
ctctgtttgg gcatgagccc cccttattat gaagggatag cctcttcagg agaggtcgct 1080
tatacctcca accatacccg atgccactgg ggggcccaag gaaagcttac cctcactgag 1140
gtctccggac tcgggtcatg catagggaag gtgcctctta cccatcaaca tctttgcaac 1200
cagaccttac ccatcaattc ctctaaaaac catcagtatc tgctcccctc aaaccatagc 1260
tggtgggcct gcagcactgg cctcaccccc tgcctctcca cctcagtttt taatcagtct 1320
aaagacttct gtgtccaggt ccagctgatc cccgcatct attaccattc tgaagaaacc 1380
ttgttacaag cctatgacaa atcaccccccc aggtttaaaa gagagcctgc ctcacttacc 1440
ctagctgtct tcctggggtt agggattgcg gcaggtatag gtactggctc aaccgcccta 1500
attaaagggc ccatagacct ccagcaaggc ctaaccagcc tccaaatcgc cattgacgct 1560
gacctccggg cccttcagga ctcaatcagc aagctagagg actcactgac ttccctatct 1620
gaggtagtac tccaaaatag gagaggcctt gacttactat tccttaaaga aggaggcctc 1680
tgcgcggccc taaaagaaga gtgctgtttt tatgtagacc actcaggtgc agtacgagac 1740
tccatgaaaa aacttaaaga aagactagat aaaagacagt tagagcgcca gaaaaaccaa 1800
aactggtatg aagggtggtt caataactcc ccttggttta ctaccctact atcaaccatc 1860
gctgggcccc tattgctcct ccttttgtta ctcactcttg ggccctgcat catcaataaa 1920
ttaatccaat tcatcaatga taggataagt gcagtcaaaa ttttagtcct tagacagaaa 1980
tatcagaccc tagataacga ggaaaacctt taa 2013

<210> SEQ ID NO 46
<211> LENGTH: 1530
<212> TYPE: DNA
<213> ORGANISM: Artificial Sequence
<220> FEATURE:
<223> OTHER INFORMATION: Envelope; FUG

<400> SEQUENCE: 46
atggttccgc aggttctttt gtttgtactc cttctgggtt tttcgttgtg tttcgggaag 60
ttccccattt acacgatacc agacgaactt ggtccctgga gccctattga catacaccat 120
ctcagctgtc caaataacct ggttgtggag gatgaaggat gtaccaacct gtccgagttc 180
tcctacatgg aactcaaagt gggatacatc tcagccatca aagtgaacgg gttcacttgc 240
acaggtgttg tgacagaggc agagacctac accaactttg ttggttatgt cacaaccaca 300
ttcaagagaa agcatttccg ccccacccca gacgcatgta gagccgcgta taactggaag 360
atggccggtg accccagata tgaagagtcc ctacacaatc cataccccga ctaccactgg 420

-continued cttcgaactg taagaaccac caaagagtcc ctcattatca tatccccaag tgtgacagat 480
ttggacccat atgacaaatc ccttcactca agggtcttcc ctggcggaaa gtgctcagga 540
ataacggtgt cctctaccta ctgctcaact aaccatgatt acaccatttg gatgcccgag 600
aatccgagac caaggacacc ttgtgacatt tttaccaata gcagagggaa gagagcatcc 660
aacgggaaca agacttgcgg ctttgtggat gaaagaggcc tgtataagtc tctaaaagga 720
gcatgcaggc tcaagttatg tggagttctt ggacttagac ttatggatgg aacatgggtc 780
gcgatgcaaa catcagatga gaccaaatgg tgccctccag atcagttggt gaatttgcac 840
gactttcgct cagacgagat cgagcatctc gttgtggagg agttagttaa gaaaagagag 900
gaatgtctgg atgcattaga gtccatcatg accaccaagt cagtaagttt cagacgtctc 960
agtcacctga gaaaacttgt cccagggttt ggaaaagcat ataccatatt caacaaaacc 1020
ttgatggagg ctgatgctca ctacaagtca gtccggacct ggaatgagat catcccctca 1080
aaagggtgtt tgaaagttgg aggaaggtgc catcctcatg tgaacggggt gtttttcaat 1140
ggtataatat tagggcctga cgaccatgtc ctaatcccag agatgcaatc atccctcctc 1200
cagcaacata tggagttgtt ggaatcttca gttatccccc tgatgcaccc cctggcagac 1260
ccttctacag ttttcaaaga aggtgatgag gctgaggatt ttgttgaagt tcacctcccc 1320
gatgtgtaca aacagatctc aggggttgac ctgggtctcc cgaactgggg aaagtatgta 1380
ttgatgactg caggggccat gattggcctg gtgttgatat tttccctaat gacatggtgc 1440
agagttggta tccatctttg cattaaatta aagcacacca agaaaaagaca gatttataca 1500 gacatagaga tgaaccgact tggaaagtaa 1530

<210> SEQ ID NO 47
<211> LENGTH: 1497
<212> TYPE: DNA
<213> ORGANISM: Artificial Sequence
<220> FEATURE:
<223> OTHER INFORMATION: Envelope; LCMV

<400> SEQUENCE: 47
atgggtcaga ttgtgacaat gtttgaggct ctgcctcaca tcatcgatga ggtgatcaac 60
attgtcatta ttgtgcttat cgtgatcacg ggtatcaagg ctgtctacaa ttttgccacc 120
tgtgggatat tcgcattgat cagtttccta cttctggctg gcaggtcctg tggcatgtac 180
ggtcttaagg gacccgacat ttacaaagga gtttaccaat ttaagtcagt ggagtttgat 240
atgtcacatc tgaacctgac catgcccaac gcatgttcag ccaacaactc ccaccattac 300
atcagtatgg ggacttctgg actagaattg accttcacca atgattccat catcagtcac 360
aacttttgca atctgacctc tgccttcaac aaaaagacct ttgaccacac actcatgagt 420
atagtttcga gcctacacct cagtatcaga gggaactcca actataaggc agtatcctgc 480
gacttcaaca atggcataac catccaatac aacttgacat tctcagatcg acaaagtgct 540
cagagccagt gtagaacctt cagaggtaga gtcctagata tgtttagaac tgccttcggg 600
gggaaataca tgaggagtgg ctggggctgg acaggctcag atggcaagac cacctggtgt 660
agccagacga gttaccaata cctgattata caaaatagaa cctgggaaaa ccactgcaca 720
tatgcaggtc cttttgggat gtccaggatt ctcctttccc aagagaagac taagttcttc 780
actaggagac tagcgggcac attcacctgg actttgtcag actcttcagg ggtggagaat 840
ccaggtggtt attgcctgac caaatggatg attcttgctg cagagcttaa gtgtttcggg 900
aacacagcag ttgcgaaatg caatgtaaat catgatgccg aattctgtga catgctgcga 960
ctaattgact acaacaaggc tgctttgagt aagttcaaag aggacgtaga atctgccttg 1020
cacttattca aaacaacagt gaattctttg atttcagatc aactactgat gaggaaccac 1080
ttgagagatc tgatgggggt gccatattgc aattactcaa agttttggta cctagaacat 1140
gcaaagaccg gcgaaactag tgtccccaag tgctggcttg tcaccaatgg ttcttactta 1200
aatgagaccc acttcagtga tcaaatcgaa caggaagccg ataacatgat tacagagatg 1260
ttgaggaagg attacataaa gaggcagggg agtacccccc tagcattgat ggaccttctg 1320
atgttttcca catctgcata tctagtcagc atcttcctgc accttgtcaa aataccaaca 1380
cacaggcaca taaaaggtgg ctcatgtcca aagccacacc gattaaccaa caaaggaatt 1440
tgtagttgtg gtgcatttaa ggtgcctggt gtaaaaaccg tctggaaaag acgctga 1497

<210> SEQ ID NO 48
<211> LENGTH: 1692
<212> TYPE: DNA
<213> ORGANISM: Artificial Sequence
<220> FEATURE:
<223> OTHER INFORMATION: Envelope; FPV

<400> SEQUENCE: 48
atgaacactc aaatcctggt tttcgccctt gtggcagtca tccccacaaa tgcagacaaa 60
atttgtcttg gacatcatgc tgtatcaaat ggcaccaaag taaacacact cactgagaga 120
ggagtagaag ttgtcaatgc aacggaaaca gtggagcgga caaacatccc caaaatttgc 180
tcaaaaggga aaagaaccac tgatcttggc caatgcggac tgttagggac cattaccgga 240
ccacctcaat gcgaccaatt tctagaattt tcagctgatc taataatcga gagacgagaa 300
ggaaatgatg tttgttaccc ggggaagttt gttaatgaag aggcattgcg acaaatcctc 360
agaggatcag gtgggattga caaagaaaca atgggattca catatagtgg aataaggacc 420
aacggaacaa ctagtgcatg tagaagatca gggtcttcat tctatgcaga aatggagtgg 480
ctcctgtcaa atacagacaa tgctgctttc ccacaaatga caaaatcata caaaaacaca 540
aggagagaat cagctctgat agtctgggga atccaccatt caggatcaac caccgaacag 600
accaaactat atgggagtgg aaataaactg ataacagtcg ggagttccaa atatcatcaa 660
tcttttgtgc cgagtccagg aacacgaccg cagataaatg gccagtccgg acggattgat 720
tttcattggt tgatcttgga tcccaatgat acagttactt ttagtttcaa tggggctttc 780
atagctccaa atcgtgccag cttcttgagg ggaaagtcca tggggatcca gagcgatgtg 840
caggttgatg ccaattgcga aggggaatgc taccacagtg gagggactat aacaagcaga 900
ttgccttttc aaaacatcaa tagcagagca gttggcaaat gcccaagata tgtaaaacag 960
gaaagtttat tattggcaac tgggatgaag aacgttcccg aaccttccaa aaaaaggaaa 1020
aaaagaggcc tgtttggcgc tatagcaggg tttattgaaa atggttggga aggtctggtc 1080
gacgggtggt acggtttcag gcatcagaat gcacaaggag aaggaactgc agcagactac 1140
aaaagcaccc aatcggcaat tgatcagata accggaaagt taaatagact cattgagaaa 1200
accaaccagc aatttgagct aatagataat gaattcactg aggtggaaaa gcagattggc 1260
aatttaatta actggaccaa agactccatc acagaagtat ggtcttacaa tgctgaactt 1320
cttgtggcaa tggaaaacca gcacactatt gatttggctg attcagagat gaacaagctg 1380
tatgagcgag tgaggaaaca attaagggaa aatgctgaag aggatggcac tggttgcttt 1440
gaaatttttc ataaatgtga cgatgattgt atggctagta taaggaacaa tacttatgat 1500
cacagcaaat acagagaaga agcgatgcaa aatagaatac aaattgaccc agtcaaattg 1560
agtagtggct acaaagatgt gatactttgg tttagcttcg gggcatcatg ctttttgctt 1620
cttgccattg caatgggcct tgttttcata tgtgtgaaga acggaaacat gcggtgcact 1680
atttgtatat aa 1692

<210> SEQ ID NO 49
<211> LENGTH: 1266
<212> TYPE: DNA
<213> ORGANISM: Artificial Sequence
<220> FEATURE:
<223> OTHER INFORMATION: Envelope; RRV

<400> SEQUENCE: 49
agtgtaacag agcactttaa tgtgtataag gctactagac catacctagc acattgcgcc 60
gattgcgggg acgggtactt ctgctatagc ccagttgcta tcgaggagat ccgagatgag 120
gcgtctgatg gcatgcttaa gatccaagtc tccgcccaaa taggtctgga caaggcaggc 180
acccacgccc acacgaagct ccgatatatg gctggtcatg atgttcagga atctaagaga 240
gattccttga gggtgtacac gtccgcagcg tgctccatac atgggacgat gggacacttc 300
atcgtcgcac actgtccacc aggcgactac ctcaaggttt cgttcgagga cgcagattcg 360
cacgtgaagg catgtaaggt ccaatacaag cacaatccat tgccggtggg tagagagaag 420
ttcgtggtta gaccacactt tggcgtagag ctgccatgca cctcatacca gctgacaacg 480
gctcccaccg acgaggagat tgacatgcat acaccgccag atataccgga tcgcaccctg 540
ctatcacaga cggcgggcaa cgtcaaaata acagcaggcg gcaggactat caggtacaac 600
tgtacctgcg gccgtgacaa cgtaggcact accagtactg acaagaccat caacacatgc 660
aagattgacc aatgccatgc tgccgtcacc agccatgaca aatggcaatt tacctctcca 720
tttgttccca gggctgatca gacagctagg aaaggcaagg tacacgttcc gttccctctg 780
actaacgtca cctgccgagt gccgttggct cgagcgccgg atgccaccta tggtaagaag 840
gaggtgaccc tgagattaca cccagatcat ccgacgctct tctcctatag gagtttagga 900
gccgaaccgc acccgtacga ggaatgggtt gacaagttct ctgagcgcat catcccagtg 960
acggaagaag ggattgagta ccagtggggc aacaacccgc cggtctgcct gtgggcgcaa 1020
ctgacgaccg agggcaaacc ccatggctgg ccacatgaaa tcattcagta ctattatgga 1080
ctataccccg ccgccactat tgccgcagta tccggggcga gtctgatggc cctcctaact 1140
ctggcggcca catgctgcat gctggccacc gcgaggagaa agtgcctaac accgtacgcc 1200
ctgacgccag gagcggtggt accgttgaca ctggggctgc tttgctgcgc accgagggcg 1260
aatgca 1266

<210> SEQ ID NO 50
<211> LENGTH: 1938
<212> TYPE: DNA
<213> ORGANISM: Artificial Sequence
<220> FEATURE:
<223> OTHER INFORMATION: Envelope; MLV 10A1

<400> SEQUENCE: 50
atggaaggtc cagcgttctc aaaacccctt aaagataaga ttaacccgtg gaagtcctta 60
atggtcatgg gggtctattt aagagtaggg atggcagaga gcccccatca ggtctttaat 120
gtaacctgga gagtcaccaa cctgatgact gggcgtaccg ccaatgccac ctccctttta 180
ggaactgtac aagatgcctt cccaagatta tattttgatc tatgtgatct ggtcggagaa 240

-continued gagtgggacc cttcagacca ggaaccatat gtcgggtatg gctgcaaata ccccggaggg 300
agaaagcgga cccggacttt tgacttttac gtgtgccctg ggcataccgt aaaatcgggg 360 tgtgggggc caagagaggg ctactgtggt gaatggggtt gtgaaaccac cggacaggct 420
tactggaagc ccacatcatc atgggaccta atctccctta agcgcggtaa cacccccctgg 480 gacacgggat gctccaaaat ggcttgtggc ccctgctacg acctctccaa agtatccaat 540
tccttccaag ggctactcg agggggcaga tgcaaccctc tagtcctaga attcactgat 600
gcaggaaaaa aggctaattg ggacgggccc aaatcgtggg gactgagact gtaccggaca 660
ggaacagatc ctattaccat gttctccctg acccgccagg tcctcaatat agggcccgc 720 atccccattg ggcctaatcc cgtgatcact ggtcaactac ccccctcccg acccgtgcag 780
atcaggctcc ccaggcctcc tcagcctcct cctacaggcg cagcctctat agtccctgag 840
actgccccac cttctcaaca acctgggacg ggagacaggc tgctaaacct ggtagaagga 900
gcctatcagg cgcttaacct caccaatccc gacaagaccc aagaatgttg gctgtgctta 960
gtgtcgggac ctccttatta cgaaggagta gcggtcgtgg gcacttatac caatcattct 1020
accgccccgg ccagctgtac ggccacttcc caacataagc ttaccctatc tgaagtgaca 1080
ggacagggcc tatgcatggg agcactacct aaaactcacc aggccttatg taacaccacc 1140
caaagtgccg gctcaggatc ctactacctt gcagcacccg ctggaacaat gtgggcttgt 1200
agcactggat tgactccctg cttgtccacc acgatgctca atctaaccac agactattgt 1260
gtattagttg agctctggcc cagaataatt taccactccc ccgattatat gtatggtcag 1320
cttgaacagc gtaccaaata taagagggag ccagtatcgt tgaccctggc ccttctgcta 1380
ggaggattaa ccatgggagg gattgcagct ggaataggga cggggaccac tgccctaatc 1440
aaaacccagc agtttgagca gcttcacgcc gctatccaga cagacctcaa cgaagtcgaa 1500
aaatcaatta ccaacctaga aaagtcactg acctcgttgt ctgaagtagt cctacagaac 1560
cgaagaggcc tagatttgct cttcctaaaa gagggaggtc tctgcgcagc cctaaaagaa 1620
gaatgttgtt tttatgcaga ccacacggga ctagtgagag acagcatggc caaactaagg 1680
gaaaggctta atcagagaca aaaactattt gagtcaggcc aaggttggtt cgaagggcag 1740
tttaatagat ccccctggtt taccacctta atctccacca tcatgggacc tctaatagta 1800
ctcttactga tcttactctt tggaccctgc attctcaatc gattggtcca atttgttaaa 1860
gacaggatct cagtggtcca ggctctggtt ttgactcaac aatatcacca gctaaaacct 1920
atagagtacg agccatga 1938

<210> SEQ ID NO 51
<211> LENGTH: 2030
<212> TYPE: DNA
<213> ORGANISM: Artificial Sequence
<220> FEATURE:
<223> OTHER INFORMATION: Envelope; Ebola

<400> SEQUENCE: 51
atgggtgtta caggaatatt gcagttacct cgtgatcgat tcaagaggac atcattcttt 60
ctttgggtaa ttatcctttt ccaaagaaca ttttccatcc cacttggagt catccacaat 120
agcacattac aggttagtga tgtcgacaaa ctggtttgcc gtgacaaact gtcatccaca 180
aatcaattga gatcagttgg actgaatctc gaagggaatg gagtggcaac tgacgtgcca 240
tctgcaacta aaagatgggg cttcaggtcc ggtgtcccac caaaggtggt caattatgaa 300

```
gctggtgaat gggctgaaaa ctgctacaat cttgaaatca aaaaacctga cgggagtgag    360

tgtctaccag cagcgccaga cgggattcgg ggcttccccc ggtgccggta tgtgcacaaa    420

gtatcaggaa cgggaccgtg tgccggagac tttgccttcc acaaagaggg tgctttcttc    480

ctgtatgacc gacttgcttc cacagttatc taccgaggaa cgactttcgc tgaaggtgtc    540

gttgcatttc tgatactgcc ccaagctaag aaggacttct tcagctcaca cccccttgaga   600

gagccggtca atgcaacgga ggacccgtct agtggctact attctaccac aattagatat    660

caagctaccg gttttggaac caatgagaca gagtatttgt tcgaggttga caatttgacc    720

tacgtccaac ttgaatcaag attcacacca cagtttctgc tccagctgaa tgagacaata    780

tatacaagtg ggaaaaggag caataccacg ggaaaactaa tttggaaggt caaccccgaa    840

attgatacaa caatcgggga gtgggccttc tgggaaacta aaaaaacctc actagaaaaa    900

ttcgcagtga agagttgtct ttcacagctg tatcaaacag agccaaaaac atcagtggtc    960

agagtccggc gcgaacttct tccgacccag ggaccaacac aacaactgaa gaccacaaaa   1020

tcatggcttc agaaaattcc tctgcaatgg ttcaagtgca cagtcaagga agggaagctg   1080

cagtgtcgca tctgacaacc cttgccacaa tctccacgag tcctcaaccc cccacaacca   1140

aaccaggtcc ggacaacagc acccacaata cacccgtgta taaacttgac atctctgagg   1200

caactcaagt tgaacaacat caccgcagaa cagacaacga cagcacagcc tccgacactc   1260

cccccgccac gaccgcagcc ggacccctaa aagcagagaa caccaacacg agcaagggta   1320

ccgacctcct ggaccccgcc accacaacaa gtccccaaaa ccacagcgag accgctggca   1380

acaacaacac tcatcaccaa gataccggag aagagagtgc cagcagcggg aagctaggct   1440

taattaccaa tactattgct ggagtcgcag gactgatcac aggcgggagg agagctcgaa   1500

gagaagcaat tgtcaatgct caacccaaat gcaaccctaa tttacattac tggactactc   1560

aggatgaagg tgctgcaatc ggactggcct ggataccata tttcgggcca gcagccgagg   1620

gaatttacat agaggggctg atgcacaatc aagatggttt aatctgtggg ttgagacagc   1680

tggccaacga gacgactcaa gctcttcaac tgttcctgag agccacaacc gagctacgca   1740

ccttttcaat cctcaaccgt aaggcaattg atttcttgct gcagcgatgg ggcggcacat   1800

gccacatttt gggaccggac tgctgtatcg aaccacatga ttggaccaag aacataacag   1860

acaaaattga tcagattatt catgattttg ttgataaaac ccttccggac cagggggaca   1920

atgacaattg gtggacagga tggagacaat ggataccggc aggtattgga gttacaggcg   1980

ttataattgc agttatcgct ttattctgta tatgcaaatt tgtcttttag               2030
```

<210> SEQ ID NO 52
<211> LENGTH: 237
<212> TYPE: DNA
<213> ORGANISM: Artificial Sequence
<220> FEATURE:
<223> OTHER INFORMATION: Polymerase III shRNA promoters; U6 promoter

<400> SEQUENCE: 52

```
tttcccatga ttccttcata tttgcatata cgatacaagg ctgttagaga gataattgga     60

attaatttga ctgtaaacac aaagatatta gtacaaaata cgtgacgtag aaagtaataa    120

tttcttgggt agtttgcagt tttaaaatta tgttttaaaa tggactatca tatgcttacc    180

gtaacttgaa agtatttcga tttcttggct ttatatatct tgtggaaagg acgaaac       237
```

<210> SEQ ID NO 53
<211> LENGTH: 243

<212> TYPE: DNA
<213> ORGANISM: Artificial Sequence
<220> FEATURE:
<223> OTHER INFORMATION: Polymerase III shRNA promoters; 7SK promoter

<400> SEQUENCE: 53
ctgcagtatt tagcatgccc cacccatctg caaggcattc tggatagtgt caaaacagcc 60
ggaaatcaag tccgtttatc tcaaacttta gcattttggg aataaatgat atttgctatg 120
ctggttaaat tagattttag ttaaatttcc tgctgaagct ctagtacgat aagcaacttg 180
acctaagtgt aaagttgaga tttccttcag gtttatatag cttgtgcgcc gcctggctac 240
ctc 243

<210> SEQ ID NO 54
<211> LENGTH: 21
<212> TYPE: DNA
<213> ORGANISM: Artificial Sequence
<220> FEATURE:
<223> OTHER INFORMATION: FDPS target sequence #1

<400> SEQUENCE: 54
gtcctggagt acaatgccat t 21

<210> SEQ ID NO 55
<211> LENGTH: 21
<212> TYPE: DNA
<213> ORGANISM: Artificial Sequence
<220> FEATURE:
<223> OTHER INFORMATION: FDPS target sequence #2

<400> SEQUENCE: 55
gcaggatttc gttcagcact t 21

<210> SEQ ID NO 56
<211> LENGTH: 21
<212> TYPE: DNA
<213> ORGANISM: Artificial Sequence
<220> FEATURE:
<223> OTHER INFORMATION: FDPS target sequence #3

<400> SEQUENCE: 56
gccatgtaca tggcaggaat t 21

<210> SEQ ID NO 57
<211> LENGTH: 21
<212> TYPE: DNA
<213> ORGANISM: Artificial Sequence
<220> FEATURE:
<223> OTHER INFORMATION: FDPS target sequence #4

<400> SEQUENCE: 57
gcagaaggag gctgagaaag t 21

<210> SEQ ID NO 58
<211> LENGTH: 49
<212> TYPE: DNA
<213> ORGANISM: Artificial Sequence
<220> FEATURE:
<223> OTHER INFORMATION: Non-targeting sequence

<400> SEQUENCE: 58
gccgctttgt aggatagagc tcgagctcta tcctacaaag cggctttttt 49

<210> SEQ ID NO 59

<211> LENGTH: 20
<212> TYPE: DNA
<213> ORGANISM: Artificial Sequence
<220> FEATURE:
<223> OTHER INFORMATION: Forward primer

<400> SEQUENCE: 59
aggaattgat ggcgagaagg 20

<210> SEQ ID NO 60
<211> LENGTH: 22
<212> TYPE: DNA
<213> ORGANISM: Artificial Sequence
<220> FEATURE:
<223> OTHER INFORMATION: Reverse primer

<400> SEQUENCE: 60
cccaaagagg tcaaggtaat ca 22

<210> SEQ ID NO 61
<211> LENGTH: 18
<212> TYPE: DNA
<213> ORGANISM: Artificial Sequence
<220> FEATURE:
<223> OTHER INFORMATION: Forward primer

<400> SEQUENCE: 61
agcgcggcta cagcttca 18

<210> SEQ ID NO 62
<211> LENGTH: 20
<212> TYPE: DNA
<213> ORGANISM: Artificial Sequence
<220> FEATURE:
<223> OTHER INFORMATION: Reverse primer

<400> SEQUENCE: 62
ggcgacgtag cacagcttct 20

<210> SEQ ID NO 63
<211> LENGTH: 130
<212> TYPE: DNA
<213> ORGANISM: Artificial Sequence
<220> FEATURE:
<223> OTHER INFORMATION: Left Inverted Terminal Repeat (Left ITR)

<400> SEQUENCE: 63
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct 130

<210> SEQ ID NO 64
<211> LENGTH: 151
<212> TYPE: DNA
<213> ORGANISM: Artificial Sequence
<220> FEATURE:
<223> OTHER INFORMATION: Right Inverted Terminal Repeat (Right ITR)

<400> SEQUENCE: 64
gagcggccgc aggaacccct agtgatggag ttggccactc cctctctgcg cgctcgctcg 60
ctcactgagg ccgggcgacc aaaggtcgcc cgacgcccgg gctttgcccg ggcggcctca 120
gtgagcgagc gagcgcgcag ctgcctgcag g 151

-continued

<210> SEQ ID NO 65
<211> LENGTH: 1227
<212> TYPE: DNA
<213> ORGANISM: Artificial Sequence
<220> FEATURE:
<223> OTHER INFORMATION: RRE/rabbit poly A beta globin

<400> SEQUENCE: 65
tctagaagga gctttgttcc ttgggttctt gggagcagca ggaagcacta tgggcgcagc 60
gtcaatgacg ctgacggtac aggccagaca attattgtct ggtatagtgc agcagcagaa 120
caatttgctg agggctattg aggcgcaaca gcatctgttg caactcacag tctggggcat 180
caagcagctc caggcaagaa tcctggctgt ggaaagatac ctaaaggatc aacagctcct 240
agatcttttt ccctctgcca aaaattatgg ggacatcatg aagccccttg agcatctgac 300
ttctggctaa taaaggaaat ttattttcat tgcaatagtg tgttggaatt ttttgtgtct 360
ctcactcgga aggacatatg ggagggcaaa tcatttaaaa catcagaatg agtatttggt 420
ttagagtttg gcaacatatg ccatatgctg gctgccatga acaaaggtgg ctataaagag 480
gtcatcagta tatgaaacag ccccctgctg tccattcctt attccataga aaagccttga 540
cttgaggtta gatttttttt atattttgtt ttgtgttatt tttttcttta acatccctaa 600
aattttcctt acatgtttta ctagccagat ttttcctcct ctcctgacta ctcccagtca 660
tagctgtccc tcttctctta tgaagatccc tcgacctgca gcccaagctt ggcgtaatca 720
tggtcatagc tgtttcctgt gtgaaattgt tatccgctca caattccaca caacatacga 780
gccggaagca taaagtgtaa agcctggggt gcctaatgag tgagctaact cacattaatt 840
gcgttgcgct cactgcccgc tttccagtcg ggaaacctgt cgtgccagcg gatccgcatc 900
tcaattagtc agcaaccata gtcccgcccc taactccgcc catcccgccc ctaactccgc 960
ccagttccgc ccattctccg ccccatggct gactaatttt ttttatttat gcagaggccg 1020
aggccgcctc ggcctctgag ctattccaga agtagtgagg aggctttttt ggaggcctag 1080
gcttttgcaa aaagctaact tgtttattgc agcttataat ggttacaaat aaagcaatag 1140
catcacaaat ttcacaaata aagcattttt ttcactgcat tctagttgtg gtttgtccaa 1200
actcatcaat gtatcttatc acccggg 1227

METHODS AND COMPOSITIONS FOR THE ACTIVATION OF GAMMA-DELTA T-CELLS

CROSS-REFERENCE TO RELATED APPLICATIONS

This application is a continuation of U.S. patent application Ser. No. 16/530,908 filed on Aug. 2, 2019 entitled "METHODS AND COMPOSITIONS FOR THE ACTIVATION OF GAMMA-DELTA T-CELLS", which is a continuation of U.S. patent application Ser. No. 16/132,247 filed on Sep. 14, 2018 entitled "METHODS AND COMPOSITIONS FOR THE ACTIVATION OF GAMMA-DELTA T-CELLS," which is a continuation of U.S. patent application Ser. No. 15/904,131 filed on Feb. 23, 2018 entitled "METHODS AND COMPOSITIONS FOR THE ACTIVATION OF GAMMA-DELTA T-CELLS", which is a continuation in part of U.S. patent application Ser. No. 15/652,080 filed on Jul. 17, 2017 entitled "METHODS AND COMPOSITIONS FOR THE ACTIVATION OF GAMMA-DELTA T-CELLS", which is a continuation of International Application No. PCT/US17/13399 filed on Jan. 13, 2017 entitled "METHODS AND COMPOSITIONS FOR THE ACTIVATION OF GAMMA-DELTA T-CELLS", which claims priority to U.S. Provisional Patent Application No. 62/279,474 filed on Jan. 15, 2016 entitled "METHODS AND COMPOSITIONS FOR THE ACTIVATION OF GAMMA-DELTA T-CELLS", the disclosures of which are incorporated herein by reference.

SEQUENCE LISTING

A Sequence Listing is enclosed with this application and is incorporated herein by reference. The text file of the Sequence Listing is named 7061203137_SL.txt and the file size is 61 kilobytes.

FIELD OF THE INVENTION

The present disclosure relates generally to the fields of gene therapy and immunotherapy, specifically in relation to increased activation and effector cell function of gamma delta ("GD") T cells.

BACKGROUND

Human T cells are distinguished on the basis of T cell receptor structure. The major populations, including CD4+ and CD8+ subsets, express a receptor composed of alpha and beta chains. A smaller subset expresses T cell receptor made from gamma and delta chains. Gamma delta ("GD") T cells make up 3-10% of circulating lymphocytes, and a Vδ2+ subset makes up 75% of GD T cells in blood. Vδ2+ cells recognize non-peptide epitopes and do not require antigen presentation by major histocompatibility complexes ("MHC") or human leukocyte antigen ("HLA"). The majority of Vδ2+ T cells also express a Vγ9 chain and are stimulated by exposure to 5-carbon pyrophosphate compounds that are intermediates in mevalonate and non-mevalonate sterol/isoprenoid synthesis pathways. The response to isopentenyl pyrophosphate (5-carbon) is universal among healthy human beings.

Another subset of GD T cells, Vδ+, make up a much smaller percentage of the T cells circulating in the blood, but Vδ+1 cells are commonly found in the epithelial mucosa and the skin.

In general, GD T cells have several functions, including killing tumor cells and pathogen-infected cells. Stimulation through their unique T cell receptor ("TCRs") composed of two glycoprotein chains, γ and δ, improves the capacity for cellular cytotoxicity, cytokine secretion and other effector functions. The TCRs of GD T cells have unique specificities and the cells themselves occur in high clonal frequencies, thus allowing rapid innate-like responses to tumors and pathogens.

Bisphosphonate drugs and other inhibitors of farnesyl diphosphate synthase ("FDPS"), which are downstream from isopentenyl pyrophosphate ("IPP") in the mevalonate pathway (see, for e.g., FIG. 1), have been used to treat various diseases, including cancers, specifically those involving bone metastasis. Bisphosphonate drugs include, for example, Zometa® (Novartis) and Fosamax® (Merck).

Certain bisphosphonates have also been investigated for stimulation of GD T cells. This may be because when FDPS is inhibited in myeloid cells, IPP begins to accumulate and geranylgeranyl pyrophosphate ("GGPP"), a downstream product of FDPS that suppresses activation of the inflammasome pathway, is reduced. The reduction in GGPP removes an inhibitor of the caspase-dependent inflammasome pathway and allows secretion of mature cytokines including interleukin-beta and interleukin-18, the latter being especially important for gamma delta T cell activation.

Thus, when FDPS is blocked, the increased IPP and decreased GGPP combine to activate Vδ2+ T cells. Vδ2+ cells activated by IPP or bisphosphonates will proliferate rapidly, express a number of cytokines and chemokines, and can function to cytotoxically destroy tumor cells or cells infected with pathogenic microorganisms.

However, bisphosphonates are associated with inflammation and osteonecrosis, as well as having poor bioavailability due to their chemistry. Likewise, IPP has a very short half-life and is difficult to synthesize. Both types of compounds require systemic administration in an individual. Accordingly, both bisphosphonates in general, and IPP specifically, leave a great deal to be desired for therapeutic purposes involving activation of GD T cells.

SUMMARY OF THE INVENTION

In one aspect, a method of activating a GD T cell is provided. The method includes infecting, in the presence of the GD T cell, a target cell with a viral delivery system that encodes at least one genetic element. In embodiments, the at least one genetic element includes a small RNA capable of inhibiting production of an enzyme involved in the mevalonate pathway. In embodiments, the enzyme is FDPS. In embodiments, when the enzyme is inhibited in the target cell, the target cell subsequently activates the GD T cell. In embodiments, the target cell is a cancer cell or a cell that has been infected with an infectious agent. In a preferred embodiment, the activation of the GD T cell results in the GD T cell killing the cancer cell or the cell infected with an infectious agent. In embodiments, the at least one encoded genetic element includes a microRNA or a shRNA. In further embodiments, the target cell is also contacted with a bisphosphonate drug. In embodiments, the bisphosphonate drug is zoledronic acid.

In another aspect, a method of treating cancer in a subject is provided. The method includes administering to the subject a therapeutically-effective amount of a viral delivery system that encodes at least one genetic element. In embodiments, the at least one genetic element includes a small RNA capable of inhibiting production of an enzyme involved in the mevalonate pathway. In further embodiments, when the enzyme is inhibited in a cancer cell in the presence of a GD T cell, the cancer cell activates the GD T cell, to thereby treat the cancer. In embodiments, the enzyme is FDPS. In embodiments, the at least one encoded genetic element includes a microRNA or a shRNA. In further embodiments, the target cell is also contacted with a bisphosphonate drug. In embodiments, the bisphosphonate drug is zoledronic acid.

In another aspect, a method of treating an infectious disease in a subject is provided. The method includes administering to the subject a therapeutically-effective amount of a viral delivery system that encodes at least one genetic element. In embodiments, the at least one genetic element includes a small RNA capable of inhibiting production of an enzyme involved in the mevalonate pathway. In further embodiments, when the enzyme is inhibited in a cell that is infected with an infectious agent in the presence of a GD T cell, the infected cell activates the GD T cell, to thereby treat the infected cell, and the infectious disease. In embodiments, the enzyme is FDPS. In embodiments, the at least one encoded genetic element includes a microRNA or a shRNA. In further embodiments, the target cell is also contacted with a bisphosphonate drug. In embodiments, the bisphosphonate drug is zoledronic acid.

In another aspect, the at least one encoded genetic element includes a shRNA having at least 80%, or at least 85%, or at least 90%, or at least 95% percent identity with GTCCTGGAGTACAATGCCATTCTCGAGAATGGCATTGTACTCCAGGACTTTTT (SEQ ID NO: 1); GCAGGATTTCGTTCAGCACTTCTCGAGAAGTGCTGAACGAAATCCTGCTTTTT (SEQ ID NO: 2); GCCATGTACATGGCAGGAATTCTCGAGAA TTCCTGCCATGTACATGGCTTTTT (SEQ ID NO: 3); or GCAGAAGGAGGCTGA GAAAGTCTCGAGACTTTCTCAGCCTCCTTCTGCTTTTT (SEQ ID NO: 4). In a preferred embodiment, the shRNA includes GTCCTGGAGTACAATGCCATTCTCGAG AATGGCATTGTACTCCAGGACTTTTT (SEQ ID NO: 1); GCAGGATTTCGTTCA GCACTTCTCGAGAAGTGCTGAACGAAATCCTGCTTTTT (SEQ ID NO: 2); GCCA TGTACATGGCAGGAATTCTCGAGAATTCCTGCCATGTACATGGCTTTTT (SEQ ID NO: 3); or GCAGAAGGAGGCTGAGAAAGTCTCGAGACTTTCTCAGCCTCCTT CTGCTTTTT (SEQ ID NO: 4).

In another aspect, the at least one encoded genetic element includes a microRNA having at least 80%, or at least 85%, or at least 90%, or at least 95% percent identity with AAGGTATATTGCTGTTGACAGTGAGCGACACTTTCTCAGCCTCCTTCTGCGTGAAGC CACAGATGGCAGAAGGAGGCTGAGAAAGTGCTGCCTACTGCCTCGGACTTCAAGGG GCT (SEQ ID NO: 5); AAGGTATATTGCTGTTGACAGTGAGCGACACT TTCTCAGCCTCCTTCTGCGTGAAGCCACAGATGGCAGAAGGGCTGAGAAAGTGCTGC CTACTGCCTCGGACTTCAAGGGGCT (SEQ ID NO: 6); TGCTGTTGACAGTG AGCGACTTTCTCAGCCTCCTTCTGCGTGAAGCCACAGATGGCAGAAGGAGGCTGAG AAAGTTGCCTACTGCCTCGGA (SEQ ID NO: 7); CCTGGAGGCTTGCTGAAG GCTGTATGCTGACTTTCTCAGCCTCCTTCTGCTTTT GGCCACTGACTGAGCAGAAGGG CTGAGAAAGTCAGGACACAAGGCCTGTTACTAGCACTCA (SEQ ID NO: 8); CATCTCCATGGCTGTACCACCTTGTCGGGACTTTCTCAGCCTCCTTCTGCCTG TTGAA TCTCATGGCAGAAGGAGGCGAGAAAGTCTGACATTTTGGTATCTTTCATCTGACCA (SEQ ID NO: 9); or GGGCCTGGCTCGAGCAGGGGGCGAGGGATACTTTCT CAGCCTCCTTCTGCTGGTCCCCTCCCCGCAGAAGG AGGCTGAGAAAGTCCTTCCCTC CCAATGACCGCGTCTTCGTCG (SEQ ID NO: 10). In a preferred embodiment, the microRNA includes AAGGTATATTGCTGTTGACAGTGAGCGACACTTTCTCAGCCT CCTTCTGCGTGAAGCCACAGATGGCAGAAGGAGGCTGAGAAAGTGCTGCCTACTGC CTCGGACTTCAAGGGGCT (SEQ ID NO: 5); AAGGTATATTGCTGTTGACAGT GAGCGACACTTTCTCAGCCTCCTTCTGCGTGAAGCCACAGATGGCAGAAGGGCTGA GAAAGTGCTGCCTACTGCCTCGGACTTCAAGGGGCT (SEQ ID NO: 6); TGCTG TTGACAGTGAGCGACTTTCTCAGCCTCCTTCTGCGTGAAGCCACAGATGGCAGAAGG AGGCTGAGAAAGTTGCCTACTGCCTCGGA (SEQ ID NO: 7); CCTGGAGGCT TGCTGAAGGCTGTATGCTGACTTTCTCAGCCTCCTTCTGC TTTTGGCCACTGACTGAG CAGAAGGGCTGAGAAAGTCAGGACACAAGGCCTGTTACTAGCACTCA (SEQ ID NO: 8); CATCTCCATGGCTGTACCACCTTGTCGGGACTTTCTCAGCCT CCTT CTGCCTGTTGAATCTCATGGCAGAAGGAGGCGAGAAAGTCTGACATTTTGGTATCTT TCATCTGACCA (SEQ ID NO: 9); or GGGCCTGGCTCGAGCAGGGGGCGAGGG ATACTTTCTCAGCCTCCTTCTGCTGGTCCCCTCCCC GCAGAAGGAGGCTGAGAAAGT CCTTCCCTCCCAATGACCGCGTCTTCGTCG (SEQ ID NO: 10).

In another aspect, a viral vector comprising at least one encoded genetic element is provided. The at least one encoded genetic element includes a small RNA capable of inhibiting production of an enzyme involved in the mevalonate pathway. In embodiments, the enzyme involved in the mevalonate pathway is farnesyl diphosphate synthase (FDPS). In embodiments, the at least one encoded genetic element includes a microRNA or a shRNA.

In another aspect, the at least one encoded genetic element includes a shRNA having at least 80%, or at least 85%, or at least 90%, or at least 95% percent identity with v In a preferred embodiment, the shRNA includes SEQ ID NO: 1; SEQ ID NO: 2; SEQ ID NO: 3; or SEQ ID NO: 4.

In another aspect, the at least one encoded genetic element includes a microRNA having at least 80%, or at least 85%, or at least 90%, or at least 95% percent identity with SEQ ID NO: 5; SEQ ID NO: 6; SEQ ID NO: 7; SEQ ID NO: 8; SEQ ID NO: 9; or SEQ ID NO: 10. In a preferred embodiment, the microRNA includes SEQ ID NO: 5; SEQ ID NO: 6; SEQ ID NO: 7; SEQ ID NO: 8; SEQ ID NO: 9; or SEQ ID NO: 10.

In embodiments, the viral vector is comprised of any vector that can effectively transduce the small RNA into a target cell. In embodiments, the viral vector is a lentiviral vector. In other embodiments, the viral vector is an adeno-associated virus vector.

In another aspect, the viral vector includes a second encoded genetic element. In embodiments, the second genetic element includes at least one cytokine or chemokine. In embodiments, the at least one cytokine is selected from the group consisting of: IL-18, TNF-α, interferon-γ, IL-1, IL-2, IL-15, IL-17, and IL-12. In embodiments, the at least one chemokine is a CC chemokine or a CXC chemokine. In further embodiments, the at least one chemokine is RANTES.

In another aspect, a lentiviral vector system for expressing a lentiviral particle is provided. The system includes a lentiviral vector, at least one envelope plasmid for expressing an envelope protein optimized for infecting a cell; and at least one helper plasmid for expressing gag, pol, and rev genes. When the lentiviral vector, the at least one envelope plasmid, and the at least one helper plasmid are transfected into a packaging cell, a lentiviral particle is produced by the packaging cell. In embodiments, the lentiviral particle is capable of infecting a targeting cell, and inhibiting an enzyme involved in the mevalonate pathway within the target cell. In embodiments, the enzyme involved in the mevalonate pathway is FDPS. In embodiments, the lentiviral vector system includes a first helper plasmid for expressing the gag and pol genes, and a second helper plasmid for expressing the rev gene. In embodiments, the envelope protein is preferably optimized for infecting a target cell. In embodiments, the target cell is a cancer cell. In other embodiments, the target cell is a cell that is infected with an infectious agent.

In another aspect a pharmaceutical combination is disclosed which includes a bisphosphonate compound; and a lentiviral particle produced by a packaging cell and capable of infecting a target cell. The lentiviral particle comprises an envelope protein capable of infecting the target cell, and: at least one encoded shRNA capable of inhibiting production of an enzyme of the mevalonate pathway, wherein the at least one encoded shRNA comprises a sequence having at least 80% percent identity with SEQ ID NO: 1; SEQ ID NO: 2; SEQ ID NO: 3; or SEQ ID NO: 4; or at least one encoded microRNA capable of inhibiting production of an enzyme of the mevalonate pathway, wherein the at least one encoded microRNA comprises a sequence having at least 80% percent identity with SEQ ID NO: 5; SEQ ID NO: 6; SEQ ID NO: 7; SEQ ID NO: 8; SEQ ID NO: 9; or SEQ ID NO: 10, wherein the pharmaceutical combination is at least one of fixed and non-fixed. In embodiments, the at least one encoded shRNA comprises a sequence having at least 85% or at least 90% or at least 95% percent identity with SEQ ID NO: 1; SEQ ID NO: 2; SEQ ID NO: 3; or SEQ ID NO: 4; or the at least one encoded microRNA comprises a sequence having at least 85% percent identity with SEQ ID NO: 5; SEQ ID NO: 6; SEQ ID NO: 7; SEQ ID NO: 8; SEQ ID NO: 9; or SEQ ID NO: 10. In embodiments, the at least one encoded shRNA comprises SEQ ID NO: 1; SEQ ID NO: 2; SEQ ID NO: 3; or SEQ ID NO: 4 or the at least one encoded microRNA comprises SEQ ID NO: 5; SEQ ID NO: 6; SEQ ID NO: 7; SEQ ID NO: 8; SEQ ID NO: 9; or SEQ ID NO: 10. In embodiments, the pharmaceutical composition comprises a fixed combination. In embodiments, the pharmaceutical composition comprises a non-fixed combination. In embodiments, the bisphosphonate drug comprises zoledronic acid. In embodiments, the bisphosphonate drug and the lentiviral particle are present in synergistically effective amounts. In embodiments, the target cell is one or more cancer cells that are present in a cancer selected from one or more of a carcinoma, a leukemia, a lymphoma, a sarcoma, a myeloma, a mesothelioma, a mixed type, or mixtures thereof. In embodiments, the target cell is one or more cancer cells that are present in a hepatocellular carcinoma. In embodiments, the target cell is capable of activating a gamma delta T cell following infection with the lentiviral particle. In embodiments, the enzyme is FDPS.

In another aspect, a method of treating a cancer in a subject using an immunotherapy-based composition is disclosed. The method includes administering a therapeutically-effective amount of a bisphosphonate drug to the subject; and administering a therapeutically-effective amount of the immunotherapy-based composition to the subject, wherein the immunotherapy-based composition comprises a lentiviral particle. The lentiviral particle comprises an envelope protein capable of infecting one or more cancer cells, and at least one encoded shRNA capable of inhibiting production of an enzyme of the mevalonate pathway, wherein the at least one encoded shRNA comprises a sequence having at least 80% percent identity with SEQ ID NO: 1; SEQ ID NO: 2; SEQ ID NO: 3; or SEQ ID NO: 4 or at least one encoded microRNA capable of inhibiting production of an enzyme of the mevalonate pathway, wherein the at least one encoded microRNA comprises a sequence having at least 80% percent identity with SEQ ID NO: 5; SEQ ID NO: 6; SEQ ID NO: 7; SEQ ID NO: 8; SEQ ID NO: 9; or SEQ ID NO: 10. In embodiments, the at least one encoded shRNA comprises a sequence having at least 85% or at least 90% or at least 95% percent identity with SEQ ID NO: 1; SEQ ID NO: 2; SEQ ID NO: 3; or SEQ ID NO: 4, or at least one encoded microRNA comprises a sequence having at least 85% or at least 90% or at least 95% percent identity with SEQ ID NO: 5; SEQ ID NO: 6; SEQ ID NO: 7; SEQ ID NO: 8; SEQ ID NO: 9; or SEQ ID NO: 10. In embodiments, the at least one encoded shRNA comprises SEQ ID NO: 1; SEQ ID NO: 2; SEQ ID NO: 3; or SEQ ID NO: 4. In embodiments, the at least one encoded microRNA comprises SEQ ID NO: 5; SEQ ID NO: 6; SEQ ID NO: 7; SEQ ID NO: 8; SEQ ID NO: 9; or SEQ ID NO: 10. In embodiments, the one or more cancer cells are present in a cancer selected from one or more of a carcinoma, a leukemia, a lymphoma, a sarcoma, a myeloma, a mesothelioma, a mixed type, or mixtures thereof. In embodiments, the bisphosphonate drug comprises zoledronic acid. In embodiments, the bisphosphonate drug and the immunotherapy-based composition are administered in a fixed combination. In embodiments, the bisphosphonate drug and the immunotherapy-based composition are administered in a non-fixed combination. In embodiments, the bisphosphonate drug and the immunotherapy-based composition are administered simultaneously. In embodiments, the bisphosphonate drug and the immunotherapy-based composition are administered sequentially. In embodiments, the bisphosphonate drug and the immunotherapy-based composition are administered in synergistically effective amounts. In embodiments, the bisphosphonate drug and the immunotherapy-based composition are administered at a synergistically effective time interval. In embodiments, the one or more cancer cells are capable of activating a gamma delta T cell resident in the subject following infection of the one or more cancer cells with the immunotherapy-based composition. In embodiments, activating the gamma delta T cell comprises increasing tumor necrosis factor (TNF)-α expression by the gamma delta T cell. In embodiments, activating the gamma delta T cell comprises increasing expression and/or secretion of cytokines, chemokines, and/or cell death ligands including but not limited to FasL and TRAIL. In embodiments, the enzyme of the mevalonate pathway is farnesyl diphosphate synthase (FDPS).

DETAILED DESCRIPTION

Overview of Disclosure

Figure 1:
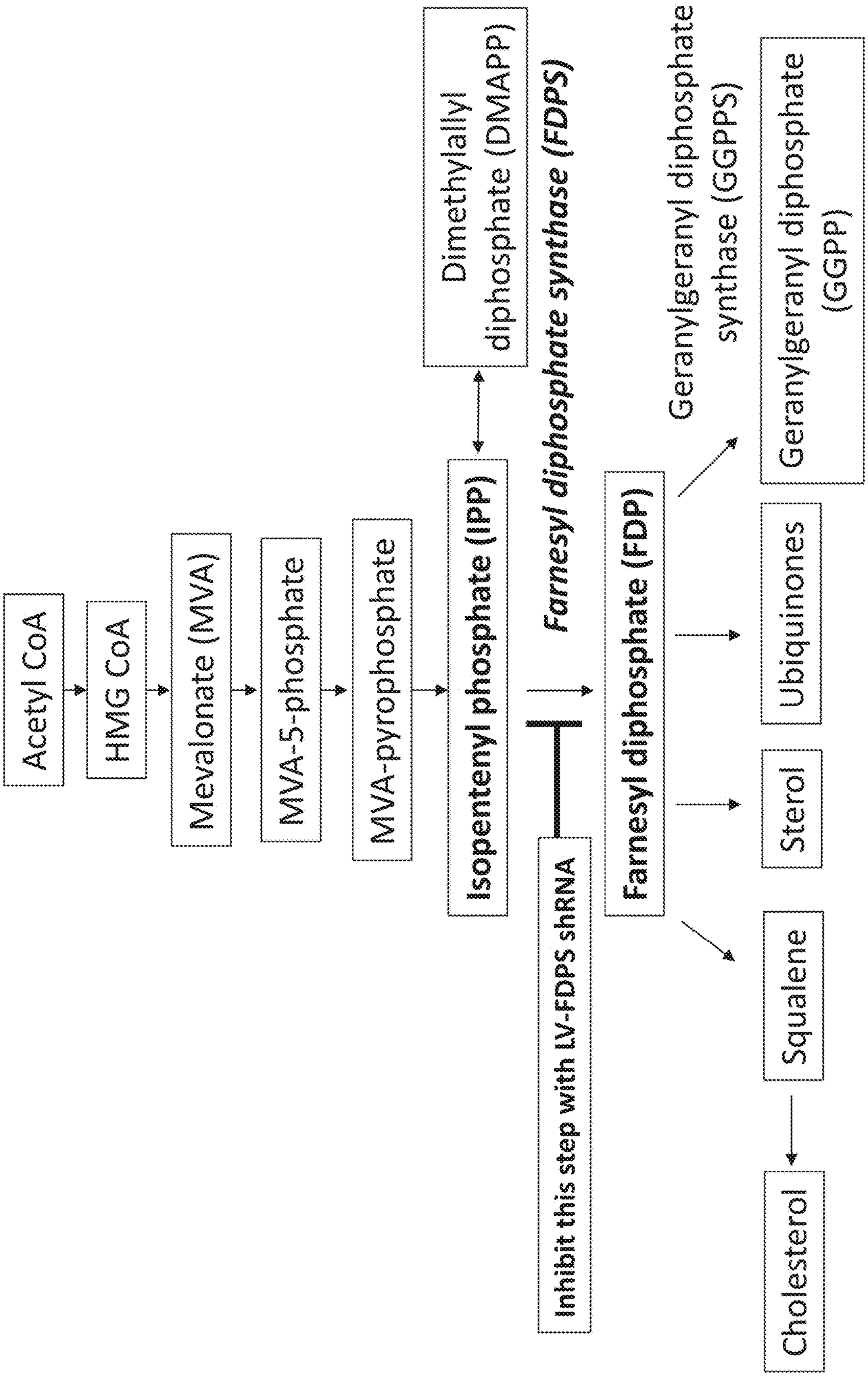
FIG. 1 depicts an overview of the major steps in the mevalonate pathway for biosynthesis of steroids and isoprenoids.

The present disclosure relates to gene therapy constructs and delivery of the same to cells, resulting in suppression of Farnesyl diphosphate synthase ("FDPS"), which is necessary to convert isopentenyl phosphate (IPP) to farnesyl diphosphate (FDP), as shown, for example, in FIG. 1. In embodiments, one or more viral vectors are provided with microRNAs or short hairpin RNAs (shRNA) that target FDPS, thereby reducing expression levels of this enzyme. The viral vectors include lentiviral vectors and AAV vectors. A consequence of modulating expression of FDPS is to increase the accumulation of IPP, which is a stimulator of GD T cell proliferation and differentiation. Accordingly, the constructs provided herein are used to activate GD T cells, and are used to treat cancers and infectious diseases.

Definitions and Interpretation

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well-known and commonly used in the art. The methods and techniques of the present disclosure are generally performed according to conventional methods well-known in the art and as described in various general and more specific references that are cited and discussed throughout the present specification unless otherwise indicated. See, e.g.: Sambrook J. & Russell D. Molecular Cloning: A Laboratory Manual, 3rd ed., Cold Spring Harbor Laboratory Press, Cold Spring Harbor, N.Y. (2000); Ausubel et al., Short Protocols in Molecular Biology: A Compendium of Methods from Current Protocols in Molecular Biology, Wiley, John & Sons, Inc. (2002); Harlow and Lane Using Antibodies: A Laboratory Manual; Cold Spring Harbor Laboratory Press, Cold Spring Harbor, N.Y. (1998); and Coligan et al., Short Protocols in Protein Science, Wiley, John & Sons, Inc. (2003). Any enzymatic reactions or purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well-known and commonly used in the art.

As used in the description and the appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or").

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

As used herein, the terms "administration of" or "administering" refer to providing an active agent to a subject in need of treatment in a form that can be introduced into that individual's body in a therapeutically useful form and therapeutically effective amount.

As used herein, the terms "bisphosphonates" and "bisphosphonate drugs" refer to therapeutic agents of various embodiments, and encompass any of aminobisphosphonates, diphosphonates, biphosphonic acids, and diphosphonic acids, as well as pharmaceutically acceptable salts and derivatives thereof. The use of a specific nomenclature in referring to bisphosphonates is not meant to limit the scope of the present invention, unless specifically indicated.

As used herein, the terms "co-administration" or "combined administration" or "combined use" or "combination therapy" or the like as utilized herein refer to administration of a therapeutic vector or a lentiviral particle and a bisphosphonate drug or a therapeutic vector or a lentiviral particle and an antibody or a therapeutic vector or a lentiviral particle and a bisphosphonate drug and an antibody to a single subject in need thereof (e.g., a patient), and are intended to include treatment regimens in which the agents are not necessarily administered by the same route of administration and/or at the same time.

As used herein, the term "fixed combination," refers to two or more active ingredients or components, including any of their respective compositions, formulations or drug forms, e.g., a therapeutic vector or a lentiviral particle and a bisphosphonate drug or any combination of these, that are administered essentially in combination to a patient, for example essentially simultaneously, in the form of a single entity or dosage or combined entities or dosages, e.g., in one tablet or in one capsule or in combined tablets or capsules or combined liquid forms.

As used herein, the term "non-fixed combination," refers to two or more active ingredients or components, including any of their respective compositions, formulations or drug forms, e.g., a therapeutic vector or a lentiviral particle and a bisphosphonate drug or any combination of these, that are administered in combination to a patient as separate entities either simultaneously, concurrently or sequentially with no specific time limits, wherein such administration provides therapeutically effective levels of the active components in the patient. The non-fixed combination can be dosed independently of each other or by use of different fixed combinations e.g., simultaneously or at different time points. The active components may be administered as separate pharmaceutical dosage forms or pharmaceutical formulations that may be, for example, sold independently of each other, with or without label instructions concerning the possibility of a combined use. Such instructions may be provided in the package equipment, e.g., leaflet or the like, or in other information, e.g., provided to physicians and medical staff. A non-fixed combination, its respective active ingredients or components, including any of their respective compositions, formulations or drug forms, or the parts thereof, can be administered simultaneously or chronologically staggered, e.g., at different time points and with equal or different time intervals for any part of the administration. Such time intervals may be chosen such that the effect on the treated disease, when treated in combination, is more effective than would be obtained by use of only any one of the active components.

As used herein, the terms "combination," "in combination" and "combination therapies," may refer generally to any or both of the "fixed combination" and "non-fixed combination" definitions and embodiments described above.

As used herein, the transitional term "comprising," when used to define compositions and methods, means that the compositions and methods include the recited elements, but does not exclude others. As used herein, "consisting essentially of," when used to define compositions and methods, means that the composition and methods include additional elements, but only if those additional elements do not materially affect the basic and novel characteristics of the composition or methods. As used herein, "consisting of," when used to define compositions and methods, means that the compositions and methods exclude more than trace elements of other ingredients for compositions and substantial method steps. Embodiments defined by each of these transitional terms are within the scope of this disclosure. For example, it is intended that the methods and compositions can include additional steps and components (comprising) or alternatively including steps and compositions of no significance (consisting essentially of) or alternatively, intending only the stated method steps or compositions (consisting of).

As used herein, the terms "expression," "expressed," or "encodes" refer to a process by which polynucleotides are transcribed into mRNA and/or the process by which the transcribed mRNA is subsequently being translated into peptides, polypeptides, or proteins. Expression may include splicing of the mRNA in a eukaryotic cell or other forms of post-transcriptional modification or post-translational modification.

As used herein, the term "farnesyl diphosphate synthase" may also be referred to herein as FDPS, and may also be referred to herein as farnesyl pyrophosphate synthase or FPPS.

As used herein, the term "gamma delta T cell" may also be referred to herein as a γδ T cell, or further as a GD T cell. The term "gamma delta T cell activation" refers to any measurable biological phenomenon associated with a gamma delta T cell that is representative of such T cell being activated. Non-limiting examples of such a biological phenomenon include an increase of cytokine production, changes in the qualitative or quantitative composition of cell surface proteins, an increase in T cell proliferation, and/or an increase in T cell effector function, such killing or a target cell or assisting another effector cell to kill a target cell.

As used herein, the terms "individual," "subject," and "patient" are used interchangeably herein, and refer to any individual mammal subject, e.g., bovine, canine, feline, equine, and/or human.

As used herein, the term "miRNA" refers to a microRNA, and also may be referred to herein as "miR".

The term "packaging cell line" refers to any cell line that can be used to express a lentiviral particle.

As used herein, the term "homology" refers to the percentage number of amino acids, nucleic acids, or analogs thereof, that are identical or constitute conservative substitutions. Homology may be determined using sequence comparison programs such as GAP (Deveraux et al., 1984, Nucleic Acids Research 12, 387-395). In this way sequences of a similar or substantially different length to those cited herein could be compared by insertion of gaps into the alignment, such gaps being determined, for example, by the comparison algorithm used by GAP.

As used herein, the term "sequence identity," which also may appear in the non-limiting context of "a sequence 50% identical to," and "having at least 80%, or at least 85%, or at least 90%, or at least 95% identity with" a given sequence, as similar pharasings, as used herein, refers to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., Nucl. Acids Res. 25:3389, 1997.

As used here, the term "percent identity," which may be used interchangeably with the term "sequence identity", in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the "percent identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

Suitable algorithms for determining percent sequence identity include the BLAST algorithm, which is described in Altschul et al., J. Mol. Biol. 215:403-410 (1990). Software for performing BLAST analyses is publicly available through the National Center for Biotechnology Information web site.

The percent identity between two nucleotide sequences can be determined using the GAP program in the GCG software package (available at http://www.gcg.com), using a NWSgapdna. CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present disclosure can further be used as a "query sequence" to perform a search against public databases to, for example, identify related sequences. Such searches can be performed using the NBLAST and)(BLAST programs (version 2.0) of Altschul, et al. (1990) *J. Mol. Biol.* 215:403-10. BLAST nucleotide searches can be performed with the NBLAST program, score=100, word length=12 to obtain nucleotide sequences homologous to the nucleic acid molecules provided in the disclosure. BLAST protein searches can be performed with the XBLAST program, score=50, wordlength=3 to obtain amino acid sequences homologous to the protein molecules of the disclosure. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g.,)(BLAST and NBLAST) can be used. See http://www.ncbi.nlm.nih.gov.

As used herein, the term "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

As used herein, the term "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see, e.g., Berge et al. (1977) *J Pharm Sci* 66:1-19).

As used herein, the term "pharmaceutically acceptable salt" refers to derivatives of compounds or other active ingredients, wherein the parent compound or active ingredient is modified by converting an existing acid or base moiety to its salt form. Non-limiting examples of pharmaceutically acceptable salts include, but are not limited to, mineral or organic acid salts of basic residues such as amines; alkali or organic salts of acidic residues such as carboxylic acids; alkali metal, alkaline metal, ammonium, and mono-, di, tri-, or tetra-C1-C30-alkyl-substituted ammonium; and the like. The pharmaceutically acceptable salts of various embodiments include the conventional non-toxic salts of the compound or active ingredient formed, for example, from nontoxic inorganic or organic acids. Suitable organic acids are, e.g., carboxylic acids or sulfonic acids, such as acetic acid, succinic acid, fumaric acid or methanesulfonic acid. The pharmaceutically acceptable salts herein can be synthesized from the parent compound or active ingredient which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "SEQ ID NO" is synonymous with the term "Sequence ID No."

As used herein, the term "small RNA" refers to non-coding RNA that are generally less than about 200 nucleotides or less in length and possess a silencing or interference function. In embodiments, the small RNA is about 175 nucleotides or less, about 150 nucleotides or less, about 125 nucleotides or less, about 100 nucleotides or less, or about 75 nucleotides or less in length. Such RNAs include microRNA (miRNA), small interfering RNA (siRNA), double stranded RNA (dsRNA), and short hairpin RNA (shRNA). In embodiments, "small RNA" are capable of inhibiting or knocking-down gene expression of a target gene, generally through pathways that result in the inhibitions or destruction of the target gene mRNA.

As used herein, the term "therapeutically effective amount" refers to a sufficient quantity of the active agents of the present disclosure, in a suitable composition, and in a suitable dosage form to treat or prevent the symptoms, progression, or onset of the complications seen in patients suffering from a given ailment, injury, disease, or condition. The therapeutically effective amount will vary depending on the state of the patient's condition or its severity, and the age, weight, etc., of the subject to be treated. A therapeutically effective amount can vary, depending on any of a number of factors, including, e.g., the route of administration, the condition of the subject, as well as other factors understood by those in the art.

As used herein, the term "therapeutic vector" includes, without limitation, reference to a lentiviral vector or an AAV vector.

As used herein, the terms "treatment" and "treating" refer to the intended targeting of a disease state and combatting of it, i.e., ameliorating or preventing the disease state. A particular treatment thus will depend on the disease state to be targeted and the current or future state of medicinal therapies and therapeutic approaches. A treatment may have associated toxicities.

Desirable effects include, but are not limited to, preventing occurrence or recurrence of disease, alleviating symptoms, suppressing, diminishing or inhibiting any direct or indirect pathological consequences of the disease, ameliorating or palliating the disease state, and causing remission or improved prognosis.

Description of Aspects of the Disclosure

In one aspect, a method of activating a GDT cell is provided. The method includes infecting, in the presence of the GD T cell, a target cell with a viral delivery system encoding at least one genetic element. In embodiments, the at least one encoded genetic element includes a small RNA capable of inhibiting production of an enzyme involved in the mevalonate pathway. In embodiments, the enzyme is FDPS. In embodiments, when the enzyme is inhibited in the target cell, the target cell activates the GD T cell. In embodiments, the target cell is a cancer cell or a cell that has been infected with an infectious agent. In embodiments, the at least one encoded genetic element includes a microRNA or a shRNA.

In embodiments, the at least one encoded genetic element includes a shRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with GTCCTGGAGTACAATGCCATTCTCGAGAATGGCATTGTACTCCAGGACTTTTT (SEQ ID NO: 1); GCAGGATTTCGTTCAGCACTTCTCGAGAAGTGCTGAACGAAATCCTGCTTTTT (SEQ ID NO: 2); GCCATGTACATGGCAGGAATTCTCGAGAA TTCCTGCCATGTACATGGCTTTTT (SEQ ID NO: 3); or GCAGAAGGAGGCTGA GAAAGTCTCGAGACTTTCTCAGCCTCCTTCTGCTTTTT (SEQ ID NO: 4). In a preferred embodiment, the shRNA includes GTCCTGGAGTACAATGCCATTCTCGAG AATGGCATTGTACTCCAGGACTTTTT (SEQ ID NO: 1); GCAGGATTTCGTTCA GCACTTCTCGAGAAGTGCTGAACGAAATCCTGCTTTTT (SEQ ID NO: 2); GCCA TGTACATGGCAGGAATTCTCGAGAATTCCTGCCATGTACATGGCTTTTT (SEQ ID NO: 3); or GCAGAAGGAGGCTGAGAAAGTCTCGAGACTTTCTCAGCCTCCTT CTGCTTTTT (SEQ ID NO: 4).

In another aspect, the at least one encoded genetic element includes a microRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with AAGGTATATTGCTGTTGACAGTGAGCGACACTTTCTCAGCCTCCTTCTGCGTGAAGC CACAGATGGCAGAAGGAGGCTGAGAAAGTGCTGCCTACTGCCTCGGACTTCAAGGG GCT (SEQ ID NO: 5); AAGGTATATTGCTGTTGACAGTGAGCGACACT TTCTCAGCCTCCTTCTGCGTGAAGCCACAGATGGCAGAAGGGCTGAGAAAGTGCTGC CTACTGCCTCGGACTTCAAGGGGCT (SEQ ID NO: 6); TGCTGTTGACAGTG AGCGACTTTCTCAGCCTCCTTCTGCGTGAAGCCACAGATGGCAGAAGGAGGCTGAG AAAGTTGCCTACTGCCTCGGA (SEQ ID NO: 7); CCTGGAGGCTTGCTGAAG GCTGTATGCTGACTTTCTCAGCCTCCTTCTGCTTTT GGCCACTGACTGAGCAGAAGGG CTGAGAAAGTCAGGACACAAGGCCTGTTACTAGCACTCA (SEQ ID NO: 8); CATCTCCATGGCTGTACCACCTTGTCGGGACTTTCTCAGCCTCCTTCTGCCTG TTGAA TCTCATGGCAGAAGGAGGCGAGAAAGTCTGACATTTTGGTATCTTTCATCTGACCA (SEQ ID NO: 9); or GGGCCTGGCTCGAGCAGGGGGCGAGGGATACTTTCT CAGCCTCCTTCTGCTGGTCCCCTCCCCGCAGAAGG AGGCTGAGAAAGTCCTTCCCTC CCAATGACCGCGTCTTCGTCG (SEQ ID NO: 10). In a preferred embodiment, the microRNA includes AAGGTATATTGCTGTTGACAGTGAGCGACACTTTCTCAGCCT CCTTCTGCGTGAAGCCACAGATGGCAGAAGGAGGCTGAGAAAGTGCTGCCTACTGC CTCGGACTTCAAGGGGCT (SEQ ID NO: 5); AAGGTATATTGCTGTTGACAGT GAGCGACACTTTCTCAGCCTCCTTCTGCGTGAAGCCACAGATGGCAGAAGGGCTGA GAAAGTGCTGCCTACTGCCTCGGACTTCAAGGGGCT (SEQ ID NO: 6); TGCTG TTGACAGTGAGCGACTTTCTCAGCCTCCTTCTGCGTGAAGCCACAGATGGCAGAAGG AGGCTGAGAAAGTTGCCTACTGCCTCGGA (SEQ ID NO: 7); CCTGGAGGCT TGCTGAAGGCTGTATGCTGACTTTCTCAGCCTCCTTCTGC TTTTGGCCACTGACTGAG CAGAAGGGCTGAGAAAGTCAGGACACAAGGCCTGTTACTAGCACTCA (SEQ ID NO: 8); CATCTC- CATGGCTGTACCACCTTGTCGGGACTTTCTCAGCCT CCTT CTGCCTGTTGAATCT-CATGGCAGAAGGAGGCGAGAAAGTCTGACAT-TTTGGTATCTT TCATCTGACCA (SEQ ID NO: 9); or GGGCCTGGCTCGAGCAGGGGGCGAGGG ATACTTTCTCAGCCTCCTTCTGCTGGTCCCCTCCCC GCAGAAGGAGGCTGAGAAAGT CCTTCCCTCC-CAATGACCGCGTCTTCGTCG (SEQ ID NO: 10).

In another aspect, the target cell is also contacted with a bisphosphonate drug. In a preferred embodiment, the bisphosphonate drug is zoledronic acid. The bisphosphonate drug may be a pharmaceutically acceptable salt, hydrate or a solvate thereof.

In another aspect, a method of treating cancer in a subject is provided. The method includes administering to the subject a therapeutically-effective amount of a viral delivery system encoding at least one genetic element. In embodiments, the at least one encoded genetic element includes a small RNA capable of inhibiting production of an enzyme involved in the mevalonate pathway. In further embodiments, when the enzyme is inhibited in a cancer cell in the presence of a GD T cell, the cancer cell activates the GD T cell, to thereby treat the cancer. In embodiments, the enzyme is FDPS. In embodiments, the at least one encoded genetic element includes a microRNA or a shRNA.

In another aspect, a method of treating an infectious disease in a subject is provided. The method includes administering to the subject a therapeutically-effective amount of a viral delivery system encoding at least one genetic element. In embodiments, the at least one encoded genetic element includes a small RNA capable of inhibiting production of an enzyme involved in the mevalonate pathway. In further embodiments, when the enzyme is inhibited in a cell that is infected with an infectious agent and is in the presence of a GD T cell, the infected cell activates the GD T cell, to thereby treat the infected cell, and the infectious disease. In embodiments, the enzyme is FDPS. In embodiments, the at least one encoded genetic element includes a microRNA or a shRNA.

In embodiments, the at least one encoded genetic element includes a shRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with SEQ ID NO: 1; SEQ ID NO: 2; SEQ ID NO: 3; or SEQ ID NO: 4. In a preferred embodiment, the shRNA includes SEQ ID NO: 1; SEQ ID NO: 2; SEQ ID NO: 3; or SEQ ID NO: 4.

In other embodiments, the at least one encoded genetic element includes a microRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with SEQ ID NO: 5; SEQ ID NO: 6; SEQ ID NO: 7; SEQ ID NO: 8; SEQ ID NO: 9; or SEQ ID NO: 10. In a preferred embodiment, the microRNA includes SEQ ID NO: 5; SEQ ID NO: 6; SEQ ID NO: 7; SEQ ID NO: 8; SEQ ID NO: 9; or SEQ ID NO: 10.

In another aspect, a viral vector comprising at least one encoded genetic element is provided. The at least one encoded genetic element includes a small RNA capable of inhibiting production of an enzyme involved in the mevalonate pathway. In embodiments, the enzyme involved in the mevalonate pathway is farnesyl diphosphate synthase (FDPS). In embodiments, the at least one encoded genetic element includes a microRNA or a shRNA.

In another aspect, the at least one encoded genetic element includes a shRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with SEQ ID NO: 1; SEQ ID NO: 2; SEQ ID NO: 3; or SEQ ID NO: 4. In a preferred embodiment, the shRNA includes SEQ ID NO: 1; SEQ ID NO: 2; SEQ ID NO: 3; or SEQ ID NO: 4.

In another aspect, the at least one encoded genetic element includes a microRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with SEQ ID NO: 5; SEQ ID NO: 6; SEQ ID NO: 7; SEQ ID NO: 8; SEQ ID NO: 9; or SEQ ID NO: 10. In a preferred embodiment, the microRNA includes SEQ ID NO: 5; SEQ ID NO: 6; SEQ ID NO: 7; SEQ ID NO: 8; SEQ ID NO: 9; or SEQ ID NO: 10.

In embodiments, the viral vector includes any vector that can effectively transduce the small RNA. In embodiments, the viral vector is a lentiviral vector. In other embodiments, the viral vector is an adeno-associated virus (AAV) vector.

In another aspect, the viral vector includes a second encoded genetic element. In embodiments, the second genetic element includes at least one cytokine or chemokine. In embodiments, the at least one cytokine is selected from the group consisting of: IL-18, TNF-α, interferon-γ, IL-1, IL-2, IL-15, IL-17, and IL-12. In embodiments, the at least one chemokine is a CC chemokine, CXC chemokine, a CX3 chemokine or a XC chemokine. In a further embodiment, the at least one chemokine is the CC chemokine, RANTES.

In another aspect, a lentiviral vector system for expressing a lentiviral particle is provided. The system includes a lentiviral vector, at least one envelope plasmid for expressing an envelope protein optimized for infecting a cell; and at least one helper plasmid for expressing gag, pol, and rev genes. When the lentiviral vector, the at least one envelope plasmid, and the at least one helper plasmid are transfected into a packaging cell, a lentiviral particle is produced by the packaging cell. In embodiments, the lentiviral particle is capable of infecting a targeting cell, and inhibiting an enzyme involved in the mevalonate pathway within the target cell. In embodiments, the enzyme involved in the mevalonate pathway is FDPS. In embodiments, the lentiviral vector system includes a first helper plasmid for expressing the gag and pol genes, and a second helper plasmid for expressing the rev gene. In embodiments, the envelope protein is preferably optimized for infecting a target cell. In embodiments, the target cell is a cancer cell. In other embodiments, the target cell is a cell that is infected with an infectious disease.

In another aspect a pharmaceutical combination is disclosed which includes a bisphosphonate compound; and a lentiviral particle produced by a packaging cell and capable of infecting a target cell. The lentiviral particle comprises an envelope protein capable of infecting the target cell, and: at least one encoded shRNA capable of inhibiting production of an enzyme of the mevalonate pathway, wherein the at least one encoded shRNA comprises a sequence having at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98% or at least 99% percent identity with SEQ ID NO: 1; SEQ ID NO: 2; SEQ ID NO: 3; or SEQ ID NO: 4; or at least one encoded microRNA capable of inhibiting production of an enzyme of the mevalonate pathway, wherein the at least one encoded microRNA comprises a sequence having at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98% or at least 99% percent identity with SEQ ID NO: 5; SEQ ID NO: 6; SEQ ID NO: 7; SEQ ID NO: 8; SEQ ID NO: 9; or SEQ ID NO: 10, wherein the pharmaceutical combination is at least one of fixed and non-fixed. In embodiments, the at least one encoded shRNA comprises SEQ ID NO: 1; SEQ ID NO: 2; SEQ ID NO: 3; or SEQ ID NO: 4 or the at least one encoded microRNA comprises SEQ ID NO: 5; SEQ ID NO: 6; SEQ ID NO: 7; SEQ ID NO: 8; SEQ ID NO: 9; or SEQ ID NO: 10. In embodiments, the pharmaceutical composition comprises a fixed combination. In embodiments, the pharmaceutical composition comprises a non-fixed combination. In embodiments, the bisphosphonate drug comprises zoledronic acid. In embodiments, the bisphosphonate drug and the lentiviral particle are present in synergistically effective amounts. In embodiments, the target cell is one or more cancer cells that are present in a cancer selected from one or more of a carcinoma, a leukemia, a lymphoma, a sarcoma, a myeloma, a mesothelioma, a mixed type, or mixtures thereof. In embodiments, the target cell is one or more cancer cells that are present in a hepatocellular carcinoma. In embodiments, the target cell is capable of activating a gamma delta T cell following infection with the lentiviral particle. In embodiments, the enzyme is FDPS.

In another aspect, a method of treating a cancer in a subject using an immunotherapy-based composition is disclosed. The method includes administering a therapeutically-effective amount of a bisphosphonate drug to the subject; and administering a therapeutically-effective amount of the immunotherapy-based composition to the subject, wherein the immunotherapy-based composition comprises a lentiviral particle. The lentiviral particle comprises an envelope protein capable of infecting one or more cancer cells, and at least one encoded shRNA capable of inhibiting production of an enzyme of the mevalonate pathway, wherein the at least one encoded shRNA comprises a sequence having at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98% or at least 99% percent identity with SEQ ID NO: 1; SEQ ID NO: 2; SEQ ID NO: 3; or SEQ ID NO: 4 or at least one encoded microRNA capable of inhibiting production of an enzyme of the mevalonate pathway, wherein the at least one encoded microRNA comprises a sequence having at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98% or at least 99% percent identity with SEQ ID NO: 5; SEQ ID NO: 6; SEQ ID NO: 7; SEQ ID NO: 8; SEQ ID NO: 9; or SEQ ID NO: 10. In embodiments, the at least one encoded shRNA comprises SEQ ID NO: 1; SEQ ID NO: 2; SEQ ID NO: 3; or SEQ ID NO: 4. In embodiments, the at least one encoded microRNA comprises SEQ ID NO: 5; SEQ ID NO: 6; SEQ ID NO: 7; SEQ ID NO: 8; SEQ ID NO: 9; or SEQ ID NO: 10. In embodiments, the one or more cancer cells are present in a cancer selected from one or more of a carcinoma, a leukemia, a lymphoma, a sarcoma, a myeloma, a mesothelioma, a mixed type, or mixtures thereof. In embodiments, the bisphosphonate drug comprises zoledronic acid. In embodiments, the bisphosphonate drug and the immunotherapy-based composition are administered in a fixed combination. In embodiments, the bisphosphonate drug and the immunotherapy-based composition are administered in a non-fixed combination. In embodiments, the bisphosphonate drug and the immunotherapy-based composition are administered simultaneously. In embodiments, the bisphosphonate drug and the immunotherapy-based composition are administered sequentially. In embodiments, the bisphosphonate drug and the immunotherapy-based composition are administered in synergistically effective amounts. In embodiments, the bisphosphonate drug and the immunotherapy-based composition are administered at a synergistically effective time interval. In embodiments, the one or more cancer cells are capable of activating a gamma delta T cell resident in the subject following infection of the one or more cancer cells with the immunotherapy-based composition. In embodiments, activating the gamma delta T cell comprises increasing tumor necrosis factor (TNF)-$\alpha$ expression by the gamma delta T cell. In embodiments, the enzyme of the mevalonate pathway is farnesyl diphosphate synthase (FDPS).

Cancer

The compositions and methods provided herein are used to treat cancer. A cell, tissue, or target may be a cancer cell, a cancerous tissue, harbor cancerous tissue, or be a subject or patient diagnosed or at risk of developing a disease or condition. In certain aspects, a cell may be an epithelial, an endothelial, a mesothelial, a glial, a stromal, or a mucosal cell. The cancer cell population can include, but is not limited to a brain, a neuronal, a blood, an endometrial, a meninges, an esophageal, a lung, a cardiovascular, a liver, a lymphoid, a breast, a bone, a connective tissue, a fat, a retinal, a thyroid, a glandular, an adrenal, a pancreatic, a stomach, an intestinal, a kidney, a bladder, a colon, a prostate, a uterine, an ovarian, a cervical, a testicular, a splenic, a skin, a smooth muscle, a cardiac muscle, or a striated muscle cell, and can also include a cancer cell population from any of the foregoing, and can be associated with one or more of carcinomas, sarcomas, myelomas, leukemias, lymphomas, mixed types or mixtures of the foregoing. In still a further aspect cancer includes, but is not limited to astrocytoma, acute myeloid leukemia, anaplastic large cell lymphoma, acute lymphoblastic leukemia, angiosarcoma, B-cell lymphoma, Burkitt's lymphoma, breast carcinoma, bladder carcinoma, carcinoma of the head and neck, cervical carcinoma, chronic lymphoblastic leukemia, chronic myeloid leukemia, colorectal carcinoma, endometrial carcinoma, esophageal squamous cell carcinoma, Ewing's sarcoma, fibrosarcoma, glioma, glioblastoma, gastrinoma, gastric carcinoma, hepatoblastoma, hepatocellular carcinoma, Kaposi's sarcoma, Hodgkin lymphoma, laryngeal squamous cell carcinoma, larynx carcinoma, leukemia, leiomyosarcoma, lipoma, liposarcoma, melanoma, mantle cell lymphoma, medulloblastoma, mesothelioma, myxofibrosarcoma, myeloid leukemia, mucosa-associated lymphoid tissue B cell lymphoma, multiple myeloma, high-risk myelodysplastic syndrome, nasopharyngeal carcinoma, neuroblastoma, neurofibroma, high-grade non-Hodgkin lymphoma, non-Hodgkin lymphoma, lung carcinoma, non-small cell lung carcinoma, ovarian carcinoma, esophageal carcinoma, osteosarcoma, pancreatic carcinoma, pheochromocytoma, prostate carcinoma, renal cell carcinoma, retinoblastoma, rhabdomyosarcoma, salivary gland tumor, schwannoma, small cell lung cancer, squamous cell carcinoma of the head and neck, testicular tumor, thyroid carcinoma, urothelial carcinoma, and Wilms tumor.

The compositions and methods provided herein are also used to treat NSCLC (non-small cell lung cancer), pediatric malignancies, cervical and other tumors caused or promoted by human papilloma virus (HPV), melanoma, Barrett's esophagus (pre-malignant syndrome), adrenal and skin cancers and auto immune, neoplastic cutaneous diseases.

Infectious Diseases

The compositions and methods disclosed herein can be used to treat infectious diseases. The term "infectious disease" includes any disease that is caused by an infectious agent. An "infectious agent" includes any exogenous pathogen including, without limitation, bacteria, fungi, viruses, mycoplasma, and parasites. Infectious agents that may be treated with compositions provided for in this disclosure include any art-recognized infectious organisms that cause pathogenesis in an animal, including such organisms as bacteria that are gram-negative or gram-positive cocci or bacilli, DNA and RNA viruses, including, but not limited to, DNA viruses such as papilloma viruses, parvoviruses, adenoviruses, herpesviruses and vaccinia viruses, and RNA viruses, such as arenaviruses, coronaviruses, rhinoviruses, respiratory syncytial viruses, influenza viruses, picomaviruses, paramyxoviruses, reoviruses, retroviruses, and rhabdoviruses. Examples of fungi that may be treated with the compositions and methods of the disclosure include fungi that grow as molds or are yeast-like, including, for example, fungi that cause diseases such as ringworm, histoplasmosis, blastomycosis, aspergillosis, cryptococcosis, sporotrichosis, coccidioidomycosis, paracoccidio-idomycosis, and candidiasis. Compositions and methods provided for herein may be utilized to treat parasitic infections including, but not limited to, infections caused by somatic tapeworms, blood flukes, tissue roundworms, ameba, and *Plasmodium, Trypanosoma, Leishmania*, and *Toxoplasma* species.

Methods of GD T Cell Activation

Provided herein are compositions and methods for activating GD T cells in an individual, as well as methods for treating tumors and infectious diseases. For instance, in embodiments, the compositions and methods provided herein can be used in methods to treat all known cancers because activated GD T cells comprise a natural mechanism for immune surveillance of tumors (See for e.g.: Pauza et al. 2014 *Frontiers in Immunol.* 5:687). Likewise, in embodiments, the compositions and methods provided herein can be used to treat infectious diseases, including but not limited to flavivirus, influenza virus, human retrovirus, mycobacteria, plasmodia and a variety of other viral, fungal and bacterial infections. (See for e.g.: Pauza and Cairo, 2015 *Cell Immunol.* 296(1).

In general, a vector system is administered to an individual to transfect or transduce a target cell population with the disclosed constructs for decreasing expression of FDPS and, in other embodiments, increasing expression of chemokines or cytokines. Administration and transfection/transduction can occur in vivo or ex vivo, with the transfected cells later administered back into the subject in the latter scenario.

Administration of the disclosed vectors and transfection or transduction of the disclosed constructs into a subject's cells result in decreased expression of FDPS, increased expression of cytokines or chemokines, accumulation of IPP and in many cases, reduced growth rates for genetically modified tumor cells. All of these features work together to activate and co-localize GD T cells to the site of a tumor or infection.

The disclosed methods can also increase the capacity of NK cells to recognize and destroy tumor cells and/or infected cells. Crosstalk between GD T cells and NK cells is an important aspect of regulating the immune and inflammatory responses. Further, GD T cells are known to trigger dendritic cell maturation, recruit B cells and macrophages, and participate in a variety of cytolytic activities, such as secretion of interferon-γ and TNF-α.

In embodiments, the disclosed compositions and methods provided herein comprise a form of gene therapy for activating GD T cells at the site of tumor or infectious disease pathology. In an aspect, the compositions and methods provided herein activate GD T cells and support their proliferation, differentiation, and functional capacities by promoting the production of specific cytokines needed for cytolytic activity capable of killing cancer cells or treating infectious diseases.

In embodiments the gene therapy sequences (e.g., FDPS shRNAs) are carried by therapeutic vectors, including but not limited to viral vectors such as lentiviruses or adeno-associated viruses, although other viral vectors can also be suitable. Gene therapy constructs may also be delivered in the form of DNA or RNA, including but not limited to plasmid forms. In embodiments, the disclosed gene therapy constructs may also be delivered in the form of protein-nucleic acid complexes or lipid nucleic acid complexes and mixtures of these formulations. For instance, a protein-nucleic acid complex can comprise nucleic acids of interest in a complex with cationic peptides such as lysine and arginine. Lipid-nucleic acids complexes can comprise lipid emulsions, micelles, liposomes, and/or mixtures of neutral and cationic lipids such as DOTMA, DOSPA, DOTAP, and DMRIE.

In embodiments, therapeutic vectors may comprise a single construct or at least two, at least three, at least four, or at least five different constructs. When more than one construct is present in a vector the constructs may be identical, or they may be different. For instance, the constructs may vary in terms of their promoters, the presence or absence of integrating elements, and/or their sequences. In some embodiments, a therapeutic vector will comprise at least one construct that encodes a small RNA capable of knocking down the expression of FDPS. In embodiments, the therapeutic vector will also encode a specific cytokine(s) and/or chemokine(s), including but not limited to TNF-α, interferon-γ, IL-1, IL-2, IL-15, IL-17, IL-18 or IL-12. In some embodiments, a single construct may encode both small RNAs capable of knocking down the expression of FDPS and specific cytokines or chemokines, including but not limited to TNF-α, interferon-γ, IL-1, IL-2, IL-15, IL-17, IL-18 or IL-12.

In embodiments, viral vectors may introduce nucleic acid constructs that become integrated into the host chromosome. Alternately, transient delivery vectors may be used to prevent chromosomal integration and limit the lifespan of gene therapy constructs.

In embodiments, the disclosed constructs and vectors comprise short hairpin RNA ("shRNA"), micro RNA ("miRNA"), or siRNA capable of reducing or knocking down expression of FDPS and/or geranyl pyrophosphate synthase ("GPPS") and/or farnesyl transferase ("FT") genes. By down regulating these genes, which control steroid and isoprenoid synthesis, isopentenyl pyrophosphate ("IPP") levels are elevated. Elevation and accumulation of IPP is a known mechanism for increasing GD T cells activation. Further, down regulation of these pyrophosphate synthase genes removes an important negative regulator of inflammasome function that in turn results in increased expression of cytokines that are important for GD T cell activation and effector cell function.

In embodiments, the disclosed constructs are regulated by specific promoters that are capable of producing interleukin-2 and/or interleukin-15 to sustain GD T cell proliferation. In addition, the disclosed constructs may be regulated by specific promoters that are capable of producing interleukin-1 beta and/or interleukin-18 and/or interferon-gamma required for GD T cell differentiation and acquisition of all effector cell function. Desirable effector cell functions include the capacity for direct cytotoxic cell killing of tumors and/or infected cells, secretion of beneficial cytokines and/or chemokines, increased expression of NK receptors required to recognize cancerous or infected cells, and increased expression of Fc receptors needed to bind targeting antibodies in order to co-localize GD T cells with cancerous or infected cell targets.

In embodiments, the disclosed methods activate GD T cells, resulting in the indirect effect of increasing the capacity for NK cells to attack and destroy cancerous cells, tumors, or infected cells. The activation of NK cells requires GD T cells that are stimulated to proliferate and differentiate, and to express 4-1BBL costimulatory ligand needed to engage the 4-1BB costimulatory receptor on NK cells. This form of crosstalk is known as an important mechanism for activating NK cells and is achieved here through the action of the disclosed methods and compositions.

In another aspect, crosstalk between GD T cells and NK cells is an important mechanism for eliminating inflammatory dendritic cells that accumulate in diseased tissues. Alone, neither GD T cells nor NK cells are capable of destroying dendritic cells, but once the aforementioned crosstalk interactions have occurred, NK cells are altered to become cytotoxic against inflammatory dendritic cells. This immuno-regulatory mechanism depends on strong activation and proliferation of GD T cells.

In embodiments, the disclosed methods for activation of GD T cells further comprise a step of suppressing pathologic inflammatory responses that may include cellular proliferation leading to atherosclerosis, chronic immune activation that stimulates tumor growth, autoimmune diseases including psoriasis and other presentations in the epidermis, inflammatory diseases of the central nervous system, and arthritis and other diseases of unregulated immune responses.

In embodiments, therapeutic vectors are administered in combination with bisphosphonate drugs. In various embodiments, such combinations achieve synergistic, positive or heightened activation of gamma delta T cells. Such positive activation may allow alternate, modified or reduced doses of bisphosphonates and may decrease adverse reactions to bisphosphonates including acute inflammatory responses and chronic diseases. Combinations of therapeutic vectors with bisphosphonates may be together or separate, with or without instructions for combined use or to combination products. The therapeutic vectors and/or bisphosphonates may be administered entirely separately and may be formulated in entirely distinct pharmaceutical dosage forms. The therapeutic vectors and/or bisphosphonates may be sold independently of each other, with or without label instructions concerning the possibility of a combined use. Such instructions also may be provided in the package equipment, e.g., leaflet or the like, or in other information, e.g., provided to physicians and medical staff (e.g., oral communications, communications in writing or the like). Such labels or other instructions can refer to either a fixed combination in one dosage unit form, or a non-fixed combination as a kit of parts for the combined administration where the therapeutic vector may be administered independently of the bisphosphonate drug, at the same time, or separately within time intervals. In various embodiments, the combination exhibits a cooperative or joint effect, or a decrease in toxicity or complications of treatment. In one embodiment the effect of the combination is synergistic. A synergistic effect is achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together, albeit subject to potential variances in timing as detailed herein.

The combinations herein may be manufactured and/or formulated by the same or different manufacturers. The active ingredients may be brought together into a combination therapy: (i) prior to release of the combination product to physicians (e.g., in the case of a kit comprising the compound of the disclosure and the other therapeutic agent); (ii) by the treating physician (or under the guidance of a physician) shortly before administration; (iii) in the actual patient, e.g., during sequential administration of the active ingredients disclosed herein.

In embodiments, a therapeutically effective amount of each of the combinations may be administered simultaneously or sequentially and in any order, and the components may be administered together or separate. For example, the method of treating a proliferative disease according to the disclosure may comprise (i) administration of a first agent such as a therapeutic vector that forms part of a lentiviral particle, and (ii) administration of a second agent such as a bisphosphonate drug in free or pharmaceutically acceptable salt form, simultaneously or sequentially in any order, in jointly therapeutically effective amounts, preferably in cooperative, jointly effective, and/or synergistically effective, amounts, e.g., in daily or intermittent dosages corresponding to the amounts described herein. The combinations may be administered separately at different times during the course of therapy or concurrently in divided or single drug forms. Furthermore, the term "administering" also encompasses the use of a pro-drug of a combination partner that converts in vivo to the combination partner as such. The instant disclosure is therefore to be understood as embracing all such regimens of simultaneous or alternating treatment and the term "administering" is to be interpreted accordingly.

In embodiments, agents (i) and (ii) can be administered using any pharmaceutically acceptable method, such as intranasal, buccal, sublingual, oral, rectal, ocular, parenteral (intravenously, intradermally, intramuscularly, subcutaneously, intraperitoneally), pulmonary, intravaginal, locally administered, topically administered, topically administered after scarification, mucosally administered, via an aerosol, in semi-solid media such as agarose or gelatin, or via a buccal or nasal spray formulation, and/or in solid media such as granules or powders including inert excipients. For example, a therapeutic vector and/or bisphosphonate drug may be administered intravenously. Further, agents (i) and (ii) can be formulated into any pharmaceutically acceptable dosage form, such as a solid dosage form, tablet, pill, lozenge, capsule, liquid dispersion, gel, aerosol, pulmonary aerosol, nasal aerosol, ointment, cream, semi-solid dosage form, a solution, an emulsion, and a suspension. For example, a bisphosphonate drug may be formulated into a tablet and administered orally.

A combination therapy according to the disclosure can besides or in addition be administered especially for cancer therapy in combination with chemotherapy, radiotherapy, immunotherapy, surgical intervention, or a combination of these. Long-term therapy is equally possible as is adjuvant therapy in the context of other treatment strategies, as described above. In embodiments, a combination therapy can also include immune adjuvants (e.g., Toll-like receptor ligands), immune stimulating toxins, or stimulatory protozoans or stimulatory bacilli (e.g., bacille Calmette-Guerin), cancer therapeutic drugs, cell-based therapies (gamma delta T cell or other cell types known to be in use or under evaluation for tumor therapy and may also include natural or genetically-engineered cells and cells cultured under) ionizing radiation or surgery. Other possible treatments are therapy to maintain the patient's status after tumor regression, or even chemo-preventive therapy, for example in patients at risk.

Constructs for GD T Cell Activation

Inhibition of FDPS results in IPP accumulation, resulting in activation of Vδ2+ GD T cells and expression of IL-18, which is also important in activating GD T cells. Inhibition of farnesyl transferase results in decreased prenylation of proteins. The disclosed constructs can be transfected or transduced into specific target cells, like tumor cells or infected cells, where they can express RNA sequences (i.e., siRNA, shRNA or microRNA) that will inhibit translation of FDPS as well as encode and express cytotoxic cytokines or chemokines.

Disclosed herein are constructs for decreasing expression of FDPS and/or FT, increasing expression of cytokines, and increasing expression of chemokines including RANTES. For instance, in some embodiments the constructs may encode for interferon-gamma, IL-1, IL-2, IL-15, IL-17, IL-18 or IL-12.

Expression of cytokines and chemokines, like those listed above, will result in localized cytotoxic destruction of tumor cells or cells infected with pathogenic organisms. Accordingly, expression of such constructs by a tumor cell or an infected cell will result in the unwanted cells assisting in its own destruction.

Likewise, if the disclosed constructs are expressed in a tumor cell or infected cell, decreasing the expression of FDPS and FT will result in activation and recruitment of GD T cells to the tumor site of site of cell infection. Increasing expression of RANTES will further attract GD T cells to intended tissue location. Because GD T cells can kill a broad range of tumors of epithelial origin as well as many leukemias and lymphomas, and are further able to produce high levels of the anti-tumor cytokine, IFNγ, recruitment of GD T cells to the site of a tumor can be a particularly effective means of inducing anti-tumor immunity.

Decreased expression of FDPS can be achieved via shRNA, microRNA, siRNA, or other means known in the art. For instance, shRNAs according to SEQ ID NOS: 1, 2, 3, or 4, or variants thereof can be used in the disclosed constructs and methods, although this example is not limiting. The coding regions for RNAs to decrease expression of FDPS and FT and the coding regions of cytokine and chemokines may be in the same construct or on different constructs.

The classical approach for the production of recombinant polypeptides or gene regulatory molecules including small RNA is the use of stable expression constructs. These constructs are based upon chromosomal integration of a transduced expression plasmid (or at least a portion thereof) into the genome of the host cell, short-duration plasmid transfection, or non-integrating viral vectors also with limited half-life. The sites of gene integration are generally random, and the number and ratio of genes integrating at any particular site are often unpredictable; likewise, non-integrating plasmids or viral vectors also generate nuclear DNA but these species usually lack sequences required for DNA replication and continuous maintenance. Thus, constructs that rely on chromosomal integration result in permanent maintenance of the recombinant gene that may exceed the therapeutic interval.

An alternative to stable expression constructs for gene expression are transient expression constructs. The expression of the latter gene expression construct is based on non-integrated plasmids, and hence the expression is typically lost as the cell undergoes division or the plasmid vectors are destroyed by endogenous nucleases.

The disclosed constructs are preferably episomal constructs that are transiently expressed. Episomal constructs are degraded or diluted over time such that they do not make permanent changes to a subject's genome, nor are they incorporated into the chromosome of a target cell. The process of episomal replication typically incorporates both host cell replication machinery and viral trans-acting factors.

Avoiding chromosomal integration reduces certain barriers to in vivo gene delivery. However, even integration-defective constructs can have a background frequency of integration, and any DNA molecule can find rare homologies to recombine with host sequences; but these rates of integration are exceptionally rare and generally not clinically significant.

Thus, in some embodiments, the disclosed vectors support active gene and/or small RNA delivery over a period of about 1, about 2, about 3, about 4, about 5, about 6, about 7, about 8, about 9, about 10, about 11, or about 12 weeks. In some embodiments, the disclosed vectors support active gene and/or small RNA delivery over a period of about 1 month, 2 months, 3 months, 4 months, 5 months, 6 months, 7 months, 8 months, 9 months, 10 months, 11 months, 12 months, or longer. Any combination of these time periods can also be used in the methods of the invention, e.g., 1 month and 1 week, or 3 months and 2 weeks.

However, in some embodiments, the constructs comprise integrating elements that depend on a retroviral integrase gene, such that the construct becomes integrated into the subject's chromosome. Retrotransposition and transposition are additional examples of mechanisms whereby mobile genetic elements become integrated or inserted into the chromosome. Plasmids may become integrated into the chromosome by recombination, and gene editing technologies including CRISPR and TALEN utilize guide RNA sequences and alter chromosomal loci by gene conversion mechanisms.

Constructs may comprise specific promoters for expressing cytokines involved in the maintenance of GD T cells (i.e., IL-2, IL-7, IL-17, and IL-15). For example, promoters that may be incorporated into the disclosed constructs include but are not limited to TATA-box promoters, CpG-box promoters, CCAAT-box promoters, TTGACA-box promoters, BRE-box promoters, INR-box promoters, AT-based promoters, CG-based promoters, ATCG-compact promoters, ATCG-balanced promoters, ATCG-middle promoters, ATCG-less promoters, AT-less promoters, CG-less promoters, AT-spike promoters, and CG-spike promoters. See Gagniuc and Ionescu-Tirgoviste, *Eukaryotic genomes may exhibit up to* 10 *generic classes of gene promoters*, BMC GENOMICS 13:512 (2012).

Therapeutic Vectors

The construct can be delivered via known transfection and/or transduction vectors, including but not limited to lentiviral vectors, gamma-retroviruses, adeno-associated virus, poxvirus, herpesvirus vectors, protein and/or lipid complexes, liposomes, micelles, and the like.

Viral vectors can be preferentially targeted to cell types that are useful for the disclosed methods (i.e., tumor cells or myeloid cells). Viral vectors can be used to transduce genes into target cells owing to specific virus envelope-host cell receptor interactions and viral mechanisms for gene expression. As a result, viral vectors have been used as vehicles for the transfer of genes into many different cell types including whole embryos, fertilized eggs, isolated tissue samples, tissue targets in situ, and cultured cell lines. The ability to introduce and express foreign genes in a cell is useful for the study of gene expression, and the elucidation of cell lineages as well as providing the potential for therapeutic interventions such as gene therapy, somatic cell reprogramming of induced pluripotent stem cells, and various types of immunotherapy. Viral components from viruses like Papovaviridae (e.g. bovine papillomavirus or BPV) or Herpesviridae (e.g. Epstein Barr Virus or EBV) or Hepadnaviridae (e.g. Hepatitis B Virus or HBV) or pox vectors including vaccinia may be used in the disclosed vectors.

Lentiviral vectors are a preferred type of vector for the disclosed compositions and methods, although the disclosure is not specifically limited to lentiviral vectors. Lentivirus is a genus of viruses that can deliver a significant amount of viral nucleic acid into a host cell. Lentiviruses are characterized as having a unique ability to infect/transduce non-dividing cells, and following transduction, lentiviruses integrate their nucleic acid into the host cell's chromosomes.

Infectious lentiviruses have three main genes coding for the virulence proteins gag, pol, and env, and two regulatory genes including tat and rev. Depending on the specific serotype and virus, there may be additional accessory genes that code for proteins involved in regulation, synthesis, and/or processing viral nucleic acids and other replicative functions.

Moreover, lentiviruses contain long terminal repeat (LTR) regions, which may be approximately 600 nt long. LTRs may be segmented into U3, R, and U5 regions. LTRs can mediate integration of retroviral DNA into the host chromosome via the action of integrase. Alternatively, without functioning integrase, the LTRs may be used to circularize the viral nucleic acid.

Viral proteins involved in early stages of lentivirus replication include reverse transcriptase and integrase. Reverse transcriptase is the virally encoded, RNA-dependent DNA polymerase. The enzyme uses a viral RNA genome as a template for the synthesis of a complementary DNA copy. Reverse transcriptase also has RNaseH activity for destruction of the RNA-template. Integrase binds both the viral cDNA generated by reverse transcriptase and the host DNA. Integrase processes the LTR before inserting the viral genome into the host DNA. Tat acts as a trans-activator during transcription to enhance initiation and elongation. The rev responsive element acts post-transcriptionally, regulating mRNA splicing and transport to the cytoplasm.

Viral vectors, in general, comprise glycoproteins and the various glycoproteins may provide specific affinities. For instance, VSV-G peptides can increase transfection into myeloid cells. Alternatively, viral vectors can also have targeting moieties, such as antibodies, attached to their shell peptides. Targeting antibodies can be specific for antigens that are overexpressed on a tumor, for instance, like HER-2, PSA, CEA, M2-PK, and CA19-9.

Other viral vector specificities are also known in the art and can be used to target particular populations of cells. For example, poxvirus vectors target to macrophages and dendritic cells.

Lentiviral Vector System

A lentiviral virion (particle) is expressed by a vector system encoding the necessary viral proteins to produce a virion (viral particle). There is at least one vector containing a nucleic acid sequence encoding the lentiviral pol proteins necessary for reverse transcription and integration, operably linked to a promoter. In another embodiment, the pol proteins are expressed by multiple vectors. There is also a vector containing a nucleic acid sequence encoding the lentiviral gag proteins necessary for forming a viral capsid operably linked to a promoter. In an embodiment, this gag nucleic acid sequence is on a separate vector than at least some of the pol nucleic acid sequence. In another embodiment, the gag nucleic acid is on a separate vector from all the pol nucleic acid sequences that encode pol proteins.

Numerous modifications can be made to the vectors, which are used to create the particles to further minimize the chance of obtaining wild type revertants. These include, but are not limited to deletions of the U3 region of the LTR, tat deletions and matrix (MA) deletions.

The gag, pol and env vector(s) do not contain nucleotides from the lentiviral genome that package lentiviral RNA, referred to as the lentiviral packaging sequence.

The vector(s) forming the particle preferably do not contain a nucleic acid sequence from the lentiviral genome that expresses an envelope protein. Preferably, a separate vector that contains a nucleic acid sequence encoding an envelope protein operably linked to a promoter is used. This env vector also does not contain a lentiviral packaging sequence. In one embodiment the env nucleic acid sequence encodes a lentiviral envelope protein.

In another embodiment the envelope protein is not from the lentivirus, but from a different virus. The resultant particle is referred to as a pseudotyped particle. By appropriate selection of envelopes one can "infect" virtually any cell. For example, one can use an env gene that encodes an envelope protein that targets an endocytic compartment such as that of the influenza virus, VSV-G, alpha viruses (Semliki forest virus, Sindbis virus), arenaviruses (lymphocytic choriomeningitis virus), flaviviruses (tick-borne encephalitis virus, Dengue virus, hepatitis C virus, GB virus), rhabdoviruses (vesicular stomatitis virus, rabies virus), paramyxoviruses (mumps or measles) and orthomyxoviruses (influenza virus). Other envelopes that can preferably be used include those from Moloney Leukemia. Virus such as MLV-E, MLV-A and GALV. These latter envelopes are particularly preferred where the host cell is a primary cell. Other envelope proteins can be selected depending upon the desired host cell. For example, targeting specific receptors such as a dopamine receptor can be used for brain delivery. Another target can be vascular endothelium. These cells can be targeted using a filovirus envelope. For example, the GP of Ebola, which by post-transcriptional modification become the GP, and $GP_2$ glycoproteins. In another embodiment, one can use different lentiviral capsids with a pseudotyped envelope (for example, FIV or SHIV [U.S. Pat. No. 5,654, 195]). A SHIV pseudotyped vector can readily be used in animal models such as monkeys.

As detailed herein, a lentiviral vector system typically includes at least one helper plasmid comprising at least one of a gag, pol, or rev gene. Each of the gag, pol and rev genes may be provided on individual plasmids, or one or more genes may be provided together on the same plasmid. In one embodiment, the gag, pol, and rev genes are provided on the same plasmid (e.g., FIG. 2). In another embodiment, the gag and pol genes are provided on a first plasmid and the rev gene is provided on a second plasmid (e.g., FIG. 3). Accordingly, both 3-vector and 4-vector systems can be used to produce a lentivirus as described in the Examples section and elsewhere herein. The therapeutic vector, the envelope plasmid and at least one helper plasmid are transfected into a packaging cell line. A non-limiting example of a packaging cell line is the 293T/17 HEK cell line. When the therapeutic vector, the envelope plasmid, and at least one helper plasmid are transfected into the packaging cell line, a lentiviral particle is ultimately produced.

In another aspect, a lentiviral vector system for expressing a lentiviral particle is disclosed. The system includes a lentiviral vector as described herein; an envelope plasmid for expressing an envelope protein optimized for infecting a cell; and at least one helper plasmid for expressing gag, pol, and rev genes, wherein when the lentiviral vector, the envelope plasmid, and the at least one helper plasmid are transfected into a packaging cell line, a lentiviral particle is produced by the packaging cell line, wherein the lentiviral particle is capable of inhibiting production of chemokine receptor CCR5 or targeting an HIV RNA sequence.

Figure 2:
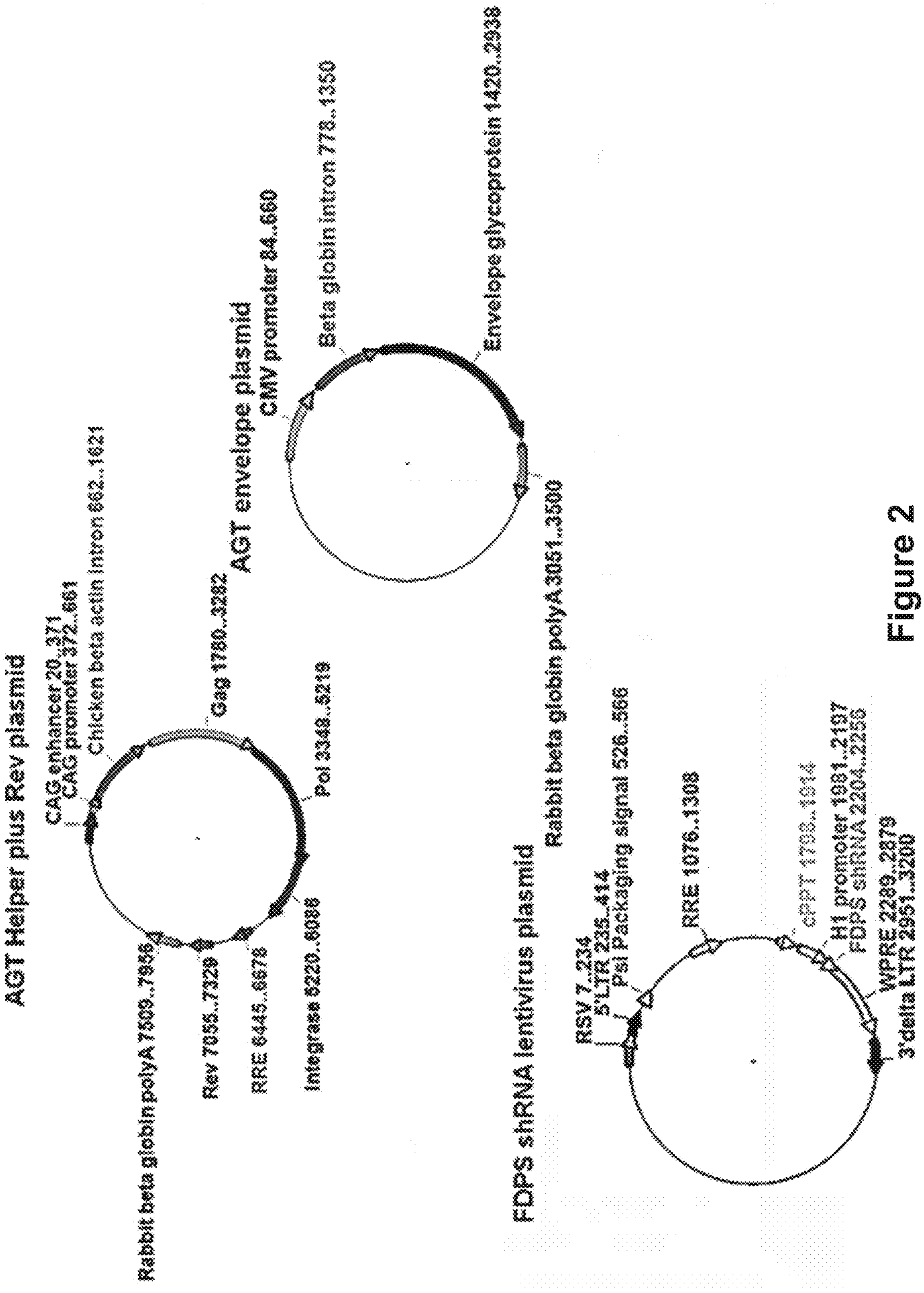
FIG. 2 depicts an exemplary 3-vector lentiviral vector system in a circularized form.

In another aspect, and as detailed in FIG. 2, the lentiviral vector, which is also referred to herein as a therapeutic vector, can include the following elements: hybrid 5' long terminal repeat (RSV/5' LTR) (SEQ ID NOS: 11-12), Psi sequence (RNA packaging site) (SEQ ID NO: 13), RRE (Rev-response element) (SEQ ID NO: 14), cPPT (polypurine tract) (SEQ ID NO: 15), H1 promoter (SEQ ID NO: 16), FDPS shRNA (SEQ ID NOS: 1, 2, 3, 4), Woodchuck Post-Transcriptional Regulatory Element (WPRE) (SEQ ID NO: 17), and 3' Delta LTR (SEQ ID NO: 18). In another aspect, sequence variation, by way of substitution, deletion, addition, or mutation can be used to modify the sequences references herein.

In another aspect, and as detailed herein, a helper plasmid has been designed to include the following elements: CAG promoter (SEQ ID NO: 19); HIV component gag (SEQ ID NO: 20); HIV component pol (SEQ ID NO: 21); HIV Int (SEQ ID NO: 22); HIV RRE (SEQ ID NO: 23); and HIV Rev (SEQ ID NO: 24). In another aspect, the helper plasmid may be modified to include a first helper plasmid for expressing the gag and pol genes, and a second and separate plasmid for expressing the rev gene. In another aspect, sequence variation, by way of substitution, deletion, addition, or mutation can be used to modify the sequences references herein.

In another aspect, and as detailed herein, an envelope plasmid has been designed to include the following elements being from left to right: RNA polymerase II promoter (CMV) (SEQ ID NO: 25) and vesicular stomatitis virus G glycoprotein (VSV-G) (SEQ ID NO: 26). In another aspect, sequence variation, by way of substitution, deletion, addition, or mutation can be used to modify the sequences references herein.

In another aspect, the plasmids used for lentiviral packaging can be modified with similar elements and the intron sequences could potentially be removed without loss of vector function. For example, the following elements can replace similar elements in the plasmids that comprise the packaging system: Elongation Factor-1 (EF-1), phosphoglycerate kinase (PGK), and ubiquitin C (UbC) promoters can replace the CMV or CAG promoter. SV40 poly A and bGH poly A can replace the rabbit beta globin poly A. The HIV sequences in the helper plasmid can be constructed from different HIV strains or clades. The VSV-G glycoprotein can be substituted with membrane glycoproteins from feline endogenous virus (RD114), gibbon ape leukemia virus (GALV), Rabies (FUG), lymphocytic choriomeningitis virus (LCMV), influenza A fowl plague virus (FPV), Ross River alphavirus (RRV), murine leukemia virus 10A1 (MLV), or Ebola virus (EboV).

Of note, lentiviral packaging systems can be acquired commercially (e.g., Lenti-vpak packaging kit from OriGene Technologies, Inc., Rockville, Md.), and can also be designed as described herein. Moreover, it is within the skill of a person skilled in the art to substitute or modify aspects of a lentiviral packaging system to improve any number of relevant factors, including the production efficiency of a lentiviral particle.

Doses and Dosage Forms

The disclosed vectors allow for short, medium, or long-term expression of genes or sequences of interest and episomal maintenance of the disclosed vectors. Accordingly, dosing regimens may vary based upon the condition being treated and the method of administration.

In one embodiment, transduction vectors may be administered to a subject in need in varying doses. Specifically, a subject may be administered about $\geq 10^6$ infectious doses (where 1 dose is needed on average to transduce 1 target cell). More specifically, a subject may be administered about $\geq 10^7$, about $\geq 10^8$, about $\geq 10^9$, or about $\geq 10^{10}$ infectious doses, or any number of doses in-between these values. Upper limits of transduction vector dosing will be determined for each disease indication and will depend on toxicity/safety profiles for each individual product or product lot.

Additionally, a vector of the present disclosure may be administered periodically, such as once or twice a day, or any other suitable time period. For example, vectors may be administered to a subject in need once a week, once every other week, once every three weeks, once a month, every other month, every three months, every six months, every nine months, once a year, every eighteen months, every two years, every thirty months, or every three years.

In one embodiment, the disclosed vectors are administered as a pharmaceutical composition. In some embodiments, the pharmaceutical composition comprising the disclosed vectors can be formulated in a wide variety of dosage forms, including but not limited to nasal, pulmonary, oral, topical, or parenteral dosage forms for clinical application. Each of the dosage forms can comprise various solubilizing agents, disintegrating agents, surfactants, fillers, thickeners, binders, diluents such as wetting agents or other pharmaceutically acceptable excipients. The pharmaceutical composition comprising a vector can also be formulated for injection, insufflation, infusion, or intradermal exposure. For instance, an injectable formulation may comprise the disclosed vectors in an aqueous or non-aqueous solution at a suitable pH and tonicity.

The disclosed vectors may be administered to a subject via direct injection into a tumor site or at a site of infection. In some embodiments, the vectors can be administered systemically. In some embodiments, the vectors can be administered via guided cannulation to tissues immediately surrounding the sites of tumor or infection.

The disclosed vector compositions can be administered using any pharmaceutically acceptable method, such as intranasal, buccal, sublingual, oral, rectal, ocular, parenteral (intravenously, intradermally, intramuscularly, subcutaneously, intraperitoneally), pulmonary, intravaginal, locally administered, topically administered, topically administered after scarification, mucosally administered, via an aerosol, in semi-solid media such as agarose or gelatin, or via a buccal or nasal spray formulation.

Further, the disclosed vector compositions can be formulated into any pharmaceutically acceptable dosage form, such as a solid dosage form, tablet, pill, lozenge, capsule, liquid dispersion, gel, aerosol, pulmonary aerosol, nasal aerosol, ointment, cream, semi-solid dosage form, a solution, an emulsion, and a suspension. Further, the composition may be a controlled release formulation, sustained release formulation, immediate release formulation, or any combination thereof. Further, the composition may be a transdermal delivery system.

In some embodiments, the pharmaceutical composition comprising a vector can be formulated in a solid dosage form for oral administration, and the solid dosage form can be powders, granules, capsules, tablets or pills. In some embodiments, the solid dosage form can include one or more excipients such as calcium carbonate, starch, sucrose, lactose, microcrystalline cellulose or gelatin. In addition, the solid dosage form can include, in addition to the excipients, a lubricant such as talc or magnesium stearate. In some embodiments, the oral dosage form can be immediate release, or a modified release form. Modified release dosage forms include controlled or extended release, enteric release, and the like. The excipients used in the modified release dosage forms are commonly known to a person of ordinary skill in the art.

In a further embodiment, the pharmaceutical composition comprising a vector can be formulated as a sublingual or buccal dosage form. Such dosage forms comprise sublingual tablets or solution compositions that are administered under the tongue and buccal tablets that are placed between the cheek and gum.

In some embodiments, the pharmaceutical composition comprising a vector can be formulated as a nasal dosage form. Such dosage forms of the present invention comprise solution, suspension, and gel compositions for nasal delivery.

In some embodiments, the pharmaceutical composition comprising a vector can be formulated in a liquid dosage form for oral administration, such as suspensions, emulsions or syrups. In some embodiments, the liquid dosage form can include, in addition to commonly used simple diluents such as water and liquid paraffin, various excipients such as humectants, sweeteners, aromatics or preservatives. In particular embodiments, the composition comprising vectors can be formulated to be suitable for administration to a pediatric patient.

In some embodiment, the pharmaceutical composition can be formulated in a dosage form for parenteral administration, such as sterile aqueous solutions, suspensions, emulsions, non-aqueous solutions or suppositories. In some embodiments, the solutions or suspensions can include propylene glycol, polyethylene glycol, vegetable oils such as olive oil or injectable esters such as ethyl oleate.

The dosage of the pharmaceutical composition can vary depending on the patient's weight, age, gender, administration time and mode, excretion rate, and the severity of disease.

In some embodiments, the treatment of cancer is accomplished by guided direct injection of the disclosed vector constructs into tumors, using needle, or intravascular cannulation. In some embodiments, the disclosed vectors are administered into the cerebrospinal fluid, blood or lymphatic circulation by venous or arterial cannulation or injection, intradermal delivery, intramuscular delivery or injection into a draining organ near the site of disease.

The following examples are given to illustrate the present invention. It should be understood, however, that the invention is not to be limited to the specific conditions or details described in these examples. All printed publications referenced herein are specifically incorporated by reference.

EXAMPLES

Example 1: Development of a Lentiviral Vector System

Figure 4:
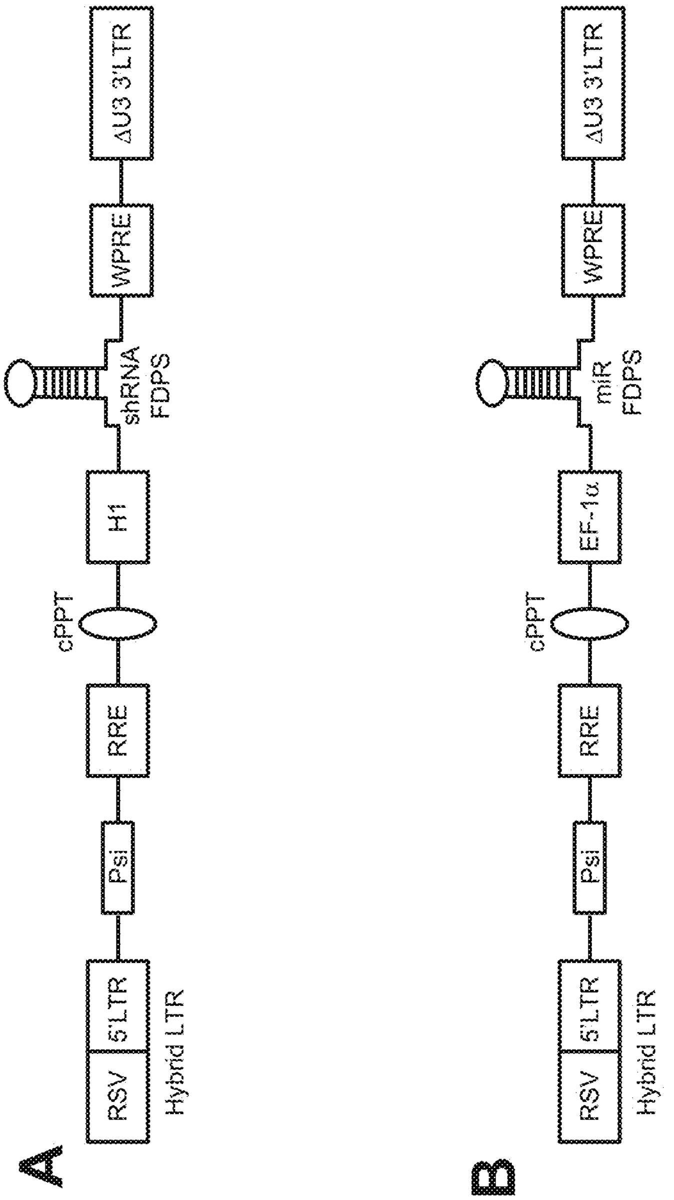
FIG. 4 depicts: (A) a linear map of a lentiviral vector expressing a FDPS shRNA targeting sequence; and (B) a linear map of a lentiviral vector expressing a synthetic microRNA with a FDPS targeting sequence.

A lentiviral vector system was developed as summarized in FIG. 4 (circularized form). Lentiviral particles were produced in 293T/17 HEK cells (purchased from American Type Culture Collection, Manassas, Va.) following transfection with the therapeutic vector, the envelope plasmid, and the helper plasmid. The transfection of 293T/17 HEK cells, which produced functional viral particles, employed the reagent Poly(ethylenimine) (PEI) to increase the efficiency of plasmid DNA uptake. The plasmids and DNA were initially added separately in culture medium without serum in a ratio of 3:1 (mass ratio of PEI to DNA). After 2-3 days, cell medium was collected and lentiviral particles were purified by high-speed centrifugation and/or filtration followed by anion-exchange chromatography. The concentration of lentiviral particles can be expressed in terms of transducing units/ml (TU/ml). The determination of TU was accomplished by measuring HIV p24 levels in culture fluids (p24 protein is incorporated into lentiviral particles), measuring the number of viral DNA copies per cell by quantitative PCR, or by infecting cells and using light (if the vectors encode luciferase or fluorescent protein markers).

As mentioned above, a 3-vector system (i.e., a 2-vector lentiviral packaging system) was designed for the production of lentiviral particles. A schematic of the 3-vector system is shown in FIG. 2. Briefly, and with reference to FIG. 2, the top-most vector is a helper plasmid, which, in this case, includes Rev. The vector appearing in the middle of FIG. 2 is the envelope plasmid. The bottom-most vector is the therapeutic vector, as described herein.

Referring more specifically to FIG. 2, the Helper plus Rev plasmid includes a CAG enhancer (SEQ ID NO: 27); a CAG promoter (SEQ ID NO: 19); a chicken beta actin intron (SEQ ID NO: 28); a HIV gag (SEQ ID NO: 20); a HIV Pol (SEQ ID NO: 21); a HIV Int (SEQ ID NO: 22); a HIV RRE (SEQ ID NO: 23); a HIV Rev (SEQ ID NO: 24); and a rabbit beta globin poly A (SEQ ID NO: 29).

The Envelope plasmid includes a CMV promoter (SEQ ID NO: 25); a beta globin intron (SEQ ID NO: 30); a VSV-G (SEQ ID NO: 28); and a rabbit beta globin poly A (SEQ ID NO: 31).

Synthesis of a 2-Vector Lentiviral Packaging System including Helper (plus Rev) and Envelope Plasmids.

Materials and Methods:

Construction of the helper plasmid: The helper plasmid was constructed by initial PCR amplification of a DNA fragment from the pNL4-3 HIV plasmid (NIH Aids Reagent Program) containing Gag, Pol, and Integrase genes. Primers were designed to amplify the fragment with EcoRI and NotI restriction sites which could be used to insert at the same sites in the pCDNA3 plasmid (Invitrogen). The forward primer was (5'-TAAGCAGAATTC ATGAATTTGCCAGGAAGAT-3') (SEQ ID NO: 32) and reverse primer was (5'-CCATACAATGAATGGACACTAGGCGGCCGCACGAAT-3') (SEQ ID NO: 33).

The sequence for the Gag, Pol, Integrase fragment was as follows:

(SEQ ID NO: 34)

```
GAATTCATGAATTTGCCAGGAAGATGGAAACCAAAAATGATAGGGGGAAT
TGGAGGTTTTATCAAAGTAAGACAGTATGATCAGATACTCATAGAAATCT
GCGGACATAAAGCTATAGGTACAGTATTAGTAGGACCTACACCTGTCAAC
ATAATTGGAAGAAATCTGTTGACTCAGATTGGCTGCACTTTAAATTTTCC
CATTAGTCCTATTGAGACTGTACCAGTAAAATTAAAGCCAGGAATGGATG
GCCCAAAAGTTAAACAATGGCCATTGACAGAAGAAAAAATAAAAGCATTA
GTAGAAATTTGTACAGAAATGGAAAAGGAAGGAAAAATTTCAAAAATTGG
GCCTGAAAATCCATACAATACTCCAGTATTTGCCATAAAGAAAAAAGACA
GTACTAAATGGAGAAAATTAGTAGATTTCAGAGAACTTAATAAGAGAACT
CAAGATTTCTGGGAAGTTCAATTAGGAATACCACATCCTGCAGGGTTAAA
ACAGAAAAAATCAGTAACAGTACTGGATGTGGGCGATGCATATTTTTCAG
TTCCCTTAGATAAAGACTTCAGGAAGTATACTGCATTTACCATACCTAGT
ATAAACAATGAGACACCAGGGATTAGATATCAGTACAATGTGCTTCCACA
GGGATGGAAAGGATCACCAGCAATATTCCAGTGTAGCATGACAAAAATCT
TAGAGCCTTTTAGAAAACAAAATCCAGACATAGTCATCTATCAATACATG
GATGATTTGTATGTAGGATCTGACTTAGAAATAGGGCAGCATAGAACAAA
AATAGAGGAACTGAGACAACATCTGTTGAGGTGGGGATTTACCACACCAG
ACAAAAAACATCAGAAAGAACCTCCATTCCTTTGGATGGGTTATGAACTC
CATCCTGATAAATGGACAGTACAGCCTATAGTGCTGCCAGAAAAGGACAG
CTGGACTGTCAATGACATACAGAAATTAGTGGGAAAATTGAATTGGGCAA
GTCAGATTTATGCAGGGATTAAAGTAAGGCAATTATGTAAACTTCTTAGG
GGAACCAAAGCACTAACAGAAGTAGTACCACTAACAGAAGAAGCAGAGCT
AGAACTGGCAGAAAACAGGGAGATTCTAAAAGAACCGGTACATGGAGTGT
ATTATGACCCATCAAAAGACTTAATAGCAGAAATACAGAAGCAGGGGCAA
GGCCAATGGACATATCAAATTTATCAAGAGCCATTTAAAAATCTGAAAAC
AGGAAAGTATGCAAGAATGAAGGGTGCCCACACTAATGATGTGAAACAAT
TAACAGAGGCAGTACAAAAAATAGCCACAGAAAGCATAGTAATATGGGGA
AAGACTCCTAAATTTAAATTACCCATACAAAAGGAAACATGGGAAGCATG
GTGGACAGAGTATTGGCAAGCCACCTGGATTCCTGAGTGGGAGTTTGTCA
```

-continued

```
ATACCCCTCCCTTAGTGAAGTTATGGTACCAGTTAGAGAAAGAACCCATA
ATAGGAGCAGAAACTTTCTATGTAGATGGGGCAGCCAATAGGGAAACTAA
ATTAGGAAAAGCAGGATATGTAACTGACAGAGGAAGACAAAAAGTTGTCC
CCCTAACGGACACAACAAATCAGAAGACTGAGTTACAAGCAATTCATCTA
GCTTTGCAGGATTCGGGATTAGAAGTAAACATAGTGACAGACTCACAATA
TGCATTGGGAATCATTCAAGCACAACCAGATAAGAGTGAATCAGAGTTAG
TCAGTCAAATAATAGAGCAGTTAATAAAAAAGGAAAAAGTCTACCTGGCA
TGGGTACCAGCACACAAAGGAATTGGAGGAAATGAACAAGTAGATAAATT
GGTCAGTGCTGGAATCAGGAAAGTACTATTTTTAGATGGAATAGATAAGG
CCCAAGAAGAACATGAGAAATATCACAGTAATTGGAGAGCAATGGCTAGT
GATTTTAACCTACCACCTGTAGTAGCAAAAGAAATAGTAGCCAGCTGTGA
TAAATGTCAGCTAAAAGGGGAAGCCATGCATGGACAAGTAGACTGTAGCC
CAGGAATATGGCAGCTAGATTGTACACATTTAGAAGGAAAAGTTATCTTG
GTAGCAGTTCATGTAGCCAGTGGATATATAGAAGCAGAAGTAATTCCAGC
AGAGACAGGGCAAGAAACAGCATACTTCCTCTTAAAATTAGCAGGAAGAT
GGCCAGTAAAAACAGTACATACAGACAATGGCAGCAATTTCACCAGTACT
ACAGTTAAGGCCGCCTGTTGGTGGGCGGGGATCAAGCAGGAATTTGGCAT
TCCCTACAATCCCCAAAGTCAAGGAGTAATAGAATCTATGAATAAAGAAT
TAAAGAAAATTATAGGACAGGTAAGAGATCAGGCTGAACATCTTAAGACA
GCAGTACAAATGGCAGTATTCATCCACAATTTTAAAAGAAAAGGGGGGAT
TGGGGGGTACAGTGCAGGGGAAAGAATAGTAGACATAATAGCAACAGACA
TACAAACTAAAGAATTACAAAAACAAATTACAAAAATTCAAAATTTTCGG
GTTTATTACAGGGACAGCAGAGATCCAGTTTGGAAAGGACCAGCAAAGCT
CCTCTGGAAAGGTGAAGGGGCAGTAGTAATACAAGATAATAGTGACATAA
AAGTAGTGCCAAGAAGAAAAGCAAAGATCATCAGGGATTATGGAAAACAG
ATGGCAGGTGATGATTGTGTGGCAAGTAGACAGGATGAGGATTAA
```

Next, a DNA fragment containing the Rev, RRE, and rabbit beta globin poly A sequence with XbaI and XmaI flanking restriction sites was synthesized by MWG Operon. The DNA fragment was then inserted into the plasmid at the XbaI and XmaI restriction sites The DNA sequence was as follows:

(SEQ ID NO: 35)

```
TCTAGAATGGCAGGAAGAAGCGGAGACAGCGACGAAGAGCTCATCAGAAC
AGTCAGACTCATCAAGCTTCTCTATCAAAGCAACCCACCTCCCAATCCCG
AGGGGACCCGACAGGCCCGAAGGAATAGAAGAAGAAGGTGGAGAGAGAGA
CAGAGACAGATCCATTCGATTAGTGAACGGATCCTTGGCACTTATCTGGG
ACGATCTGCGGAGCCTGTGCCTCTTCAGCTACCACCGCTTGAGAGACTTA
CTCTTGATTGTAACGAGGATTGTGGAACTTCTGGGACGCAGGGGGTGGGA
AGCCCTCAAATATTGGTGGAATCTCCTACAATATTGGAGTCAGGAGCTAA
AGAATAGAGGAGCTTTGTTCCTTGGGTTCTTGGGAGCAGCAGGAAGCACT
ATGGGCGCAGCGTCAATGACGCTGACGGTACAGGCCAGACAATTATTGTC
```

-continued

TGGTATAGTGCAGCAGCAGAACAATTTGCTGAGGGCTATTGAGGCGCAAC

AGCATCTGTTGCAACTCACAGTCTGGGGCATCAAGCAGCTCCAGGCAAGA

ATCCTGGCTGTGGAAAGATACCTAAAGGATCAACAGCTCCTAGATCTTTT

TCCCTCTGCCAAAAATTATGGGGACATCATGAAGCCCCTTGAGCATCTGA

CTTCTGGCTAATAAAGGAAATTTATTTTCATTGCAATAGTGTGTTGGAAT

TTTTTGTGTCTCTCACTCGGAAGGACATATGGGAGGGCAAATCATTTAAA

ACATCAGAATGAGTATTTGGTTTAGAGTTTGGCAACATATGCCATATGCT

GGCTGCCATGAACAAAGGTGGCTATAAAGAGGTCATCAGTATATGAAACA

GCCCCCTGCTGTCCATTCCTTATTCCATAGAAAAGCCTTGACTTGAGGTT

AGATTTTTTTTATATTTTGTTTTGTGTTATTTTTTTCTTTAACATCCCTA

AAATTTTCCTTACATGTTTTACTAGCCAGATTTTTCCTCCTCTCCTGACT

ACTCCCAGTCATAGCTGTCCCTCTTCTCTTATGAAGATCCCTCGACCTGC

AGCCCAAGCTTGGCGTAATCATGGTCATAGCTGTTTCCTGTGTGAAATTG

TTATCCGCTCACAATTCCACACAACATACGAGCCGGAAGCATAAAGTGTA

AAGCCTGGGGTGCCTAATGAGTGAGCTAACTCACATTAATTGCGTTGCGC

TCACTGCCCGCTTTCCAGTCGGGAAACCTGTCGTGCCAGCGGATCCGCAT

CTCAATTAGTCAGCAACCATAGTCCCGCCCCTAACTCCGCCCATCCCGCC

CCTAACTCCGCCCAGTTCCGCCCATTCTCCGCCCCATGGCTGACTAATTT

TTTTTATTTATGCAGAGGCCGAGGCCGCCTCGGCCTCTGAGCTATTCCAG

AAGTAGTGAGGAGGCTTTTTTGGAGGCCTAGGCTTTTGCAAAAAGCTAAC

TTGTTTATTGCAGCTTATAATGGTTACAAATAAAGCAATAGCATCACAAA

TTTCACAAATAAAGCATTTTTTTCACTGCATTCTAGTTGTGGTTTGTCCA

AACTCATCAATGTATCTTATCAGCGGCCGCCCCGGG

Finally, the CMV promoter of pCDNA3.1 was replaced with the CAG enhancer/promoter plus a chicken beta actin intron sequence. A DNA fragment containing the CAG enhancer/promoter/intron sequence with MluI and EcoRI flanking restriction sites was synthesized by MWG Operon. The DNA fragment was then inserted into the plasmid at the MluI and EcoRI restriction sites. The DNA sequence was as follows:

(SEQ ID NO: 36)

ACGCGTTAGTTATTAATAGTAATCAATTACGGGGTCATTAGTTCATAGCC

CATATATGGAGTTCCGCGTTACATAACTTACGGTAAATGGCCCGCCTGGC

TGACCGCCCAACGACCCCCGCCCATTGACGTCAATAATGACGTATGTTCC

CATAGTAACGCCAATAGGGACTTTCCATTGACGTCAATGGGTGGACTATT

TACGGTAAACTGCCCACTTGGCAGTACATCAAGTGTATCATATGCCAAGT

ACGCCCCCTATTGACGTCAATGACGGTAAATGGCCCGCCTGGCATTATGC

CCAGTACATGACCTTATGGGACTTTCCTACTTGGCAGTACATCTACGTAT

TAGTCATCGCTATTACCATGGGTCGAGGTGAGCCCCACGTTCTGCTTCAC

TCTCCCCATCTCCCCCCCCTCCCCACCCCCAATTTTGTATTTATTTATTT

TTTAATTATTTTGTGCAGCGATGGGGGCGGGGGGGGGGGGGGCGCGCGCC

AGGCGGGGCGGGGCGGGGCGAGGGGCGGGGCGGGGCGAGGCGGAGAGGTG

CGGCGGCAGCCAATCAGAGCGGCGCGCTCCGAAAGTTTCCTTTTATGGCG

AGGCGGCGGCGGCGGCGGCCCTATAAAAAGCGAAGCGCGCGGCGGGCGGG

AGTCGCTGCGTTGCCTTCGCCCCGTGCCCCGCTCCGCGCCGCCTCGCGCC

GCCCGCCCCGGCTCTGACTGACCGCGTTACTCCCACAGGTGAGCGGGCGG

GACGGCCCTTCTCCTCCGGGCTGTAATTAGCGCTTGGTTTAATGACGGCT

CGTTTCTTTTCTGTGGCTGCGTGAAAGCCTTAAAGGGCTCCGGGAGGGCC

CTTTGTGCGGGGGGGAGCGGCTCGGGGGGTGCGTGCGTGTGTGTGTGCGT

GGGGAGCGCCGCGTGCGGCCCGCGCTGCCCGGCGGCTGTGAGCGCTGCGG

GCGCGGCGCGGGGCTTTGTGCGCTCCGCGTGTGCGCGAGGGGAGCGCGGC

CGGGGGCGGTGCCCCGCGGTGCGGGGGGGCTGCGAGGGGAACAAAGGCTG

CGTGCGGGGTGTGTGCGTGGGGGGGTGAGCAGGGGGTGTGGGCGCGGCGG

TCGGGCTGTAACCCCCCCCTGCACCCCCCTCCCCGAGTTGCTGAGCACGG

CCCGGCTTCGGGTGCGGGGCTCCGTGCGGGGCGTGGCGCGGGGCTCGCCG

TGCCGGGCGGGGGGTGGCGGCAGGTGGGGGTGCCGGGCGGGGCGGGGCCG

CCTCGGGCCGGGGAGGGCTCGGGGGAGGGGCGCGGCGGCCCCGGAGCGCC

GGCGGCTGTCGAGGCGCGGCGAGCCGCAGCCATTGCCTTTTATGGTAATC

GTGCGAGAGGGCGCAGGGACTTCCTTTGTCCCAAATCTGGCGGAGCCGAA

ATCTGGGAGGCGCCGCCGCACCCCCTCTAGCGGGCGCGGGCGAAGCGGTG

CGGCGCCGGCAGGAAGGAAATGGGCGGGGAGGGCCTTCGTGCGTCGCCGC

GCCGCCGTCCCCTTCTCCATCTCCAGCCTCGGGGCTGCCGCAGGGGGACG

GCTGCCTTCGGGGGGGACGGGGCAGGGCGGGGTTCGGCTTCTGGCGTGTG

ACCGGCGGGAATTC

Construction of the VSV-G Envelope Plasmid:

The vesicular stomatitis Indiana virus glycoprotein (VSV-G) sequence was synthesized by MWG Operon with flanking EcoRI restriction sites. The DNA fragment was then inserted into the pCDNA3.1 plasmid (Invitrogen) at the EcoRI restriction site and the correct orientation was determined by sequencing using a CMV specific primer. The DNA sequence was as follows:

(SEQ ID NO: 37)

GAATTCATGAAGTGCCTTTTGTACTTAGCCTTTTTATTCATTGGGGTGA

ATTGCAAGTTCACCATAGTTTTTCCACACAACCAAAAAGGAAACTGGAA

AAATGTTCCTTCTAATTACCATTATTGCCCGTCAAGCTCAGATTTAAAT

TGGCATAATGACTTAATAGGCACAGCCTTACAAGTCAAAATGCCCAAGA

GTCACAAGGCTATTCAAGCAGACGGTTGGATGTGTCATGCTTCCAAATG

GGTCACTACTTGTGATTTCCGCTGGTATGGACCGAAGTATATAACACAT

TCCATCCGATCCTTCACTCCATCTGTAGAACAATGCAAGGAAAGCATTG

AACAAACGAAACAAGGAACTTGGCTGAATCCAGGCTTCCCTCCTCAAAG

TTGTGGATATGCAACTGTGACGGATGCCGAAGCAGTGATTGTCCAGGTG

ACTCCTCACCATGTGCTGGTTGATGAATACACAGGAGAATGGGTTGATT

CACAGTTCATCAACGGAAAATGCAGCAATTACATATGCCCCACTGTCCA

TAACTCTACAACCTGGCATTCTGACTATAAGGTCAAAGGGCTATGTGAT

-continued

TCTAACCTCATTTCCATGGACATCACCTTCTTCTCAGAGGACGGAGAGC

TATCATCCCTGGGAAAGGAGGGCACAGGGTTCAGAAGTAACTACTTTGC

TTATGAAACTGGAGGCAAGGCCTGCAAAATGCAATACTGCAAGCATTGG

GGAGTCAGACTCCCATCAGGTGTCTGGTTCGAGATGGCTGATAAGGATC

TCTTTGCTGCAGCCAGATTCCCTGAATGCCCAGAAGGGTCAAGTATCTC

TGCTCCATCTCAGACCTCAGTGGATGTAAGTCTAATTCAGGACGTTGAG

AGGATCTTGGATTATTCCCTCTGCCAAGAAACCTGGAGCAAAATCAGAG

CGGGTCTTCCAATCTCTCCAGTGGATCTCAGCTATCTTGCTCCTAAAAA

CCCAGGAACCGGTCCTGCTTTCACCATAATCAATGGTACCCTAAAATAC

TTTGAGACCAGATACATCAGAGTCGATATTGCTGCTCCAATCCTCTCAA

GAATGGTCGGAATGATCAGTGGAACTACCACAGAAAGGGAACTGTGGGA

TGACTGGGCACCATATGAAGACGTGGAAATTGGACCCAATGGAGTTCTG

AGGACCAGTTCAGGATATAAGTTTCCTTTATACATGATTGGACATGGTA

TGTTGGACTCCGATCTTCATCTTAGCTCAAAGGCTCAGGTGTTCGAACA

TCCTCACATTCAAGACGCTGCTTCGCAACTTCCTGATGATGAGAGTTTA

TTTTTGGTGATACTGGGCTATCCAAAAATCCAATCGAGCTTGTAGAAG

GTTGGTTCAGTAGTTGGAAAAGCTCTATTGCCTCTTTTTTCTTTATCAT

AGGGTTAATCATTGGACTATTCTTGGTTCTCCGAGTTGGTATCCATCTT

TGCATTAAATTAAAGCACACCAAGAAAAGACAGATTTATACAGACATAG

AGATGAGAATTC

Figure 3:
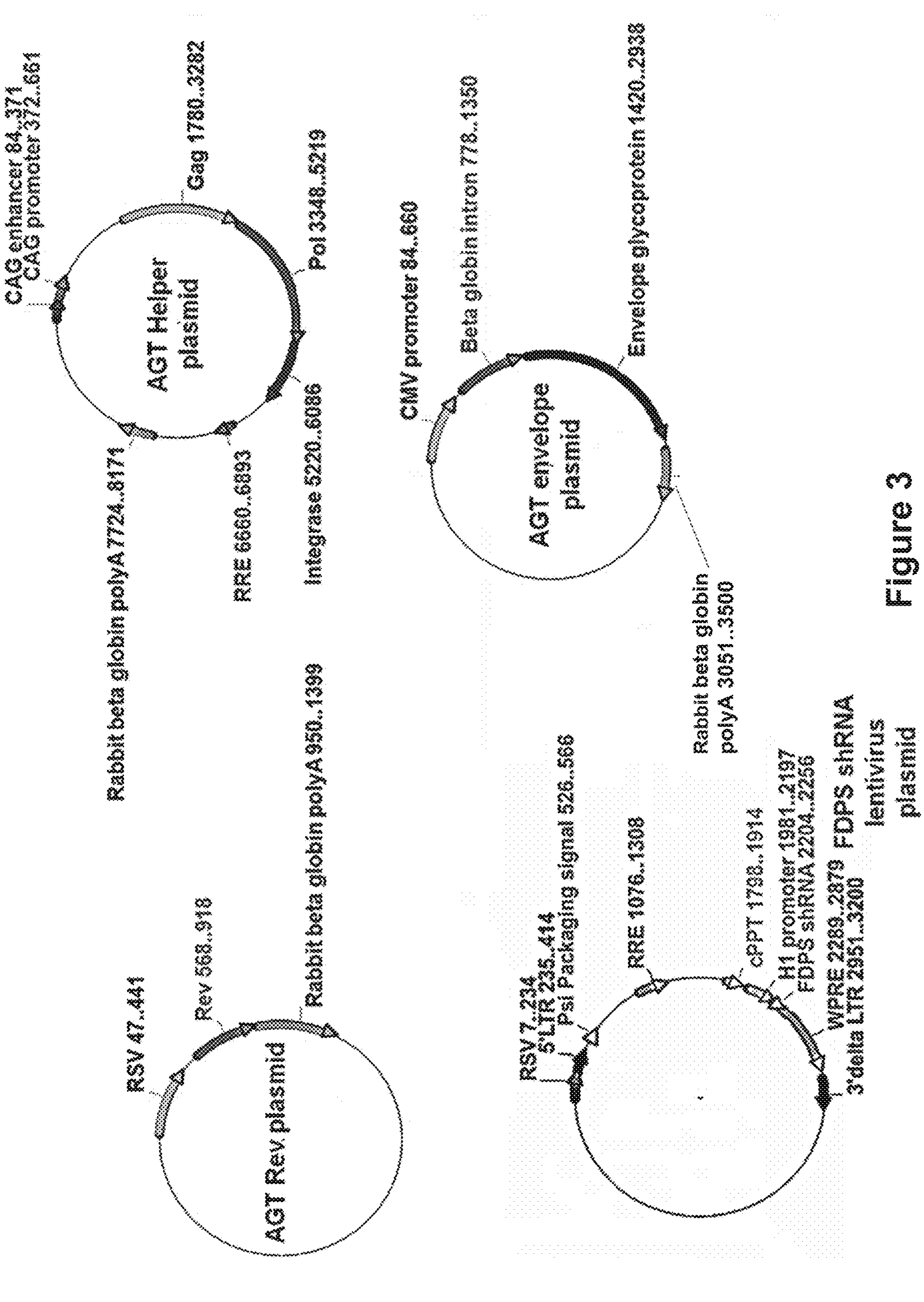
FIG. 3 depicts an exemplary 4-vector lentiviral vector system in a circularized form.

A 4-vector system (i.e., a 3-vector lentiviral packaging system) has also been designed and produced using the methods and materials described herein. A schematic of the 4-vector system is shown in FIG. 3. Briefly, and with reference to FIG. 3, the top-most vector is a helper plasmid, which, in this case, does not include Rev. The vector second from the top is a separate Rev plasmid. The vector second from the bottom is the envelope plasmid. The bottom-most vector is the previously described therapeutic vector.

Referring, in part, to FIG. 2, the Helper plasmid includes a CAG enhancer (SEQ ID NO: 27); a CAG promoter (SEQ ID NO: 19); a chicken beta actin intron (SEQ ID NO: 28); a HIV gag (SEQ ID NO: 20); a HIV Pol (SEQ ID NO: 21); a HIV Int (SEQ ID NO: 22); a HIV RRE (SEQ ID NO: 23); and a rabbit beta globin poly A (SEQ ID NO: 29).

The Rev plasmid includes a RSV promoter and a HIV Rev (SEQ ID NO: 38); and a rabbit beta globin poly A (SEQ ID NO: 29).

The Envelope plasmid includes a CMV promoter (SEQ ID NO: 25); a beta globin intron (SEQ ID NO: 30); a VSV-G (SEQ ID NO: 28); and a rabbit beta globin poly A (SEQ ID NO: 29).

Synthesis of a 3-Vector Lentiviral Packaging System including Helper, Rev, and Envelope Plasmids.

Materials and Methods:

Construction of the Helper Plasmid without Rev:

The Helper plasmid without Rev was constructed by inserting a DNA fragment containing the RRE and rabbit beta globin poly A sequence. This sequence was synthesized by MWG Operon with flanking XbaI and XmaI restriction sites. The RRE/rabbit poly A beta globin sequence was then inserted into the Helper plasmid at the XbaI and XmaI restriction sites. The DNA sequence is as follows:

(SEQ ID NO: 65)

TCTAGAAGGAGCTTTGTTCCTTGGGTTCTTGGGAGCAGCAGGAAGCACTA

TGGGCGCAGCGTCAATGACGCTGACGGTACAGGCCAGACAATTATTGTCT

GGTATAGTGCAGCAGCAGAACAATTTGCTGAGGGCTATTGAGGCGCAACA

GCATCTGTTGCAACTCACAGTCTGGGGCATCAAGCAGCTCCAGGCAAGAA

TCCTGGCTGTGGAAAGATACCTAAAGGATCAACAGCTCCTAGATCTTTTT

CCCTCTGCCAAAAATTATGGGGACATCATGAAGCCCCTTGAGCATCTGAC

TTCTGGCTAATAAAGGAAATTTATTTTCATTGCAATAGTGTGTTGGAATT

TTTTGTGTCTCTCACTCGGAAGGACATATGGGAGGGCAAATCATTTAAAA

CATCAGAATGAGTATTTGGTTTAGAGTTTGGCAACATATGCCATATGCTG

GCTGCCATGAACAAAGGTGGCTATAAAGAGGTCATCAGTATATGAAACAG

CCCCCTGCTGTCCATTCCTTATTCCATAGAAAAGCCTTGACTTGAGGTTA

GATTTTTTTTATATTTTGTTTTGTGTTATTTTTTTCTTTAACATCCCTAA

AATTTTCCTTACATGTTTTACTAGCCAGATTTTTCCTCCTCTCCTGACTA

CTCCCAGTCATAGCTGTCCCTCTTCTCTTATGAAGATCCCTCGACCTGCA

GCCCAAGCTTGGCGTAATCATGGTCATAGCTGTTTCCTGTGTGAAATTGT

TATCCGCTCACAATTCCACACAACATACGAGCCGGAAGCATAAAGTGTAA

AGCCTGGGGTGCCTAATGAGTGAGCTAACTCACATTAATTGCGTTGCGCT

CACTGCCCGCTTTCCAGTCGGGAAACCTGTCGTGCCAGCGGATCCGCATC

TCAATTAGTCAGCAACCATAGTCCCGCCCCTAACTCCGCCCATCCCGCCC

CTAACTCCGCCCAGTTCCGCCCATTCTCCGCCCCATGGCTGACTAATTTT

TTTTATTTATGCAGAGGCCGAGGCCGCCTCGGCCTCTGAGCTATTCCAGA

AGTAGTGAGGAGGCTTTTTTGGAGGCCTAGGCTTTTGCAAAAAGCTAACT

TGTTTATTGCAGCTTATAATGGTTACAAATAAAGCAATAGCATCACAAAT

TTCACAAATAAAGCATTTTTTTCACTGCATTCTAGTTGTGGTTTGTCCAA

ACTCATCAATGTATCTTATCACCCGGG

Construction of the Rev Plasmid:

The RSV promoter and HIV Rev sequence was synthesized as a single DNA fragment by MWG Operon with flanking MfeI and XbaI restriction sites. The DNA fragment was then inserted into the pCDNA3.1 plasmid (Invitrogen) at the MfeI and XbaI restriction sites in which the CMV promoter is replaced with the RSV promoter. The DNA sequence was as follows:

(SEQ ID NO: 38)

CAATTGCGATGTACGGGCCAGATATACGCGTATCTGAGGGGACTAGGGTGT

GTTTAGGCGAAAAGCGGGGCTTCGGTTGTACGCGGTTAGGAGTCCCCTCAG

GATATAGTAGTTTCGCTTTTGCATAGGGAGGGGGAAATGTAGTCTTATGCA

ATACACTTGTAGTCTTGCAACATGGTAACGATGAGTTAGCAACATGCCTTA

CAAGGAGAGAAAAAGCACCGTGCATGCCGATTGGTGGAAGTAAGGTGGTAC

GATCGTGCCTTATTAGGAAGGCAACAGACAGGTCTGACATGGATTGGACGA

ACCACTGAATTCCGCATTGCAGAGATAATTGTATTTAAGTGCCTAGCTCGA

TACAATAAACGCCATTTGACCATTCACCACATTGGTGTGCACCTCCAAGCT

CGAGCTCGTTTAGTGAACCGTCAGATCGCCTGGAGACGCCATCCACGCTGT

-continued

```
TTTGACCTCCATAGAAGACACCGGGACCGATCCAGCCTCCCCTCGAAGCTA
GCGATTAGGCATCTCCTATGGCAGGAAGAAGCGGAGACAGCGACGAAGAAC
TCCTCAAGGCAGTCAGACTCATCAAGTTTCTCTATCAAAGCAACCCACCTC
CCAATCCCGAGGGGACCCGACAGGCCCGAAGGAATAGAAGAAGAAGGTGGA
GAGAGAGACAGAGACAGATCCATTCGATTAGTGAACGGATCCTTAGCACTT
ATCTGGGACGATCTGCGGAGCCTGTGCCTCTTCAGCTACCACCGCTTGAGA
GACTTACTCTTGATTGTAACGAGGATTGTGGAACTTCTGGGACGCAGGGGG
TGGGAAGCCCTCAAATATTGGTGGAATCTCCTACAATATTGGAGTCAGGAG
CTAAAGAATAGTCTAGA
```

The plasmids for the 2-vector and 3-vector packaging systems could be modified with similar elements and the intron sequences could potentially be removed without loss of vector function. For example, the following elements could replace similar elements in the 2-vector and 3-vector packaging system:

Promoters: Elongation Factor-1 (EF-1) (SEQ ID NO: 39), phosphoglycerate kinase (PGK) (SEQ ID NO: 40), and ubiquitin C (UbC) (SEQ ID NO: 41) can replace the CMV (SEQ ID NO: 25) or CAG promoter (SEQ ID NO: 19). These sequences can also be further varied by addition, substitution, deletion or mutation.

Poly A sequences: SV40 poly A (SEQ ID NO: 42) and bGH poly A (SEQ ID NO: 43) can replace the rabbit beta globin poly A (SEQ ID NO: 29). These sequences can also be further varied by addition, substitution, deletion or mutation.

HIV Gag, Pol, and Integrase sequences: The HIV sequences in the Helper plasmid can be constructed from different HIV strains or clades. For example, HIV Gag (SEQ ID NO: 20); HIV Pol (SEQ ID NO: 21); and HIV Int (SEQ ID NO: 22) from the Bal strain can be interchanged with the gag, pol, and int sequences contained in the helper/helper plus Rev plasmids as outlined herein. These sequences can also be further varied by addition, substitution, deletion or mutation.

Envelope: The VSV-G glycoprotein can be substituted with membrane glycoproteins from feline endogenous virus (RD114) (SEQ ID NO: 44), gibbon ape leukemia virus (GALV) (SEQ ID NO: 45), Rabies (FUG) (SEQ ID NO: 46), lymphocytic choriomeningitis virus (LCMV) (SEQ ID NO: 47), influenza A fowl plague virus (FPV) (SEQ ID NO: 48), Ross River alphavirus (RRV) (SEQ ID NO: 49), murine leukemia virus 10A1 (MLV) (SEQ ID NO: 50), or Ebola virus (EboV) (SEQ ID NO: 51). Sequences for these envelopes are identified in the sequence portion herein. Further, these sequences can also be further varied by addition, substitution, deletion or mutation.

In summary, the 3-vector versus 4-vector systems can be compared and contrasted, in part, as follows. The 3-vector lentiviral vector system contains: 1. Helper plasmid: HIV Gag, Pol, Integrase, and Rev/Tat; 2. Envelope plasmid: VSV-G/FUG envelope; and 3. Therapeutic vector: RSV 5'LTR, Psi Packaging Signal, Gag fragment, RRE, Env fragment, cPPT, WPRE, and 3'δ LTR. The 4-vector lentiviral vector system contains: 1. Helper plasmid: HIV Gag, Pol, and Integrase; 2. Rev plasmid: Rev; 3. Envelope plasmid: VSV-G/FUG envelope; and 4. Therapeutic vector: RSV 5'LTR, Psi Packaging Signal, Gag fragment, RRE, Env fragment, cPPT, WPRE, and 3' delta LTR. Sequences corresponding with the above elements are identified in the sequence listings portion herein.

Example 2: Development of a Lentiviral Vector that Expresses FDPS

The purpose of this Example was to develop an FDPS lentivirus vector.

Inhibitory RNA Design: The sequence of Homo sapiens Farnesyl diphosphate synthase (FDPS) (NM_002004.3) mRNA was used to search for potential siRNA or shRNA candidates to knockdown FDPS levels in human cells. Potential RNA interference sequences were chosen from candidates selected by siRNA or shRNA design programs such as from GPP Web Portal hosted by the Broad Institute (http://portals.broadinstitute.org/gpp/public/) or the BLOCK-iT RNAi Designer from Thermo Scientific (https://rnaidesigner.thermofisher.com/rnaiexpress/). Individual selected shRNA sequences were inserted into a lentiviral vector immediately 3 prime to a RNA polymerase III promoter such as H1 (SEQ ID NO: 16), U6 (SEQ ID NO: 52), or 7SK (SEQ ID NO: 53) to regulate shRNA expression. These lentivirus shRNA constructs were used to transduce cells and measure the change in specific mRNA levels. The shRNA most potent for reducing mRNA levels were embedded individually within a microRNA backbone to allow for expression by either the EF-1alpha or CMV RNA polymerase II promoters. The microRNA backbone was selected from mirbase.org. RNA sequences were also synthesized as synthetic siRNA oligonucleotides and introduced directly into cells without using a lentiviral vector.

Vector Construction: For FDPS shRNA, oligonucleotide sequences containing BamHI and EcoRI restriction sites were synthesized by Eurofins MWG Operon. Overlapping sense and antisense oligonucleotide sequences were mixed and annealed during cooling from 70 degrees Celsius to room temperature. The lentiviral vector was digested with the restriction enzymes BamHI and EcoRI for one hour at 37 degrees Celsius. The digested lentiviral vector was purified by agarose gel electrophoresis and extracted from the gel using a DNA gel extraction kit from Thermo Scientific. The DNA concentrations were determined and vector to oligo (3:1 ratio) were mixed, allowed to anneal, and ligated. The ligation reaction was performed with T4 DNA ligase for 30 minutes at room temperature. 2.5 microliters of the ligation mix were added to 25 microliters of STBL3 competent bacterial cells. Transformation was achieved after heat-shock at 42 degrees Celsius. Bacterial cells were spread on agar plates containing ampicillin and drug-resistant colonies (indicating the presence of ampicillin-resistance plasmids) were recovered and expanded in LB broth. To check for insertion of the oligo sequences, plasmid DNA was extracted from harvested bacteria cultures with the Thermo Scientific DNA mini prep kit. Insertion of shRNA sequences in the lentiviral vector was verified by DNA sequencing using a specific primer for the promoter used to regulate shRNA expression. Using the following target sequences, exemplary shRNA sequences were determined to knock-down FDPS:

```
        (FDPS target sequence #1; SEQ ID NO: 54)
GTCCTGGAGTACAATGCCATT;

           (FDPS shRNA sequence #1; SEQ ID NO: 1)
GTCCTGGAGTACAATGCCATTCTCGAGAATGGCATTGTACTCCAGGACT
TTTT;
```

-continued (FDPS target sequence #2; SEQ ID NO: 55)
GCAGGATTTCGTTCAGCACTT;

(FDPS shRNA sequence #2; SEQ ID NO: 2)
GCAGGATTTCGTTCAGCACTTCTCGAGAAGTGCTGAACGAAATCCTGCT
TTTT;

(FDPS target sequence #3; SEQ ID NO: 56)
GCCATGTACATGGCAGGAATT;

(FDPS shRNA sequence #3; SEQ ID NO: 3)
GCCATGTACATGGCAGGAATTCTCGAGAATTCCTGCCATGTACATGGCT
TTTT;

(FDPS target sequence #4; SEQ ID NO: 57)
GCAGAAGGAGGCTGAGAAAGT;
and (FDPS shRNA sequence #4; SEQ ID NO: 4)
GCAGAAGGAGGCTGAGAAAGTCTCGAGACTTTCTCAGCCTCCTTCTGCT
TTTT.

shRNA sequences were then assembled into a synthetic microRNA (miR) under control of the EF-1 alpha promoter. Briefly, a miR hairpin sequences, such as miR30, miR21, or miR185 as detailed below, was obtained from mirbase.org. The 19-22 mer shRNA target sequence was used to construct the synthetic miR sequence. The miR sequence was arranged as an anti-sense-target-sequence-hairpin loop sequence (specific for each microRNA)—sense target sequence.

The following miR sequences were developed:

(miR30 FDPS sequence #1; SEQ ID NO: 5)
AAGGTATATTGCTGTTGACAGTGAGCGACACTTTCTCAGCCTCCTTCTG
CGTGAAGCCACAGATGGCAGAAGGAGGCTGAGAAAGTGCTGCCTACTGC
CTCGGACTTCAAGGGGCT (miR30 FDPS sequence #2; SEQ ID NO: 6)
AAGGTATATTGCTGTTGACAGTGAGCGACACTTTCTCAGCCTCCTTCTG
CGTGAAGCCACAGATGGCAGAAGGGCTGAGAAAGTGCTGCCTACTGCCT
CGGACTTCAAGGGGCT (miR30 FDPS sequence #3; SEQ ID NO: 7)
TGCTGTTGACAGTGAGCGACTTTCTCAGCCTCCTTCTGCGTGAAGCCAC
AGATGGCAGAAGGAGGCTGAGAAAGTTGCCTACTGCCTCGGA (miR155 FDPS sequence #1; SEQ ID NO: 8)
CCTGGAGGCTTGCTGAAGGCTGTATGCTGACTTTCTCAGCCTCCTTCTG
CTTTTGGCCACTGACTGAGCAGAAGGGCTGAGAAAGTCAGGACACAAGG
CCTGTTACTAGCACTCA (miR21 FDPS sequence #1; SEQ ID NO: 9)
CATCTCCATGGCTGTACCACCTTGTCGGGACTTTCTCAGCCTCCTTCTG
CCTGTTGAATCTCATGGCAGAAGGAGGCGAGAAAGTCTGACATTTTGGT
ATCTTTCATCTGACCA (miR185 FDPS sequence #1; SEQ ID NO: 10)
GGGCCTGGCTCGAGCAGGGGGCGAGGGATACTTTCTCAGCCTCCTTCTG
CTGGTCCCCTCCCCGCAGAAGGAGGCTGAGAAAGTCCTTCCCTCCCAAT
GACCGCGTCTTCGTCG Example 3—Knock-Down of FDPS for 3 Days in THP1 Monocytic Leukemia by shRNA #4

Figure 5:
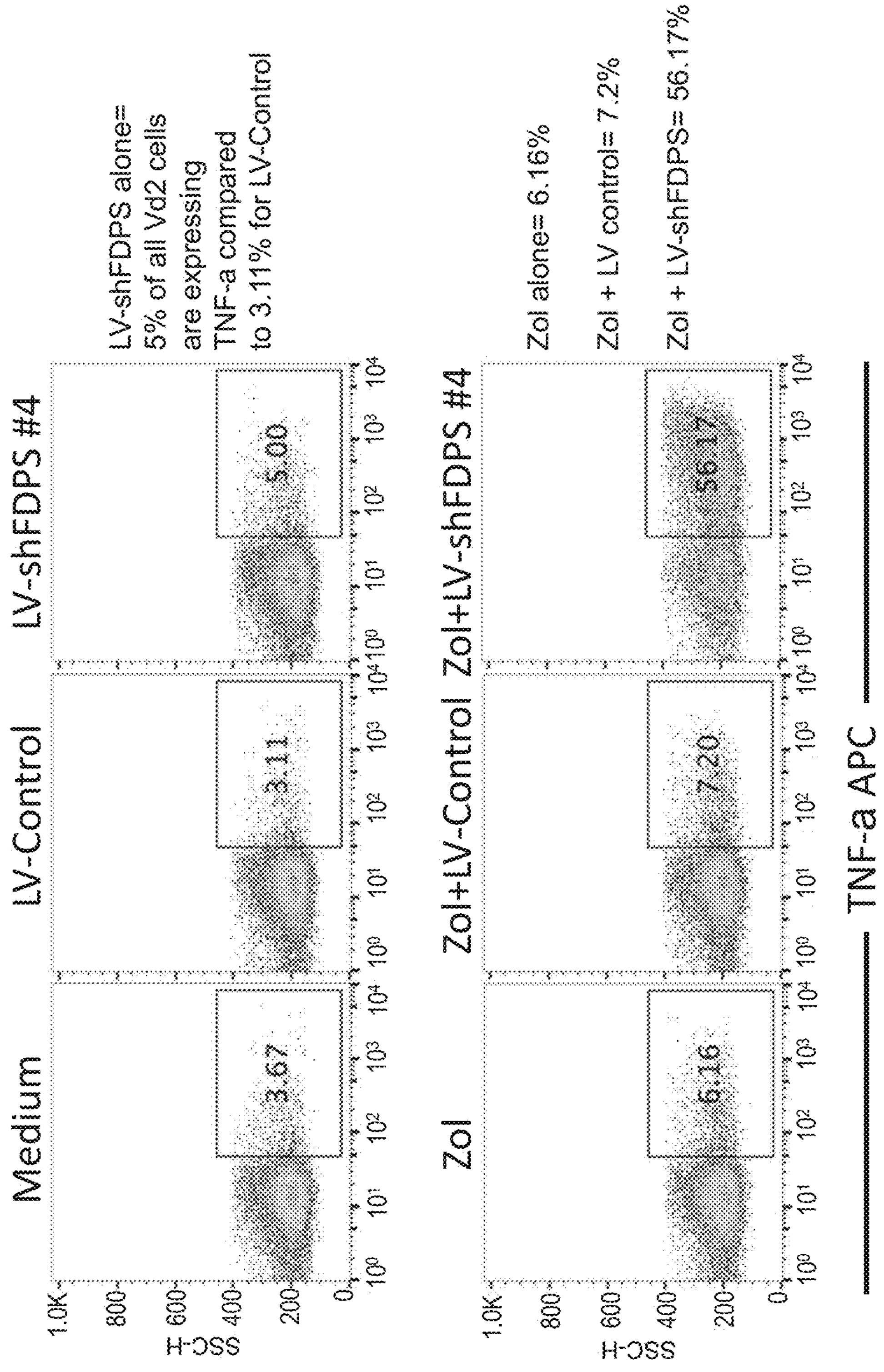
FIG. 5 depicts data demonstrating activation of Vδ2+ T cells THP-1 leukemia cells with a lentivirus expressing FDPS shRNA #4 (SEQ ID NO: 4), as described herein.

This Example illustrates that knock-down of FDPS in THP1 monocytic leukemia cells by lentiviral (LV)—expressing FDPS shRNA #4 stimulates TNF-α expression in gamma delta T cells, as shown in FIG. 5.

THP1 cells ($1\times10^5$ cells) were transduced with LV-control or LV-FDPS shRNA #4 for 3 days. Two days after transduction, cells were treated with or without 1 μM zoledronic acid. After 24 hours, the transduced THP-1 cells were co-cultured with $5\times10^5$ PBMC cells and IL-2 in a round bottom 96 well plate for 4 hours. The PBMC cells were pre-stimulated with zoledronic acid and IL-2 for 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated, and Vδ2+ and TNF-α+ cells were selected on a dot blot. The activated cytotoxic Vγ9Vδ2 T cells appeared in the upper right quadrant of flow cytograms. Without zoledronic acid, LV-control stimulated 3.1% of TNF-α expressing Vγ9Vδ2 T cells and LV-FDPS shRNA #4 stimulated 5%. With zoledronic acid treatment, LV-control stimulated 7.2% of TNF-α expressing Vγ9Vδ2 T cells and LV-FDPS shRNA #4 stimulated 56.2%.

Example 4—Knock-Down of FDPS for 14 Days in THP1 Leukemia Cells by shRNA #4

Figure 6:
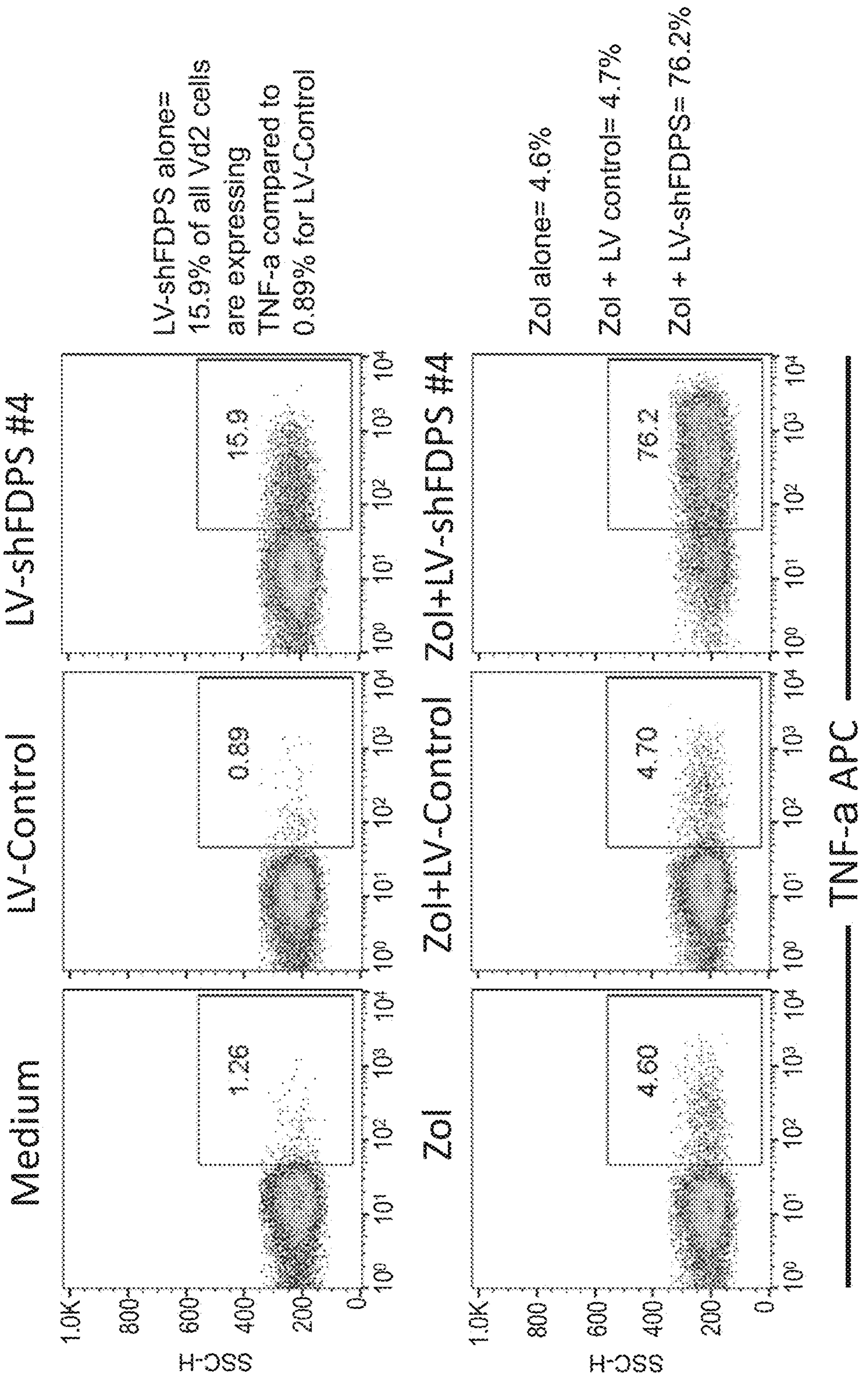
FIG. 6 depicts data demonstrating activation of Vδ2+ T cells by THP-1 leukemia cells with a lentivirus expressing FDPS shRNA #4 (SEQ ID NO: 4), as described herein.

This Example illustrates that Knock-down of FDPS for 14 days in THP1 leukemia cells by lentiviral (LV)—expressing FDPS shRNA #4 stimulates TNF-α expression in GD T cells, as shown in FIG. 6.

THP1 cells ($1\times10^5$ cells) were transduced with LV-control or LV-FDPS shRNA #4 for 14 days. Two days after transduction, cells were treated with or without 1 μM zoledronic acid. After 24 hours, the transduced THP-1 cells were co-cultured with $5\times10^5$ PBMC cells and IL-2 in a round bottom 96 well plate for 4 hours. The PBMC cells were pre-stimulated with zoledronic acid and IL-2 for 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated, and Vδ2+ and TNF-α+ cells were selected on a dot blot. The activated cytotoxic Vγ9Vδ2 T cells appeared in the upper right quadrant of flow cytograms. Without zoledronic acid, LV-control stimulated 0.9% of TNF-α expressing Vγ9Vδ2 T cells and LV-FDPS shRNA #4 (SEQ ID NO: 4) stimulated 15.9%. With zoledronic acid treatment, LV-control stimulated 4.7% of TNF-α expressing Vγ9Vδ2 T cells and LV-FDPS shRNA #4 (SEQ ID NO: 4) stimulated 76.2%.

Example 5—Knock-Down of FDPS for 3 Days in PC3 Prostate Carcinoma Cells by shRNA #1

Figure 7:
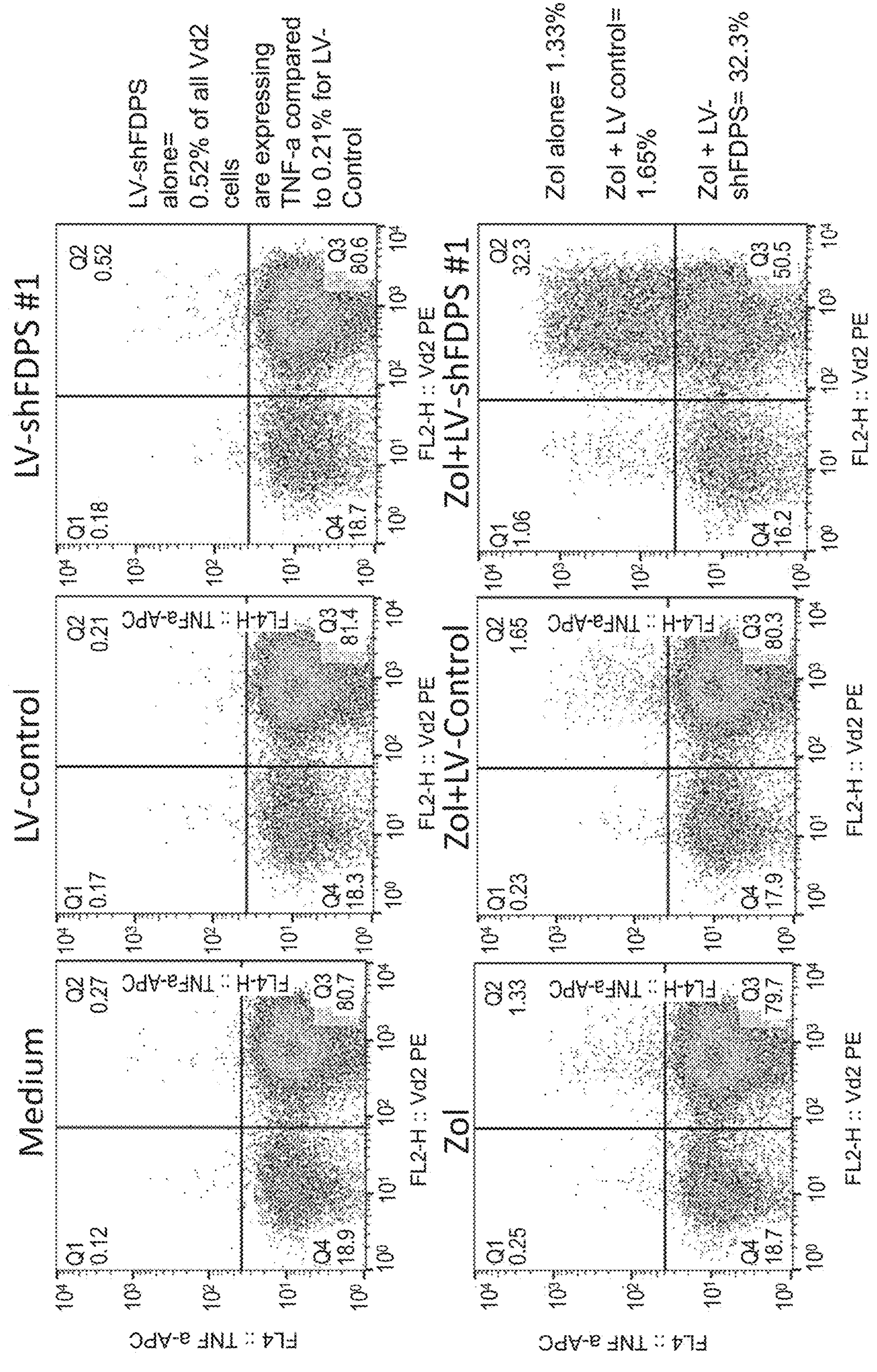
FIG. 7 depicts data demonstrating activation of Vδ2+ T cells by PC3 prostate carcinoma cells with a lentivirus expressing FDPS shRNA #1 (SEQ ID NO: 1), as described herein.

This Example illustrates that knock-down of FDPS for 3 days in PC3 prostate carcinoma cells by lentiviral (LV)—expressing FDPS shRNA #1 stimulates TNF-α expression in GD T cells, as shown in FIG. 7.

PC3 cells were transduced with LV-control or LV-FDPS shRNA #1 (SEQ ID NO: 1) for 3 days. Two days after transduction, cells were treated with or without 1 μM zoledronic acid. After 24 hours, the transduced PC3 cells were co-cultured with $5\times10^5$ PBMC cells and IL-2 in a round bottom 96 well plate for 4 hours. The PBMC cells were pre-stimulated with zoledronic acid and IL-2 for 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated, and Vδ2+ and TNF-α+ cells were selected on a dot blot. The activated cytotoxic Vγ9Vδ2 T cells appeared in the upper right quadrant of flow cytograms. Without zoledronic acid, LV-control stimulated 0.2% of TNF-α expressing Vγ9Vδ2 T cells and LV-FDPS shRNA #1 stimulated 0.5%. With zoledronic acid treatment, LV-control stimulated 1.7% of TNF-α expressing Vγ9Vδ2 T cells and LV-FDPS shRNA #1 (SEQ ID NO: 1) stimulated 32.2%.

Example 6—Knock-Down of FDPS for 3 Days in PC3 Prostate Carcinoma Cells by shRNA #4

Figure 8:
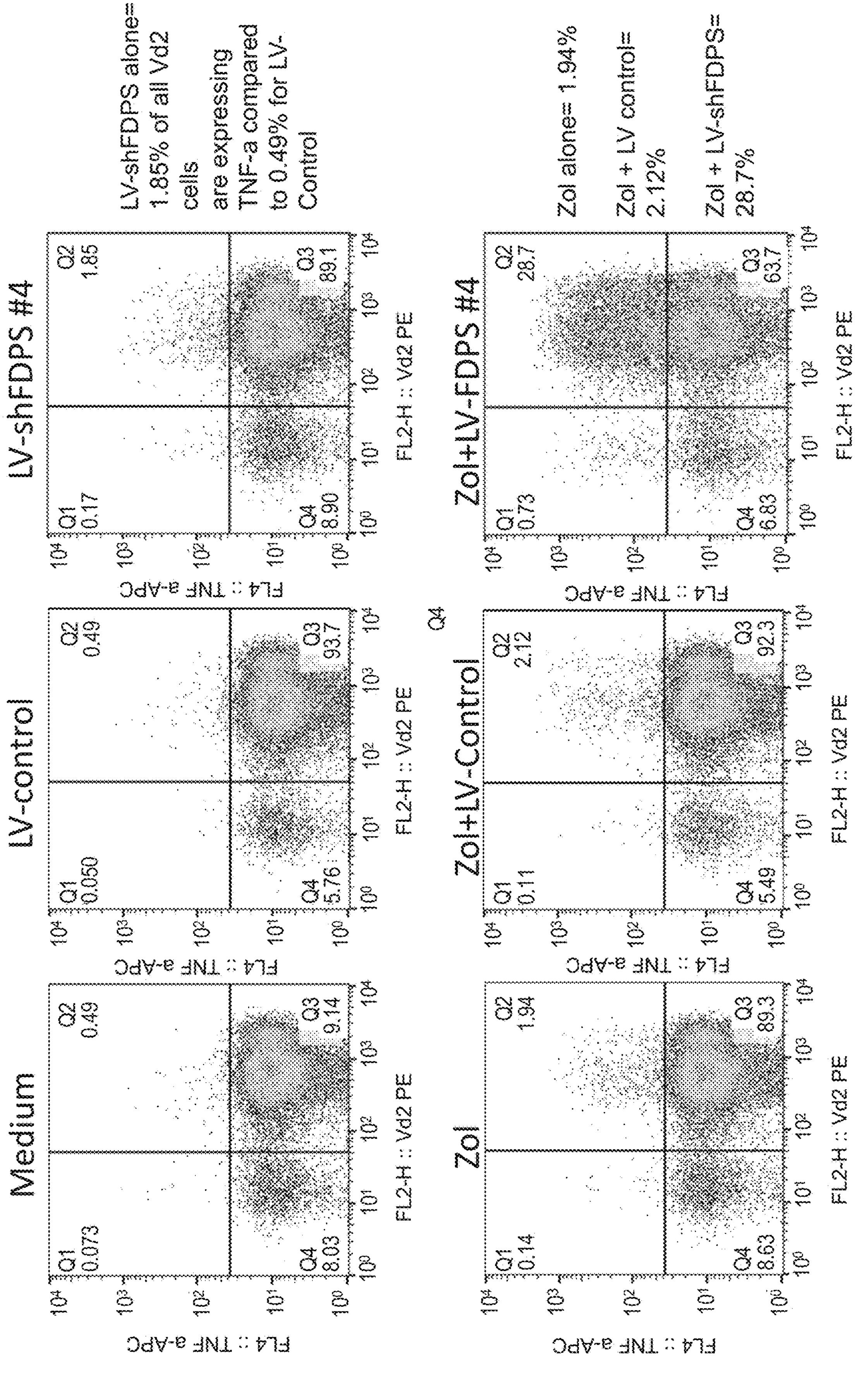
FIG. 8 depicts data demonstrating activation of Vδ2+ T cells by PC3 prostate carcinoma cells with a lentivirus expressing FDPS shRNA #4 (SEQ ID NO: 4), as described herein.

This Example illustrates that Knock-down of FDPS for 3 days in PC3 prostate carcinoma cells by lentiviral (LV)—expressing FDPS shRNA #4 stimulates TNF-α expression in GD T cells, as shown in FIG. 8.

PC3 cells were transduced with LV-control or LV-FDPS shRNA #4 (SEQ ID NO: 4) for 3 days. Two days after transduction, cells were treated with or without 1 μM zoledronic acid. After 24 hours, the transduced PC3 cells were co-cultured with $5\times10^5$ PBMC cells and IL-2 in a round bottom 96 well plate for 4 hours. The PBMC cells were pre-stimulated with zoledronic acid and IL-2 for 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated, and Vδ2+ and TNF-α+ cells were selected on a dot blot. The activated cytotoxic Vγ9Vδ2 T cells appeared in the upper right quadrant of flow cytograms. Without zoledronic acid, LV-control stimulated 0.5% of TNF-α expressing Vγ9Vδ2 T cells and LV-FDPS shRNA #4 (SEQ ID NO: 4) stimulated 1.9%. With zoledronic acid treatment, LV-control stimulated 2.1% of TNF-α expressing Vγ9Vδ2 T cells and LV-FDPS shRNA #4 stimulated 28.7%.

Example 7—Knock-Down of FDPS for 3 Days in HepG2 Liver Carcinoma Cells by shRNA #1 and #4

Figure 9:
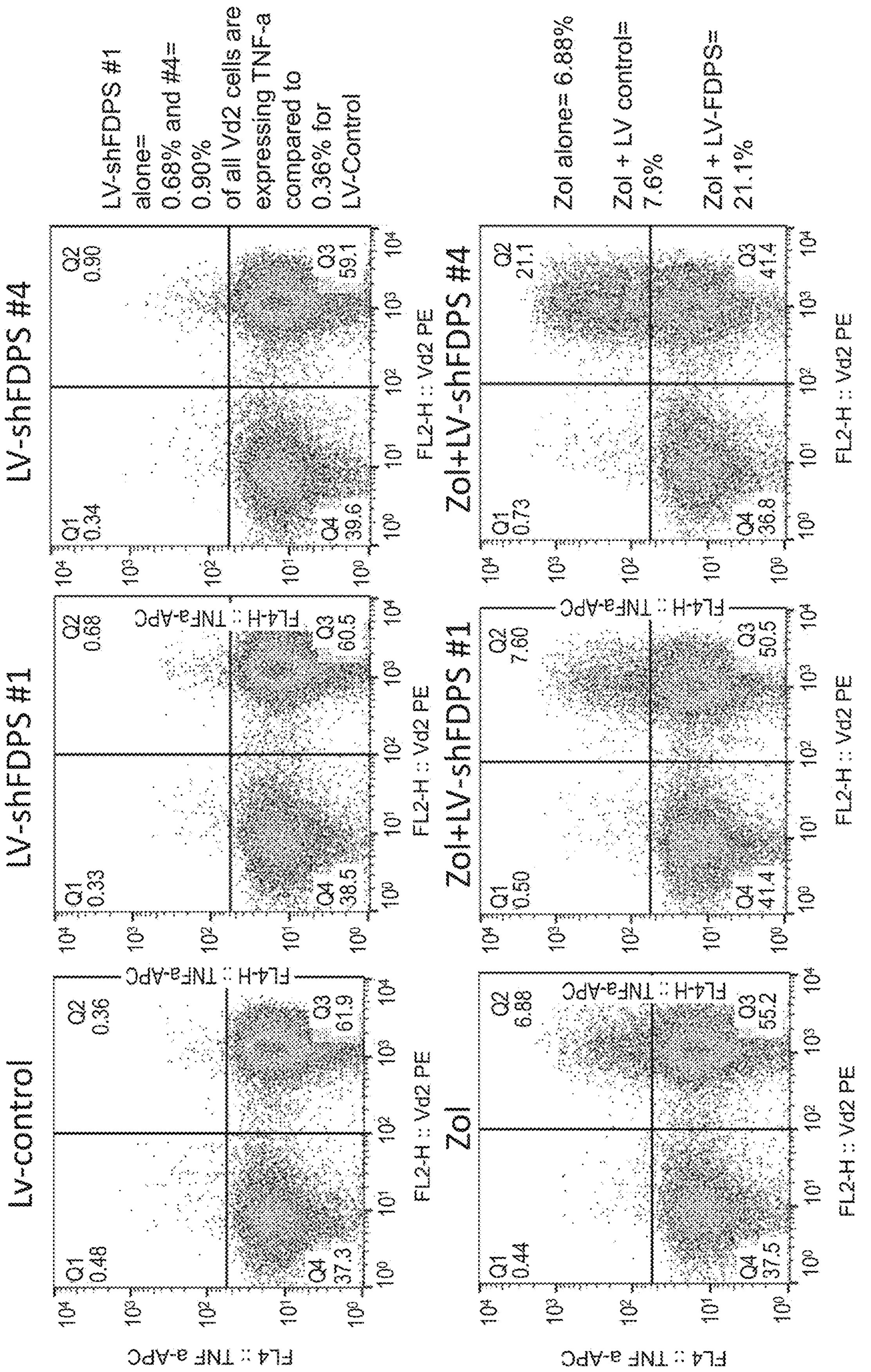
FIG. 9 depicts data demonstrating activation of Vδ2+ T cells by HepG2 carcinoma cells with a lentivirus expressing FDPS shRNA #1 (SEQ ID NO: 1) or FDPS shRNA #4 (SEQ ID NO: 4), as described herein.

This Example illustrates that Knock-down of FDPS for 3 days in HepG2 liver carcinoma cells by lentiviral (LV)—expressing FDPS shRNA #1 (SEQ ID NO: 1) and shRNA #4 (SEQ ID NO: 4) stimulates TNF-α expression in GD T cells, as shown in FIG. 9.

HepG2 cells were transduced with LV-control, LV-FDPS shRNA #1 (SEQ ID NO: 1), or LV-FDPS shRNA #4 (SEQ ID NO: 4) for 3 days. Two days after transduction, cells were treated with or without 1 μM zoledronic acid. After 24 hours, the transduced HepG2 cells were co-cultured with $5\times10^5$ PBMC cells and IL-2 in a round bottom 96 well plate for 4 hours. The PBMC cells were pre-stimulated with zoledronic acid and IL-2 for 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated, and Vδ2+ and TNF-α+ cells were selected on a dot blot. The activated cytotoxic Vγ9Vδ2 T cells appeared in the upper right quadrant of flow cytograms. Without zoledronic acid, LV-control stimulated 0.4% of TNF-α expressing Vγ9Vδ2 T cells and LV-FDPS shRNA #1 (SEQ ID NO: 1) and #4 (SEQ ID NO: 4) stimulated 0.7% and 0.9%, respectively. With zoledronic acid treatment, LV-control stimulated 6.9% of TNF-α expressing Vγ9Vδ2 T cells and LV-FDPS shRNA #1 and #4 stimulated 7.6% and 21.1%, respectively.

Example 8—Knock-Down of FDPS for 3 Days in THP1 Leukemia by MicroRNA-30

Figure 10:
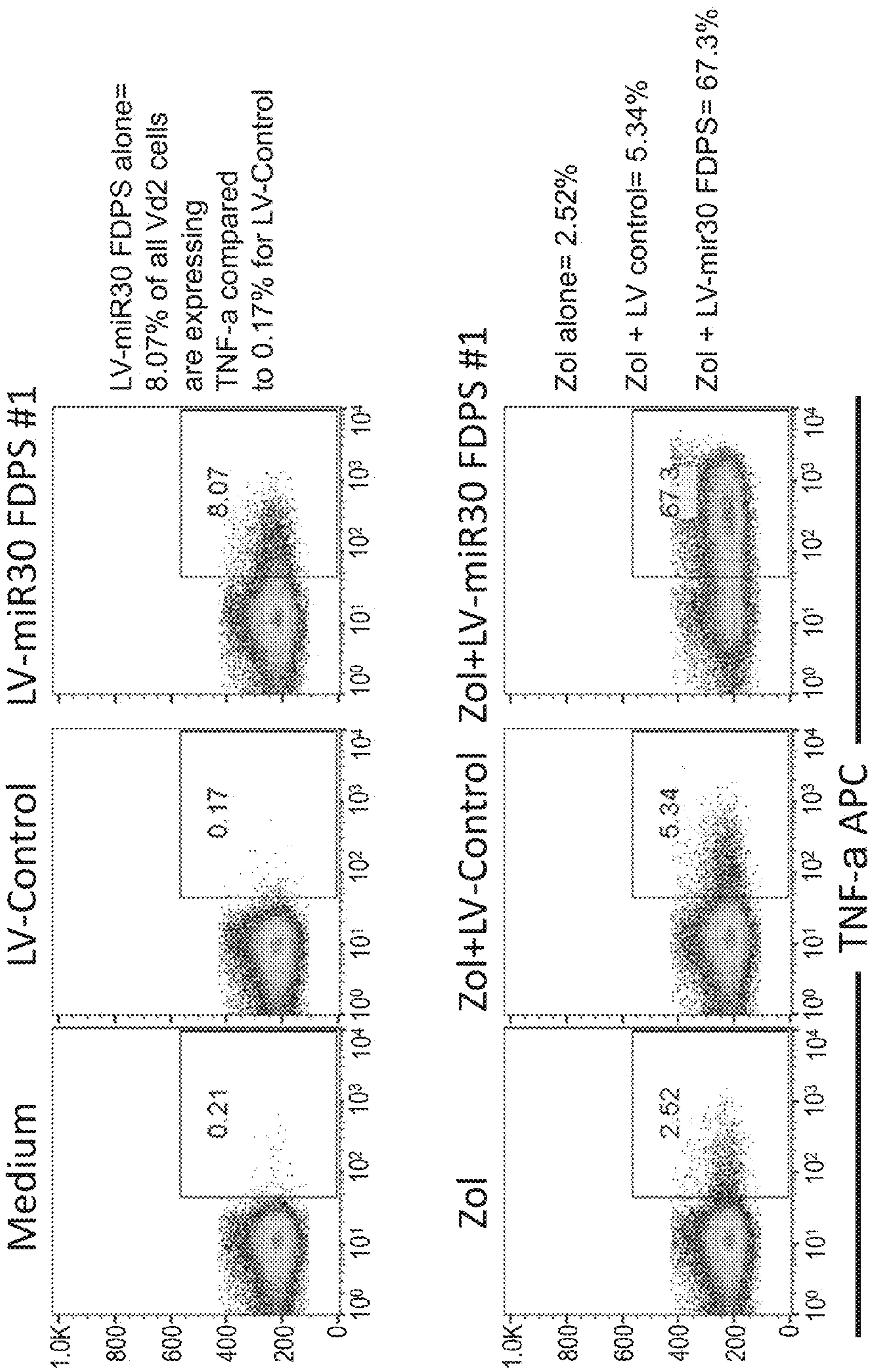
FIG. 10 depicts data demonstrating activation of Vδ2+ T cells by THP-1 leukemia cells with a lentivirus expressing miR30 FDPS #1 (SEQ ID NO: 5), as described herein.

This Example illustrates that Knock-down of FDPS for 3 days in THP1 leukemia cells by lentiviral (LV)—expressing FDPS-targeted synthetic microRNA-30 stimulates TNF-α expression in gamma delta T cells, as shown in FIG. 10.

THP1 cells ($1\times10^5$ cells) were transduced with LV-control or LV-miR30 FDPS #1 (SEQ ID NO: 5) for 3 days. Two days after transduction, cells were treated with or without 1 μM zoledronic acid. After 24 hours, the transduced THP-1 cells were co-cultured with $5\times10^5$ PBMC cells and IL-2 in a round bottom 96 well plate for 4 hours. The PBMC cells were pre-stimulated with zoledronic acid and IL-2 for 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated, and Vδ2+ and TNF-α+ cells were selected on a dot blot. The activated cytotoxic Vγ9Vδ2 T cells appeared in the upper right quadrant of flow cytograms. Without zoledronic acid, LV-control stimulated 0.2% of TNF-α expressing Vγ9Vδ2 T cells and LV-miR30 FDPS stimulated 8.1%. With zoledronic acid treatment, LV-control stimulated 5.3% of TNF-α expressing Vγ9Vδ2 T cells and LV-miR30 FDPS #1 (SEQ ID NO: 5) stimulated 67.3%.

Example 9: E:T Ratios Resulting from Mixture of THP-1 Cells, Cultured Human GD T Cells, and/or Zometa (Zol)

Figure 11:
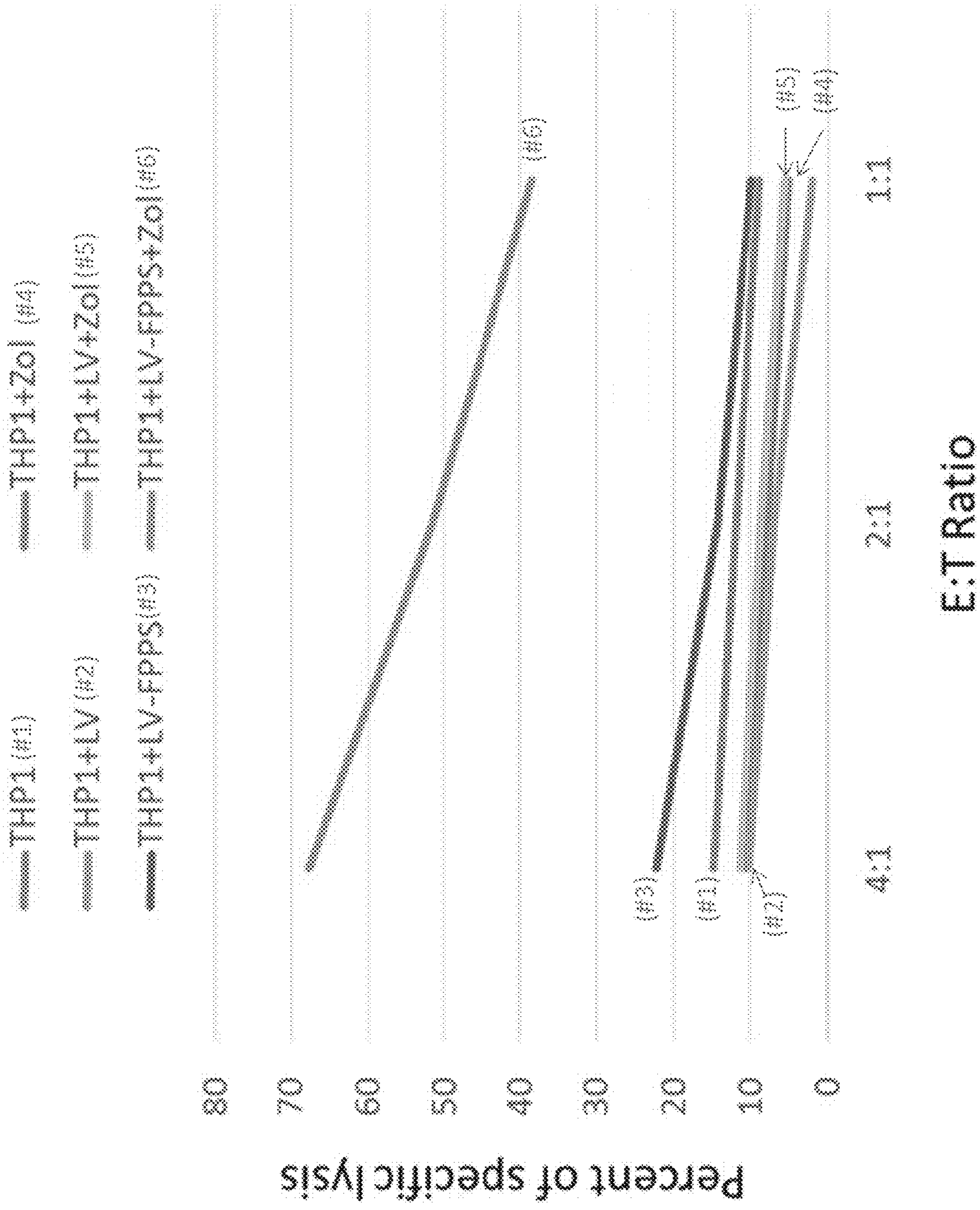
FIG. 11 depicts data demonstrating the percent of specific lysis versus an E:T ratio for a variety of experimental conditions, as described herein.

This Example demonstrates results from mixing treated THP-1 monocytoid tumor cells with cultured human GD T cells, as shown in FIG. 11.

The monocytoid cell line THP-1 was treated with control lentivirus vector (LV), LV suppressing farnesyl diphosphate synthase gene expression (LV-FDPS), zoledronic acid (Zol) or combinations. The legend, as shown in FIG. 11, was: lentiviral control vectors (LV-Control), lentiviral vectors expressing microRNA to down regulate FDPS (LV-FPPS), Zometa (Zol), Zometa plus lentiviral control (Zol+LV-Control), or Zometa plus lentiviral vectors expressing microRNA to down regulate FPPS (Zol+LV-FPPS).

Human GD T cells were cultured from an anonymous donor and added to treated THP-1 cells in 4:1, 2:1 or 1:1 ratios (GD T:THP-1) for 4 hours. Cell killing was measured by a fluorescence assay. When THP-1 cells were treated with a combination of LV-FDPS and Zol, cytotoxic T cell killing by GD T cells was increased greatly compared to either treatment alone. When LV-FDPS treatment alone was compared to Zol treatment alone, the LV-FDPS lead to greater killing but was >3-fold below tumor cell killing after combination treatment. The combined LV-FDPS plus Zol treatment caused nearly 70% tumor cell killing with 4:1 ratio; this was more than 3-fold higher than the second best treatment (LV-FDPS alone).

Figure 12:
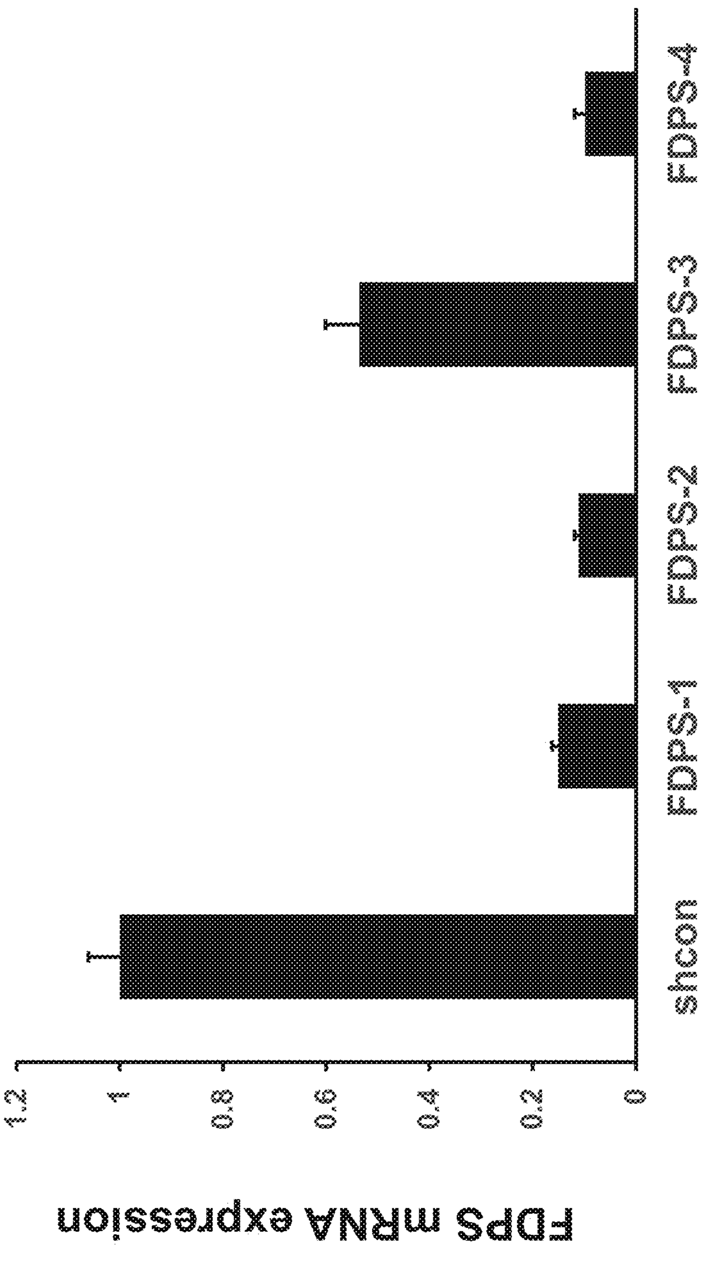
FIG. 12 depicts data demonstrating lentiviral-delivered shRNA-based RNA interference targeting the human FDPS gene.

Example 10—Lentiviral-Delivered shRNA-Based RNA Interference Targeting the Human Farnesyl Diphosphate Synthase (FDPS) Gene HepG2 human hepatocellular carcinoma cells were infected with lentiviral vectors containing the H1 promoter and either a non-targeting or four different FDPS shRNA sequences, as shown in FIG. 12. After 48 hours, RNA was extracted from the cells and converted to cDNA. Expression of FDPS cDNA was determined by quantitative PCR using SYBR Green and FDPS primers. FDPS expression was normalized to actin levels for each sample. FDPS-targeting lentiviral vectors containing the H1 promoter and either a non-targeting sequence (5'-GCCGCTTTGTAGGA-TAGAGCTCGAGCTCTATCCTACAAAGCGGCTTTTT-3') (SEQ ID NO: 58)
or one of four different FDPS shRNA sequences
GTCCTGGAGTACAATGCCATTCTCGAGAATGGCAT-TGTACTCCAGGACTTTTT (FDPS shRNA sequence #1; SEQ ID NO: 1);
GCAGGATTTCGTTCAGCACTTCTCGAGAAGTGCT-GAACGAAATCCTGCTTTTT (FDPS shRNA sequence #2; SEQ ID NO: 2);
GCCATGTACATGGCAGGAATTCTCGAGAAT-TCCTGCCATGTACATGGCTTTTT (FDPS shRNA sequence #3; SEQ ID NO: 3); and
GCAGAAGGAGGCTGAGAAAGTCTCGA-GACTTTCTCAGCCTCCTTCTGCTTTTT (FDPS shRNA sequence #4; SEQ ID NO: 4) were produced in 293 T cells.

HepG2 human hepatocellular carcinoma cells were then infected with lentiviral vectors to determine the efficacy of FDPS knock-down. After 48 hours, RNA was extracted from the cells using the RNeasy RNA isolation kit (Qiagen) and converted to cDNA with the SuperScript VILO cDNA synthesis kit (Thermo Scientific). Expression of FDPS cDNA was determined by quantitative PCR on an Applied Biosystems StepOne qPCR machine using a SYBR Green PCR mix (Thermo Scientific) and FDPS primers (Forward primer: 5'-AGGAATTGATGGCGAGAAGG-3' (SEQ ID NO: 59) and Reverse primer: 5'-CCCAAAGAGGT-CAAGGTAATCA-3' (SEQ ID NO: 60)). FDPS expression was normalized to actin levels for each sample using the actin primers (Forward primer: 5'-AGCGCGGCTA-CAGCTTCA-3' (SEQ ID NO: 61) and Reverse primer: 5'-GGCGACGTAGCACAGCTTCT-3') (SEQ ID NO: 62). The relative FDPS RNA expression of the shCon sample is set at 100%. There was an 85% (FDPS sequence #1), 89% (FDPS sequence #2), 46% (FDPS sequence #3), and 98% (FDPS sequence #4) decrease in FDPS expression.

Figure 13:
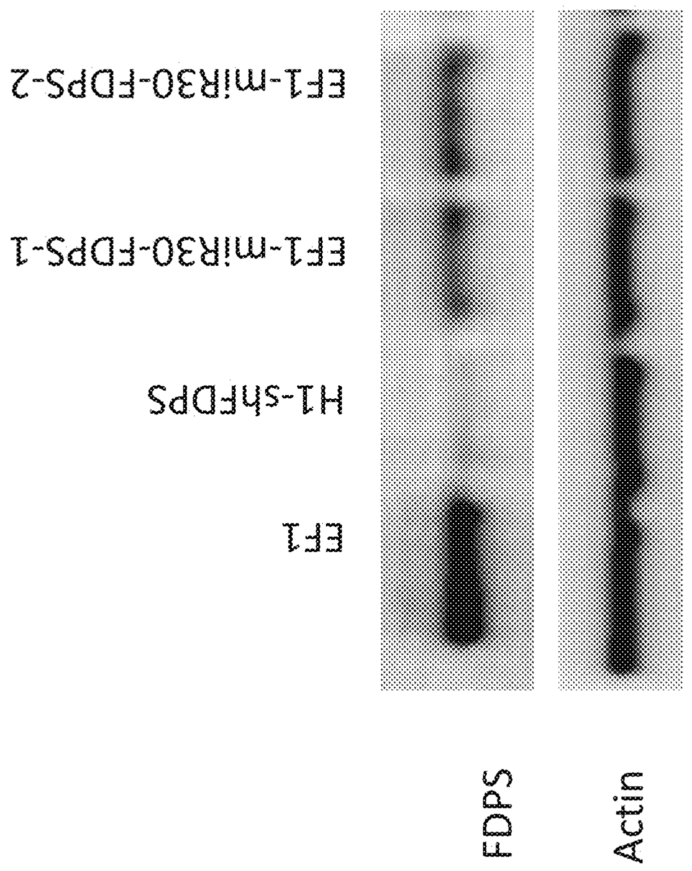
FIG. 13 depicts data demonstrating lentiviral-delivered miR-based RNA interference targeting the human FDPS gene.

Example 11—Lentiviral-Delivered miR-based RNA Interference Targeting the Human Farnesyl Diphosphate Synthase (FDPS) Gene As shown in FIG. 13, HepG2 human hepatocellular carcinoma cells were infected with lentiviral vectors containing either the H1 promoter (SEQ ID NO: 16) the FDPS shRNA #4 (SEQ ID NO: 4) sequence or the EF-1α promoter (SEQ ID NO: 40) and miR30-based FDPS sequences. After 48 hours, cells were lysed and an immunoblot was performed using an anti-FDPS (Thermo Scientific) and an anti-actin (Sigma) antibody as a protein loading control.

More specifically, HepG2 human hepatocellular carcinoma cells were infected with lentiviral vectors containing either the H1 promoter (SEQ ID NO: 16) and the FDPS shRNA sequence
GCAGAAGGAGGCTGAGAAAGTCTCGA-GACTTTCTCAGCCTCCTTCTGCTTTTT (FDPS shRNA sequence #4; SEQ ID NO: 4) or the EF-1alpha promoter (SEQ ID NO: 39) and miR30-based FDPS sequences
AAGGTATATTGCTGTTGACAGT-GAGCGACACTTTCTCAGCCTCCTTCTGCGT-GAAGC CACAGATGGCAGAAGGAGGCT-GAGAAAGTGCTGCCTACTGCCTCGGACTTCAAG GG GCT (miR30 FDPS sequence #1; SEQ ID NO: 5) and
AAGGTATATTGCTGTTGACAGT-GAGCGACACTTTCTCAGCCTCCTTCTGCGT-GAAGC CACAGATGGCAGAAGGGCT-GAGAAAGTGCTGCCTACTGCCTCGGACTTCAAG GGGC T (miR30 FDPS sequence #2; SEQ ID NO: 6).

After 48 hours, cells were lysed with NP-40 lysis buffer and protein was quantified with the Bio-Rad protein assay reagent. Protein samples at 50 micrograms were electrophoresed on 4-12% Bis-Tris gels (Thermo Scientific and transferred to PVDF membranes (EMD Millipore). An immunoblot was performed using an anti-FDPS (Thermo Scientific) and an anti-actin (Sigma) antibody as a protein loading control. Antibodies were bound with HRP-conjugated secondary antibodies and detected with a Licor c-DiGit Blot scanner using the Immobilon Western ECL reagent (EMD Millipore). The densitometry of the immunoblot bands were quantified with the NIH image software. The LV control with the EF-1 promoter was set at 100%. There was a 68% (LV-shFDPS #4), 43% (LV-miR FDPS #1), and 38% (LV-miR FDPS #3) reduction of FDPS protein expression.

Example 12—Knock-Down of FDPS for 3 Days in HepG2 Liver Carcinoma Cells by Adeno-Associated Virus (AAV)—Expressing FDPS shRNA #4

Figure 14:
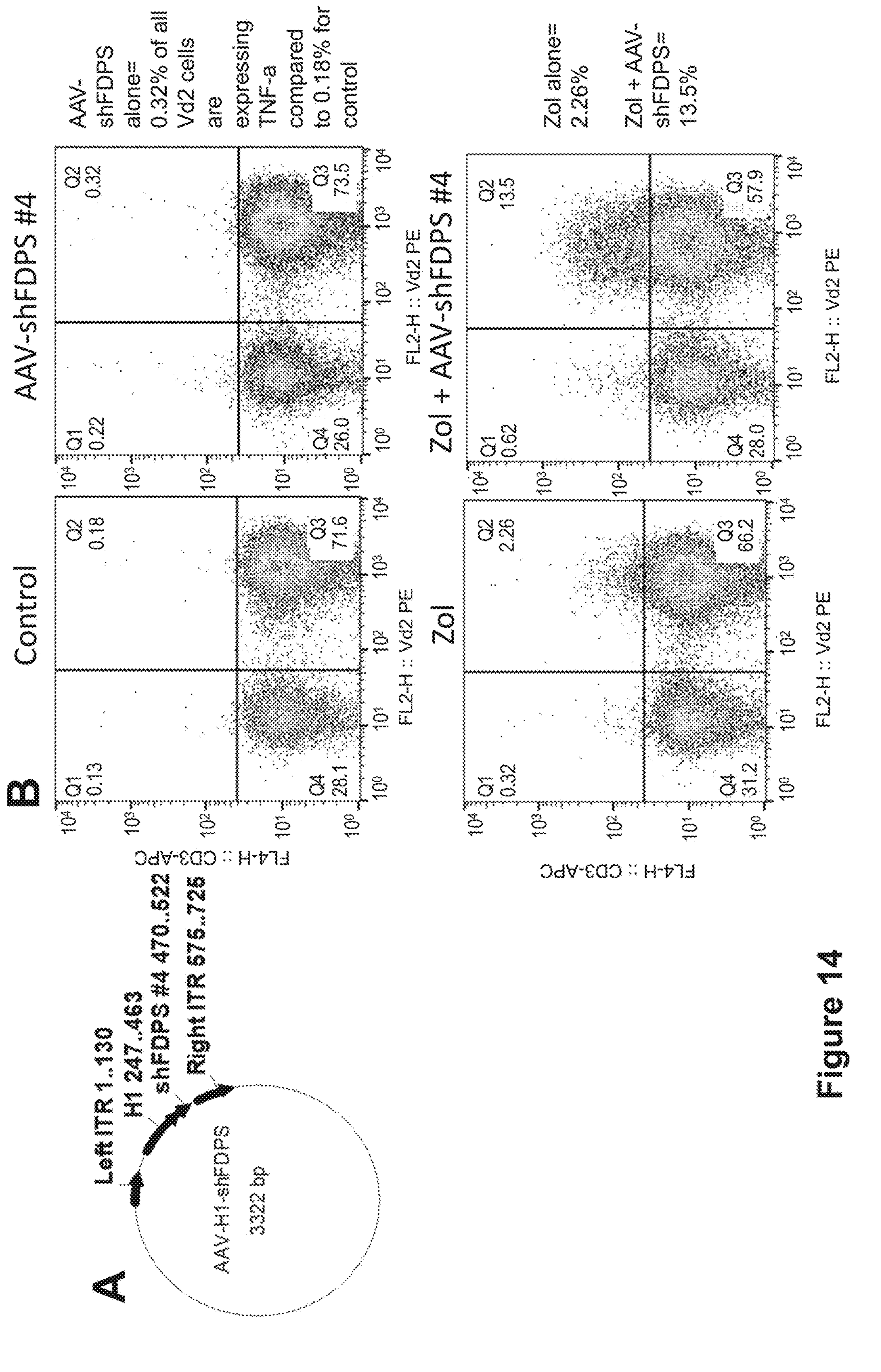
FIG. 14 depicts data demonstrating activation of Vδ2+ T cells by HepG2 carcinoma cells with an adeno-associated virus expressing FDPS shRNA #4 (SEQ ID NO: 4), as described herein.

This Example illustrates that knock-down of FDPS for 3 days in HepG2 liver carcinoma cells by adeno-associated virus (AAV)—expressing FDPS shRNA #4 (SEQ ID NO: 4) stimulates TNF-α expression in GD T cells (FIG. 14, Panel B).

HepG2 cells were transduced with control or AAV-FDPS shRNA #4 (SEQ ID NO: 8) for 3 days. Two days after transduction, cells were treated with or without 1 μM zoledronic acid. After 24 hours, the transduced HepG2 cells were co-cultured with $5\times10^5$ PBMC cells and IL-2 in a round bottom 96 well plate for 4 hours. The PBMC cells were pre-stimulated with zoledronic acid and IL-2 for 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated, and Vδ2+ and TNF-α+ cells were selected on a dot blot. The activated cytotoxic Vγ9Vδ2 T cells appeared in the upper right quadrant of flow cytograms (FIG. 14, Panel B).

AAV Vector Construction. FDPS shRNA sequence #4 (SEQ ID NO: 4) was inserted into the pAAV plasmid (Cell Biolabs). FDPS oligonucleotide sequences containing BamHI and EcoRI restriction sites were synthesized by Eurofins MWG Operon. Overlapping sense and antisense oligonucleotide sequences were mixed and annealed during cooling from 70 degrees Celsius to room temperature. The pAAV was digested with the restriction enzymes BamHI and EcoRI for one hour at 37 degrees Celsius. The digested pAAV plasmid was purified by agarose gel electrophoresis and extracted from the gel using a DNA gel extraction kit from Thermo Scientific. The DNA concentrations were determined and vector to oligo (3:1 ratio) were mixed, allowed to anneal, and ligated. The ligation reaction was performed with T4 DNA ligase for 30 minutes at room temperature. 2.5 microliters of the ligation mix were added to 25 microliters of STBL3 competent bacterial cells. Transformation was achieved after heat-shock at 42 degrees Celsius. Bacterial cells were spread on agar plates containing ampicillin and drug-resistant colonies (indicating the presence of ampicillin-resistance plasmids) were recovered and expanded in LB broth. To check for insertion of the oligo sequences, plasmid DNA was extracted from harvested bacteria cultures with the Thermo Scientific DNA mini prep kit. Insertion of shRNA sequences in the pAAV plasmid was verified by DNA sequencing using a specific primer for the promoter used to regulate shRNA expression. An exemplary AAV vector with a H1 promoter (SEQ ID NO: 16), shFDPS sequence (e.g., SEQ ID NO: 4), Left Inverted Terminal Repeat (Left ITR; SEQ ID NO: 63), and Right Inverted Terminal Repeat (Right ITR; SEQ ID NO: 64) can be found in FIG. 14, Panel A).

Production of AAV particles. The AAV-FDPS shRNA plasmid was combined with the plasmids pAAV-RC2 (Cell Biolabs) and pHelper (Cell Biolabs). The pAAV-RC2 plasmid contains the Rep and AAV2 capsid genes and pHelper contains the adenovirus E2A, E4, and VA genes. To produce AAV particles, these plasmids were transfected in the ratio 1:1:1 (pAAV-shFDPS:pAAV-RC2:pHelper) into 293T cells. For transfection of cells in 150 mm dishes (BD Falcon), 10 micrograms of each plasmid were added together in 1 ml of DMEM. In another tube, 60 microliters of the transfection reagent PEI (1 microgram/ml) (Polysciences) was added to 1 ml of DMEM. The two tubes were mixed together and allowed to incubate for 15 minutes. Then the transfection mixture was added to cells and the cells were collected after 3 days. The cells were lysed by freeze/thaw lysis in dry ice/isopropanol. Benzonase nuclease (Sigma) was added to the cell lysate for 30 minutes at 37 degrees Celsius. Cell debris were then pelleted by centrifugation at 4 degrees Celsius for 15 minutes at 12,000 rpm. The supernatant was collected and then added to target cells.

Example 13—Decreased RAP1 Prenylation in the Cells Transduced with LV-shFDPS and Treated with Zoledronic Acid This Example illustrates that lentiviral-delivered shRNA targeting the human farnesyl diphosphate synthase (FDPS) gene and zoledronic acid synergize to inhibit farnesyl diphosphate production.

Figure 15:
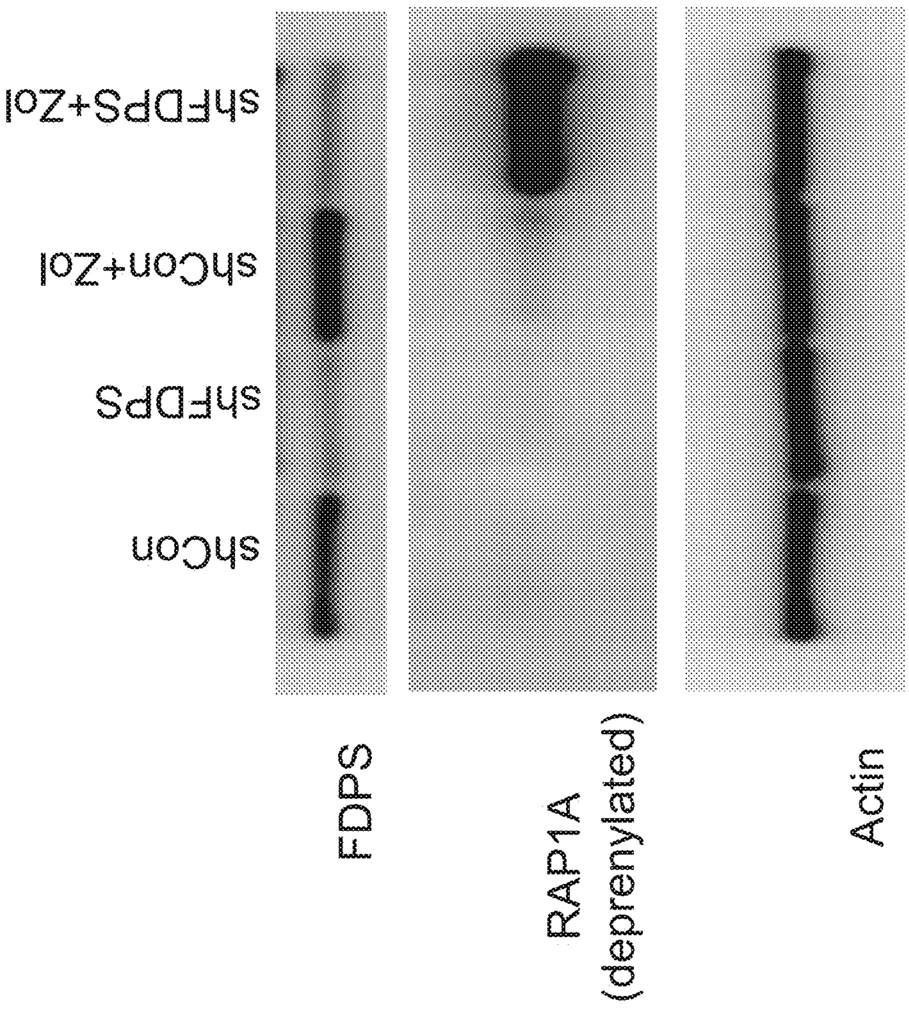
FIG. 15 depicts immunoblot data demonstrating lack of RAP1 prenylation in the cells transduced with LV-shFDPS and treated with zoledronic acid.

FDPS is an enzyme in the isoprenoid synthesis pathway that catalyzes the production of farnesyl diphosphate. Inhibiting the enzyme activity of FDPS by zoledronic acid or reduced protein expression by shRNA-mediated knockdown will result in reduced farnesyl diphosphate levels. Farnesylation of cellular proteins requires farnesyl diphosphate. RAP1A is a protein that is modified by farnesylation, which can be used as a biomarker for levels of cellular farnesyl diphosphate. An antibody that specifically recognizes reduced RAP1A farnesylation was used to measure FDPS activity after transduction with LV-shFDPS alone or in combination with zoledronic acid. HepG2 human hepatocellular carcinoma cells were infected with lentiviral vectors containing FDPS shRNA sequence #4. For the zoledronic acid treated cells, zoledronic acid (Sigma) was added for the last 24 hours. After 48 hours, cells were lysed with NP-40 lysis buffer and protein was quantified with the Bio-Rad protein assay reagent. Protein samples at 50 micrograms were electrophoresed on 4-12% Bis-Tris gels (Thermo Scientific and transferred to PVDF membranes (EMD Millipore). As shown in FIG. 15, an immunoblot was performed using an anti-FDPS (Thermo Scientific), anti-RAP1A (Santa Cruz), and an anti-actin (Sigma) antibody as a protein loading control. Antibodies were bound with HRP-conjugated secondary antibodies and detected with a Licor c-DiGit Blot scanner using the Immobilon Western ECL reagent (EMD Millipore). An increase in the RAP1A band intensity correlates with reduced farnesylation. RAP1A defarnesylation occurred only in the cells transduced with LV-shFDPS and treated with zoledronic acid.

Example 14—Treatment of a Subject with Cancer

LV-FDPS is a Genetic Medicine Delivered by a Lentivirus Vector Via Local Administration to the Site of Late Stage, Non-Resectable Hepatocellular Carcinoma A Phase I clinical trial will test safety and feasibility of delivering LV-FDPS to the site of hepatocellular carcinoma (HCC) using ultrasound guided cannulation of the liver in patients without concomitant radiotherapy or chemotherapy. It is rationally predicted that this study will result in the successful treatment of HCC. The study is an open label, 4×3 dose escalation (4 dose ranges, up to 3 subjects per dose) to identify the maximum tolerable dose of LV-FDPS in patients 18 years or older with Stage III/IV non-resectable HCC.

LV-FDPS is a genetic therapy designed to reduce expression in tumor cells of the enzyme farnesyl diphosphate synthase. Experimental studies show that tumor cells modified by LV-FDPS induce the anti-tumor activity of human gamma delta T cells, including the capacity for tumor killing by cellular cytotoxicity.

Subjects with target lesions ≥1 cm in longest diameter (measured by helical CT) and ≤4.9 cm maximum diameter and meeting inclusion and exclusion criteria detailed below, are enrolled into the next available dosing category. A maximum of 3 subjects are recruited for each dosage group. The dose is number of transducing units of LV-FDPS as described in the product release criteria, delivered via intrahepatic cannulation in a single bolus with volume not to exceed 25 mL. The minimum dose is $1\times10^9$ transducing units and escalation is 10-fold to a next dose of $1\times10^{10}$ transducing units, the next dose is $1\times10^{11}$ transducing units, and a maximum dose of $1\times10^{12}$ transducing units based on reported experience with recombinant adenovirus therapy for HCC (Sangro et al., A phase I clinic trial of thymidine kinase-based gene therapy in advanced hepatocellular carcinoma, 2010, *Cancer Gene Ther.* 17:837-43). Subjects are enrolled, treated and evaluated for 3 months. All safety evaluations are completed for each group prior to enrolling and treating subjects at the next higher dose level. Enrollment and dose escalation continue until a maximum tolerable dose is achieved or the study is terminated.

Cannulation is via the left subclavian artery until tip of catheter is at the proper hepatic artery junction. Cannulation is guided by ultrasonography as described (Lin et al., Clinical effects of intra-arterial infusion chemotherapy with cisplatin, mitomycin C, leucovor and 5-Fluorouracil for unresectable advanced hepatocellular carcinoma, 2004, *J. Chin. Med. Assoc.* 67:602-10).

Primary Outcome Measures

Safety: Systemic and locoregional adverse events are graded according to CTCAS and coded according to MedRA. The adverse events data for all subjects at a single dose range will be evaluated prior to dose escalation. The final safety assessment incorporates data from all dose ranges.

Secondary Outcome Measures

Lesion distribution and retention of LV-FDPS following locoregional administration and subsequent biopsy or necropsy to obtain tissues.

Objective response rate (ORR) in target and measurable non-local lesions (if present) by physical analysis, medical imaging or biopsy during 3 months after treatment.

Levels of LV-FDPS in blood stream during 10 minutes, 30 minutes, 1 hour and 1 day after local injection.

Changes in markers of hepatic function including ALP, ALT, ASAT, total bilirubin and GGT during 3 months after treatment.

Disease free survival beyond historical control (no LV-FDPS) patients in ad hoc analysis.

Inclusion Criteria

Greater than 18 years and including both males and females.

Diagnosis confirmed by histology or cytology or based on currently accepted clinical standards of hepatocellular carcinoma of parenchyma cell origin that is not amenable, at the time of screening, to resection, transplant or other potentially curative therapies.

Treating physician determines that the lesion is amenable to locoregional targeted delivery.

Target lesion must represent measurable disease with a unidimensional longest diameter of ≥1.0 cm by computed tomography; the maximum longest diameter is ≤5.0 cm.

Karnofsky performance score 60-80% of ECOG values.

Life expectancy ≥12 weeks.

Hematopoietic function: WBC≥2,500/$mm^3$; ANC≥1000/$mm^3$; Hemoglobin≥8 g/dL; Platelet count≥50,000/$mm^3$; Coagulation INR≤1.3.

AST and ALT <5 times ULN; ALPS <5 time ULN. Bilirubin ≤1.5 times ULV; Creatine ≤1.5 times ULN and eGFR ≥50.

Thyroid function: Total T3 or free T3, total T4 or free T4 and THC≤CTCAE Grade 2 abnormality.

Renal, cardiovascular and respiratory function adequate in the opinion of the attending physician.

Immunological function: Circulating Vgamma9Vdelta2+ T cells≥30/$mm^3$; no immunodeficiency disease.

Negative for HIV by serology and viral RNA test.

Written informed consent.

Exclusion Criteria

Target lesion contiguous with, encompasses or infiltrates blood vessel.

Primary HCC amenable to resection, transplantation or other potentially curative therapies.

Hepatic surgery or chemoembolization within the past 4 months.

Hepatic radiation or whole body radiation therapy within past 4 months.

Chemotherapy with 4 weeks or any use of nitrosourea, mitomycin C or cisplatin.

Current or within past 4 weeks receipt of bisphosphonate therapy

Investigational agents within 4 weeks or <5 drug half-lives.

Impaired wound healing due to diabetes.

Significant psychiatric illness, alcohol dependence or illicit drug use.

Unwilling to comply with study protocols and reporting requirements.

Bisphosphonate treatment within past 4 months.

Presence of clinically significant cardiovascular, cerebrovascular (stroke), immunological (except hepatitis B or C virus infection, viral hepatitis or cirrhosis), endocrine or central nervous system disorders; current encephalopathy; variceal bleeding requiring hospitalization or transfusion within past 4 months.

History of HIV or acquired immune deficiency syndrome.

Current or prior treatment with antiretroviral medications.

Pregnant, lactating or refusal to adopt barrier or chemical contraceptive use throughout trial and follow-up interval.

LV-FDPS is a Genetic Medicine Delivered by a Lentivirus Vector Via Local Administration to the Site of Late Stage, Non-Resectable Hepatocellular Carcinoma—Adjunct Administration of Bisphosphonate A Phase I clinical trial will test safety and feasibility of delivering LV-FDPS to the site of hepatocellular carcinoma (HCC) using ultrasound guided cannulation of the liver in patients with concomitant bisphosphonate chemotherapy. It is rationally predicted that this study will result in the successful treatment of HCC. The study is an open label, 4×3 dose escalation (4 dose ranges, up to 3 subjects per dose) to identify the maximum tolerable dose of LV-FDPS in patients 18 years or older with Stage III/IV non-resectable HCC.

LV-FDPS is a genetic therapy designed to reduce expression in tumor cells of the enzyme farnesyl diphosphate synthase. Experimental studies show that tumor cells modified by LV-FDPS induce the anti-tumor activity of human gamma delta T cells, including the capacity for tumor killing by cellular cytotoxicity. Prior experimental studies also showed the potential for positive interactions of LV-FDPS and specific bisphosphonate drugs that may be prescribed in primary or metastatic diseases. For this study, subjects will receive dose escalating amounts of LV-FDPS with continuous standard of care dosing with Aredia® (pamidronate), Zometa® (zoledronic acid) or Actonel® (risedronate) according to physician advice and subject preference.

Subjects with target lesions ≥1 cm in longest diameter (measured by helical CT) and ≤4.9 cm maximum diameter and meeting inclusion and exclusion criteria detailed below, are enrolled and started on bisphosphonate therapy. 30 days later size of the target lesion is re-evaluated to ensure subjects still meet starting criteria for LV-FDPS. Subjects without objective clinical response on bisphosphonate are enrolled into the next available LV-FDPS dosing category. A maximum of 3 subjects are recruited for each dosage group and all continue on bisphosphonate for the study duration unless otherwise advised by the attending physician. The LV-FDPS dose is a number of transducing units of LV-FDPS as described in the product release criteria, delivered via intrahepatic cannulation in a single bolus with volume not to exceed 25 mL. The minimum dose is $1\times10^9$ transducing units and escalation is 10-fold to a next dose of $1\times10^{10}$ transducing units, the next dose is $1\times10^{11}$ transducing units, and a maximum dose of $1\times10^{12}$ transducing units based on reported experience with recombinant adenovirus therapy for HCC (Sangro, et al., A phase I clinic trial of thymidine kinase-based gene therapy in advanced hepatocellular carcinoma, 2010, *Cancer Gene Ther.* 17:837-43). Subjects are enrolled, treated and evaluated for 3 months. All safety evaluations are completed for each group prior to enrolling and treating subjects at the next higher dose level. Enrollment and dose escalation continue until a maximum tolerable dose is achieved or the study is terminated.

Cannulation is via the left subclavian artery until tip of catheter is at the proper hepatic artery junction. Cannulation is guided by ultrasonography as described (Lin et al., Clinical effects of intra-arterial infusion chemotherapy with cisplatin, mitomycin C, leucovor and 5-Fluorouracil for unresectable advanced hepatocellular carcinoma, 2004, *J. Chin. Med. Assoc.* 67:602-10).

Primary Outcome Measures

Safety: Systemic and locoregional adverse events are graded according to CTCAS and coded according to MedRA. The adverse events data for all subjects at a single dose range will be evaluated prior to dose escalation. The final safety assessment incorporates data from all dose ranges.

Secondary Outcome Measures

- Lesion distribution and retention of LV-FDPS following locoregional administration and subsequent biopsy or necropsy to obtain tissues.
- Objective response rate (ORR) in target and measurable non-local lesions (if present) by physical analysis, medical imaging or biopsy during 3 months after treatment.
- Levels of LV-FDPS in blood stream during 10 minutes, 30 minutes, 1 hour and 1 day after local injection.
- Changes in markers of hepatic function including ALP, ALT, ASAT, total bilirubin and GGT during 3 months after treatment.
- Disease free survival beyond historical control (no LV-FDPS) patients in ad hoc analysis.

Inclusion Criteria

- Greater than 18 years and including both males and females.
- Diagnosis confirmed by histology or cytology or based on currently accepted clinical standards of hepatocellular carcinoma of parenchyma cell origin that is not amenable, at the time of screening, to resection, transplant or other potentially curative therapies.
- Treating physician determines that the lesion is amenable to locoregional targeted delivery.
- Target lesion must represent measurable disease with a unidimensional longest diameter of ≥1.0 cm by computed tomography; the maximum longest diameter is ≤5.0 cm.
- Karnofsky performance score 60-80% of ECOG values.
- Life expectancy ≥12 weeks.
- Hematopoietic function: WBC≥2,500/$mm^3$; ANC≥1000/$mm^3$; Hemoglobin≥8 g/dL; Platelet count≥50,000/$mm^3$; Coagulation INR≤1.3.
- AST and ALT <5 times ULN; ALPS <5 time ULN. Bilirubin ≤1.5 times ULV; Creatine ≤1.5 times ULN and eGFR ≥50.
- Thyroid function: Total T3 or free T3, total T4 or free T4 and THC≤CTCAE Grade 2 abnormality.
- Renal, cardiovascular and respiratory function adequate in the opinion of the attending physician.
- Immunological function: Circulating Vgamma9Vdelta2+ T cells≥30/$mm^3$; no immunodeficiency disease.
- Negative for HIV by serology and viral RNA test.
- Written informed consent.

Exclusion Criteria

- Intolerant to or unwilling to continue bisphosphonate adjunct therapy.
- Objective clinical response after bisphosphonate therapy.
- Target lesion contiguous with, encompasses or infiltrates blood vessel.
- Primary HCC amenable to resection, transplantation or other potentially curative therapies.
- Hepatic surgery or chemoembolization within the past 4 months.
- Hepatic radiation or whole body radiation therapy within past 4 months.
- Chemotherapy excluding bisphosphonate, within 4 weeks or any use of nitrosourea, mitomycin C or cisplatin.
- Investigational agents within 4 weeks or <5 drug half-lives.
- Impaired wound healing due to diabetes.
- Significant psychiatric illness, alcohol dependence or illicit drug use.
- Unwilling to comply with study protocols and reporting requirements.
- Presence of clinically significant cardiovascular, cerebrovascular (stroke), immunological (except hepatitis B or C virus infection, viral hepatitis or cirrhosis), endocrine or central nervous system disorders; current encephalopathy; variceal bleeding requiring hospitalization or transfusion within past 4 months.
- History of HIV or acquired immune deficiency syndrome.
- Current or prior treatment with antiretroviral medications.
- Pregnant, lactating or refusal to adopt barrier or chemical contraceptive use throughout trial and follow-up interval.

Example 15—Treatment of a Subject with Chronic Viral Disease(s) of the Liver LV-FDPS is a Genetic Medicine Delivered by a Lentivirus Vector Via Local Administration to Liver for the Treatment of Hepatitis B Virus, Hepatitis C Virus, HIV or Other Viral Infection of the Liver A Phase I clinical trial will test safety and feasibility of delivering LV-FDPS to virally infected liver using ultrasound guided cannulation. It is rationally predicted that this study will result in the successful treatment of infections of the liver. The study is an open label, 4×3 dose escalation (4 dose ranges, up to 3 subjects per dose) to identify the maximum tolerable dose of LV-FDPS in patients 18 years or older with chronic viral disease of the liver that is resistant to chemotherapy.

LV-FDPS is a genetic therapy designed to reduce expression in tumor cells of the enzyme farnesyl diphosphate synthase. Experimental studies show that tumor cells modified by LV-FDPS induce human gamma delta T cells, including a capacity for cellular cytotoxicity against virally-infected cells.

Subjects with confirmed viral infection of the liver including hepatitis B virus, hepatitis C virus, HIV or other viruses are enrolled into the next available LV-FDPS dosing category. A maximum of 3 subjects are recruited for each dosage group. The LV-FDPS dose is a number of transducing units of LV-FDPS as described in the product release criteria, delivered via intrahepatic cannulation in a single bolus with volume not to exceed 25 mL. The minimum dose is $1\times10^9$ transducing units and escalation is 10-fold to a next dose of $1\times10^{10}$ transducing units, the next dose is $1\times10^{11}$ transducing units, and a maximum dose of $1\times10^{12}$ transducing units based on reported experience with recombinant adenovirus therapy for HCC (Sangro, et al., A phase I clinic trial of thymidine kinase-based gene therapy in advanced hepatocellular carcinoma, 2010, *Cancer Gene Ther.* 17:837-43). Subjects are enrolled, treated and evaluated for 3 months. All safety evaluations are completed for each group prior to enrolling and treating subjects at the next higher dose level. Enrollment and dose escalation continue until a maximum tolerable dose is achieved or the study is terminated.

Cannulation is via the left subclavian artery until tip of catheter is at the proper hepatic artery junction. Cannulation is guided by ultrasonography as described (Lin et al., Clinical effects of intra-arterial infusion chemotherapy with cisplatin, mitomycin C, leucovor and 5-Fluorouracil for unresectable advanced hepatocellular carcinoma, 2004, *J. Chin. Med. Assoc.* 67:602-10).

Primary Outcome Measures

Safety: Systemic and locoregional adverse events are graded according to CTCAS and coded according to MedRA. The adverse events data for all subjects at a single dose range will be evaluated prior to dose escalation. The final safety assessment incorporates data from all dose ranges.

Secondary Outcome Measures

- Lesion distribution and retention of LV-FDPS following locoregional administration and subsequent biopsy or necropsy to obtain tissues.
- Objective response rate (ORR) measured as a Sustained Viral Response (SVR) within the organ or systemically during 3 months after treatment.
- Levels of LV-FDPS in blood stream during 10 minutes, 30 minutes, 1 hour and 1 day after local injection.
- Changes in markers of hepatic function including ALP, ALT, ASAT, total bilirubin and GGT during 3 months after treatment.
- Disease free survival beyond historical control (no LV-FDPS) patients in ad hoc analysis.

Inclusion Criteria

- Greater than 18 years and including both males and females.
- Diagnosis confirmed by histology or cytology or based on currently accepted clinical standards of chronic viral infection of the liver that is not amenable, at the time of screening, to resection, transplant or other potentially curative therapies.
- Treating physician determines that the lesion is amenable to locoregional targeted delivery.
- Karnofsky performance score 60-80% of ECOG values.
- Life expectancy ≥12 weeks.
- Hematopoietic function: WBC≥2,500/$mm^3$; ANC≥1000/$mm^3$; Hemoglobin≥8 g/dL; Platelet count≥50,000/$mm^3$; Coagulation INR≤1.3.
- AST and ALT <5 times ULN; ALPS <5 time ULN. Bilirubin ≤1.5 times ULV; Creatine ≤1.5 times ULN and eGFR ≥50.
- Thyroid function: Total T3 or free T3, total T4 or free T4 and THC≤CTCAE Grade 2 abnormality.
- Renal, cardiovascular and respiratory function adequate in the opinion of the attending physician.
- Immunological function: Circulating Vgamma9Vdelta2+ T cells≥30/$mm^3$; no immunodeficiency disease.
- Negative for HIV by serology and viral RNA test.
- Written informed consent.

Exclusion Criteria

- Chronic viral disease amenable to resection, transplantation or other potentially curative therapies.
- Hepatic surgery or chemoembolization within the past 4 months.
- Hepatic radiation or whole body radiation therapy within past 4 months.
- Investigational agents within 4 weeks or <5 drug half-lives.
- Current (within past 4 weeks) or ongoing receipt of bisphosphonate therapy.
- Impaired wound healing due to diabetes.
- Significant psychiatric illness, alcohol dependence or illicit drug use.
- Unwilling to comply with study protocols and reporting requirements.
- Presence of clinically significant cardiovascular, cerebrovascular (stroke), immunological (except virus infection, viral hepatitis or cirrhosis), endocrine or central nervous system disorders; current encephalopathy; variceal bleeding requiring hospitalization or transfusion within past 4 months.
- Pregnant, lactating or refusal to adopt barrier or chemical contraceptive use throughout trial and follow-up interval.

LV-FDPS is a Genetic Medicine Delivered by a Lentivirus Vector Via Local Administration to Liver for the Treatment of Hepatitis B Virus, Hepatitis C Virus, HIV or other Viral Infection of the Liver—Concomitant Adjunct Bisphosphonate Therapy A Phase I clinical trial will test safety and feasibility of delivering LV-FDPS to virally infected liver using ultrasound guided cannulation. It is rationally predicted that this study will result in the successful treatment of infections of the liver. The study is an open label, 4×3 dose escalation (4 dose ranges, up to 3 subjects per dose) to identify the maximum tolerable dose of LV-FDPS in patients 18 years or older with chronic viral disease of the liver that is resistant to chemotherapy.

LV-FDPS is a genetic therapy designed to reduce expression in tumor cells of the enzyme farnesyl diphosphate synthase. Experimental studies show that tumor cells modified by LV-FDPS induce human gamma delta T cells, including a capacity for cellular cytotoxicity against virally-infected cells. Prior experimental studies also showed the potential for positive interactions of LV-FDPS and specific bisphosphonate drugs that may be prescribed during infectious disease. For this study, subjects will receive dose escalating amounts of LV-FDPS with continuous standard of care dosing with Aredia® (pamidronate), Zometa® (zoledronic acid) or Actonel® (risedronate) according to physician advice and subject preference.

Subjects with confirmed viral infection of the liver including hepatitis B virus, hepatitis C virus, HIV or other viruses will initiate bisphosphonate therapy for 45 days before re-screening to meet enrollment criteria for LV-FDPS treatment of infectious disease. Eligible subjects are enrolled into the next available LV-FDPS dosing category. A maximum of 3 subjects are recruited for each dosage group. The LV-FDPS dose is a number of transducing units of LV-FDPS as described in the product release criteria, delivered via intrahepatic cannulation in a single bolus with volume not to exceed 25 mL. The minimum dose is $1\times10^9$ transducing units and escalation is 10-fold to a next dose of $1\times10^{10}$ transducing units, the next dose is $1\times10^{11}$ transducing units, and a maximum dose of $1\times10^{12}$ transducing units based on reported experience with recombinant adenovirus therapy for HCC (Sangro, et al., A phase I clinic trial of thymidine kinase-based gene therapy in advanced hepatocellular carcinoma, 2010, *Cancer Gene Ther.* 17:837-43). Subjects are enrolled, treated and evaluated for 3 months. All safety evaluations are completed for each group prior to enrolling and treating subjects at the next higher dose level. Enrollment and dose escalation continue until a maximum tolerable dose is achieved or the study is terminated.

Cannulation is via the left subclavian artery until tip of catheter is at the proper hepatic artery junction. Cannulation is guided by ultrasonography as described (Lin et al., Clinical effects of intra-arterial infusion chemotherapy with cisplatin, mitomycin C, leucovor and 5-Fluorouracil for unresectable advanced hepatocellular carcinoma, 2004, *J. Chin. Med. Assoc.* 67:602-10).

Primary Outcome Measures

Safety: Systemic and locoregional adverse events are graded according to CTCAS and coded according to MedRA. The adverse events data for all subjects at a single dose range will be evaluated prior to dose escalation. The final safety assessment incorporates data from all dose ranges.

Secondary Outcome Measures

- Lesion distribution and retention of LV-FDPS following locoregional administration and subsequent biopsy or necropsy to obtain tissues.
- Objective response rate (ORR) measured as a Sustained Viral Response (SVR) within the organ or systemically during 3 months after treatment.
- Levels of LV-FDPS in blood stream during 10 minutes, 30 minutes, 1 hour and 1 day after local injection.
- Changes in markers of hepatic function including ALP, ALT, ASAT, total bilirubin and GGT during 3 months after treatment.
- Disease free survival beyond historical control (no LV-FDPS) patients in ad hoc analysis.

Inclusion Criteria

- Greater than 18 years and including both males and females.
- Diagnosis confirmed by histology or cytology or based on currently accepted clinical standards of chronic viral infection of the liver that is not amenable, at the time of screening, to resection, transplant or other potentially curative therapies.
- Treating physician determines that the lesion is amenable to locoregional targeted delivery.
- Karnofsky performance score 60-80% of ECOG values.
- Life expectancy ≥12 weeks.
- Hematopoietic function: WBC≥2,500/$mm^3$; ANC≥1000/$mm^3$; Hemoglobin≥8 g/dL; Platelet count≥50,000/$mm^3$; Coagulation INR≤1.3.
- AST and ALT <5 times ULN; ALPS <5 time ULN. Bilirubin <1.5 times ULV; Creatine ≤1.5 times ULN and eGFR ≥50.
- Thyroid function: Total T3 or free T3, total T4 or free T4 and THC≤CTCAE Grade 2 abnormality.
- Renal, cardiovascular and respiratory function adequate in the opinion of the attending physician.
- Immunological function: Circulating Vgamma9Vdelta2+ T cells≥30/$mm^3$; no immunodeficiency disease.
- Negative for HIV by serology and viral RNA test.
- Written informed consent.

Exclusion Criteria

- Chronic viral disease amenable to resection, transplantation or other potentially curative therapies.
- Hepatic surgery or chemoembolization within the past 4 months.
- Hepatic radiation or whole body radiation therapy within past 4 months.
- Investigational agents within 4 weeks or <5 drug half-lives.
- Impaired wound healing due to diabetes.
- Significant psychiatric illness, alcohol dependence or illicit drug use.
- Unwilling to comply with study protocols and reporting requirements.
- Presence of clinically significant cardiovascular, cerebrovascular (stroke), immunological (except virus infection, viral hepatitis or cirrhosis), endocrine or central nervous system disorders; current encephalopathy; variceal bleeding requiring hospitalization or transfusion within past 4 months.
- Pregnant, lactating or refusal to adopt barrier or chemical contraceptive use throughout trial and follow-up interval Sequences The following sequences are referred to herein:

| SEQ ID NO: | Description | Sequence |
|---|---|---|
| 1 | FDPS shRNA sequence #1 | GTCCTGGAGTACAATGCCATTCTCGAGAATGGCATTGTA CTCCAGGACTTTTT |
| 2 | FDPS shRNA sequence #2 | GCAGGATTTCGTTCAGCACTTCTCGAGAAGTGCTGAACG AAATCCTGCTTTTT |
| 3 | FDPS shRNA sequence #3 | GC CATGTACATGGCAGGAATTCTCGAGAATTCCTGCCAT GTACATGGCTTTTT |
| 4 | FDPS shRNA sequence #4 | GCAGAAGGAGGCTGAGAAAGTCTCGAGACTTTCTCAGCC TCCTTCTGCTTTTT |
| 5 | miR30 FDPS sequence #1 | AAGGTATATTGCTGTTGACAGTGAGCGACACTTTCTCAG CCTCCTTCTGCGTGAAGCCACAGATGGCAGAAGGAGGCT GAGAAAGTGCTGCCTACTGCCTCGGACTTCAAGGGGCT |
| 6 | miR30 FDPS sequence #2 | AAGGTATATTGCTGTTGACAGTGAGCGACACTTTCTCAG CCTCCTTCTGCGTGAAGCCACAGATGGCAGAAGGGCTGA GAAAGTGCTGCCTACTGCCTCGGACTTCAAGGGGCT |
| 7 | miR30 FDPS sequence #3 | TGCTGTTGACAGTGAGCGACTTTCTCAGCCTCCTTCTGCG TGAAGCCACAGATGGCAGAAGGAGGCTGAGAAAGTTGC CTACTGCCTCGGA |
| 8 | miR155 FDPS sequence #1 | CCTGGAGGCTTGCTGAAGGCTGTATGCTGACTTTCTCAG CCTCCTTCTGCTTTTGGCCACTGACTGAGCAGAAGGGCT GAGAAAGTCAGGACACAAGGCCTGTTACTAGCACTCA |
| 9 | miR21 FDPS sequence #1 | CATCTCCATGGCTGTACCACCTTGTCGGGACTTTCTCAGC CTCCTTCTGCCTGTTGAATCTCATGGCAGAAGGAGGCGA GAAAGTCTGACATTTTGGTATCTTTCATCTGACCA |

-continued

| SEQ ID NO: | Description | Sequence |
|---|---|---|
| 10 | miR185 FDPS sequence #1 | GGGCCTGGCTCGAGCAGGGGGCGAGGGATACTTTCTCAG CCTCCTTCTGCTGGTCCCCTCCCCGCAGAAGGAGGCTGA GAAAGTCCTTCCCTCCCAATGACCGCGTCTTCGTCG |
| 11 | Rous Sarcoma virus (RSV) promoter | GTAGTCTTATGCAATACTCTTGTAGTCTTGCAACATGGTA ACGATGAGTTAGCAACATGCCTTACAAGGAGAGAAAAA GCACCGTGCATGCCGATTGGTGGAAGTAAGGTGGTACGA TCGTGCCTTATTAGGAAGGCAACAGACGGGTCTGACATG GATTGGACGAACCACTGAATTGCCGCATTGCAGAGATAT TGTATTTAAGTGCCTAGCTCGATACAATAAACG |
| 12 | 5' Long terminal repeat (LTR) | GGTCTCTCTGGTTAGACCAGATCTGAGCCTGGGAGCTCT CTGGCTAACTAGGGAACCCACTGCTTAAGCCTCAATAAA GCTTGCCTTGAGTGCTTCAAGTAGTGTGTGCCCGTCTGTT GTGTGACTCTGGTAACTAGAGATCCCTCAGACCCTTTTA GTCAGTGTGGAAAATCTCTAGCA |
| 13 | Psi Packaging signal | TACGCCAAAAATTTTGACTAGCGGAGGCTAGAAGGAGA GAG |
| 14 | Rev response element (RRE) | AGGAGCTTTGTTCCTTGGGTTCTTGGGAGCAGCAGGAAG CACTATGGGCGCAGCCTCAATGACGCTGACGGTACAGGC CAGACAATTATTGTCTGGTATAGTGCAGCAGCAGAACAA TTTGCTGAGGGCTATTGAGGCGCAACAGCATCTGTTGCA ACTCACAGTCTGGGGCATCAAGCAGCTCCAGGCAAGAAT CCTGGCTGTGGAAAGATACCTAAAGGATCAACAGCTCC |
| 15 | Central polypurine tract (cPPT) | TTTTAAAAGAAAAGGGGGGATTGGGGGGTACAGTGCAG GGGAAAGAATAGTAGACATAATAGCAACAGACATACAA ACTAAAGAATTACAAAAACAAATTACAAAATTCAAAATT TTA |
| 16 | Polymerase III shRNA promoters; H1 promoter | GAACGCTGACGTCATCAACCCGCTCCAAGGAATCGCGGG CCCAGTGTCACTAGGCGGGAACACCCAGCGCGCGTGCGC CCTGGCAGGAAGATGGCTGTGAGGGACAGGGGAGTGGC GCCCTGCAATATTTGCATGTCGCTATGTGTTCTGGGAAAT CACCATAAACGTGAAATGTCTTTGGATTTGGGAATCTTA TAAGTTCTGTATGAGACCACTT |
| 17 | Long WPRE sequence | AATCAACCTCTGATTACAAAATTTGTGAAAGATTGACTG GTATTCTTAACTATGTTGCTCCTTTTACGCTATGTGGATA CGCTGCTTTAATGCCTTTGTATCATGCTATTGCTTCCCGT ATGGCTTTCATTTTCTCCTCCTTGTATAAATCCTGGTTGC TGTCTCTTTATGAGGAGTTGTGGCCCGTTGTCAGGCAAC GTGGCGTGGTGTGCACTGTGTTTGCTGACGCAACCCCCA CTGGTTGGGGCATTGCCACCACCTGTCAGCTCCTTTCCGG GACTTTCGCTTTCCCCCTCCCTATTGCCACGGCGGAACTC ATCGCCGCCTGCCTTGCCCGCTGCTGGACAGGGGCTCGG CTGTTGGGCACTGACAATTCCGTGGTGTTGTCGGGGAAA TCATCGTCCTTTCCTTGGCTGCTCGCCTGTGTTGCCACCT GGATTCTGCGCGGGACGTCCTTCTGCTACGTCCCTTCGGC CCTCAATCCAGCGGACCTTCCTTCCCGCGGCCTGCTGCC GGCTCTGCGGCCTCTTCCGCGTCTTCGCCTTCGCCCTCAG ACGAGTCGGATCTCCCTTTGGGCCGCCTCCCCGCCT |
| 18 | 3' delta LTR | TGGAAGGGCTAATTCACTCCCAACGAAGATAAGATCTGC TTTTTGCTTGTACTGGGTCTCTCTGGTTAGACCAGATCTG AGCCTGGGAGCTCTCTGGCTAACTAGGGAACCCACTGCT TAAGCCTCAATAAAGCTTGCCTTGAGTGCTTCAAGTAGT GTGTGCCCGTCTGTTGTGTGACTCTGGTAACTAGAGATC CCTCAGACCCTTTTAGTCAGTGTGGAAAATCTCTAGCAG TAGTAGTTCATGTCA |
| 19 | Helper/Rev; Chicken beta actin (CAG) promoter; Transcription | GCTATTACCATGGGTCGAGGTGAGCCCCACGTTCTGCTT CACTCTCCCCATCTCCCCCCCCTCCCCACCCCCAATTTTG TATTTATTTATTTTTTAATTATTTTGTGCAGCGATGGGGG CGGGGGGGGGGGGGGCGCGCGCCAGGCGGGGCGGGGC GGGGCGAGGGGCGGGGCGGGGCGAGGCGGAGAGGTGC GGCGGCAGCCAATCAGAGCGGCGCGCTCCGAAAGTTTCC TTTTATGGCGAGGCGGCGGCGGCGGCGGCCCTATAAAAA GCGAAGCGCGCGGCGGGCG |
| 20 | Helper/Rev; HIV Gag; Viral capsid | ATGGGTGCGAGAGCGTCAGTATTAAGCGGGGGAGAATT AGATCGATGGGAAAAAATTCGGTTAAGGCCAGGGGGAA AGAAAAAATATAAATTAAAACATATAGTATGGGCAAGC AGGGAGCTAGAACGATTCGCAGTTAATCCTGGCCTGTTA |

-continued

| SEQ ID NO: | Description | Sequence |
|---|---|---|
| | | GAAACATCAGAAGGCTGTAGACAAATACTGGGACAGCT<br>ACAACCATCCCTTCAGACAGGATCAGAAGAACTTAGATC<br>ATTATATAATACAGTAGCAACCCTCTATTGTGTGCATCA<br>AAGGATAGAGATAAAAGACACCAAGGAAGCTTTAGACA<br>AGATAGAGGAAGAGCAAAACAAAAGTAAGAAAAAAGC<br>ACAGCAAGCAGCAGCTGACACAGGACACAGCAATCAGG<br>TCAGCCAAAATTACCCTATAGTGCAGAACATCCAGGGGC<br>AAATGGTACATCAGGCCATATCACCTAGAACTTTAAATG<br>CATGGGTAAAAGTAGTAGAAGAGAAGGCTTTCAGCCCA<br>GAAGTGATACCCATGTTTTCAGCATTATCAGAAGGAGCC<br>ACCCCACAAGATTTAAACACCATGCTAAACACAGTGGGG<br>GGACATCAAGCAGCCATGCAAATGTTAAAAGAGACCAT<br>CAATGAGGAAGCTGCAGAATGGGATAGAGTGCATCCAG<br>TGCATGCAGGGCCTATTGCACCAGGCCAGATGAGAGAA<br>CCAAGGGGAAGTGACATAGCAGGAACTACTAGTACCCTT<br>CAGGAACAAATAGGATGGATGACACATAATCCACCTATC<br>CCAGTAGGAGAAATCTATAAAAGATGGATAATCCTGGG<br>ATTAAATAAAATAGTAAGAATGTATAGCCCTACCAGCAT<br>TCTGGACATAAGACAAGGACCAAAGGAACCCTTTAGAG<br>ACTATGTAGACCGATTCTATAAAACTCTAAGAGCCGAGC<br>AAGCTTCACAAGAGGTAAAAAATTGGATGACAGAAACC<br>TTGTTGGTCCAAAATGCGAACCCAGATTGTAAGACTATT<br>TTAAAAGCATTGGGACCAGGAGCGACACTAGAAGAAAT<br>GATGACAGCATGTCAGGGAGTGGGGGGACCCGGCCATA<br>AAGCAAGAGTTTTGGCTGAAGCAATGAGCCAAGTAACA<br>AATCCAGCTACCATAATGATACAGAAAGGCAATTTTAGG<br>AACCAAAGAAAGACTGTTAAGTGTTTCAATTGTGGCAAA<br>GAAGGGCACATAGCCAAAAATTGCAGGGCCCCTAGGAA<br>AAAGGGCTGTTGGAAATGTGGAAAGGAAGGACACCAAA<br>TGAAAGATTGTACTGAGAGACAGGCTAATTTTTTAGGGA<br>AGATCTGGCCTTCCCACAAGGGAAGGCCAGGGAATTTTC<br>TTCAGAGCAGACCAGAGCCAACAGCCCCACCAGAAGAG<br>AGCTTCAGGTTTGGGGAAGAGACAACAACTCCCTCTCAG<br>AAGCAGGAGCCGATAGACAAGGAACTGTATCCTTTAGCT<br>TCCCTCAGATCACTCTTTGGCAGCGACCCCTCGTCACAAT<br>AA |
| 21 | Helper/Rev; HIV Pol; Protease and reverse transcriptase | ATGAATTTGCCAGGAAGATGGAAACCAAAAATGATAGG<br>GGGAATTGGAGGTTTTATCAAAGTAGGACAGTATGATCA<br>GATACTCATAGAAATCTGCGGACATAAAGCTATAGGTAC<br>AGTATTAGTAGGACCTACACCTGTCAACATAATTGGAAG<br>AAATCTGTTGACTCAGATTGGCTGCACTTTAAATTTTCCC<br>ATTAGTCCTATTGAGACTGTACCAGTAAAATTAAAGCCA<br>GGAATGGATGGCCCAAAAGTTAAACAATGGCCATTGAC<br>AGAAGAAAAAATAAAAGCATTAGTAGAAATTTGTACAG<br>AAATGGAAAAGGAAGGAAAAATTTCAAAAATTGGGCCT<br>GAAAATCCATACAATACTCCAGTATTTGCCATAAAGAAA<br>AAAGACAGTACTAAATGGAGAAAATTAGTAGATTTCAG<br>AGAACTTAATAAGAGAACTCAAGATTTCTGGGAAGTTCA<br>ATTAGGAATACCACATCCTGCAGGGTTAAAACAGAAAA<br>AATCAGTAACAGTACTGGATGTGGGCGATGCATATTTTT<br>CAGTTCCCTTAGATAAAGACTTCAGGAAGTATACTGCAT<br>TTACCATACCTAGTATAAACAATGAGACACCAGGGATTA<br>GATATCAGTACAATGTGCTTCCACAGGGATGGAAAGGAT<br>CACCAGCAATATTCCAGTGTAGCATGACAAAAATCTTAG<br>AGCCTTTTAGAAAACAAAATCCAGACATAGTCATCTATC<br>AATACATGGATGATTTGTATGTAGGATCTGACTTAGAAA<br>TAGGGCAGCATAGAACAAAAATAGAGGAACTGAGACAA<br>CATCTGTTGAGGTGGGGATTTACCACACCAGACAAAAA<br>CATCAGAAAGAACCTCCATTCCTTTGGATGGGTTATGAA<br>CTCCATCCTGATAAATGGACAGTACAGCCTATAGTGCTG<br>CCAGAAAAGGACAGCTGGACTGTCAATGACATACAGAA<br>ATTAGTGGGAAAATTGAATTGGGCAAGTCAGATTTATGC<br>AGGGATTAAAGTAAGGCAATTATGTAAACTTCTTAGGGG<br>AACCAAAGCACTAACAGAAGTAGTACCACTAACAGAAG<br>AAGCAGAGCTAGAACTGGCAGAAAACAGGGAGATTCTA<br>AAAGAACCGGTACATGGAGTGTATTATGACCCATCAAAA<br>GACTTAATAGCAGAAATACAGAAGCAGGGGCAAGGCCA<br>ATGGACATATCAAATTTATCAAGAGCCATTTAAAAATCT<br>GAAAACAGGAAAATATGCAAGAATGAAGGGTGCCCACA<br>CTAATGATGTGAAACAATTAACAGAGGCAGTACAAAAA<br>ATAGCCACAGAAAGCATAGTAATATGGGGAAAGACTCC<br>TAAATTTAAATTACCCATACAAAAGGAAACATGGGAAG<br>CATGGTGGACAGAGTATTGGCAAGCCACCTGGATTCCTG<br>AGTGGGAGTTTGTCAATACCCCTCCCTTAGTGAAGTTAT<br>GGTACCAGTTAGAGAAAGAACCCATAATAGGAGCAGAA |

-continued

| SEQ ID NO: | Description | Sequence |
|---|---|---|
| | | ACTTTCTATGTAGATGGGGCAGCCAATAGGGAAACTAAA TTAGGAAAAGCAGGATATGTAACTGACAGAGGAAGACA AAAAGTTGTCCCCCTAACGGACACAACAAATCAGAAGA CTGAGTTACAAGCAATTCATCTAGCTTTGCAGGATTCGG GATTAGAAGTAAACATAGTGACAGACTCACAATATGCAT TGGGAATCATTCAAGCACAACCAGATAAGAGTGAATCA GAGTTAGTCAGTCAAATAATAGAGCAGTTAATAAAAAA GGAAAAAGTCTACCTGGCATGGGTACCAGCACACAAAG GAATTGGAGGAAATGAACAAGTAGATGGGTTGGTCAGT GCTGGAATCAGGAAAGTACTA |
| 22 | Helper Rev; HIV Integrase; Integration of viral RNA | TTTTTAGATGGAATAGATAAGGCCCAAGAAGAACATGA GAAATATCACAGTAATTGGAGAGCAATGGCTAGTGATTT TAACCTACCACCTGTAGTAGCAAAAGAAATAGTAGCCAG CTGTGATAAATGTCAGCTAAAAGGGGAAGCCATGCATG GACAAGTAGACTGTAGCCCAGGAATATGGCAGCTAGATT GTACACATTTAGAAGGAAAAGTTATCTTGGTAGCAGTTC ATGTAGCCAGTGGATATATAGAAGCAGAAGTAATTCCAG CAGAGACAGGGCAAGAAACAGCATACTTCCTCTTAAAAT TAGCAGGAAGATGGCCAGTAAAAACAGTACATACAGAC AATGGCAGCAATTTCACCAGTACTACAGTTAAGGCCGCC TGTTGGTGGGCGGGGATCAAGCAGGAATTTGGCATTCCC TACAATCCCCAAAGTCAAGGAGTAATAGAATCTATGAAT AAAGAATTAAAGAAAATTATAGGACAGGTAAGAGATCA GGCTGAACATCTTAAGACAGCAGTACAAATGGCAGTATT CATCCACAATTTTAAAAGAAAAGGGGGGATTGGGGGGT ACAGTGCAGGGGAAAGAATAGTAGACATAATAGCAACA GACATACAAACTAAAGAATTACAAAAACAAATTACAAA AATTCAAAATTTTCGGGTTTATTACAGGGACAGCAGAGA TCCAGTTTGGAAAGGACCAGCAAAGCTCCTCTGGAAAGG TGAAGGGGCAGTAGTAATACAAGATAATAGTGACATAA AAGTAGTGCCAAGAAGAAAAGCAAAGATCATCAGGGAT TATGGAAAACAGATGGCAGGTGATGATTGTGTGGCAAGT AGACAGGATGAGGATTAA |
| 23 | Helper/Rev; HIV RRE; Binds Rev element | AGGAGCTTTGTTCCTTGGGTTCTTGGGAGCAGCAGGAAG CACTATGGGCGCAGCGTCAATGACGCTGACGGTACAGGC CAGACAATTATTGTCTGGTATAGTGCAGCAGCAGAACAA TTTGCTGAGGGCTATTGAGGCGCAACAGCATCTGTTGCA ACTCACAGTCTGGGGCATCAAGCAGCTCCAGGCAAGAAT CCTGGCTGTGGAAAGATACCTAAAGGATCAACAGCTCCT |
| 24 | Helper/Rev; HIV Rev; Nuclear export and stabilize viral mRNA | ATGGCAGGAAGAAGCGGAGACAGCGACGAAGAACTCCT CAAGGCAGTCAGACTCATCAAGTTTCTCTATCAAAGCAA CCCACCTCCCAATCCCGAGGGGACCCGACAGGCCCGAA GGAATAGAAGAAGAAGGTGGAGAGAGAGACAGAGACA GATCCATTCGATTAGTGAACGGATCCTTAGCACTTATCT GGGACGATCTGCGGAGCCTGTGCCTCTTCAGCTACCACC GCTTGAGAGACTTACTCTTGATTGTAACGAGGATTGTGG AACTTCTGGGACGCAGGGGGTGGGAAGCCCTCAAATATT GGTGGAATCTCCTACAATATTGGAGTCAGGAGCTAAAGA ATAG |
| 25 | Envelope; CMV promoter; Transcription | ACATTGATTATTGACTAGTTATTAATAGTAATCAATTACG GGGTCATTAGTTCATAGCCCATATATGGAGTTCCGCGTT ACATAACTTACGGTAAATGGCCCGCCTGGCTGACCGCCC AACGACCCCCGCCCATTGACGTCAATAATGACGTATGTT CCCATAGTAACGCCAATAGGGACTTTCCATTGACGTCAA TGGGTGGAGTATTTACGGTAAACTGCCCACTTGGCAGTA CATCAAGTGTATCATATGCCAAGTACGCCCCCTATTGAC GTCAATGACGGTAAATGGCCCGCCTGGCATTATGCCCAG TACATGACCTTATGGGACTTTCCTACTTGGCAGTACATCT ACGTATTAGTCATCGCTATTACCATGGTGATGCGGTTTTG GCAGTACATCAATGGGCGTGGATAGCGGTTTGACTCACG GGGATTTCCAAGTCTCCACCCCATTGACGTCAATGGGAG TTTGTTTTGGCACCAAAATCAACGGGACTTTCCAAAATG TCGTAACAACTCCGCCCCATTGACGCAAATGGGCGGTAG GCGTGTACGGTGGGAGGTCTATATAAGC |
| 26 | Envelope; VSV-G; Glycoprotein envelope-cell entry | ATGAAGTGCCTTTTGTACTTAGCCTTTTTATTCATTGGGG TGAATTGCAAGTTCACCATAGTTTTTCCACACAACCAAA AAGGAAACTGGAAAAATGTTCCTTCTAATTACCATTATT GCCCGTCAAGCTCAGATTTAAATTGGCATAATGACTTAA TAGGCACAGCCTTACAAGTCAAAATGCCCAAGAGTCACA AGGCTATTCAAGCAGACGGTTGGATGTGTCATGCTTCCA AATGGGTCACTACTTGTGATTTCCGCTGGTATGGACCGA |

-continued

| SEQ ID NO: | Description | Sequence |
|---|---|---|
| | | AGTATATAACACATTCCATCCGATCCTTCACTCCATCTGT AGAACAATGCAAGGAAAGCATTGAACAAACGAAACAAG GAACTTGGCTGAATCCAGGCTTCCCTCCTCAAAGTTGTG GATATGCAACTGTGACGGATGCCGAAGCAGTGATTGTCC AGGTGACTCCTCACCATGTGCTGGTTGATGAATACACAG GAGAATGGGTTGATTCACAGTTCATCAACGGAAAATGCA GCAATTACATATGCCCCACTGTCCATAACTCTACAACCT GGCATTCTGACTATAAGGTCAAAGGGCTATGTGATTCTA ACCTCATTTCCATGGACATCACCTTCTTCTCAGAGGACG GAGAGCTATCATCCCTGGGAAAGGAGGGCACAGGGTTC AGAAGTAACTACTTTGCTTATGAAACTGGAGGCAAGGCC TGCAAAATGCAATACTGCAAGCATTGGGGAGTCAGACTC CCATCAGGTGTCTGGTTCGAGATGGCTGATAAGGATCTC TTTGCTGCAGCCAGATTCCCTGAATGCCCAGAAGGGTCA AGTATCTCTGCTCCATCTCAGACCTCAGTGGATGTAAGT CTAATTCAGGACGTTGAGAGGATCTTGGATTATTCCCTCT GCCAAGAAACCTGGAGCAAAATCAGAGCGGGTCTTCCA ATCTCTCCAGTGGATCTCAGCTATCTTGCTCCTAAAAACC CAGGAACCGGTCCTGCTTTCACCATAATCAATGGTACCC TAAAATACTTTGAGACCAGATACATCAGAGTCGATATTG CTGCTCCAATCCTCTCAAGAATGGTCGGAATGATCAGTG GAACTACCACAGAAAGGGAACTGTGGGATGACTGGGCA CCATATGAAGACGTGGAAATTGGACCCAATGGAGTTCTG AGGACCAGTTCAGGATATAAGTTTCCTTTATACATGATT GGACATGGTATGTTGGACTCCGATCTTCATCTTAGCTCA AAGGCTCAGGTGTTCGAACATCCTCACATTCAAGACGCT GCTTCGCAACTTCCTGATGATGAGAGTTTATTTTTTGGTG ATACTGGGCTATCCAAAAATCCAATCGAGCTTGTAGAAG GTTGGTTCAGTAGTTGGAAAAGCTCTATTGCCTCTTTTTT CTTTATCATAGGGTTAATCATTGGACTATTCTTGGTTCTC CGAGTTGGTATCCATCTTTGCATTAAATTAAAGCACACC AAGAAAAGACAGATTTATACAGACATAGAGATGA |
| 27 | Helper/Rev; CMV early (CAG) enhancer; Enhance Transcription | TAGTTATTAATAGTAATCAATTACGGGGTCATTAGTTCAT AGCCCATATATGGAGTTCCGCGTTACATAACTTACGGTA AATGGCCCGCCTGGCTGACCGCCCAACGACCCCCGCCCA TTGACGTCAATAATGACGTATGTTCCCATAGTAACGCCA ATAGGGACTTTCCATTGACGTCAATGGGTGGACTATTTA CGGTAAACTGCCCACTTGGCAGTACATCAAGTGTATCAT ATGCCAAGTACGCCCCCTATTGACGTCAATGACGGTAAA TGGCCCGCCTGGCATTATGCCCAGTACATGACCTTATGG GACTTTCCTACTTGGCAGTACATCTACGTATTAGTCATC |
| 28 | Helper/Rev; Chicken beta actin intron; Enhance gene expression | GGAGTCGCTGCGTTGCCTTCGCCCCGTGCCCCGCTCCGC GCCGCCTCGCGCCGCCCGCCCCGGCTCTGACTGACCGCG TTACTCCCACAGGTGAGCGGGCGGGACGGCCCTTCTCCT CCGGGCTGTAATTAGCGCTTGGTTTAATGACGGCTCGTTT CTTTTCTGTGGCTGCGTGAAAGCCTTAAAGGGCTCCGGG AGGGCCCTTTGTGCGGGGGGGAGCGGCTCGGGGGGTGC GTGCGTGTGTGTGTGCGTGGGGAGCGCCGCGTGCGGCCC GCGCTGCCCGGCGGCTGTGAGCGCTGCGGGCGCGGCGC GGGGCTTTGTGCGCTCCGCGTGTGCGCGAGGGGAGCGCG GCCGGGGGCGGTGCCCCGCGGTGCGGGGGGGCTGCGAG GGGAACAAAGGCTGCGTGCGGGGTGTGTGCGTGGGGGG GTGAGCAGGGGGTGTGGGCGCGGCGGTCGGGCTGTAAC CCCCCCCTGCACCCCCCTCCCCGAGTTGCTGAGCACGGC CCGGCTTCGGGTGCGGGGCTCCGTGCGGGGCGTGGCGCG GGGCTCGCCGTGCCGGGCGGGGGGTGGCGGCAGGTGGG GGTGCCGGGCGGGGCGGGGCCGCCTCGGGCCGGGGAGG GCTCGGGGGAGGGGCGCGGCGGCCCCGGAGCGCCGGCG GCTGTCGAGGCGCGGCGAGCCGCAGCCATTGCCTTTTAT GGTAATCGTGCGAGAGGGCGCAGGGACTTCCTTTGTCCC AAATCTGGCGGAGCCGAAATCTGGGAGGCGCCGCCGCA CCCCCTCTAGCGGGCGCGGGCGAAGCGGTGCGGCGCCG GCAGGAAGGAAATGGGCGGGGAGGGCCTTCGTGCGTCG CCGCGCCGCCGTCCCCTTCTCCATCTCCAGCCTCGGGGCT GCCGCAGGGGGACGGCTGCCTTCGGGGGGGACGGGGCA GGGCGGGGTTCGGCTTCTGGCGTGTGACCGGCGG |
| 29 | Helper/Rev; Rabbit beta globin poly A; RNA stability | AGATCTTTTTCCCTCTGCCAAAAATTATGGGGACATCAT GAAGCCCCTTGAGCATCTGACTTCTGGCTAATAAAGGAA ATTTATTTTCATTGCAATAGTGTGTTGGAATTTTTTGTGT CTCTCACTCGGAAGGACATATGGGAGGGCAAATCATTTA AAACATCAGAATGAGTATTTGGTTTAGAGTTTGGCAACA TATGCCATATGCTGGCTGCCATGAACAAAGGTGGCTATA AAGAGGTCATCAGTATATGAAACAGCCCCCTGCTGTCCA |

-continued

| SEQ ID NO: | Description | Sequence |
|---|---|---|
| | | TTCCTTATTCCATAGAAAAGCCTTGACTTGAGGTTAGATT TTTTTTATATTTTGTTTTGTGTTATTTTTTTCTTTAACATCC CTAAAATTTTCCTTACATGTTTTACTAGCCAGATTTTTCC TCCTCTCCTGACTACTCCCAGTCATAGCTGTCCCTCTTCT CTTATGAAGATC |
| 30 | Envelope; Beta globin intron; Enhance gene expression | GTGAGTTTGGGGACCCTTGATTGTTCTTTCTTTTTCGCTA TTGTAAAATTCATGTTATATGGAGGGGGCAAAGTTTTCA GGGTGTTGTTTAGAATGGGAAGATGTCCCTTGTATCACC ATGGACCCTCATGATAATTTTGTTTCTTTCACTTTCTACT CTGTTGACAACCATTGTCTCCTCTTATTTTCTTTTCATTTT CTGTAACTTTTTCGTTAAACTTTAGCTTGCATTTGTAACG AATTTTTAAATTCACTTTTGTTTATTTGTCAGATTGTAAG TACTTTCTCTAATCACTTTTTTTTCAAGGCAATCAGGGTA TATTATATTGTACTTCAGCACAGTTTTAGAGAACAATTGT TATAATTAAATGATAAGGTAGAATATTTCTGCATATAAA TTCTGGCTGGCGTGGAAATATTCTTATTGGTAGAAACAA CTACACCCTGGTCATCATCCTGCCTTTCTCTTTATGGTTA CAATGATATACACTGTTTGAGATGAGGATAAAATACTCT GAGTCCAAACCGGGCCCCTCTGCTAACCATGTTCATGCC TTCTTCTCTTTCCTACAG |
| 31 | Envelope; Rabbit beta globin poly A; RNA stability | AGATCTTTTTCCCTCTGCCAAAAATTATGGGGACATCAT GAAGCCCCTTGAGCATCTGACTTCTGGCTAATAAAGGAA ATTTATTTTCATTGCAATAGTGTGTTGGAATTTTTTGTGT CTCTCACTCGGAAGGACATATGGGAGGGCAAATCATTTA AAACATCAGAATGAGTATTTGGTTTAGAGTTTGGCAACA TATGCCCATATGCTGGCTGCCATGAACAAAGGTTGGCTA TAAAGAGGTCATCAGTATATGAAACAGCCCCCTGCTGTC CATTCCTTATTCCATAGAAAAGCCTTGACTTGAGGTTAG ATTTTTTTTATATTTTGTTTTGTGTTATTTTTTTCTTTAACA TCCCTAAAATTTTCCTTACATGTTTTACTAGCCAGATTTT TCCTCCTCTCCTGACTACTCCCAGTCATAGCTGTCCCTCT TCTCTTATGGAGATC |
| 32 | Primer | TAAGCAGAATTCATGAATTTGCCAGGAAGAT |
| 33 | Primer | CCATACAATGAATGGACACTAGGCGGCCGCACGAAT |
| 34 | Gag, Pol, Integrase fragment | GAATTCATGAATTTGCCAGGAAGATGGAAACCAAAAAT GATAGGGGGAATTGGAGGTTTTATCAAAGTAAGACAGT ATGATCAGATACTCATAGAAATCTGCGGACATAAAGCTA TAGGTACAGTATTAGTAGGACCTACACCTGTCAACATAA TTGGAAGAAATCTGTTGACTCAGATTGGCTGCACTTTAA ATTTTCCCATTAGTCCTATTGAGACTGTACCAGTAAAATT AAAGCCAGGAATGGATGGCCCAAAAGTTAAACAATGGC CATTGACAGAAGAAAAAATAAAAGCATTAGTAGAAATT TGTACAGAAATGGAAAAGGAAGGAAAAATTTCAAAAAT TGGGCCTGAAAATCCATACAATACTCCAGTATTTGCCAT AAAGAAAAAAGACAGTACTAAATGGAGAAAATTAGTAG ATTTCAGAGAACTTAATAAGAGAACTCAAGATTTCTGGG AAGTTCAATTAGGAATACCACATCCTGCAGGGTTAAAAC AGAAAAAATCAGTAACAGTACTGGATGTGGGCGATGCA TATTTTTCAGTTCCCTTAGATAAAGACTTCAGGAAGTATA CTGCATTTACCATACCTAGTATAAACAATGAGACACCAG GGATTAGATATCAGTACAATGTGCTTCCACAGGGATGGA AAGGATCACCAGCAATATTCCAGTGTAGCATGACAAAA ATCTTAGAGCCTTTTAGAAAACAAAATCCAGACATAGTC ATCTATCAATACATGGATGATTTGTATGTAGGATCTGAC TTAGAAATAGGGCAGCATAGAACAAAAATAGAGGAACT GAGACAACATCTGTTGAGGTGGGGATTTACCACACCAGA CAAAAAACATCAGAAAGAACCTCCATTCCTTTGGATGGG TTATGAACTCCATCCTGATAAATGGACAGTACAGCCTAT AGTGCTGCCAGAAAAGGACAGCTGGACTGTCAATGACA TACAGAAATTAGTGGGAAAATTGAATTGGGCAAGTCAG ATTTATGCAGGGATTAAAGTAAGGCAATTATGTAAACTT CTTAGGGGAACCAAAGCACTAACAGAAGTAGTACCACT AACAGAAGAAGCAGAGCTAGAACTGGCAGAAAACAGGG AGATTCTAAAAGAACCGGTACATGGAGTGTATTATGACC CATCAAAAGACTTAATAGCAGAAATACAGAAGCAGGGG CAAGGCCAATGGACATATCAAATTTATCAAGAGCCATTT AAAAATCTGAAAACAGGAAAGTATGCAAGAATGAAGGG TGCCCACACTAATGATGTGAAACAATTAACAGAGGCAGT ACAAAAAATAGCCACAGAAAGCATAGTAATATGGGGAA AGACTCCTAAATTTAAATTACCCATACAAAAGGAAACAT GGGAAGCATGGTGGACAGAGTATTGGCAAGCCACCTGG |

-continued

| SEQ ID NO: | Description | Sequence |
|---|---|---|
| | | ATTCCTGAGTGGGAGTTTGTCAATACCCCTCCCTTAGTGA AGTTATGGTACCAGTTAGAGAAAGAACCCATAATAGGA GCAGAAACTTTCTATGTAGATGGGGCAGCCAATAGGGA AACTAAATTAGGAAAAGCAGGATATGTAACTGACAGAG GAAGACAAAAAGTTGTCCCCCTAACGGACACAACAAAT CAGAAGACTGAGTTACAAGCAATTCATCTAGCTTTGCAG GATTCGGGATTAGAAGTAAACATAGTGACAGACTCACA ATATGCATTGGGAATCATTCAAGCACAACCAGATAAGAG TGAATCAGAGTTAGTCAGTCAAATAATAGAGCAGTTAAT AAAAAAGGAAAAAGTCTACCTGGCATGGGTACCAGCAC ACAAAGGAATTGGAGGAAATGAACAAGTAGATAAATTG GTCAGTGCTGGAATCAGGAAAGTACTATTTTTAGATGGA ATAGATAAGGCCCAAGAAGAACATGAGAAATATCACAG TAATTGGAGAGCAATGGCTAGTGATTTTAACCTACCACC TGTAGTAGCAAAAGAAATAGTAGCCAGCTGTGATAAAT GTCAGCTAAAAGGGGAAGCCATGCATGGACAAGTAGAC TGTAGCCCAGGAATATGGCAGCTAGATTGTACACATTTA GAAGGAAAAGTTATCTTGGTAGCAGTTCATGTAGCCAGT GGATATATAGAAGCAGAAGTAATTCCAGCAGAGACAGG GCAAGAAACAGCATACTTCCTCTTAAAATTAGCAGGAAG ATGGCCAGTAAAAACAGTACATACAGACAATGGCAGCA ATTTCACCAGTACTACAGTTAAGGCCGCCTGTTGGTGGG CGGGGATCAAGCAGGAATTTGGCATTCCCTACAATCCCC AAAGTCAAGGAGTAATAGAATCTATGAATAAAGAATTA AAGAAAATTATAGGACAGGTAAGAGATCAGGCTGAACA TCTTAAGACAGCAGTACAAATGGCAGTATTCATCCACAA TTTTAAAAGAAAAGGGGGGATTGGGGGGTACAGTGCAG GGGAAAGAATAGTAGACATAATAGCAACAGACATACAA ACTAAAGAATTACAAAAACAAATTACAAAAATTCAAAA TTTTCGGGTTTATTACAGGGACAGCAGAGATCCAGTTTG GAAAGGACCAGCAAAGCTCCTCTGGAAAGGTGAAGGGG CAGTAGTAATACAAGATAATAGTGACATAAAAGTAGTG CCAAGAAGAAAAGCAAAGATCATCAGGGATTATGGAAA ACAGATGGCAGGTGATGATTGTGTGGCAAGTAGACAGG ATGAGGATTAA |
| 35 | DNA Fragment containing Rev, RRE and rabbit beta globin poly A | TCTAGAATGGCAGGAAGAAGCGGAGACAGCGACGAAGA GCTCATCAGAACAGTCAGACTCATCAAGCTTCTCTATCA AAGCAACCCACCTCCCAATCCCGAGGGGACCCGACAGG CCCGAAGGAATAGAAGAAGAAGGTGGAGAGAGAGACA GAGACAGATCCATTCGATTAGTGAACGGATCCTTGGCAC TTATCTGGGACGATCTGCGGAGCCTGTGCCTCTTCAGCT ACCACCGCTTGAGAGACTTACTCTTGATTGTAACGAGGA TTGTGGAACTTCTGGGACGCAGGGGGTGGGAAGCCCTCA AATATTGGTGGAATCTCCTACAATATTGGAGTCAGGAGC TAAAGAATAGAGGAGCTTTGTTCCTTGGGTTCTTGGGAG CAGCAGGAAGCACTATGGGCGCAGCGTCAATGACGCTG ACGGTACAGGCCAGACAATTATTGTCTGGTATAGTGCAG CAGCAGAACAATTTGCTGAGGGCTATTGAGGCGCAACA GCATCTGTTGCAACTCACAGTCTGGGGCATCAAGCAGCT CCAGGCAAGAATCCTGGCTGTGGAAAGATACCTAAAGG ATCAACAGCTCCTAGATCTTTTTCCCTCTGCCAAAAATTA TGGGGACATCATGAAGCCCCTTGAGCATCTGACTTCTGG CTAATAAAGGAAATTTATTTTCATTGCAATAGTGTGTTG GAATTTTTTGTGTCTCTCACTCGGAAGGACATATGGGAG GGCAAATCATTTAAAACATCAGAATGAGTATTTGGTTTA GAGTTTGGCAACATATGCCATATGCTGGCTGCCATGAAC AAAGGTGGCTATAAAGAGGTCATCAGTATATGAAACAG CCCCCTGCTGTCCATTCCTTATTCCATAGAAAAGCCTTGA CTTGAGGTTAGATTTTTTTTATATTTTGTTTTGTGTTATTT TTTTCTTTAACATCCCTAAAATTTTCCTTACATGTTTTACT AGCCAGATTTTTCCTCCTCTCCTGACTACTCCCAGTCATA GCTGTCCCTCTTCTCTTATGAAGATCCCTCGACCTGCAGC CCAAGCTTGGCGTAATCATGGTCATAGCTGTTTCCTGTGT GAAATTGTTATCCGCTCACAATTCCACACAACATACGAG CCGGAAGCATAAAGTGTAAAGCCTGGGGTGCCTAATGA GTGAGCTAACTCACATTAATTGCGTTGCGCTCACTGCCC GCTTTCCAGTCGGGAAACCTGTCGTGCCAGCGGATCCGC ATCTCAATTAGTCAGCAACCATAGTCCCGCCCCTAACTC CGCCCATCCCGCCCCTAACTCCGCCCAGTTCCGCCCATTC TCCGCCCCATGGCTGACTAATTTTTTTTATTTATGCAGAG GCCGAGGCCGCCTCGGCCTCTGAGCTATTCCAGAAGTAG TGAGGAGGCTTTTTTGGAGGCCTAGGCTTTTGCAAAAAG CTAACTTGTTTATTGCAGCTTATAATGGTTACAAATAAA |

-continued

| SEQ ID NO: | Description | Sequence |
|---|---|---|
| | | GCAATAGCATCACAAATTTCACAAATAAAGCATTTTTTT CACTGCATTCTAGTTGTGGTTTGTCCAAACTCATCAATGT ATCTTATCAGCGGCCGCCCCGGG |
| 36 | DNA fragment containing the CAG enhancer/promoter/ intron sequence | ACGCGTTAGTTATTAATAGTAATCAATTACGGGGTCATT AGTTCATAGCCCATATATGGAGTTCCGCGTTACATAACT TACGGTAAATGGCCCGCCTGGCTGACCGCCCAACGACCC CCGCCCATTGACGTCAATAATGACGTATGTTCCCATAGT AACGCCAATAGGGACTTTCCATTGACGTCAATGGGTGGA CTATTTACGGTAAACTGCCCACTTGGCAGTACATCAAGT GTATCATATGCCAAGTACGCCCCCTATTGACGTCAATGA CGGTAAATGGCCCGCCTGGCATTATGCCCAGTACATGAC CTTATGGGACTTTCCTACTTGGCAGTACATCTACGTATTA GTCATCGCTATTACCATGGGTCGAGGTGAGCCCCACGTT CTGCTTCACTCTCCCCATCTCCCCCCCCTCCCCACCCCCA ATTTTGTATTTATTTATTTTTTAATTATTTTGTGCAGCGAT GGGGGCGGGGGGGGGGGGGGCGCGCGCCAGGCGGGGC GGGGCGGGGCGAGGGGCGGGGCGGGGCGAGGCGGAGA GGTGCGGCGGCAGCCAATCAGAGCGGCGCGCTCCGAAA GTTTCCTTTTATGGCGAGGCGGCGGCGGCGGCGGCCCTA TAAAAAGCGAAGCGCGCGGCGGGCGGGAGTCGCTGCGT TGCCTTCGCCCCGTGCCCCGCTCCGCGCCGCCTCGCGCC GCCCGCCCCGGCTCTGACTGACCGCGTTACTCCCACAGG TGAGCGGGCGGGACGGCCCTTCTCCTCCGGGCTGTAATT AGCGCTTGGTTTAATGACGGCTCGTTTCTTTTCTGTGGCT GCGTGAAAGCCTTAAAGGGCTCCGGGAGGGCCCTTTGTG CGGGGGGGAGCGGCTCGGGGGGTGCGTGCGTGTGTGTG TGCGTGGGGAGCGCCGCGTGCGGCCCGCGCTGCCCGGCG GCTGTGAGCGCTGCGGGCGCGGCGCGGGGCTTTGTGCGC TCCGCGTGTGCGCGAGGGGAGCGCGGCCGGGGGCGGTG CCCCGCGGTGCGGGGGGGCTGCGAGGGGAACAAAGGCT GCGTGCGGGGTGTGTGCGTGGGGGGGTGAGCAGGGGGT GTGGGCGCGGCGGTCGGGCTGTAACCCCCCCCTGCACCC CCCTCCCCGAGTTGCTGAGCACGGCCCGGCTTCGGGTGC GGGGCTCCGTGCGGGGCGTGGCGCGGGGCTCGCCGTGCC GGGCGGGGGGTGGCGGCAGGTGGGGGTGCCGGGCGGGG CGGGGCCGCCTCGGGCCGGGGAGGGCTCGGGGGAGGGG CGCGGCGGCCCCGGAGCGCCGGCGGCTGTCGAGGCGCG GCGAGCCGCAGCCATTGCCTTTTATGGTAATCGTGCGAG AGGGCGCAGGGACTTCCTTTGTCCCAAATCTGGCGGAGC CGAAATCTGGGAGGCGCCGCCGCACCCCCTCTAGCGGGC GCGGGCGAAGCGGTGCGGCGCCGGCAGGAAGGAAATGG GCGGGGAGGGCCTTCGTGCGTCGCCGCGCCGCCGTCCCC TTCTCCATCTCCAGCCTCGGGGCTGCCGCAGGGGGACGG CTGCCTTCGGGGGGGACGGGGCAGGGCGGGGTTCGGCTT CTGGCGTGTGACCGGCGGGAATTC |
| 37 | DNA fragment containing VSV-G | GAATTCATGAAGTGCCTTTTGTACTTAGCCTTTTTATTCA TTGGGGTGAATTGCAAGTTCACCATAGTTTTTCCACACA ACCAAAAAGGAAACTGGAAAAATGTTCCTTCTAATTACC ATTATTGCCCGTCAAGCTCAGATTTAAATTGGCATAATG ACTTAATAGGCACAGCCTTACAAGTCAAAATGCCCAAGA GTCACAAGGCTATTCAAGCAGACGGTTGGATGTGTCATG CTTCCAAATGGGTCACTACTTGTGATTTCCGCTGGTATGG ACCGAAGTATATAACACATTCCATCCGATCCTTCACTCC ATCTGTAGAACAATGCAAGGAAAGCATTGAACAAACGA AACAAGGAACTTGGCTGAATCCAGGCTTCCCTCCTCAAA GTTGTGGATATGCAACTGTGACGGATGCCGAAGCAGTGA TTGTCCAGGTGACTCCTCACCATGTGCTGGTTGATGAAT ACACAGGAGAATGGGTTGATTCACAGTTCATCAACGGAA AATGCAGCAATTACATATGCCCCACTGTCCATAACTCTA CAACCTGGCATTCTGACTATAAGGTCAAAGGGCTATGTG ATTCTAACCTCATTTCCATGGACATCACCTTCTTCTCAGA GGACGGAGAGCTATCATCCCTGGGAAAGGAGGGCACAG GGTTCAGAAGTAACTACTTTGCTTATGAAACTGGAGGCA AGGCCTGCAAAATGCAATACTGCAAGCATTGGGGAGTC AGACTCCCATCAGGTGTCTGGTTCGAGATGGCTGATAAG GATCTCTTTGCTGCAGCCAGATTCCCTGAATGCCCAGAA GGGTCAAGTATCTCTGCTCCATCTCAGACCTCAGTGGAT GTAAGTCTAATTCAGGACGTTGAGAGGATCTTGGATTAT TCCCTCTGCCAAGAAACCTGGAGCAAAATCAGAGCGGGT CTTCCAATCTCTCCAGTGGATCTCAGCTATCTTGCTCCTA AAAACCCAGGAACCGGTCCTGCTTTCACCATAATCAATG GTACCCTAAAATACTTTGAGACCAGATACATCAGAGTCG ATATTGCTGCTCCAATCCTCTCAAGAATGGTCGGAATGA TCAGTGGAACTACCACAGAAAGGGAACTGTGGGATGAC |

-continued

| SEQ ID NO: | Description | Sequence |
|---|---|---|
| | | TGGGCACCATATGAAGACGTGGAAATTGGACCCAATGG<br>AGTTCTGAGGACCAGTTCAGGATATAAGTTTCCTTTATA<br>CATGATTGGACATGGTATGTTGGACTCCGATCTTCATCTT<br>AGCTCAAAGGCTCAGGTGTTCGAACATCCTCACATTCAA<br>GACGCTGCTTCGCAACTTCCTGATGATGAGAGTTTATTTT<br>TTGGTGATACTGGGCTATCCAAAAATCCAATCGAGCTTG<br>TAGAAGGTTGGTTCAGTAGTTGGAAAAGCTCTATTGCCT<br>CTTTTTTCTTTATCATAGGGTTAATCATTGGACTATTCTT<br>GGTTCTCCGAGTTGGTATCCATCTTTGCATTAAATTAAAG<br>CACACCAAGAAAAGACAGATTTATACAGACATAGAGAT<br>GAGAATTC |
| 38 | RSV promoter and HIV Rev | CAATTGCGATGTACGGGCCAGATATACGCGTATCTGAGG<br>GGACTAGGGTGTGTTTAGGCGAAAAGCGGGGCTTCGGTT<br>GTACGCGGTTAGGAGTCCCCTCAGGATATAGTAGTTTCG<br>CTTTTGCATAGGGAGGGGGAAATGTAGTCTTATGCAATA<br>CACTTGTAGTCTTGCAACATGGTAACGATGAGTTAGCAA<br>CATGCCTTACAAGGAGAGAAAAAGCACCGTGCATGCCG<br>ATTGGTGGAAGTAAGGTGGTACGATCGTGCCTTATTAGG<br>AAGGCAACAGACAGGTCTGACATGGATTGGACGAACCA<br>CTGAATTCCGCATTGCAGAGATAATTGTATTTAAGTGCC<br>TAGCTCGATACAATAAACGCCATTTGACCATTCACCACA<br>TTGGTGTGCACCTCCAAGCTCGAGCTCGTTTAGTGAACC<br>GTCAGATCGCCTGGAGACGCCATCCACGCTGTTTTGACC<br>TCCATAGAAGACACCGGGACCGATCCAGCCTCCCCTCGA<br>AGCTAGCGATTAGGCATCTCCTATGGCAGGAAGAAGCG<br>GAGACAGCGACGAAGAACTCCTCAAGGCAGTCAGACTC<br>ATCAAGTTTCTCTATCAAAGCAACCCACCTCCCAATCCC<br>GAGGGGACCCGACAGGCCCGAAGGAATAGAAGAAGAA<br>GGTGGAGAGAGAGACAGAGACAGATCCATTCGATTAGT<br>GAACGGATCCTTAGCACTTATCTGGGACGATCTGCGGAG<br>CCTGTGCCTCTTCAGCTACCACCGCTTGAGAGACTTACTC<br>TTGATTGTAACGAGGATTGTGGAACTTCTGGGACGCAGG<br>GGGTGGGAAGCCCTCAAATATTGGTGGAATCTCCTACAA<br>TATTGGAGTCAGGAGCTAAAGAATAGTCTAGA |
| 39 | Elongation Factor-1 alpha (EF1-alpha) promoter | CCGGTGCCTAGAGAAGGTGGCGCGGGGTAAACTGGGAA<br>AGTGATGTCGTGTACTGGCTCCGCCTTTTTCCCGAGGGTG<br>GGGGAGAACCGTATATAAGTGCAGTAGTCGCCGTGAAC<br>GTTCTTTTTCGCAACGGGTTTGCCGCCAGAACACAGGTA<br>AGTGCCGTGTGTGGTTCCCGCGGGCCTGGCCTCTTTACG<br>GGTTATGGCCCTTGCGTGCCTTGAATTACTTCCACGCCCC<br>TGGCTGCAGTACGTGATTCTTGATCCCGAGCTTCGGGTT<br>GGAAGTGGGTGGGAGAGTTCGAGGCCTTGCGCTTAAGG<br>AGCCCCTTCGCCTCGTGCTTGAGTTGAGGCCTGGCCTGG<br>GCGCTGGGGCCGCCGCGTGCGAATCTGGTGGCACCTTCG<br>CGCCTGTCTCGCTGCTTTCGATAAGTCTCTAGCCATTTAA<br>AATTTTTGATGACCTGCTGCGACGCTTTTTTTCTGGCAAG<br>ATAGTCTTGTAAATGCGGGCCAAGATCTGCACACTGGTA<br>TTTCGGTTTTTGGGGCCGCGGGCGGCGACGGGGCCCGTG<br>CGTCCCAGCGCACATGTTCGGCGAGGCGGGGCCTGCGAG<br>CGCGGCCACCGAGAATCGGACGGGGGTAGTCTCAAGCT<br>GGCCGGCCTGCTCTGGTGCCTGGCCTCGCGCCGCCGTGT<br>ATCGCCCCGCCCTGGGCGGCAAGGCTGGCCCGGTCGGCA<br>CCAGTTGCGTGAGCGGAAAGATGGCCGCTTCCCGGCCCT<br>GCTGCAGGGAGCTCAAAATGGAGGACGCGGCGCTCGGG<br>AGAGCGGGCGGGTGAGTCACCCACACAAAGGAAAAGGG<br>CCTTTCCGTCCTCAGCCGTCGCTTCATGTGACTCCACGGA<br>GTACCGGGCGCCGTCCAGGCACCTCGATTAGTTCTCGAG<br>CTTTTGGAGTACGTCGTCTTTAGGTTGGGGGGAGGGGTT<br>TTATGCGATGGAGTTTCCCCACACTGAGTGGGTGGAGAC<br>TGAAGTTAGGCCAGCTTGGCACTTGATGTAATTCTCCTTG<br>GAATTTGCCCTTTTTGAGTTTGGATCTTGGTTCATTCTCA<br>AGCCTCAGACAGTGGTTCAAAGTTTTTTTCTTCCATTTCA<br>GGTGTCGTGA |
| 40 | Promoter; PGK | GGGGTTGGGGTTGCGCCTTTTCCAAGGCAGCCCTGGGTT<br>TGCGCAGGGACGCGGCTGCTCTGGGCGTGGTTCCGGGAA<br>ACGCAGCGGCGCCGACCCTGGGTCTCGCACATTCTTCAC<br>GTCCGTTCGCAGCGTCACCCGGATCTTCGCCGCTACCCTT<br>GTGGGCCCCCCGGCGACGCTTCCTGCTCCGCCCCTAAGT<br>CGGGAAGGTTCCTTGCGGTTCGCGGCGTGCCGGACGTGA<br>CAAACGGAAGCCGCACGTCTCACTAGTACCCTCGCAGAC<br>GGACAGCGCCAGGGAGCAATGGCAGCGCGCCGACCGCG<br>ATGGGCTGTGGCCAATAGCGGCTGCTCAGCAGGGCGCGC<br>CGAGAGCAGCGGCCGGGAAGGGGCGGTGCGGGAGGCGG |

-continued

| SEQ ID NO: | Description | Sequence |
|---|---|---|
| | | GGTGTGGGGCGGTAGTGTGGGCCCTGTTCCTGCCCGCGC<br>GGTGTTCCGCATTCTGCAAGCCTCCGGAGCGCACGTCGG<br>CAGTCGGCTCCCTCGTTGACCGAATCACCGACCTCTCTCC<br>CCAG |
| 41 | Promoter; UbC | GCGCCGGGTTTTGGCGCCTCCCGCGGGCGCCCCCCTCCT<br>CACGGCGAGCGCTGCCACGTCAGACGAAGGGCGCAGGA<br>GCGTTCCTGATCCTTCCGCCCGGACGCTCAGGACAGCGG<br>CCCGCTGCTCATAAGACTCGGCCTTAGAACCCCAGTATC<br>AGCAGAAGGACATTTTAGGACGGGACTTGGGTGACTCTA<br>GGGCACTGGTTTTCTTTCCAGAGAGCGGAACAGGCGAGG<br>AAAAGTAGTCCCTTCTCGGCGATTCTGCGGAGGGATCTC<br>CGTGGGGCGGTGAACGCCGATGATTATATAAGGACGCG<br>CCGGGTGTGGCACAGCTAGTTCCGTCGCAGCCGGGATTT<br>GGGTCGCGGTTCTTGTTTGTGGATCGCTGTGATCGTCACT<br>TGGTGAGTTGCGGGCTGCTGGGCTGGCCGGGGCTTTCGT<br>GGCCGCCGGGCCGCTCGGTGGGACGGAAGCGTGTGGAG<br>AGACCGCCAAGGGCTGTAGTCTGGGTCCGCGAGCAAGG<br>TTGCCCTGAACTGGGGGTTGGGGGGAGCGCACAAAATG<br>GCGGCTGTTCCCGAGTCTTGAATGGAAGACGCTTGTAAG<br>GCGGGCTGTGAGGTCGTTGAAACAAGGTGGGGGGCATG<br>GTGGGCGGCAAGAACCCAAGGTCTTGAGGCCTTCGCTAA<br>TGCGGGAAAGCTCTTATTCGGGTGAGATGGGCTGGGGCA<br>CCATCTGGGGACCCTGACGTGAAGTTTGTCACTGACTGG<br>AGAACTCGGGTTTGTCGTCTGGTTGCGGGGGCGGCAGTT<br>ATGCGGTGCCGTTGGGCAGTGCACCCGTACCTTTGGGAG<br>CGCGCGCCTCGTCGTGTCGTGACGTCACCCGTTCTGTTGG<br>CTTATAATGCAGGGTGGGGCCACCTGCCGGTAGGTGTGC<br>GGTAGGCTTTTCTCCGTCGCAGGACGCAGGGTTCGGGCC<br>TAGGGTAGGCTCTCCTGAATCGACAGGCGCCGGACCTCT<br>GGTGAGGGGAGGGATAAGTGAGGCGTCAGTTTCTTTGGT<br>CGGTTTTATGTACCTATCTTCTTAAGTAGCTGAAGCTCCG<br>GTTTTGAACTATGCGCTCGGGGTTGGCGAGTGTGTTTTGT<br>GAAGTTTTTTAGGCACCTTTTGAAATGTAATCATTTGGGT<br>CAATATGTAATTTTCAGTGTTAGACTAGTAAA |
| 42 | Poly A; SV40 | GTTTATTGCAGCTTATAATGGTTACAAATAAAGCAATAG<br>CATCACAAATTTCACAAATAAAGCATTTTTTTCACTGCAT<br>TCTAGTTGTGGTTTGTCCAAACTCATCAATGTATCTTATC<br>A |
| 43 | Poly A; bGH | GACTGTGCCTTCTAGTTGCCAGCCATCTGTTGTTTGCCCC<br>TCCCCCGTGCCTTCCTTGACCCTGGAAGGTGCCACTCCCA<br>CTGTCCTTTCCTAATAAAATGAGGAAATTGCATCGCATT<br>GTCTGAGTAGGTGTCATTCTATTCTGGGGGGTGGGGTGG<br>GGCAGGACAGCAAGGGGGAGGATTGGGAAGACAATAGC<br>AGGCATGCTGGGGATGCGGTGGGCTCTATGG |
| 44 | Envelope; RD 114 | ATGAAACTCCCAACAGGAATGGTCATTTTATGTAGCCTA<br>ATAATAGTTCGGGCAGGGTTTGACGACCCCCGCAAGGCT<br>ATCGCATTAGTACAAAAACAACATGGTAAACCATGCGA<br>ATGCAGCGGAGGGCAGGTATCCGAGGCCCCACCGAACT<br>CCATCCAACAGGTAACTTGCCCAGGCAAGACGGCCTACT<br>TAATGACCAACCAAAAATGGAAATGCAGAGTCACTCCA<br>AAAAATCTCACCCCTAGCGGGGGAGAACTCCAGAACTG<br>CCCCTGTAACACTTTCCAGGACTCGATGCACAGTTCTTGT<br>TATACTGAATACCGGCAATGCAGGGCGAATAATAAGAC<br>ATACTACACGGCCACCTTGCTTAAAATACGGTCTGGGAG<br>CCTCAACGAGGTACAGATATTACAAAACCCCAATCAGCT<br>CCTACAGTCCCCTTGTAGGGGCTCTATAAATCAGCCCGT<br>TTGCTGGAGTGCCACAGCCCCCATCCATATCTCCGATGG<br>TGGAGGACCCCTCGATACTAAGAGAGTGTGGACAGTCCA<br>AAAAAGGCTAGAACAAATTCATAAGGCTATGCATCCTGA<br>ACTTCAATACCACCCCTTAGCCCTGCCCAAAGTCAGAGA<br>TGACCTTAGCCTTGATGCACGGACTTTTGATATCCTGAAT<br>ACCACTTTTAGGTTACTCCAGATGTCCAATTTTAGCCTTG<br>CCCAAGATTGTTGGCTCTGTTTAAAACTAGGTACCCCTA<br>CCCCTCTTGCGATACCCACTCCCTCTTTAACCTACTCCCT<br>AGCAGACTCCCTAGCGAATGCCTCCTGTCAGATTATACC<br>TCCCCTCTTGGTTCAACCGATGCAGTTCTCCAACTCGTCC<br>TGTTTATCTTCCCCTTTCATTAACGATACGGAACAAATAG<br>ACTTAGGTGCAGTCACCTTTACTAACTGCACCTCTGTAGC<br>CAATGTCAGTAGTCCTTTATGTGCCCTAAACGGGTCAGT<br>CTTCCTCTGTGGAAATAACATGGCATACACCTATTTACCC<br>CAAAACTGGACAGGACTTTGCGTCCAAGCCTCCCTCCTC<br>CCCGACATTGACATCATCCCGGGGGATGAGCCAGTCCCC |

-continued

| SEQ ID NO: | Description | Sequence |
|---|---|---|
| | | ATTCCTGCCATTGATCATTATATACATAGACCTAAACGA GCTGTACAGTTCATCCCTTTACTAGCTGGACTGGGAATC ACCGCAGCATTCACCACCGGAGCTACAGGCCTAGGTGTC TCCGTCACCCAGTATACAAAATTATCCCATCAGTTAATA TCTGATGTCCAAGTCTTATCCGGTACCATACAAGATTTAC AAGACCAGGTAGACTCGTTAGCTGAAGTAGTTCTCCAAA ATAGGAGGGGACTGGACCTACTAACGGCAGAACAAGGA GGAATTTGTTTAGCCTTACAAGAAAAATGCTGTTTTTATG CTAACAAGTCAGGAATTGTGAGAAACAAAATAAGAACC CTACAAGAAGAATTACAAAAACGCAGGGAAAGCCTGGC ATCCAACCCTCTCTGGACCGGGCTGCAGGGCTTTCTTCC GTACCTCCTACCTCTCCTGGGACCCCTACTCACCCTCCTA CTCATACTAACCATTGGGCCATGCGTTTTCAATCGATTGG TCCAATTTGTTAAAGACAGGATCTCAGTGGTCCAGGCTC TGGTTTTGACTCAGCAATATCACCAGCTAAAACCCATAG AGTACGAGCCATGA |
| 45 | Envelope; GALV | ATGCTTCTCACCTCAAGCCCGCACCACCTTCGGCACCAG ATGAGTCCTGGGAGCTGGAAAAGACTGATCATCCTCTTA AGCTGCGTATTCGGAGACGGCAAAACGAGTCTGCAGAA TAAGAACCCCCACCAGCCTGTGACCCTCACCTGGCAGGT ACTGTCCCAAACTGGGGACGTTGTCTGGGACAAAAAGGC AGTCCAGCCCCTTTGGACTTGGTGGCCCTCTCTTACACCT GATGTATGTGCCCTGGCGGCCGGTCTTGAGTCCTGGGAT ATCCCGGGATCCGATGTATCGTCCTCTAAAAGAGTTAGA CCTCCTGATTCAGACTATACTGCCGCTTATAAGCAAATC ACCTGGGGAGCCATAGGGTGCAGCTACCCTCGGGCTAGG ACCAGGATGGCAAATTCCCCCTTCTACGTGTGTCCCCGA GCTGGCCGAACCCATTCAGAAGCTAGGAGGTGTGGGGG GCTAGAATCCCTATACTGTAAAGAATGGAGTTGTGAGAC CACGGGTACCGTTTATTGGCAACCCAAGTCCTCATGGGA CCTCATAACTGTAAAATGGGACCAAAATGTGAAATGGG AGCAAAAAATTTCAAAAGTGTGAACAAACCGGCTGGTGT AACCCCCTCAAGATAGACTTCACAGAAAAAGGAAAACT CTCCAGAGATTGGATAACGGAAAAAACCTGGGAATTAA GGTTCTATGTATATGGACACCCAGGCATACAGTTGACTA TCCGCTTAGAGGTCACTAACATGCCGGTTGTGGCAGTGG GCCCAGACCCTGTCCTTGCGGAACAGGGACCTCCTAGCA AGCCCCTCACTCTCCCTCTCTCCCCACGGAAAGCGCCGC CCACCCCTCTACCCCCGGCGGCTAGTGAGCAAACCCCTG CGGTGCATGGAGAAACTGTTACCCTAAACTCTCCGCCTC CCACCAGTGGCGACCGACTCTTTGGCCTTGTGCAGGGGG CCTTCCTAACCTTGAATGCTACCAACCCAGGGGCCACTA AGTCTTGCTGGCTCTGTTTGGGCATGAGCCCCCCTTATTA TGAAGGGATAGCCTCTTCAGGAGAGGTCGCTTATACCTC CAACCATACCCGATGCCACTGGGGGGCCCAAGGAAAGC TTACCCTCACTGAGGTCTCCGGACTCGGGTCATGCATAG GGAAGGTGCCTCTTACCCATCAACATCTTTGCAACCAGA CCTTACCCATCAATTCCTCTAAAAACCATCAGTATCTGCT CCCCTCAAACCATAGCTGGTGGGCCTGCAGCACTGGCCT CACCCCCTGCCTCTCCACCTCAGTTTTTAATCAGTCTAAA GACTTCTGTGTCCAGGTCCAGCTGATCCCCCGCATCTATT ACCATTCTGAAGAAACCTTGTTACAAGCCTATGACAAAT CACCCCCCAGGTTTAAAAGAGAGCCTGCCTCACTTACCC TAGCTGTCTTCCTGGGGTTAGGGATTGCGGCAGGTATAG GTACTGGCTCAACCGCCCTAATTAAAGGGCCCATAGACC TCCAGCAAGGCCTAACCAGCCTCCAAATCGCCATTGACG CTGACCTCCGGGCCCTTCAGGACTCAATCAGCAAGCTAG AGGACTCACTGACTTCCCTATCTGAGGTAGTACTCCAAA ATAGGAGAGGCCTTGACTTACTATTCCTTAAAGAAGGAG GCCTCTGCGCGGCCCTAAAAGAAGAGTGCTGTTTTTATG TAGACCACTCAGGTGCAGTACGAGACTCCATGAAAAAA CTTAAAGAAAGACTAGATAAAAGACAGTTAGAGCGCCA GAAAAACCAAAACTGGTATGAAGGGTGGTTCAATAACT CCCCTTGGTTTACTACCCTACTATCAACCATCGCTGGGCC CCTATTGCTCCTCCTTTTGTTACTCACTCTTGGGCCCTGC ATCATCAATAAATTAATCCAATTCATCAATGATAGGATA AGTGCAGTCAAAATTTTAGTCCTTAGACAGAAATATCAG ACCCTAGATAACGAGGAAAACCTTTAA |
| 46 | Envelope; FUG | ATGGTTCCGCAGGTTCTTTTGTTTGTACTCCTTCTGGGTT TTTCGTTGTGTTTCGGGAAGTTCCCCATTTACACGATACC AGACGAACTTGGTCCCTGGAGCCCTATTGACATACACCA TCTCAGCTGTCCAAATAACCTGGTTGTGGAGGATGAAGG ATGTACCAACCTGTCCGAGTTCTCCTACATGGAACTCAA AGTGGGATACATCTCAGCCATCAAAGTGAACGGGTTCAC |

-continued

| SEQ ID NO: | Description | Sequence |
|---|---|---|
| | | TTGCACAGGTGTTGTGACAGAGGCAGAGACCTACACCAA CTTTGTTGGTTATGTCACAACCACATTCAAGAGAAAGCA TTTCCGCCCCACCCCAGACGCATGTAGAGCCGCGTATAA CTGGAAGATGGCCGGTGACCCCAGATATGAAGAGTCCCT ACACAATCCATACCCCGACTACCACTGGCTTCGAACTGT AAGAACCACCAAAGAGTCCCTCATTATCATATCCCCAAG TGTGACAGATTTGGACCCATATGACAAATCCCTTCACTC AAGGGTCTTCCCTGGCGGAAAGTGCTCAGGAATAACGGT GTCCTCTACCTACTGCTCAACTAACCATGATTACACCATT TGGATGCCCGAGAATCCGAGACCAAGGACACCTTGTGAC ATTTTTACCAATAGCAGAGGGAAGAGAGCATCCAACGG GAACAAGACTTGCGGCTTTGTGGATGAAAGAGGCCTGTA TAAGTCTCTAAAAGGAGCATGCAGGCTCAAGTTATGTGG AGTTCTTGGACTTAGACTTATGGATGGAACATGGGTCGC GATGCAAACATCAGATGAGACCAAATGGTGCCCTCCAG ATCAGTTGGTGAATTTGCACGACTTTCGCTCAGACGAGA TCGAGCATCTCGTTGTGGAGGAGTTAGTTAAGAAAAGAG AGGAATGTCTGGATGCATTAGAGTCCATCATGACCACCA AGTCAGTAAGTTTCAGACGTCTCAGTCACCTGAGAAAAC TTGTCCCAGGGTTTGGAAAAGCATATACCATATTCAACA AAACCTTGATGGAGGCTGATGCTCACTACAAGTCAGTCC GGACCTGGAATGAGATCATCCCCTCAAAAGGGTGTTTGA AAGTTGGAGGAAGGTGCCATCCTCATGTGAACGGGGTGT TTTTCAATGGTATAATATTAGGGCCTGACGACCATGTCCT AATCCCAGAGATGCAATCATCCCTCCTCCAGCAACATAT GGAGTTGTTGGAATCTTCAGTTATCCCCCTGATGCACCCC CTGGCAGACCCTTCTACAGTTTTCAAAGAAGGTGATGAG GCTGAGGATTTTGTTGAAGTTCACCTCCCCGATGTGTAC AAACAGATCTCAGGGGTTGACCTGGGTCTCCCGAACTGG GGAAAGTATGTATTGATGACTGCAGGGGCCATGATTGGC CTGGTGTTGATATTTTCCCTAATGACATGGTGCAGAGTTG GTATCCATCTTTGCATTAAATTAAAGCACACCAAGAAAA GACAGATTTATACAGACATAGAGATGAACCGACTTGGA AAGTAA |
| 47 | Envelope; LCMV | ATGGGTCAGATTGTGACAATGTTTGAGGCTCTGCCTCAC ATCATCGATGAGGTGATCAACATTGTCATTATTGTGCTTA TCGTGATCACGGGTATCAAGGCTGTCTACAATTTTGCCA CCTGTGGGATATTCGCATTGATCAGTTTCCTACTTCTGGC TGGCAGGTCCTGTGGCATGTACGGTCTTAAGGGACCCGA CATTTACAAAGGAGTTTACCAATTTAAGTCAGTGGAGTT TGATATGTCACATCTGAACCTGACCATGCCCAACGCATG TTCAGCCAACAACTCCCACCATTACATCAGTATGGGGAC TTCTGGACTAGAATTGACCTTCACCAATGATTCCATCATC AGTCACAACTTTTGCAATCTGACCTCTGCCTTCAACAAA AAGACCTTTGACCACACACTCATGAGTATAGTTTCGAGC CTACACCTCAGTATCAGAGGGAACTCCAACTATAAGGCA GTATCCTGCGACTTCAACAATGGCATAACCATCCAATAC AACTTGACATTCTCAGATCGACAAAGTGCTCAGAGCCAG TGTAGAACCTTCAGAGGTAGAGTCCTAGATATGTTTAGA ACTGCCTTCGGGGGGAAATACATGAGGAGTGGCTGGGG CTGGACAGGCTCAGATGGCAAGACCACCTGGTGTAGCCA GACGAGTTACCAATACCTGATTATACAAAATAGAACCTG GGAAAACCACTGCACATATGCAGGTCCTTTTGGGATGTC CAGGATTCTCCTTTCCCAAGAGAAGACTAAGTTCTTCAC TAGGAGACTAGCGGGCACATTCACCTGGACTTTGTCAGA CTCTTCAGGGGTGGAGAATCCAGGTGGTTATTGCCTGAC CAAATGGATGATTCTTGCTGCAGAGCTTAAGTGTTTCGG GAACACAGCAGTTGCGAAATGCAATGTAAATCATGATGC CGAATTCTGTGACATGCTGCGACTAATTGACTACAACAA GGCTGCTTTGAGTAAGTTCAAAGAGGACGTAGAATCTGC CTTGCACTTATTCAAAACAACAGTGAATTCTTTGATTTCA GATCAACTACTGATGAGGAACCACTTGAGAGATCTGATG GGGGTGCCATATTGCAATTACTCAAAGTTTTGGTACCTA GAACATGCAAAGACCGGCGAAACTAGTGTCCCCAAGTG CTGGCTTGTCACCAATGGTTCTTACTTAAATGAGACCCA CTTCAGTGATCAAATCGAACAGGAAGCCGATAACATGAT TACAGAGATGTTGAGGAAGGATTACATAAAGAGGCAGG GGAGTACCCCCCTAGCATTGATGGACCTTCTGATGTTTTC CACATCTGCATATCTAGTCAGCATCTTCCTGCACCTTGTC AAAATACCAACACACAGGCACATAAAAGGTGGCTCATG TCCAAAGCCACACCGATTAACCAACAAAGGAATTTGTAG TTGTGGTGCATTTAAGGTGCCTGGTGTAAAAACCGTCTG GAAAAGACGCTGA |

-continued

| SEQ ID NO: | Description | Sequence |
|---|---|---|
| 48 | Envelope; FPV | ATGAACACTCAAATCCTGGTTTTCGCCCTTGTGGCAGTC<br>ATCCCCACAAATGCAGACAAAATTTGTCTTGGACATCAT<br>GCTGTATCAAATGGCACCAAAGTAAACACACTCACTGAG<br>AGAGGAGTAGAAGTTGTCAATGCAACGGAAACAGTGGA<br>GCGGACAAACATCCCCAAAATTTGCTCAAAAGGGAAAA<br>GAACCACTGATCTTGGCCAATGCGGACTGTTAGGGACCA<br>TTACCGGACCACCTCAATGCGACCAATTTCTAGAATTTTC<br>AGCTGATCTAATAATCGAGAGACGAGAAGGAAATGATG<br>TTTGTTACCCGGGGAAGTTTGTTAATGAAGAGGCATTGC<br>GACAAATCCTCAGAGGATCAGGTGGATTGACAAAGAA<br>ACAATGGGATTCACATATAGTGGAATAAGGACCAACGG<br>AACAACTAGTGCATGTAGAAGATCAGGGTCTTCATTCTA<br>TGCAGAAATGGAGTGGCTCCTGTCAAATACAGACAATGC<br>TGCTTTCCCACAAATGACAAAATCATACAAAAACACAAG<br>GAGAGAATCAGCTCTGATAGTCTGGGGAATCCACCATTC<br>AGGATCAACCACCGAACAGACCAAACTATATGGGAGTG<br>GAAATAAACTGATAACAGTCGGGAGTTCCAAATATCATC<br>AATCTTTTGTGCCGAGTCCAGGAACACGACCGCAGATAA<br>ATGGCCAGTCCGGACGGATTGATTTTCATTGGTTGATCTT<br>GGATCCCAATGATACAGTTACTTTTAGTTTCAATGGGGC<br>TTTCATAGCTCCAAATCGTGCCAGCTTCTTGAGGGGAAA<br>GTCCATGGGGATCCAGAGCGATGTGCAGGTTGATGCCAA<br>TTGCGAAGGGGAATGCTACCACAGTGGAGGGACTATAA<br>CAAGCAGATTGCCTTTTCAAAACATCAATAGCAGAGCAG<br>TTGGCAAATGCCCAAGATATGTAAAACAGGAAAGTTTAT<br>TATTGGCAACTGGGATGAAGAACGTTCCCGAACCTTCCA<br>AAAAAAGGAAAAAAAGAGGCCTGTTTGGCGCTATAGCA<br>GGGTTTATTGAAAATGGTTGGGAAGGTCTGGTCGACGGG<br>TGGTACGGTTTCAGGCATCAGAATGCACAAGGAGAAGG<br>AACTGCAGCAGACTACAAAAGCACCCAATCGGCAATTG<br>ATCAGATAACCGGAAAGTTAAATAGACTCATTGAGAAA<br>ACCAACCAGCAATTTGAGCTAATAGATAATGAATTCACT<br>GAGGTGGAAAAGCAGATTGGCAATTTAATTAACTGGACC<br>AAAGACTCCATCACAGAAGTATGGTCTTACAATGCTGAA<br>CTTCTTGTGGCAATGGAAAACCAGCACACTATTGATTTG<br>GCTGATTCAGAGATGAACAAGCTGTATGAGCGAGTGAG<br>GAAACAATTAAGGGAAAATGCTGAAGAGGATGGCACTG<br>GTTGCTTTGAAATTTTTCATAAATGTGACGATGATTGTAT<br>GGCTAGTATAAGGAACAATACTTATGATCACAGCAAATA<br>CAGAGAAGAAGCGATGCAAAATAGAATACAAATTGACC<br>CAGTCAAATTGAGTAGTGGCTACAAAGATGTGATACTTT<br>GGTTTAGCTTCGGGGCATCATGCTTTTTGCTTCTTGCCAT<br>TGCAATGGGCCTTGTTTTCATATGTGTGAAGAACGGAAA<br>CATGCGGTGCACTATTTGTATATAA |
| 49 | Envelope; RRV | AGTGTAACAGAGCACTTTAATGTGTATAAGGCTACTAGA<br>CCATACCTAGCACATTGCGCCGATTGCGGGGACGGGTAC<br>TTCTGCTATAGCCCAGTTGCTATCGAGGAGATCCGAGAT<br>GAGGCGTCTGATGGCATGCTTAAGATCCAAGTCTCCGCC<br>CAAATAGGTCTGGACAAGGCAGGCACCCACGCCCACAC<br>GAAGCTCCGATATATGGCTGGTCATGATGTTCAGGAATC<br>TAAGAGAGATTCCTTGAGGGTGTACACGTCCGCAGCGTG<br>CTCCATACATGGGACGATGGGACACTTCATCGTCGCACA<br>CTGTCCACCAGGCGACTACCTCAAGGTTTCGTTCGAGGA<br>CGCAGATTCGCACGTGAAGGCATGTAAGGTCCAATACAA<br>GCACAATCCATTGCCGGTGGGTAGAGAGAAGTTCGTGGT<br>TAGACCACACTTTGGCGTAGAGCTGCCATGCACCTCATA<br>CCAGCTGACAACGGCTCCCACCGACGAGGAGATTGACAT<br>GCATACACCGCCAGATATACCGGATCGCACCCTGCTATC<br>ACAGACGGCGGGCAACGTCAAAATAACAGCAGGCGGCA<br>GGACTATCAGGTACAACTGTACCTGCGGCCGTGACAACG<br>TAGGCACTACCAGTACTGACAAGACCATCAACACATGCA<br>AGATTGACCAATGCCATGCTGCCGTCACCAGCCATGACA<br>AATGGCAATTTACCTCTCCATTTGTTCCCAGGGCTGATCA<br>GACAGCTAGGAAAGGCAAGGTACACGTTCCGTTCCCTCT<br>GACTAACGTCACCTGCCGAGTGCCGTTGGCTCGAGCGCC<br>GGATGCCACCTATGGTAAGAAGGAGGTGACCCTGAGATT<br>ACACCCAGATCATCCGACGCTCTTCTCCTATAGGAGTTT<br>AGGAGCCGAACCGCACCCGTACGAGGAATGGGTTGACA<br>AGTTCTCTGAGCGCATCATCCCAGTGACGGAAGAAGGGA<br>TTGAGTACCAGTGGGGCAACAACCCGCCGGTCTGCCTGT<br>GGGCGCAACTGACGACCGAGGGCAAACCCCATGGCTGG<br>CCACATGAAATCATTCAGTACTATTATGGACTATACCCC<br>GCCGCCACTATTGCCGCAGTATCCGGGGCGAGTCTGATG<br>GCCCTCCTAACTCTGGCGGCCACATGCTGCATGCTGGCC |

-continued

| SEQ ID NO: | Description | Sequence |
|---|---|---|
| | | ACCGCGAGGAGAAAGTGCCTAACACCGTACGCCCTGAC |
| | | GCCAGGAGCGGTGGTACCGTTGACACTGGGGCTGCTTTG |
| | | CTGCGCACCGAGGGCGAATGCA |
| 50 | Envelope; MLV | ATGGAAGGTCCAGCGTTCTCAAAACCCCTTAAAGATAAG |
| | 10A1 | ATTAACCCGTGGAAGTCCTTAATGGTCATGGGGGTCTAT |
| | | TTAAGAGTAGGGATGGCAGAGAGCCCCCATCAGGTCTTT |
| | | AATGTAACCTGGAGAGTCACCAACCTGATGACTGGGCGT |
| | | ACCGCCAATGCCACCTCCCTTTTAGGAACTGTACAAGAT |
| | | GCCTTCCCAAGATTATATTTTGATCTATGTGATCTGGTCG |
| | | GAGAAGAGTGGGACCCTTCAGACCAGGAACCATATGTC |
| | | GGGTATGGCTGCAAATACCCCGGAGGGAGAAAGCGGAC |
| | | CCGGACTTTTGACTTTTACGTGTGCCCTGGGCATACCGTA |
| | | AAATCGGGGTGTGGGGGGCCAAGAGAGGGCTACTGTGG |
| | | TGAATGGGGTTGTGAAACCACCGGACAGGCTTACTGGAA |
| | | GCCCACATCATCATGGGACCTAATCTCCCTTAAGCGCGG |
| | | TAACACCCCCTGGGACACGGGATGCTCCAAAATGGCTTG |
| | | TGGCCCCTGCTACGACCTCTCCAAAGTATCCAATTCCTTC |
| | | CAAGGGGCTACTCGAGGGGGCAGATGCAACCCTCTAGTC |
| | | CTAGAATTCACTGATGCAGGAAAAAAGGCTAATTGGGA |
| | | CGGGCCCAAATCGTGGGGACTGAGACTGTACCGGACAG |
| | | GAACAGATCCTATTACCATGTTCTCCCTGACCCGCCAGG |
| | | TCCTCAATATAGGGCCCCGCATCCCCATTGGGCCTAATC |
| | | CCGTGATCACTGGTCAACTACCCCCCTCCCGACCCGTGC |
| | | AGATCAGGCTCCCCAGGCCTCCTCAGCCTCCTCCTACAG |
| | | GCGCAGCCTCTATAGTCCCTGAGACTGCCCCACCTTCTC |
| | | AACAACCTGGGACGGGAGACAGGCTGCTAAACCTGGTA |
| | | GAAGGAGCCTATCAGGCGCTTAACCTCACCAATCCCGAC |
| | | AAGACCCAAGAATGTTGGCTGTGCTTAGTGTCGGGACCT |
| | | CCTTATTACGAAGGAGTAGCGGTCGTGGGCACTTATACC |
| | | AATCATTCTACCGCCCCGGCCAGCTGTACGGCCACTTCC |
| | | CAACATAAGCTTACCCTATCTGAAGTGACAGGACAGGGC |
| | | CTATGCATGGGAGCACTACCTAAAACTCACCAGGCCTTA |
| | | TGTAACACCACCCAAAGTGCCGGCTCAGGATCCTACTAC |
| | | CTTGCAGCACCCGCTGGAACAATGTGGGCTTGTAGCACT |
| | | GGATTGACTCCCTGCTTGTCCACCACGATGCTCAATCTA |
| | | ACCACAGACTATTGTGTATTAGTTGAGCTCTGGCCCAGA |
| | | ATAATTTACCACTCCCCCGATTATATGTATGGTCAGCTTG |
| | | AACAGCGTACCAAATATAAGAGGGAGCCAGTATCGTTG |
| | | ACCCTGGCCCTTCTGCTAGGAGGATTAACCATGGGAGGG |
| | | ATTGCAGCTGGAATAGGGACGGGGACCACTGCCCTAATC |
| | | AAAACCCAGCAGTTTGAGCAGCTTCACGCCGCTATCCAG |
| | | ACAGACCTCAACGAAGTCGAAAAATCAATTACCAACCTA |
| | | GAAAAGTCACTGACCTCGTTGTCTGAAGTAGTCCTACAG |
| | | AACCGAAGAGGCCTAGATTTGCTCTTCCTAAAAGAGGGA |
| | | GGTCTCTGCGCAGCCCTAAAAGAAGAATGTTGTTTTTAT |
| | | GCAGACCACACGGGACTAGTGAGAGACAGCATGGCCAA |
| | | ACTAAGGGAAAGGCTTAATCAGAGACAAAAACTATTTG |
| | | AGTCAGGCCAAGGTTGGTTCGAAGGGCAGTTTAATAGAT |
| | | CCCCCTGGTTTACCACCTTAATCTCCACCATCATGGGACC |
| | | TCTAATAGTACTCTTACTGATCTTACTCTTTGGACCCTGC |
| | | ATTCTCAATCGATTGGTCCAATTTGTTAAAGACAGGATC |
| | | TCAGTGGTCCAGGCTCTGGTTTTGACTCAACAATATCAC |
| | | CAGCTAAAACCTATAGAGTACGAGCCATGA |
| 51 | Envelope; Ebola | ATGGGTGTTACAGGAATATTGCAGTTACCTCGTGATCGA |
| | | TTCAAGAGGACATCATTCTTTCTTTGGGTAATTATCCTTT |
| | | TCCAAAGAACATTTTCCATCCCACTTGGAGTCATCCACA |
| | | ATAGCACATTACAGGTTAGTGATGTCGACAAACTGGTTT |
| | | GCCGTGACAAACTGTCATCCACAAATCAATTGAGATCAG |
| | | TTGGACTGAATCTCGAAGGGAATGGAGTGGCAACTGAC |
| | | GTGCCATCTGCAACTAAAAGATGGGGCTTCAGGTCCGGT |
| | | GTCCCACCAAAGGTGGTCAATTATGAAGCTGGTGAATGG |
| | | GCTGAAAACTGCTACAATCTTGAAATCAAAAAACCTGAC |
| | | GGGAGTGAGTGTCTACCAGCAGCGCCAGACGGGATTCG |
| | | GGGCTTCCCCCGGTGCCGGTATGTGCACAAAGTATCAGG |
| | | AACGGGACCGTGTGCCGGAGACTTTGCCTTCCACAAAGA |
| | | GGGTGCTTTCTTCCTGTATGACCGACTTGCTTCCACAGTT |
| | | ATCTACCGAGGAACGACTTTCGCTGAAGGTGTCGTTGCA |
| | | TTTCTGATACTGCCCCAAGCTAAGAAGGACTTCTTCAGC |
| | | TCACACCCCTTGAGAGAGCCGGTCAATGCAACGGAGGA |
| | | CCCGTCTAGTGGCTACTATTCTACCACAATTAGATATCA |
| | | AGCTACCGGTTTTGGAACCAATGAGACAGAGTATTTGTT |
| | | CGAGGTTGACAATTTGACCTACGTCCAACTTGAATCAAG |
| | | ATTCACACCACAGTTTCTGCTCCAGCTGAATGAGACAAT |
| | | ATATACAAGTGGGAAAAGGAGCAATACCACGGGAAAAC |

-continued

| SEQ ID NO: | Description | Sequence |
|---|---|---|
| | | TAATTTGGAAGGTCAACCCCGAAATTGATACAACAATCG GGGAGTGGGCCTTCTGGGAAACTAAAAAAACCTCACTA GAAAAATTCGCAGTGAAGAGTTGTCTTTCACAGCTGTAT CAAACAGAGCCAAAAACATCAGTGGTCAGAGTCCGGCG CGAACTTCTTCCGACCCAGGGACCAACACAACAACTGAA GACCACAAAATCATGGCTTCAGAAAATTCCTCTGCAATG GTTCAAGTGCACAGTCAAGGAAGGGAAGCTGCAGTGTC GCATCTGACAACCCTTGCCACAATCTCCACGAGTCCTCA ACCCCCCACAACCAAACCAGGTCCGGACAACAGCACCC ACAATACACCCGTGTATAAACTTGACATCTCTGAGGCAA CTCAAGTTGAACAACATCACCGCAGAACAGACAACGAC AGCACAGCCTCCGACACTCCCCCCGCCACGACCGCAGCC GGACCCCTAAAAGCAGAGAACACCAACACGAGCAAGGG TACCGACCTCCTGGACCCCGCCACCACAACAAGTCCCCA AAACCACAGCGAGACCGCTGGCAACAACAACACTCATC ACCAAGATACCGGAGAAGAGAGTGCCAGCAGCGGGAAG CTAGGCTTAATTACCAATACTATTGCTGGAGTCGCAGGA CTGATCACAGGCGGGAGGAGAGCTCGAAGAGAAGCAAT TGTCAATGCTCAACCCAAATGCAACCCTAATTTACATTA CTGGACTACTCAGGATGAAGGTGCTGCAATCGGACTGGC CTGGATACCATATTTCGGGCCAGCAGCCGAGGGAATTTA CATAGAGGGGCTGATGCACAATCAAGATGGTTTAATCTG TGGGTTGAGACAGCTGGCCAACGAGACGACTCAAGCTCT TCAACTGTTCCTGAGAGCCACAACCGAGCTACGCACCTT TTCAATCCTCAACCGTAAGGCAATTGATTTCTTGCTGCAG CGATGGGGCGGCACATGCCACATTTTGGGACCGGACTGC TGTATCGAACCACATGATTGGACCAAGAACATAACAGAC AAAATTGATCAGATTATTCATGATTTTGTTGATAAAACC CTTCCGGACCAGGGGGACAATGACAATTGGTGGACAGG ATGGAGACAATGGATACCGGCAGGTATTGGAGTTACAG GCGTTATAATTGCAGTTATCGCTTTATTCTGTATATGCAA ATTTGTCTTTTAG |
| 52 | Polymerase III shRNA promoters; U6 promoter | TTTCCCATGATTCCTTCATATTTGCATATACGATACAAGG CTGTTAGAGAGATAATTGGAATTAATTTGACTGTAAACA CAAAGATATTAGTACAAAATACGTGACGTAGAAAGTAA TAATTTCTTGGGTAGTTTGCAGTTTTAAAATTATGTTTTA AAATGGACTATCATATGCTTACCGTAACTTGAAAGTATT TCGATTTCTTGGCTTTATATATCTTGTGGAAAGGACGAA AC |
| 53 | Polymerase III shRNA promoters; 7SK promoter | CTGCAGTATTTAGCATGCCCCACCCATCTGCAAGGCATT CTGGATAGTGTCAAAACAGCCGGAAATCAAGTCCGTTTA TCTCAAACTTTAGCATTTTGGGAATAAATGATATTTGCTA TGCTGGTTAAATTAGATTTTAGTTAAATTTCCTGCTGAAG CTCTAGTACGATAAGCAACTTGACCTAAGTGTAAAGTTG AGATTTCCTTCAGGTTTATATAGCTTGTGCGCCGCCTGGC TACCTC |
| 54 | FDPS target sequence #1 | GTCCTGGAGTACAATGCCATT |
| 55 | FDPS target sequence #2 | GCAGGATTTCGTTCAGCACTT |
| 56 | FDPS target sequence #3 | GCCATGTACATGGCAGGAATT |
| 57 | FDPS target sequence #4 | GCAGAAGGAGGCTGAGAAAGT |
| 58 | Non-targeting sequence | GCCGCTTTGTAGGATAGAGCTCGAGCTCTATCCTACAAA GCGGCTTTTT |
| 59 | Forward primer | AGGAATTGATGGCGAGAAGG |
| 60 | Reverse primer | CCCAAAGAGGTCAAGGTAATCA |
| 61 | Forward primer | AGCGCGGCTACAGCTTCA |
| 62 | Reverse primer | GGCGACGTAGCACAGCTTCT |
| 63 | Left Inverted Terminal Repeat (Left ITR) | CCTGCAGGCAGCTGCGCGCTCGCTCGCTCACTGAGGCCG CCCGGGCGTCGGGCGACCTTTGGTCGCCCGGCCTCAGTG AGCGAGCGAGCGCGCAGAGAGGGAGTGGCCAACTCCAT CACTAGGGGTTCCT |

-continued

| SEQ ID NO: | Description | Sequence |
|---|---|---|
| 64 | Right Inverted Terminal Repeat (Right ITR) | GAGCGGCCGCAGGAACCCCTAGTGATGGAGTTGGCCACT<br>CCCTCTCTGCGCGCTCGCTCGCTCACTGAGGCCGGGCGA<br>CCAAAGGTCGCCCGACGCCCGGGCTTTGCCCGGGCGGCC<br>TCAGTGAGCGAGCGAGCGCGCAGCTGCCTGCAGG |
| 65 | RRE/rabbit poly A beta globin | TCTAGAAGGAGCTTTGTTCCTTGGGTTCTTGGGAGCAGC<br>AGGAAGCACTATGGGCGCAGCGTCAATGACGCTGACGG<br>TACAGGCCAGACAATTATTGTCTGGTATAGTGCAGCAGC<br>AGAACAATTTGCTGAGGGCTATTGAGGCGCAACAGCATC<br>TGTTGCAACTCACAGTCTGGGGCATCAAGCAGCTCCAGG<br>CAAGAATCCTGGCTGTGGAAAGATACCTAAAGGATCAA<br>CAGCTCCTAGATCTTTTTCCCTCTGCCAAAAATTATGGGG<br>ACATCATGAAGCCCCTTGAGCATCTGACTTCTGGCTAAT<br>AAAGGAAATTTATTTTCATTGCAATAGTGTGTTGGAATTT<br>TTTGTGTCTCTCACTCGGAAGGACATATGGGAGGGCAAA<br>TCATTTAAAACATCAGAATGAGTATTTGGTTTAGAGTTT<br>GGCAACATATGCCATATGCTGGCTGCCATGAACAAAGGT<br>GGCTATAAAGAGGTCATCAGTATATGAAACAGCCCCCTG<br>CTGTCCATTCCTTATTCCATAGAAAAGCCTTGACTTGAGG<br>TTAGATTTTTTTTATATTTTGTTTTGTGTTATTTTTTTCTTT<br>AACATCCCTAAAATTTTCCTTACATGTTTTACTAGCCAGA<br>TTTTTCCTCCTCTCCTGACTACTCCCAGTCATAGCTGTCC<br>CTCTTCTCTTATGAAGATCCCTCGACCTGCAGCCCAAGCT<br>TGGCGTAATCATGGTCATAGCTGTTTCCTGTGTGAAATTG<br>TTATCCGCTCACAATTCCACACAACATACGAGCCGGAAG<br>CATAAAGTGTAAAGCCTGGGGTGCCTAATGAGTGAGCTA<br>ACTCACATTAATTGCGTTGCGCTCACTGCCCGCTTTCCAG<br>TCGGGAAACCTGTCGTGCCAGCGGATCCGCATCTCAATT<br>AGTCAGCAACCATAGTCCCGCCCCTAACTCCGCCCATCC<br>CGCCCCTAACTCCGCCCAGTTCCGCCCATTCTCCGCCCCA<br>TGGCTGACTAATTTTTTTTATTTATGCAGAGGCCGAGGCC<br>GCCTCGGCCTCTGAGCTATTCCAGAAGTAGTGAGGAGGC<br>TTTTTTGGAGGCCTAGGCTTTTGCAAAAAGCTAACTTGTT<br>TATTGCAGCTTATAATGGTTACAAATAAAGCAATAGCAT<br>CACAAATTTCACAAATAAAGCATTTTTTTCACTGCATTCT<br>AGTTGTGGTTTGTCCAAACTCATCAATGTATCTTATCACC<br>CGGG |

While certain of the preferred embodiments of the present invention have been described and specifically exemplified above, it is not intended that the invention be limited to such embodiments. Various modifications may be made thereto without departing from the scope and spirit of the present invention.

What is claimed is:

1. A method of activating a GD T cell comprising:

contacting a target cell with a bisphosphonate drug; and infecting, in the presence of the GD T cell, the target cell with a viral delivery system that encodes at least one genetic element comprising a small RNA capable of inhibiting production of FDP S, wherein the GD T cell is activated.

2. The method of claim 1, further comprising killing of the target cell by the activated GD T cell.

3. The method of claim 1, wherein the target cell is a cancer cell.

4. The method of claim 3, wherein the cancer cell is derived from a carcinoma, a leukemia, a lymphoma, a sarcoma, a myeloma, a mesothelioma, a mixed type, or mixtures thereof.

5. The method of claim 1, wherein activating the GD T cell comprises increasing tumor necrosis factor TNF-α expression by the GD T cell.

6. The method of claim 1, wherein the small RNA is a microRNA or a shRNA.

7. The method of claim 6, wherein the shRNA comprises a sequence having at least 80% identity with SEQ ID NO: 1, SEQ ID NO: 2, SEQ ID NO: 3, or SEQ ID NO: 4.

8. The method of claim 7, wherein the shRNA comprises SEQ ID NO: 1, SEQ ID NO: 2, SEQ ID NO: 3, or SEQ ID NO: 4.

9. The method of claim 6, wherein the microRNA comprises a sequence having at least 80% identity with SEQ ID NO: 5, SEQ ID NO: 6, SEQ ID NO: 7, SEQ ID NO: 8, SEQ ID NO: 9, or SEQ ID NO: 10.

10. The method of claim 9, wherein the microRNA comprises SEQ ID NO: 5, SEQ ID NO: 6, SEQ ID NO: 7, SEQ ID NO: 8, SEQ ID NO: 9, or SEQ ID NO: 10.

11. The method of claim 1, wherein the bisphosphonate drug comprises zoledronic acid.

12. The method of claim 1, wherein the contacting step and the infecting step occur simultaneously.

13. The method of claim 1, wherein the contacting step and the infecting step occur sequentially.

14. A method of activating a lymphocyte cell comprising:

contacting a target cell with a bisphosphonate drug; and infecting, in the presence of the lymphocyte cell, the target cell with a viral delivery system that encodes at least one genetic element comprising a small RNA capable of inhibiting production of an enzyme of the mevalonate pathway, wherein the lymphocyte cell is activated.

15. The method of claim 14, further comprising killing of the target cell by the activated lymphocyte.

16. The method of claim 14, wherein the enzyme of the mevalonate pathway is FDPS.

17. The method of claim 14, wherein the lymphocyte is a GD T cell.

18. The method of claim 17, wherein activating the lymphocyte comprise increasing TNF-α expression by the GD T cell.

19. The method of claim 14, wherein the target cell is a cancer cell.

20. The method of claim 19, wherein the cancer cell is derived from a carcinoma, a leukemia, a lymphoma, a sarcoma, a myeloma, a mesothelioma, a mixed type, or mixtures thereof.

* * * * *